US010874541B2

(12) United States Patent
Seres et al.

(10) Patent No.: US 10,874,541 B2
(45) Date of Patent: Dec. 29, 2020

(54) OSTOMY MONITORING SYSTEM AND METHOD

(71) Applicant: 11 Health and Technologies Inc., Tustin, CA (US)

(72) Inventors: Michael Seres, Radlett (GB); Anupriya Jai Tilak Naik, Irvine, CA (US); David Ramirez-Ayala, Baldwin Park, CA (US); Yumeng Wu, Tustin, CA (US); Bryan Went, Camarillo, CA (US); Erick Went, Camarillo, CA (US); Sabrina Kaefer, Tustin, CA (US); Irina Dorofeeva, Riverside, CA (US); Tianbin Zhao, Irvine, CA (US)

(73) Assignee: 11 Health and Technologies Limited, Borehamwood (GB)

( * ) Notice: Subject to any disclaimer, the term of this patent is extended or adjusted under 35 U.S.C. 154(b) by 10 days.

(21) Appl. No.: 16/184,764

(22) Filed: Nov. 8, 2018

(65) Prior Publication Data
US 2019/0133810 A1 May 9, 2019

Related U.S. Application Data

(60) Provisional application No. 62/584,018, filed on Nov. 9, 2017, provisional application No. 62/584,611, filed (Continued)

(51) Int. Cl.
*A61F 5/445* (2006.01)
*A61F 5/443* (2006.01)
(Continued)

(52) U.S. Cl.
CPC .............. *A61F 5/443* (2013.01); *A61B 5/002* (2013.01); *A61B 5/01* (2013.01); *A61B 5/14539* (2013.01);
(Continued)

(58) Field of Classification Search
CPC .... A61F 5/445; A61F 5/448; A61F 2013/002; A61F 2013/00953; A61B 5/6802; A61B 2562/0271
See application file for complete search history.

(56) References Cited

U.S. PATENT DOCUMENTS

| 28,341 A | 5/1860 | Bennett |
| 3,507,282 A | 4/1970 | Burding |

(Continued)

FOREIGN PATENT DOCUMENTS

| EP | 1188157 B1 | 12/2005 |
| EP | 1610715 B1 | 11/2018 |

(Continued)

OTHER PUBLICATIONS

International Search Report and Written Opinion in in corresponding International Patent Application No. PCT/US2018/059884, dated Apr. 26, 2019, in 17 pages.

(Continued)

*Primary Examiner* — Peter S Vasat
*Assistant Examiner* — Meagan Ngo
(74) *Attorney, Agent, or Firm* — Knobbe, Martens, Olson & Bear, LLP

(57) ABSTRACT

An ostomy bag can include one or more sensors for measuring one or more metrics. An ostomy wafer can also include one or more sensors for measuring one or more metrics. The sensors can be temperature sensors and/or capacitive sensors, for example, and the metrics can include bag fill, leakage, skin irritation, and phase of stoma output, among others.

23 Claims, 74 Drawing Sheets
(46 of 74 Drawing Sheet(s) Filed in Color)

Related U.S. Application Data on Nov. 10, 2017, provisional application No. 62/637,974, filed on Mar. 2, 2018, provisional application No. 62/650,511, filed on Mar. 30, 2018, provisional application No. 62/675,360, filed on May 23, 2018.

(51) Int. Cl.

| | | |
|---|---|---|
| *A61F 5/44* | (2006.01) | |
| *A61B 5/00* | (2006.01) | |
| *A61F 5/441* | (2006.01) | |
| *A61B 5/01* | (2006.01) | |
| *A61B 5/145* | (2006.01) | |
| *A61B 7/00* | (2006.01) | |
| *A61F 5/448* | (2006.01) | |
| *G01F 23/26* | (2006.01) | |
| *G01K 13/02* | (2006.01) | |
| *A61F 13/42* | (2006.01) | |
| *A61F 13/02* | (2006.01) | |

(52) U.S. Cl.
CPC ............ *A61B 5/445* (2013.01); *A61B 5/4848* (2013.01); *A61B 5/6802* (2013.01); *A61B 5/746* (2013.01); *A61B 7/008* (2013.01); *A61F 5/441* (2013.01); *A61F 5/4404* (2013.01); *A61F 5/445* (2013.01); *A61F 5/448* (2013.01); *G01F 23/261* (2013.01); *G01K 13/02* (2013.01); *A61B 5/4875* (2013.01); *A61B 5/742* (2013.01); *A61B 5/7405* (2013.01); *A61B 5/7455* (2013.01); *A61B 2562/0271* (2013.01); *A61F 13/0213* (2013.01); *A61F 13/0246* (2013.01); *A61F 13/42* (2013.01)

(56) References Cited

U.S. PATENT DOCUMENTS

| | | | |
|---|---|---|---|
| 4,231,369 A | | 11/1980 | Sorensen et al. |
| 4,382,441 A | | 5/1983 | Svedman |
| 4,518,388 A | | 5/1985 | Jensen |
| 5,181,905 A | | 1/1993 | Flam |
| 5,260,692 A | | 11/1993 | Claren |
| 5,722,965 A | * | 3/1998 | Kuczynski ............... A61F 5/443 604/338 |
| 6,025,725 A | | 2/2000 | Gershenfeld et al. |
| 6,171,289 B1 | * | 1/2001 | Millot ..................... A61F 5/443 604/336 |
| 6,927,316 B1 | | 8/2005 | Faries, Jr. et al. |
| 6,963,772 B2 | | 11/2005 | Bloom et al. |
| 6,984,993 B2 | | 1/2006 | Ariav |
| 7,094,220 B2 | | 8/2006 | Tanghoj et al. |
| 7,422,577 B2 | | 9/2008 | Udayakumar et al. |
| D597,606 S | | 8/2009 | Chin et al. |
| 7,734,411 B2 | | 6/2010 | Shelley et al. |
| 7,947,003 B2 | | 5/2011 | Bonnefin et al. |
| 8,011,505 B2 | | 9/2011 | Murray et al. |
| 8,066,693 B2 | | 11/2011 | Tanghoj et al. |
| 8,207,393 B2 | | 6/2012 | Bach |
| 8,230,993 B2 | | 7/2012 | Tanghoej |
| D665,421 S | | 8/2012 | Morrow et al. |
| 8,303,554 B2 | | 11/2012 | Tsai et al. |
| 8,377,019 B2 | | 2/2013 | Schertiger |
| 8,382,732 B2 | | 2/2013 | Oberholtzer et al. |
| 8,398,602 B2 | | 3/2013 | Ilo et al. |
| 8,398,615 B2 | | 3/2013 | Torstensen et al. |
| 8,409,171 B2 | | 4/2013 | Hannon et al. |
| 8,460,259 B2 | | 6/2013 | Tsai |
| 8,500,707 B2 | | 8/2013 | Murray |
| 8,603,189 B2 | | 12/2013 | Behan et al. |
| 8,636,645 B2 | | 1/2014 | Daniel |
| 8,636,679 B2 | | 1/2014 | Linnane et al. |
| 8,637,072 B2 | | 1/2014 | Kershaw et al. |
| 8,679,581 B2 | | 3/2014 | Sambasivam et al. |
| 8,684,983 B2 | | 4/2014 | Andersen et al. |
| 8,740,865 B2 | | 6/2014 | Krystek et al. |
| 8,808,175 B2 | | 8/2014 | Deitch et al. |
| 8,845,606 B2 | | 9/2014 | Nguyen-Demary et al. |
| 8,939,952 B2 | | 1/2015 | Weig |
| 9,050,387 B2 | | 6/2015 | Chang et al. |
| 9,072,862 B2 | | 7/2015 | Murray et al. |
| 9,095,407 B2 | | 8/2015 | Deegan et al. |
| 9,216,104 B2 | | 12/2015 | Thirstrup et al. |
| 9,241,824 B2 | | 1/2016 | Ellering |
| 9,248,214 B2 | | 2/2016 | Lykke et al. |
| 9,259,512 B2 | | 2/2016 | Udayakumar et al. |
| 9,296,835 B2 | | 3/2016 | Madsen et al. |
| 9,342,485 B2 | | 5/2016 | Tart et al. |
| 9,353,211 B2 | | 5/2016 | Madsen et al. |
| D758,443 S | | 6/2016 | Kang |
| 9,399,633 B2 | | 7/2016 | Madsen et al. |
| 9,427,548 B2 | | 8/2016 | Triel |
| D771,660 S | | 11/2016 | Zimmerman et al. |
| 9,526,816 B2 | | 12/2016 | Toth |
| D777,733 S | | 1/2017 | Loosli et al. |
| 9,549,839 B2 | | 1/2017 | Schertiger et al. |
| 9,562,305 B2 | | 2/2017 | Bonnefin et al. |
| D781,299 S | | 3/2017 | Yun et al. |
| 9,585,784 B2 | | 3/2017 | Matthiassen et al. |
| 9,636,286 B2 | | 5/2017 | Grundhofer |
| 9,642,737 B2 | | 5/2017 | Seres et al. |
| 9,649,230 B1 | | 5/2017 | Li |
| 9,687,313 B2 | | 6/2017 | Todd et al. |
| 9,717,490 B2 | | 8/2017 | Deitch |
| D797,797 S | | 9/2017 | Gandhi et al. |
| 9,763,833 B2 | | 9/2017 | Taylor et al. |
| 9,770,548 B2 | | 9/2017 | Gilman |
| 9,795,484 B2 | | 10/2017 | Daniel |
| 9,801,754 B2 | | 10/2017 | Masters et al. |
| 9,848,866 B2 | | 12/2017 | Daniel |
| 9,861,781 B2 | | 1/2018 | Murray et al. |
| 9,877,818 B2 | | 1/2018 | Poucher et al. |
| 9,956,079 B2 | | 5/2018 | Daniel |
| 9,962,282 B2 | | 5/2018 | Chang et al. |
| 9,968,480 B2 | | 5/2018 | Nyberg |
| 9,974,682 B2 | | 5/2018 | Schertiger et al. |
| 9,999,537 B2 | | 6/2018 | Ekfeldt et al. |
| 10,045,877 B2 | | 8/2018 | Weig |
| 10,045,878 B2 | | 8/2018 | Freiding |
| 10,058,638 B2 | | 8/2018 | Gravesen et al. |
| D829,225 S | | 9/2018 | Gandhi et al. |
| 10,065,014 B2 | | 9/2018 | Hagel |
| 10,071,012 B2 | | 9/2018 | Larson et al. |
| 10,076,394 B2 | | 9/2018 | Browning |
| 10,076,438 B2 | | 9/2018 | Bendix et al. |
| 10,076,636 B2 | | 9/2018 | Murray et al. |
| 10,076,660 B2 | | 9/2018 | Gyrn |
| 10,092,250 B2 | | 10/2018 | Tucker et al. |
| 10,092,441 B2 | | 10/2018 | Lee |
| 10,105,255 B2 | | 10/2018 | Fattman et al. |
| 10,117,783 B2 | | 11/2018 | Cotton et al. |
| 10,118,018 B2 | | 11/2018 | Foley et al. |
| 10,118,019 B2 | | 11/2018 | Murray et al. |
| 10,123,908 B2 | | 11/2018 | Everland et al. |
| 10,136,981 B2 | | 11/2018 | Poucher et al. |
| 10,166,136 B2 | | 1/2019 | Poucher |
| 10,166,137 B2 | | 1/2019 | Nguyen-Demary et al. |
| 10,166,138 B2 | | 1/2019 | Cline et al. |
| 10,166,366 B2 | | 1/2019 | Murray et al. |
| 10,179,823 B2 | | 1/2019 | Kershaw et al. |
| 10,182,914 B2 | | 1/2019 | Daniel |
| 10,183,112 B2 | | 1/2019 | Foley et al. |
| D841,660 S | | 2/2019 | Mercado |
| 10,194,938 B2 | | 2/2019 | Byager |
| 10,195,066 B2 | | 2/2019 | Behan |
| 10,195,069 B2 | | 2/2019 | Jepsen et al. |
| 10,195,075 B2 | | 2/2019 | Scott et al. |
| 10,207,031 B2 | | 2/2019 | Toth |
| 10,207,076 B2 | | 2/2019 | Foley et al. |
| D843,404 S | | 3/2019 | Spector |
| 10,219,953 B2 | | 3/2019 | Dewitt et al. |
| 10,220,185 B2 | | 3/2019 | Sadik et al. |
| 10,226,317 B2 | | 3/2019 | Deitch et al. |
| 10,226,318 B2 | | 3/2019 | McClurg |

(56) References Cited

U.S. PATENT DOCUMENTS

| | | |
|---|---|---|
| 10,231,876 B2 | 3/2019 | Igwebuike et al. |
| 10,238,526 B2 | 3/2019 | Daniel et al. |
| 10,251,770 B2 | 4/2019 | Chang et al. |
| 10,251,773 B2 | 4/2019 | Schertiger et al. |
| 10,251,973 B2 | 4/2019 | Lam et al. |
| 10,252,291 B2 | 4/2019 | Madsen et al. |
| 10,278,691 B2 | 5/2019 | McClurg et al. |
| 10,278,800 B2 | 5/2019 | Suslian et al. |
| 10,278,822 B2 | 5/2019 | Daniel |
| 10,278,857 B2 | 5/2019 | Hansen et al. |
| 10,285,847 B2 | 5/2019 | Lesko et al. |
| 10,294,317 B2 | 5/2019 | Sambasivam et al. |
| 10,299,956 B2 | 5/2019 | Schertiger et al. |
| 10,321,983 B2 | 6/2019 | Sobrino-Serrano et al. |
| 10,322,024 B2 | 6/2019 | Chang |
| 10,322,026 B2 | 6/2019 | Hansen et al. |
| 10,335,185 B2 | 7/2019 | Uihlein |
| 10,335,309 B2 | 7/2019 | Becker et al. |
| 10,342,890 B2 | 7/2019 | Bray |
| 10,363,027 B2 | 7/2019 | Dravis et al. |
| 10,369,268 B2 | 8/2019 | Frostaa et al. |
| 10,376,637 B2 | 8/2019 | Gyrn et al. |
| 10,383,730 B2 | 8/2019 | Daniel |
| 10,391,197 B2 | 8/2019 | Woods |
| D860,222 S | 9/2019 | Cen |
| 10,398,429 B2 | 9/2019 | Poucher et al. |
| 10,398,558 B2 | 9/2019 | Crabb |
| 10,406,277 B2 | 9/2019 | Gregory |
| 10,406,322 B2 | 9/2019 | O'Flynn et al. |
| 10,420,859 B2 | 9/2019 | Rostami et al. |
| 10,426,584 B2 | 10/2019 | McClurg |
| 10,426,918 B2 | 10/2019 | Foley et al. |
| 10,434,015 B2 | 10/2019 | Taylor et al. |
| 10,434,241 B2 | 10/2019 | Hvid et al. |
| 10,434,282 B2 | 10/2019 | Kearns et al. |
| 10,441,454 B2 | 10/2019 | Tanghoej et al. |
| 10,449,025 B2 | 10/2019 | Browning et al. |
| 10,449,082 B2 | 10/2019 | Johnsen |
| 10,449,328 B2 | 10/2019 | Tanghoej et al. |
| 10,449,329 B2 | 10/2019 | Foley et al. |
| 10,456,230 B2 | 10/2019 | Schuchardt et al. |
| 10,463,833 B2 | 11/2019 | Clarke et al. |
| 10,470,917 B2 | 11/2019 | Chang et al. |
| 10,470,918 B2 | 11/2019 | Bendix |
| 10,470,936 B2 | 11/2019 | Wohlgemuth et al. |
| 10,478,203 B2 | 11/2019 | Uihlein |
| 10,478,329 B2 | 11/2019 | Oberholtzer et al. |
| D869,479 S | 12/2019 | Pillalamarri et al. |
| 10,493,101 B2 | 12/2019 | Percival et al. |
| 10,493,230 B2 | 12/2019 | Guldager et al. |
| 10,493,231 B2 | 12/2019 | McMenamin et al. |
| 10,499,938 B2 | 12/2019 | Torchio et al. |
| 10,500,084 B2 | 12/2019 | Hansen et al. |
| 10,500,315 B2 | 12/2019 | Chang et al. |
| 10,507,126 B2 | 12/2019 | Matthison-Hansen et al. |
| 10,507,318 B2 | 12/2019 | Jin et al. |
| 10,512,256 B2 | 12/2019 | Kavanagh et al. |
| 10,517,754 B2 | 12/2019 | Praame et al. |
| 10,531,690 B2 | 1/2020 | Dooly et al. |
| 10,531,977 B2* | 1/2020 | Schoess .............. A61F 5/4404 |
| 10,532,148 B2 | 1/2020 | Frostaa et al. |
| 10,543,133 B2 | 1/2020 | Shaw et al. |
| 10,561,817 B2 | 2/2020 | Hannon et al. |
| 10,569,047 B2 | 2/2020 | Farrell et al. |
| 10,576,262 B2 | 3/2020 | Tsai et al. |
| 10,583,029 B2 | 3/2020 | Chang |
| 10,588,747 B2 | 3/2020 | Allen et al. |
| 10,588,773 B2 | 3/2020 | Tsai et al. |
| 2003/0199783 A1 | 10/2003 | Bloom et al. |
| 2004/0073151 A1 | 4/2004 | Weston |
| 2005/0065485 A1 | 3/2005 | Andersen et al. |
| 2005/0143696 A1* | 6/2005 | Pedersen .............. A61F 5/441 |
| | | 604/332 |
| 2008/0275327 A1 | 11/2008 | Faarbaek et al. |
| 2008/0288026 A1 | 11/2008 | Cross et al. |
| 2010/0030167 A1* | 2/2010 | Thirstrup .............. A61F 5/445 |
| | | 604/318 |
| 2011/0224653 A1 | 9/2011 | Torstensen et al. |
| 2013/0226117 A1* | 8/2013 | Hansen .............. A61F 5/443 |
| | | 604/338 |
| 2013/0274696 A1 | 10/2013 | Lam |
| 2013/0324952 A1 | 12/2013 | Krystek et al. |
| 2014/0039429 A1 | 2/2014 | Stroebech et al. |
| 2014/0128826 A1* | 5/2014 | Klein .............. A61F 5/443 |
| | | 604/344 |
| 2015/0051587 A1 | 2/2015 | Rolsted et al. |
| 2015/0250639 A1 | 9/2015 | Thirstrup et al. |
| 2015/0297861 A1 | 10/2015 | Passalaqua et al. |
| 2015/0306342 A1 | 10/2015 | Rostami et al. |
| 2015/0351690 A1* | 12/2015 | Toth .............. A61B 5/6833 |
| | | 600/373 |
| 2016/0113810 A1 | 4/2016 | Hanuka et al. |
| 2016/0158056 A1 | 6/2016 | Davis et al. |
| 2016/0220743 A1 | 8/2016 | Guthrie et al. |
| 2016/0310642 A1 | 10/2016 | Clarke et al. |
| 2017/0000642 A1 | 1/2017 | Cisko et al. |
| 2017/0079576 A1 | 3/2017 | Stroebech et al. |
| 2017/0105657 A1 | 4/2017 | Eid |
| 2017/0140103 A1* | 5/2017 | Angelides .......... A61F 5/4404 |
| 2017/0224523 A1 | 8/2017 | Bendix |
| 2017/0239384 A1 | 8/2017 | Lam et al. |
| 2017/0340804 A1 | 11/2017 | Hvid et al. |
| 2017/0348137 A1 | 12/2017 | Hvid et al. |
| 2018/0008451 A1 | 1/2018 | Stroebech |
| 2018/0021474 A1 | 1/2018 | Stroebech et al. |
| 2018/0043086 A1 | 2/2018 | Foley et al. |
| 2018/0104089 A1 | 4/2018 | Nyberg et al. |
| 2018/0116859 A1 | 5/2018 | Strobech et al. |
| 2018/0133359 A1 | 5/2018 | Hossain et al. |
| 2018/0133360 A1 | 5/2018 | Bingol et al. |
| 2018/0147093 A1 | 5/2018 | Igwebuike et al. |
| 2018/0169377 A1 | 6/2018 | Hickmott et al. |
| 2018/0177626 A1 | 6/2018 | Israelson |
| 2018/0229013 A1 | 8/2018 | Tsai |
| 2018/0235802 A1 | 8/2018 | Nguyen-Demary et al. |
| 2018/0243466 A1 | 8/2018 | Israelson et al. |
| 2018/0250120 A1 | 9/2018 | Behan |
| 2018/0250156 A1 | 9/2018 | Lam |
| 2018/0250157 A1 | 9/2018 | Masters et al. |
| 2018/0250170 A1 | 9/2018 | Oelund et al. |
| 2018/0256020 A1 | 9/2018 | Taylor et al. |
| 2018/0256402 A1 | 9/2018 | Janis |
| 2018/0263804 A1 | 9/2018 | Stroebech et al. |
| 2018/0263805 A1 | 9/2018 | Lam et al. |
| 2018/0272105 A1 | 9/2018 | Triel et al. |
| 2018/0280659 A1 | 10/2018 | Kearns et al. |
| 2018/0289527 A1 | 10/2018 | Vila |
| 2018/0289852 A1 | 10/2018 | Woods |
| 2018/0311066 A1 | 11/2018 | Hansen et al. |
| 2018/0311420 A1 | 11/2018 | Cotton |
| 2018/0318125 A1 | 11/2018 | Casado et al. |
| 2018/0318126 A1 | 11/2018 | Weig |
| 2018/0318127 A1 | 11/2018 | Nielsen et al. |
| 2018/0325718 A1 | 11/2018 | Ekfeldt et al. |
| 2018/0333290 A1 | 11/2018 | Jones et al. |
| 2018/0333518 A1 | 11/2018 | Gravesen et al. |
| 2018/0338849 A1 | 11/2018 | Behan |
| 2018/0353317 A1 | 12/2018 | Bendix et al. |
| 2018/0360645 A1 | 12/2018 | Fattman et al. |
| 2018/0362690 A1 | 12/2018 | Sambasivam et al. |
| 2018/0369010 A1 | 12/2018 | Lee |
| 2018/0369474 A1 | 12/2018 | Falleboe et al. |
| 2019/0000324 A1* | 1/2019 | Laugaard Nielsen ...................... |
| | | A61B 5/6833 |
| 2019/0000627 A1 | 1/2019 | Wolf |
| 2019/0015186 A1 | 1/2019 | Poucher et al. |
| 2019/0015242 A1 | 1/2019 | Oeelund |
| 2019/0021912 A1 | 1/2019 | Cotton et al. |
| 2019/0029868 A1 | 1/2019 | Grum-Schwensen et al. |
| 2019/0030214 A1 | 1/2019 | Montes de Oca et al. |
| 2019/0046718 A1 | 2/2019 | Henry et al. |
| 2019/0070034 A1 | 3/2019 | Udayakumar |
| 2019/0083295 A1 | 3/2019 | Cisko et al. |
| 2019/0083746 A1 | 3/2019 | Murray et al. |

(56) References Cited

U.S. PATENT DOCUMENTS

| | | |
|---|---|---|
| 2019/0099284 A1 | 4/2019 | Augustyn et al. |
| 2019/0105462 A1 | 4/2019 | Schertiger |
| 2019/0117441 A1 | 4/2019 | Hansen et al. |
| 2019/0117824 A1 | 4/2019 | Hansen et al. |
| 2019/0117876 A1 | 4/2019 | Foley et al. |
| 2019/0125570 A1 | 5/2019 | Jones et al. |
| 2019/0126004 A1 | 5/2019 | O'Brien et al. |
| 2019/0133811 A1 | 5/2019 | Seres et al. |
| 2019/0133812 A1 | 5/2019 | Seres et al. |
| 2019/0133813 A1 | 5/2019 | Cline et al. |
| 2019/0133830 A1 | 5/2019 | Bishop et al. |
| 2019/0134256 A1 | 5/2019 | Stroebech |
| 2019/0134280 A1 | 5/2019 | Toth |
| 2019/0142623 A1* | 5/2019 | Schoess ............. A61F 5/445 604/336 |
| 2019/0142642 A1 | 5/2019 | Burnet et al. |
| 2019/0151063 A1 | 5/2019 | Deitch et al. |
| 2019/0151134 A1 | 5/2019 | Tsai et al. |
| 2019/0151158 A1 | 5/2019 | Dewitt et al. |
| 2019/0151515 A1 | 5/2019 | Selby et al. |
| 2019/0151605 A1 | 5/2019 | McMenamin et al. |
| 2019/0151610 A1 | 5/2019 | Fletter |
| 2019/0153168 A1 | 5/2019 | Behan et al. |
| 2019/0159940 A1 | 5/2019 | Selby et al. |
| 2019/0167303 A1 | 6/2019 | Byager |
| 2019/0167485 A9 | 6/2019 | Oelund et al. |
| 2019/0192066 A1 | 6/2019 | Schoess et al. |
| 2019/0201236 A1 | 7/2019 | Scott et al. |
| 2019/0201589 A1 | 7/2019 | Farrell et al. |
| 2019/0224402 A1 | 7/2019 | Henry et al. |
| 2019/0231581 A1 | 8/2019 | Chang |
| 2019/0247220 A1 | 8/2019 | Lesko et al. |
| 2019/0247549 A1 | 8/2019 | Nielsen |
| 2019/0254864 A1 | 8/2019 | Czaplewski et al. |
| 2019/0262026 A1 | 8/2019 | Uihlein |
| 2019/0262166 A1 | 8/2019 | Becker et al. |
| 2019/0274672 A1 | 9/2019 | Allen |
| 2019/0287424 A1 | 9/2019 | Taylor et al. |
| 2019/0290220 A9 | 9/2019 | Tucker et al. |
| 2019/0290472 A1 | 9/2019 | Schertiger et al. |
| 2019/0290806 A1 | 9/2019 | Farrell et al. |
| 2019/0298895 A1 | 10/2019 | Selby et al. |
| 2019/0307904 A1 | 10/2019 | Ballamy |
| 2019/0308935 A1 | 10/2019 | Fristrup et al. |
| 2019/0321587 A1 | 10/2019 | McMenamin et al. |
| 2019/0328380 A1 | 10/2019 | Poucher et al. |
| 2019/0328572 A1 | 10/2019 | Weinberg et al. |
| 2019/0343617 A1 | 11/2019 | Sobrino-Serrano et al. |
| 2019/0358015 A1 | 11/2019 | Deitch et al. |
| 2019/0358016 A1 | 11/2019 | Deitch et al. |
| 2019/0374163 A1 | 12/2019 | Faarbaek et al. |
| 2019/0374372 A1 | 12/2019 | Seres et al. |
| 2019/0380882 A1 | 12/2019 | Taylor et al. |
| 2019/0381273 A1 | 12/2019 | Kearns et al. |
| 2019/0381276 A1 | 12/2019 | Foley et al. |
| 2019/0388226 A1 | 12/2019 | Crabb et al. |
| 2020/0001043 A1 | 1/2020 | Heneghan et al. |
| 2020/0015996 A1 | 1/2020 | Schertiger |
| 2020/0016366 A1 | 1/2020 | Murray et al. |
| 2020/0016380 A1 | 1/2020 | Murray et al. |
| 2020/0030152 A1 | 1/2020 | Wohlgemuth et al. |
| 2020/0030497 A1 | 1/2020 | Chang et al. |
| 2020/0030521 A1 | 1/2020 | Gregory |
| 2020/0038226 A1 | 2/2020 | Gotten et al. |
| 2020/0038529 A1 | 2/2020 | Farrell et al. |
| 2020/0038535 A1 | 2/2020 | Montes De Oca et al. |
| 2020/0046540 A1 | 2/2020 | Cisko et al. |
| 2020/0046541 A1 | 2/2020 | Sund et al. |
| 2020/0046543 A1 | 2/2020 | Scalise et al. |
| 2020/0054795 A1 | 2/2020 | Farrell et al. |
| 2020/0060863 A1 | 2/2020 | Sund et al. |
| 2020/0061282 A1 | 2/2020 | Hvid et al. |
| 2020/0061335 A1 | 2/2020 | Guldager |
| 2020/0069455 A1 | 3/2020 | Oberholtzer et al. |
| 2020/0078030 A1 | 3/2020 | Torchio et al. |
| 2020/0078510 A1 | 3/2020 | Henry et al. |
| 2020/0093632 A1 | 3/2020 | Kavanagh et al. |

FOREIGN PATENT DOCUMENTS

| | | |
|---|---|---|
| EP | 3100702 B1 | 12/2018 |
| EP | 3427673 A1 | 1/2019 |
| EP | 2787939 B1 | 3/2019 |
| EP | 3226775 B1 | 3/2019 |
| EP | 2977074 B1 | 5/2019 |
| EP | 3292839 B1 | 5/2019 |
| EP | 2977075 B1 | 6/2019 |
| EP | 3028673 B1 | 7/2019 |
| EP | 3001983 B1 | 8/2019 |
| EP | 3539511 A1 | 9/2019 |
| EP | 2480169 B1 | 11/2019 |
| EP | 3001976 B1 | 11/2019 |
| EP | 3001980 B1 | 11/2019 |
| EP | 3563807 A1 | 11/2019 |
| EP | 3574870 A1 | 12/2019 |
| EP | 3351208 B1 | 1/2020 |
| EP | 3116559 B1 | 2/2020 |
| EP | 3001981 B1 | 3/2020 |
| EP | 3092025 B1 | 3/2020 |
| GB | 2431239 A | 4/2007 |
| IN | 200000444 P1 | 1/2006 |
| JP | J11319082 A | 11/1999 |
| WO | WO 90/11501 A1 | 10/1990 |
| WO | WO 94/15190 A1 | 7/1994 |
| WO | WO 1995/051173 A2 | 10/1999 |
| WO | WO 00/00232 A1 | 1/2000 |
| WO | WO 2000/007653 A1 | 2/2000 |
| WO | WO 01/13830 A1 | 3/2001 |
| WO | WO 00/000082 A1 | 8/2001 |
| WO | WO 03/026540 A1 | 4/2003 |
| WO | WO 2003/048998 A2 | 6/2003 |
| WO | WO 2004/047630 A1 | 6/2004 |
| WO | WO 2005/004944 A1 | 1/2005 |
| WO | WO 2005/032652 A1 | 4/2005 |
| WO | WO 2005/051316 A2 | 6/2005 |
| WO | WO 2005/099644 A2 | 10/2005 |
| WO | WO 2007/098762 A1 | 9/2007 |
| WO | WO 2012/059906 A1 | 5/2012 |
| WO | WO 2014/102537 A1 | 7/2014 |
| WO | WO 2015/148035 A1 | 10/2015 |
| WO | WO 2017/136314 A1 | 8/2017 |
| WO | WO 2017/152921 A1 | 9/2017 |
| WO | WO 2017/168249 A2 | 10/2017 |
| WO | WO 2017/192685 A1 | 11/2017 |
| WO | WO 2017/222780 A1 | 12/2017 |
| WO | WO 2018/009818 A1 | 1/2018 |
| WO | WO 2018/009880 A1 | 1/2018 |
| WO | WO 2018/028756 A1 | 2/2018 |
| WO | WO 2018/071804 A2 | 4/2018 |
| WO | WO 2018/111713 A1 | 6/2018 |
| WO | WO 2018/149463 A2 | 8/2018 |
| WO | WO 2018/156502 A2 | 8/2018 |
| WO | WO 2018/156589 A2 | 8/2018 |
| WO | WO 2018/177488 A1 | 10/2018 |
| WO | WO 2018/183128 A1 | 10/2018 |
| WO | WO 2018/187427 A1 | 10/2018 |
| WO | WO 2018/188706 A1 | 10/2018 |
| WO | WO 2018/188707 A1 | 10/2018 |
| WO | WO 2018/188708 A1 | 10/2018 |
| WO | WO 2018/188709 A1 | 10/2018 |
| WO | WO 2018/188710 A1 | 10/2018 |
| WO | WO 2018/201152 A1 | 11/2018 |
| WO | WO 2018/204767 A1 | 11/2018 |
| WO | WO 2018/210391 A1 | 11/2018 |
| WO | WO 2018/226417 A1 | 12/2018 |
| WO | WO 2018/227066 A1 | 12/2018 |
| WO | WO 2019/005836 A1 | 1/2019 |
| WO | WO 2019/014344 A1 | 1/2019 |
| WO | WO 2019/034222 A1 | 2/2019 |
| WO | WO 2019/040694 A1 | 2/2019 |
| WO | WO 2019/051412 A1 | 3/2019 |
| WO | WO 2019/057256 A1 | 3/2019 |
| WO | WO 2019/083839 A1 | 5/2019 |

(56) References Cited

FOREIGN PATENT DOCUMENTS

| | | |
|---|---|---|
| WO | WO 2019/089875 A1 | 5/2019 |
| WO | WO 2019/090239 A1 | 5/2019 |
| WO | WO 2019/091526 A1 | 5/2019 |
| WO | WO 2019/091527 A1 | 5/2019 |
| WO | WO 2019/091528 A1 | 5/2019 |
| WO | WO 2019/091529 A1 | 5/2019 |
| WO | WO 2019/091532 A1 | 5/2019 |
| WO | WO 2019/094635 A1 | 5/2019 |
| WO | WO 2019/097288 A1 | 5/2019 |
| WO | WO 2019/099662 A1 | 5/2019 |
| WO | WO 2019/099845 A1 | 5/2019 |
| WO | WO 2019/099975 A2 | 5/2019 |
| WO | WO 2019/108337 A1 | 6/2019 |
| WO | WO 2019/113077 A1 | 6/2019 |
| WO | WO 2019/113203 A1 | 6/2019 |
| WO | WO 2019/120424 A1 | 6/2019 |
| WO | WO 2019/120425 A1 | 6/2019 |
| WO | WO 2019/120427 A1 | 6/2019 |
| WO | WO 2019/120428 A1 | 6/2019 |
| WO | WO 2019/120429 A1 | 6/2019 |
| WO | WO 2019/120430 A1 | 6/2019 |
| WO | WO 2019/120431 A1 | 6/2019 |
| WO | WO 2019/120432 A1 | 6/2019 |
| WO | WO 2019/120433 A1 | 6/2019 |
| WO | WO 2019/120435 A1 | 6/2019 |
| WO | WO 2019/120437 A1 | 6/2019 |
| WO | WO 2019/120438 A1 | 6/2019 |
| WO | WO 2019/120439 A1 | 6/2019 |
| WO | WO 2019/120444 A1 | 6/2019 |
| WO | WO 2019/120445 A1 | 6/2019 |
| WO | WO 2019/120446 A1 | 6/2019 |
| WO | WO 2019/120447 A1 | 6/2019 |
| WO | WO 2019/120448 A1 | 6/2019 |
| WO | WO 2019/120450 A1 | 6/2019 |
| WO | WO 2019/120451 A1 | 6/2019 |
| WO | WO 2019/120452 A1 | 6/2019 |
| WO | WO 2019/120453 A1 | 6/2019 |
| WO | WO 2019/120458 A1 | 6/2019 |
| WO | WO 2019/123003 A1 | 6/2019 |
| WO | WO 2019/123004 A1 | 6/2019 |
| WO | WO 2019/123005 A1 | 6/2019 |
| WO | WO 2019/134726 A1 | 7/2019 |
| WO | WO 2019/149330 A1 | 8/2019 |
| WO | WO 2019/161859 A1 | 8/2019 |
| WO | WO 2019/161860 A1 | 8/2019 |
| WO | WO 2019/161861 A1 | 8/2019 |
| WO | WO 2019/161862 A1 | 8/2019 |
| WO | WO 2019/161863 A1 | 8/2019 |
| WO | WO 2019/174687 A1 | 9/2019 |
| WO | WO 2019/174692 A1 | 9/2019 |
| WO | WO 2019/174693 A1 | 9/2019 |
| WO | WO 2019/174694 A1 | 9/2019 |
| WO | WO 2019/174695 A1 | 9/2019 |
| WO | WO 2019/174696 A1 | 9/2019 |
| WO | WO 2019/174697 A1 | 9/2019 |
| WO | WO 2019/174698 A1 | 9/2019 |
| WO | WO 2019/214787 A1 | 11/2019 |
| WO | WO 2019/214788 A1 | 11/2019 |
| WO | WO 2019/221830 A1 | 11/2019 |
| WO | WO 2019/222644 A1 | 11/2019 |
| WO | WO 2019/222652 A1 | 11/2019 |
| WO | WO 2019/238180 A1 | 12/2019 |
| WO | WO 2019/238181 A1 | 12/2019 |
| WO | WO 2019/238182 A1 | 12/2019 |
| WO | WO 2019/238183 A1 | 12/2019 |
| WO | WO 2019/238195 A1 | 12/2019 |
| WO | WO 2019/238196 A1 | 12/2019 |
| WO | WO 2019/238197 A1 | 12/2019 |
| WO | WO 2019/238198 A1 | 12/2019 |
| WO | WO 2019/242828 A1 | 12/2019 |
| WO | WO 2019/245679 A1 | 12/2019 |
| WO | WO 2020/007429 A1 | 1/2020 |
| WO | WO 2020/007430 A1 | 1/2020 |
| WO | WO 2020/015804 A1 | 1/2020 |
| WO | WO 2020/035121 A1 | 2/2020 |
| WO | WO 2020/048576 A1 | 3/2020 |
| WO | WO 2020/051548 A1 | 3/2020 |
| WO | WO 2020/055998 A1 | 3/2020 |
| WO | WO 2020/057705 A1 | 3/2020 |

OTHER PUBLICATIONS

Invitation to Pay Additional Fees in corresponding International Patent Application No. PCT/US2018/059884, dated Feb. 20, 2019, in 12 pages.
Dale, M., et al., "The Effect of Cold Therapy on Pain, Swelling, and Range of Motion after Anterior Cruciate Ligament Reconstructive Surgery," Arthroscopy: The Journal of Arthroscopic & Related Surgery, vol. 10, Issue 5, Oct. 1994, pp. 530-533.
Hunter, Tim B., et al., "Medical Devices of the Abdomen and Pelvis," RadioGraphics 2005; 25:503-523.
GhaseelCom Jo, by Oioo, app704.com, last updated Jul. 17, 2018 (retrieved on Dec. 30, 2019), retrieved from the Internet, https://www.app704.com/1272706062.
Legacy Flext Alerts, appadvice.com (online), last updated Oct. 26, 2018 (retrieved on Dec. 30, 2018), retrieved from the Internet, https://appadvice.com/app/legacy-flex-alert/869412041.
Setaku: Laundry On-Demand!, by Han, behance.net (online), published on Sep. 7, 2015 (retrieved on Dec. 30, 2019), retrieved from the Internet, https://www.behance.net/gallery/30159963/Setaku-Laundry-on-demand?tracking_source=project_owner_other_projects.

\* cited by examiner

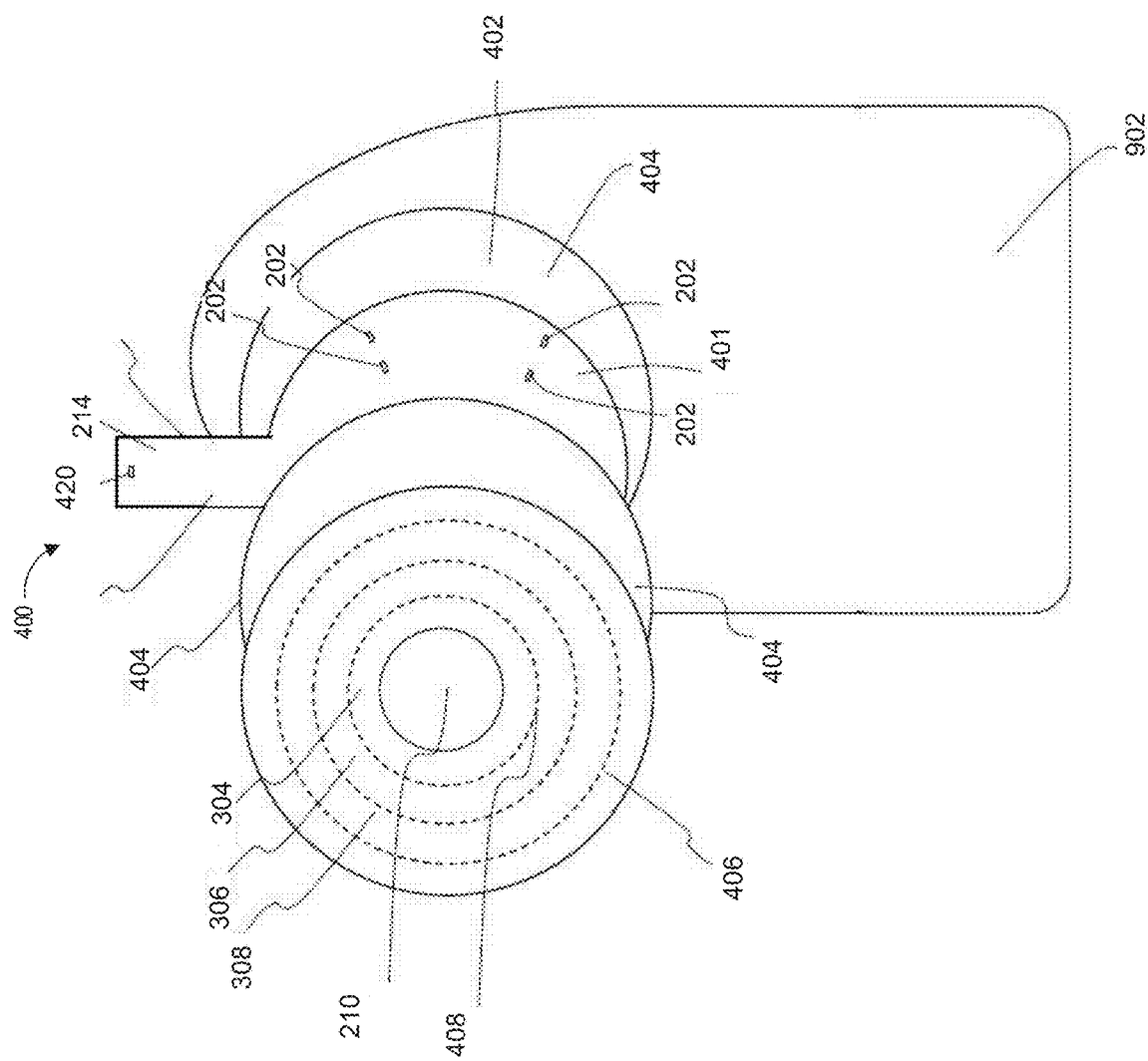

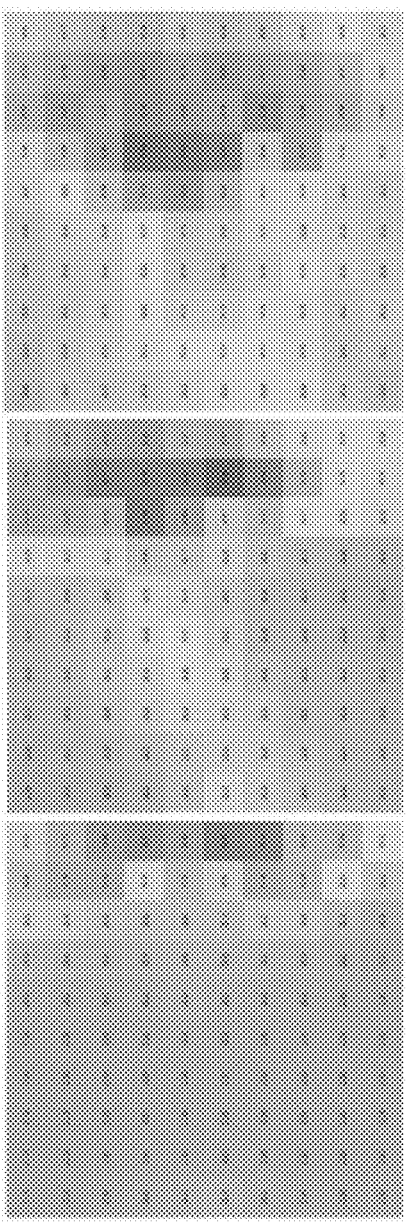

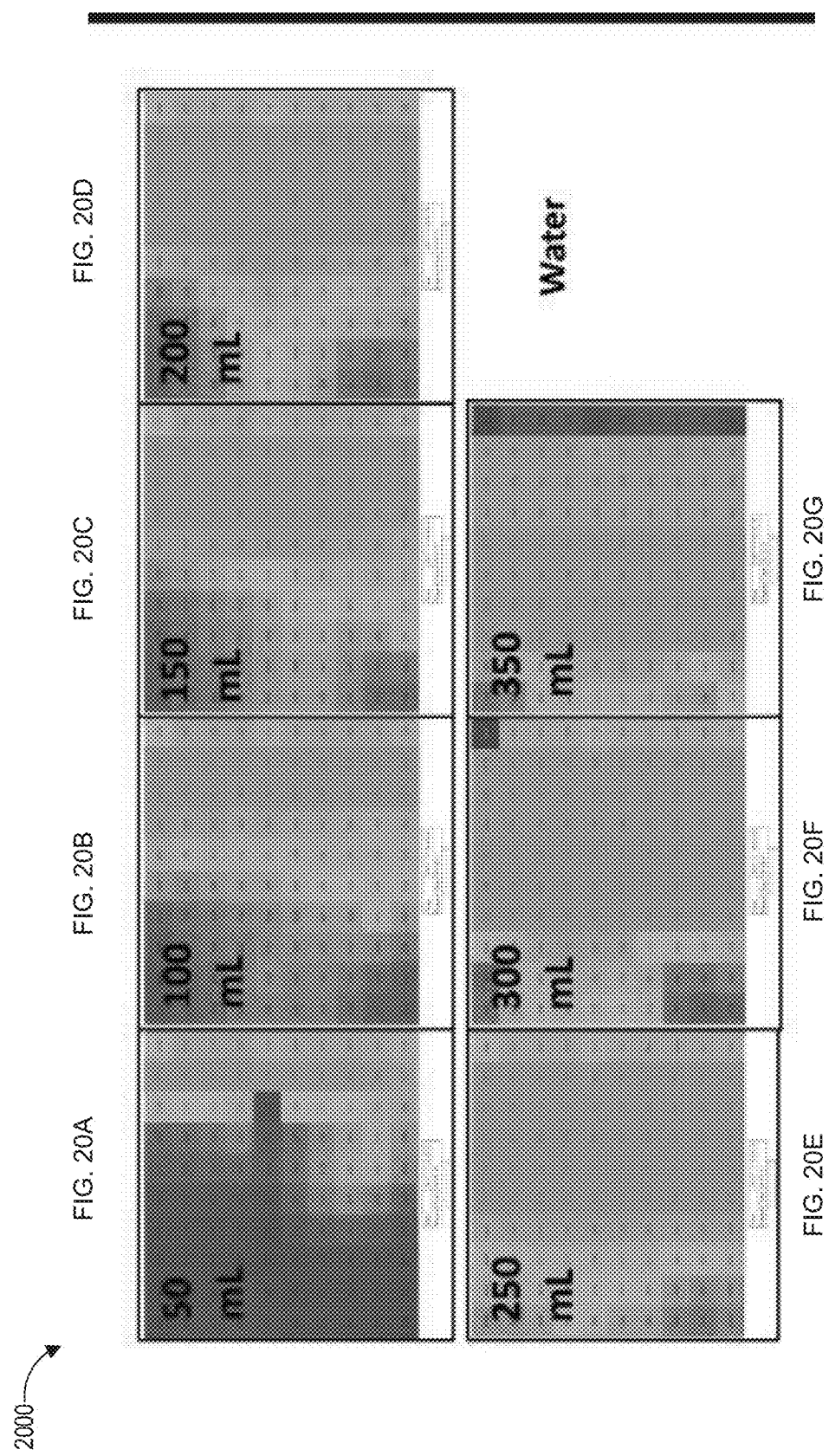

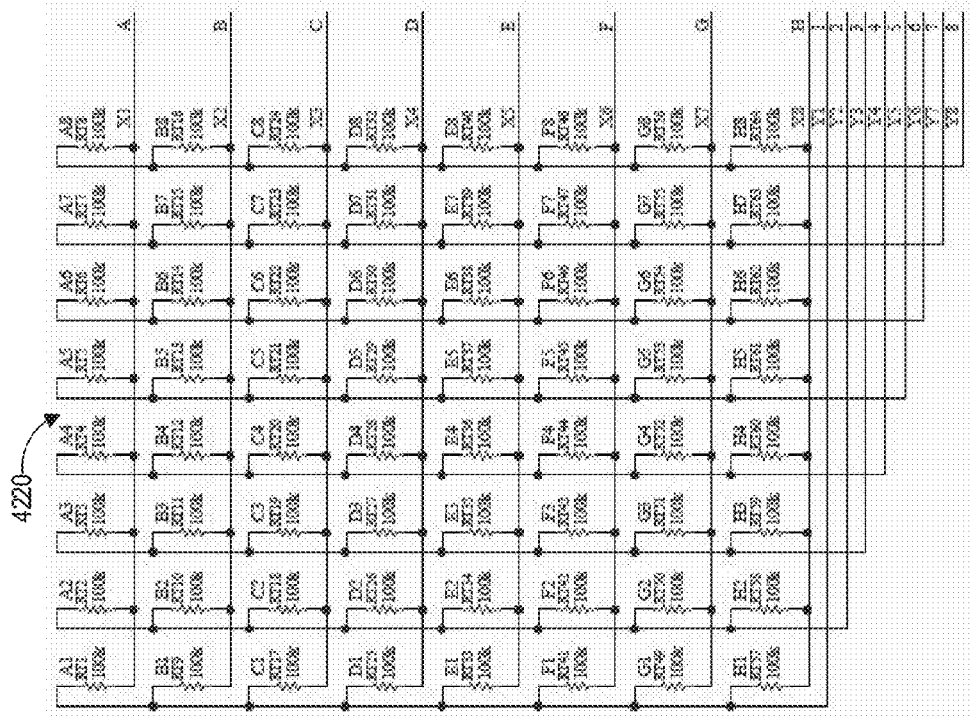
FIG. 42B
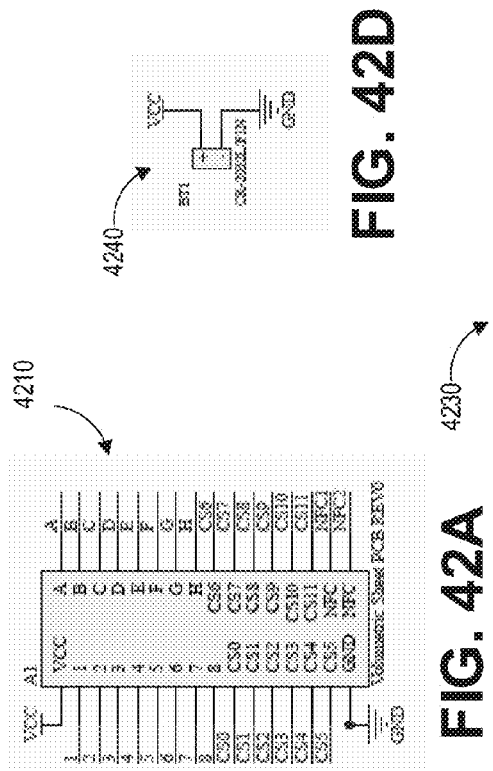
FIG. 42D
FIG. 42A
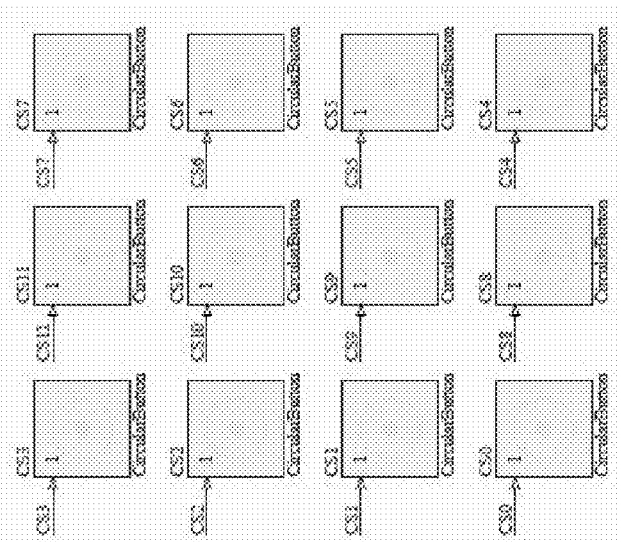
FIG. 42C

| 103 | 121 |
|---|---|
| 112 | 128 |
| 114 | 135 |
| 99 | 117 |
| 102 | 105 |
| 98 | 103 |

FIG. 49B

| 103 | 121 |
|---|---|
| 118 | 137 |
| 114 | 135 |
| 100 | 117 |
| 102 | 116 |
| 102 | 113 |

FIG. 49A

OSTOMY MONITORING SYSTEM AND METHOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Skin inflammation is a common symptom of irritated skin, caused, for example, by exposure to UV radiation, ionizing radiation, allergens, chemical irritants, biological irritants or by mechanical trauma. The process of such skin inflammation (also called "acute" inflammation) is complex and responds to help the skin fight infection. However, it is known that when the skin is exposed to a triggering stimulus, such as radiation, an irritant or an allergen, blood flow to the site of irritation is increased due to signaling of cytokines and chemokines which leads to vasodilatation of the cutaneous blood vessels, causing redness and an increase in skin temperature. As a result of the initial triggering event, an amplified large inflammatory response is stimulated that, while designed to help the skin fight infection from invading bacteria, actually causes considerable damage to the skin if left untreated.

SUMMARY

In some configurations, an ostomy wafer can include an adhesive layer configured to adhere to skin around a stoma of a living person; a flexible sensor layer coupled with the adhesive layer, the flexible sensor layer comprising a plurality of temperature sensors; and a plurality of conductors wired to the plurality of temperature sensors, the plurality of conductors configured to be electrically coupled with an electronics hub so that signals from the plurality of temperature sensors are electrically communicated to the electronics hub.

In some configurations, the ostomy wafer can further comprise a third layer configured to cover the flexible sensor layer such that the flexible sensor layer is sandwiched between the adhesive layer and the third layer.

In some configurations, the third layer can include an adhesive configured to adhere to an ostomy bag.

In some configurations, the wafer can include a Tupperware click mechanism for coupling with an ostomy bag.

In some configurations, the temperature sensors can be arranged in concentric partial rings or concentric partial rings.

In some configurations, one or more of the concentric partial rings can be severable so as to fit the ostomy wafer to different sized stomas.

In some configurations, the concentric partial rings can comprise two or more rings. In some configurations, the concentric partial rings can comprise two rings. In some configurations, the concentric partial rings can comprise four rings.

In some configurations, the plurality of conductors can comprise a serpentine portion. In some configurations, the plurality of conductors can comprise curved portions between the temperature sensors. In some configurations, the plurality of conductors can comprise half circle portions between the temperature sensors.

In some configurations, the plurality of temperature sensors can be electrically connected in a matrix circuit.

In some configurations, the wafer can further include one or more capacitive sensors.

In some configurations, the one or more capacitive sensors can be disposed on the flexible sensor layer or a second flexible sensor layer.

In some configurations, the one or more capacitive sensors can be configured to detect moisture in adhesives of the adhesive layer.

In some configurations, the ostomy wafer can comprise a neck and a body.

In some configurations, a first temperature sensor of the plurality of temperature sensors can be disposed on the neck as a reference sensor.

In some configurations, all other ones of the temperature sensors other than the first temperature sensor can be disposed on the body.

In some configurations, the conductors can be disposed in part on the neck.

In some configurations, the temperature sensors can comprise first temperature sensors disposed in a first region closer to a center of the body and second temperature sensors disposed in a second region farther from a center of the body.

In some configurations, the second temperature sensors can be used as reference temperature sensors.

In some configurations, the temperature sensors can be disposed in an approximate menorah configuration.

In some configurations, the adhesive layer can comprise hydrocolloid adhesives.

In some configurations, the wafer can further include a border ring surrounding the adhesive layer, the border ring comprising an adhesive side configured to adhere to the skin around the stoma.

In some configurations, the adhesive side of the border ring can comprise acrylic adhesives or hydrocolloid adhesives.

In some configurations, the adhesives on the border ring can be thinner than adhesives on the adhesive layer.

In some configurations, the border ring can have a greater outer diameter than the adhesive layer.

In some configurations, the wafer can be used in combination with an ostomy bag comprising a plurality of sensors.

In some configurations, an ostomy bag can include two walls joined together along a seam around at least a portion of an edge of the ostomy bag, a first one of the walls configured to be placed facing skin of a user and a second one of the walls configured to face away from the user when the first wall faces the skin of the user; an opening in the first wall, the opening configured to be disposed around a stoma of the user and to receive effluent from the stoma; and one or more sensor layers disposed in, on, or between one of the two walls of the ostomy bag, the one or more sensor layers comprising a plurality of temperature sensors and a plurality of capacitive sensors, wherein the plurality of temperature sensors can measure a temperature change due to the effluent entering the bag, and wherein the plurality of capacitive sensors can measure a capacitance change due to the effluent entering the bag, the one or more sensors layer further comprising one or more wireless communication antennas, wherein when in use, the one or more antennas can be in electrical communication with one or more antennas on an ostomy wafer configured to couple the first one of the walls of the ostomy bag to the skin of the user, and/or one or more antennas on a hub configured to be coupled to the ostomy bag on the second one of the walls.

In some configurations, the capacitive sensors can be arranged in a pattern of lines at non-90 degree angles with respect to one another.

In some configurations, the capacitive sensors can be configured to detect a fill level of the effluent in the bag when the bag is in an upright position and tilted.

In some configurations, the plurality of capacitive sensors can comprise 12-48 capacitive sensors.

In some configurations, the plurality of temperature sensors can comprise 20-64 temperature sensors.

In some configurations, an inner side of one or both of the two walls of the ostomy bag can be coated with a lubricating material.

In some configurations, the lubricating material can be hydrophilic or hydrophobic.

In some configurations, the coating can be done by spraying or dipping.

In some configurations, the coating can be effective throughout a life cycle of the bag.

In some configurations, the plurality of temperature sensors and the plurality of capacitive sensors can be located on one sensor layer.

In some configurations, the bag can include comprising an electronics hub configured to receive signals from the temperature sensors or capacitive sensors.

In some configurations, the electronics hub can comprise a wireless transmitter configured to transmit the signals to a user device.

In some configurations, the electronics hub can have an approximately crescent shape to aid weight distribution. In some configurations, the electronics hub can have a substantially disc shape.

In some configurations, the electronics hub can comprise (1) a hardware processor configured to convert the signals to temperature values and (2) a wireless transmitter configured to transmit the temperature values to a user device.

In some configurations, the electronics hub can include one or more ports, and optionally wherein the one or more ports are Universal Serial Bus (USB) ports.

In some configurations, the electronics hub can be disposed in any of the following locations: on the second wall, in an approximate center of the second wall, at a top portion of the ostomy bag, or in a pocket formed in the first wall or the second wall.

In some configurations, the electronics hub can comprise a temperature sensor configured to measure an ambient temperature.

In some configurations, the bag can include one or more of the following: a capacitive sensor, a flex sensor, an odor sensor, a microfluidic sensor, a camera, an infrared camera, an audio sensor, or a gas sensor.

In some configurations, the temperature sensors can be thermistors or IR temperature sensors.

In some configurations, the temperature sensors can be arranged in a matrix circuit.

In some configurations, the bag can include curved conductors connecting the temperature sensors.

In some configurations, the bag can include a temperature sensors cover disposed below the opening in the first wall.

In some configurations, a medical kit can include three groups of ostomy bags of any of the preceding claims, a first group of ostomy bags comprising diagnostic bag, a second group of ostomy bags comprising analytics bags, and a third group of ostomy bags comprising maintenance bags. In some configurations, the first, second, and third groups of ostomy bags can each comprise temperature sensors and capacitive sensors configured to measure output volume, leak, and/or hydration status. In some configurations, the first and second groups of ostomy bags can each further comprise an optical sensor and the third group of ostomy bags do not include an optical sensor. In some configurations, the first group of ostomy bags can further comprise a microfluidic sensor and the second and third groups of ostomy bags do not include a microfluidic sensor.

In some configurations, an ostomy bag can include two walls joined together along a seam around at least a portion of an edge of the ostomy bag, a first one of the walls configured to be placed facing skin of a user and a second one of the walls configured to face away from the user when the first wall faces the skin of the user; an opening in the first wall, the opening configured to be disposed around a stoma of the user and to receive effluent from the stoma; a sensor layer disposed in, on, or between one of the two walls of the ostomy bag, the sensor layer comprising a plurality of temperature sensors and a plurality of capacitive sensors, wherein the plurality of temperature sensors can measure a temperature change due to the effluent entering the bag, and wherein the plurality of capacitive sensors can measure a capacitance change due to the effluent entering the bag, the sensor layer further comprising one or more wireless communication antennas, wherein when in use, the one or more antennas are in electrical communication with one or more antennas on an ostomy wafer configured to couple the first one of the walls of the ostomy bag to the skin of the user, and/or one or more antennas on a hub configured to be coupled to the ostomy bag on the second one of the walls; and an insulation layer disposed between the sensor layer and one of the two walls of the ostomy bag.

In some configurations, the insulation layer can be disposed between the sensor layer and each one of the two walls of the ostomy bag.

In some configurations, the insulation layer can comprise a foam or a fibrous material.

In some configurations, the bag can include the insulation layer comprises polyester or polyurethane.

In some configurations, the bag can include the insulation layer is configured to insulate the plurality of temperature sensors from heat from the user's body.

In some configurations, the bag can include the insulation layer is configured to insulate the plurality of temperature sensors or the plurality of capacitive sensors from ambient signal noises.

In some configurations, a method of detecting an ostomy leak can include under control of a hardware processor, sensing temperature readings of a temperature sensor disposed in an ostomy wafer; detecting a rapid change in the sensed temperature occurring within a threshold time; and outputting an indicating that a leak has occurred at a location in the ostomy wafer corresponding with the temperature sensor.

In some configurations, the sensing and detecting can comprise temperature readings with a plurality of temperature sensors disposed about the ostomy wafer.

In some configurations, the plurality of temperature sensors can be disposed in one or more rings or partial rings.

In some configurations, the method can further include measuring capacitance values of a plurality of capacitive sensors disposed on the wafer.

In some configurations, the method can further include determining a moisture content of adhesives on a user-facing adhesive layer of the wafer, wherein a decrease in the moisture content is indicative of the wafer becoming loose.

In some configurations, the temperate readings can be presented as a heat map.

In some configurations, the method can be implanted with any of the features of an ostomy device disclosed herein.

In some configurations, a method of detecting skin irritation around a stoma can include under control of a hardware processor, sensing a first group of temperature readings of a first plurality of temperature sensors disposed about an ostomy wafer; sensing a second group of temperature readings of a second plurality of temperature sensors disposed about an ostomy wafer, the second plurality of temperature sensors located further away from the stoma than the first plurality of temperature sensors; detecting a difference in the temperature of the first and second groups of temperature readings, the first group of temperature readings being greater than the second group of temperature readings; and outputting an indicating that irritation has occurred at or near the stoma.

In some configurations, the temperate readings can be presented as a heat map.

In some configurations, the plurality of temperature sensors can be disposed in a matrix in the ostomy wafer.

In some configurations, the detecting can be performed using a comparator.

In some configurations, the hardware processor can be further configured to consider the temperature change to correspond to effluent but to reject a change in the second group of temperature readings that does not correspond to temperature changes flowing from the first plurality of temperature sensors to the second plurality of temperature sensors.

In some configurations, the hardware processor can be further configured to reject a change in the second group of temperature readings that is below a threshold rate.

In some configurations, the hardware processor can be further configured to calibrate based on detecting body temperature prior to flow of the effluent.

In some configurations, the hardware processor can be further configured to detect a phase of the effluent based on a speed of the change in temperature readings.

In some configurations, the hardware processor can be further configured to cause temperature readings changes that are due to gas to be ignored.

In some configurations, the method can be implanted with any of the features of an ostomy device disclosed herein.

In some configurations, a method of detecting fill of an ostomy bag can include under control of a hardware processor, sensing capacitance values of a plurality of capacitive sensors disposed in an ostomy bag; calculating a level of the fill of the bag based at least in part on the capacitance values; and outputting an indicating that a volume of bag fill has increased responsive to detecting change in the capacitance values.

In some configurations, the calculating can be performed by machine learning.

In some configurations, the calculating can be performed by a trained neural network model.

In some configurations, the method can further include sensing temperature values with a plurality of temperature sensors disposed in the ostomy bag, wherein the calculating is based in part on the temperature values.

In some configurations, the method can further include creating a plurality of event flags, wherein the plurality of event flags can comprise detection of infusion, detection of drain, and detection of the bag on a user.

In some configurations, the detection of infusion can be based on readings from temperature sensors located near an opening of the bag configured to be disposed over a user's stoma.

In some configurations, infusion can be detected when the readings from the temperature sensors located near the opening of the bag exceed an infusion criteria.

In some configurations, the calculating can be performed upon infusion being detected.

In some configurations, the detection of drain can be based on readings from temperature and/or capacitive sensors located near a bottom of the ostomy bag.

In some configurations, drain can be detected when the readings from the temperature and/or capacitive located near the bottom of the ostomy bag exceed a drain criteria.

In some configurations, the detection of the bag on the user can be based on the temperature sensors located near an opening of the bag configured to be disposed over a user's stoma.

In some configurations, the method can further include calibrating the capacitive sensors upon one or more of: detecting the drain, or detecting the bag on the user and first readings from the capacitive sensors have been taken.

In some configurations, the method can further include smoothing spikes in raw volume calculations.

In some configurations, the method can further include causing to be displayed on a user device in electrical communication with the bag one or more of: a volume of bag fill, a restroom location, or a hydration tracker.

In some configurations, the method can further include detecting phasing of effluent in an ostomy bag under control of a hardware processor by sensing temperature values of a plurality of temperature sensors disposed in an ostomy bag, the plurality of temperature sensors being in contact with the output; and determining a phase of the effluent based in part on the temperature values.

In some configurations, the hardware processor can be further configured to detect a phase of the effluent based on a speed of the change in temperature.

In some configurations, the hardware processor can be further configured to cause temperature value changes that are due to gas to be ignored.

In some configurations, a heavier thermal print on the heat map can indicate a more viscous effluent.

In some configurations, the trained neural network model can be configured to recognize borders between effluents of different phases on the heat map.

In some configurations, the hardware processor can be further configured to subtract a volume of effluent due to gas from a volume calculation based on the fill detection.

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as taught or suggested herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14A shows the layered ostomy wafer of FIG. 4 placed on an example ostomy bag.

FIGS. 19A-19F show an infusion of applesauce at different volumes in a standing position.

FIGS. 20A-20G show an infusion of water in a standing position at various volumes from 50 mL up to 350 mL at 50 mL increments.

FIG. 42A illustrates an example schematic circuit diagram of a bag PCB.

FIG. 42B illustrates an example schematic circuit diagram of temperature sensors on a sensor layer of an ostomy bag.

FIG. 42C illustrates an example schematic circuit diagram of capacitive sensors on a sensor layer of an ostomy bag.

FIG. 42D illustrates an example schematic circuit diagram of a battery on a sensor layer of an ostomy bag.

FIG. 49A illustrates example readings of capacitive sensors on an ostomy bag after first measurement.

FIG. 49B illustrates example readings of capacitive sensors on an ostomy bag after draining of the bag.

DETAILED DESCRIPTION

Introduction

Figure 1A:
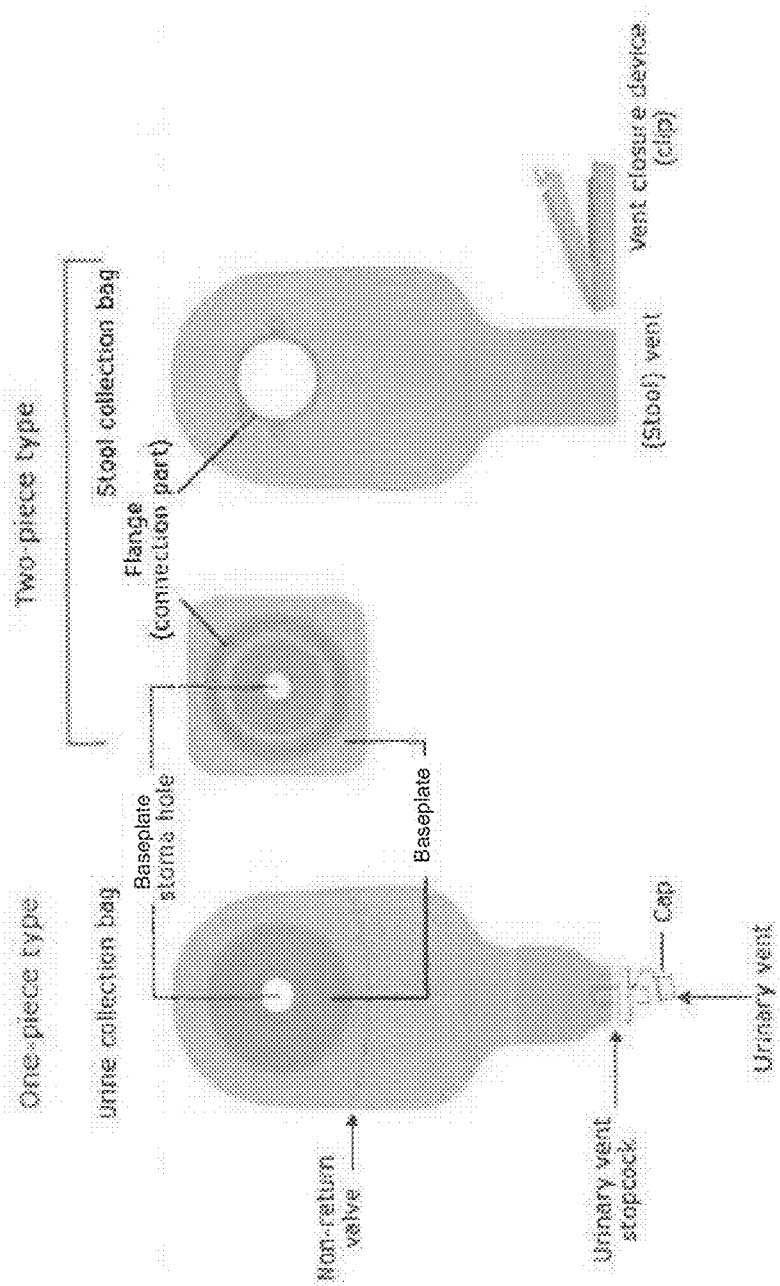
FIG. 1A illustrates schematically prior art example ostomy bags.

Systems and examples described herein relate to systems and methods for detecting skin inflammation, for example, for detecting skin inflammation around a wound. Systems and examples also relate to an ostomy system for detecting peristomal skin inflammation due, for example, to leakage at the ostomy site.

For skin wounds, such as post-operative surgical wounds, skin inflammation can also be the first indication of infection. Since infected wounds can have serious local and systemic complications for a patient, fast detection and treatment of infection is paramount. Often however, patients fail to recognize the first signs of skin inflammation and can become unwell before seeking medical advice.

Stoma patients, in particular, are at risk of suffering skin inflammation from both irritation and infection. Any leakage of waste leaving the body through the stoma (for example, the "stomal output") onto the peristomal skin can lead to irritant dermatitis, fungal infections, fungal dermatitis or folliculitis. In addition, the wearing of an ostomy device can cause irritation to the skin on the outside of the abdomen wall due to mechanical trauma resulting from an ill-fitting appliance and/or from the constant removal and re-attachment of the ostomy device.

This disclosure describes examples of systems and methods for detecting skin inflammation around a stoma, as well as leakage around the stoma. The systems and methods can be used in the context of an ostomy system for detecting peristomal skin inflammation of colostomies, ileostomies, urostomies, and the like. One example system can include an ostomy wafer that includes one or more sensors that provide outputs responsive to skin inflammation and/or leakage. The sensors can be temperature sensors, capacitive sensor(s), or other types of sensors, many examples of which are discussed in detail below.

An increase in temperature output by temperature sensors in the ostomy wafer can correspond with effluent leaking onto the peristomal skin (for example, leaking under the ostomy wafer). An increase in temperature output by the temperature sensors can also correspond with an increase in skin irritation due to the effluent leakage. Thus, the system can detect changes in temperature that may be indicative of effluent leakage and/or possible skin irritation, prior to a user noticing leakage or skin irritation. The system can output an indication to a user based on, among other things, the detected temperature changes. The indication may include an audible and/or visual representation of the changes in temperature, a warning, alert, or alarm regarding impending or detecting skin irritation. As will be described in greater detail below, capacitive sensors may be used on the wafer instead of and/or in addition to temperature sensors to detect the presence of moisture.

Another problem facing ostomy patients is leakage at the ostomy site, for example, due to overfilling of the ostomy bag. It can be difficult for some users to detect when an ostomy bag is full. This is particularly the case because an ostomy bag typically reaches its designed capacity before it appears full to a user. The designed capacity of an ostomy bag may be less than its apparent capacity to avoid leakage back into the stoma. In addition, a user may forget to check the ostomy bag and thus may accidentally permit the bag to overflow. Leakage can be uncomfortable, embarrassing, and damaging to clothing and skin, creating the irritation discussed above.

This disclosure also describes systems and methods for detecting ostomy bag fill. One example system includes an ostomy bag that includes one or more sensors for detecting bag fill. The one or more sensors can include temperature sensors. The temperature sensors can output temperature measurements indicative of changes in temperature responsive to effluent entering the ostomy bag. The system can output an indication to a user based on the detected temperature changes. The indication may include an audible and/or visual representation of the changes in temperature, a warning, alert, or alarm.

The system can also include one or more volumetric sensors (for example, capacitive sensors, or others). The system can output an indication to empty and/or change the bag to a user based on, for example, detected capacitance changes in one or more capacitive sensors, which can be on the ostomy bag. For example, a capacitive sensor can include an electrode in electrical communication with a capacitive sensor chip for monitoring the capacitance of the electrode.

The ostomy wafer described above may be used together with the ostomy bag described above. The ostomy wafer may also be integrated together with the ostomy bag. Further, an example system may also include one or more wireless transmitters that transmit data from the ostomy wafer and/or ostomy bag to another device, such as a hub, a user device, a clinician device, and/or a back-end system. For example, the ostomy wafer and/or the ostomy bag can wirelessly transmit data to a hub coupled to the ostomy bag, and the hub can transmit the received data to a back-end system (such as cloud servers). A user device (for example, a smartphone or tablet) can download the data and other information from the remote server.

This disclosure also describes many other example sensors, parameters that may be detected using those sensors, and variations of ostomy wafers and ostomy bags.

Overview

This section provides a detailed overview of various problems affecting ostomy patients as well as an overview of some of the solutions provided by this disclosure. More detailed example features are described below with respect to the drawings, starting under the heading entitled "Example Ostomy Monitoring System."

An ostomy bag can be a medical bag that collects human waste (either stools, urine, or both) from patients who cannot excrete waste naturally due to medical issues, which include, among others, cancer, trauma, inflammatory bowel disease (IBD), bowel obstruction, infection and fecal incontinence. In such cases, a surgical procedure is performed whereby a waste passage is created. This waste passage can be the ureter (called an urostomy), the small bowel or ileum (called an ileostomy, part of the small intestine) or the large bowel or colon (called a colostomy, part of the large intestine), which may be diverted to an artificial opening in the abdominal wall, thus resulting in part of the specific internal anatomy, to lie partially outside the body wall. This procedure can be referred to as an ostomy, and the part of the waste passage which is seen on the outside of the body can be referred to as a stoma.

A prior art image of example ostomy bags is presented in FIG. 1A. In FIG. 1A, two ostomy bags are shown. These bags include a one-piece bag to the left and a two-piece bag to the right. The one-piece bag (on the left) has a baseplate (also sometimes referred to as a faceplate or called an ostomy wafer or simply wafer) already attached and integrated onto the bag. The two-piece bag has a separate wafer and bag (and thus includes an attachment or flange). In the case of the one-piece bag, it is usable only once, and when it is time to change the bag, the full appliance needs to be disposed. In the case of the two-piece bag, the bag can be disposed without having to take off the wafer. Some people prefer this two-piece set-up, leaving the wafer on their bodies while removing only the bag, as removal of the wafer (which may contain a high-tac adhesive) can be a form of mechanical strain on the skin, which some prefer to avoid. When the bag is worn on the user, the wafer side in the one-piece bag, or the wafer-interfacing side of the two-piece bag, can face the user's body. The wafer can sit around the stoma (thus, the stoma sits in a stoma hole in the wafer) and can be made from a biocompatible hydrocolloid or hydrocolloid adhesive-based material, which are both skin friendly and so can stick to the skin easily once the stoma is in place through the stoma hole. Many other example wafer and bag materials are described in greater detail below. Both diagrams are examples of drainable bags, in that they have vents at the bottom of the bag for the patient to remove the waste when it is time to empty their bags. Some bags do not have a vent and so cannot be drained. Thus, when full, such bags are disposed without the function to be able to drain them. The average wear time of an ostomy bag/pouch can be 1-3 days or 3-5 days. The average wear time of a baseplate can be about 3-5 days.

The type of waste released by patients with the three different forms of ostomies (urostomy, ileostomy, and colostomy) can be different. Urostomy waste includes urine, ileostomy waste can include stools of porridge-like consistency, and waste from colostomy patients can include firm stools. The size of the stoma that is created by the stoma surgeon may be determined by the specific type of ostomy that the patient has. For example, a colostomy is the divergence of the colon (large intestine) to the opening in the abdominal wall and hence the stoma size (for example, the diameter) may be expected to be quite large. This is in contrast to an ileostomy patient, who would have his/her ileum (part of the small intestine) diverted to an opening in the abdominal wall. Because of the smaller size of the small intestine, the stoma size is likely to be smaller.

Currently bags in the medical bag industry (which includes ostomy bags, blood bags, saline bags, catheters, etc.) function solely as plastic bag type collection vessels which can be emptied and re-used, or disposed and replaced by a new one. Other than that, they have no advanced functionality or uses, for example clinical diagnostic capabilities. Thus, for example, analytical urine and stool tests are currently conducted in a lab facility by the physical collection of samples from the patient, which are subsequently sent to various diagnostic labs for clinical laboratory analysis.

This disclosure describes several different example bags and wafers that can include sensors and optionally electronics. The electronics on the bags and/or wafers can perform a significant amount of analytical analysis (for example, calculation of at least some of the leak and/or skin irritation detection metrics disclosed herein). The sensors and electronics on the bag and/or wafer can transmit sensor signals (which can be unprocessed and/or minimally processed or conditioned signals) to a back-end system (such as cloud servers) for calculation of the metrics (for example, the temperature and/or capacitance change). With systems incorporating such bags and wafers, the measurement of other metrics can be done within the bag itself (optionally together with an external device such as a patient's phone), without the need for third party intervention, such as a lab, to conduct the analysis. Thus, this disclosure describes some examples of a "lab on a bag." The bag can effectively be able to give each patient as well as his/her physician and/or nurse and/or caretaker, in-situ patient clinical information.

An example of such clinical information can be electrolyte levels such as sodium (Na+), calcium (Ca2+), or potassium (K+) levels, the loss of which can be indicative of patient hydration levels as well as acting as markers for diabetes, renal and liver dysfunction as well as cardiac and other diseases. Another clinical marker that may be used on bags herein is the pH level, for example in urine, which can give indication of UTIs (Urinary Tract Infections) as well as ketosis and severe diarrhea. Other types of substances in the output can be monitored, such as presence of drugs.

Other metrics can be of incredible value to both the patient and his/her medical team in charge, as well as possible care giver. In response to this, the bag and/or wafer can also measure the physical information associated with events which occur on a daily basis in the lives of ostomy patients. This physical information can encompass data on the fullness of the bag as well as monitoring the volume of output in the ostomy bag, the flow rate in the effluent/output, its physical phase and the viscosity of the effluent, and finally peristomal skin irritation and leakage of the effluent, both around the site of the stoma and in the hydrocolloid wafer. A brief overview of examples of these metrics follows.

Bag Fill and Volumetric Measure:

Data and indicators regarding the fullness of the bag can be useful metrics for patients, providing early indication that his/her bag needs to be emptied, which can prevent the patient from potentially unfortunate and embarrassing incidents such as overfilling of the bag and can prevent the effluent from contacting the skin around the stoma site thus causing irritation or infection. Such incidences can impact patients socially and psychologically. Further, volumetric output can have a strong correlation to the patient in terms of their diet and hydration and therefore can be a good indirect indicator of the functionality of the GI (Gastro Intestinal) system and its ability to absorb nutritious components such as vitamins, proteins, glucose, minerals, and the like whilst being indicative of its throughput in removing the waste from the patient's body. Thus, a quantitative measure of the volumetric output from the stoma can indirectly give clinical guidance of the functioning of the GI system.

However, the output of each patient can be a very subjective metric, with some patients having significantly more output and others significantly less. Linearity may not always be the case in the relationship between input and output, with some patients having significant output in comparison to what is going into their bodies. Thus, the combined information of the input of the patients with their output, could lead to early signs of for example dehydration (for example, by losing significantly more water through the measured output than that which is going into the body via fluid intake).

A mobile application and/or web site can be provided to patients, which can include a platform of different trackers such as food and hydration trackers. With the application optionally being able to record metrics such as diet and hydration (via user interaction and trackers within the app) and the bag sensor(s) able to indicate the volume in the bag, this integrated platform can work together to give early signs of dehydration, dietary issues or even GI dysfunction in patients. Dehydration can be a significant metric because it is one of the most common reasons why patients are readmitted into the hospital in the first three months following ostomy surgery. Thus, providing features that can help patients become aware of their output can enable patients to better monitor and prevent dehydration, significantly improving quality of care and life while at the same time potentially reducing the post-operative costs associated in hospital re-admissions following initial stoma surgery.

Flow Rate, the Physical Phase and the Viscosity of the Effluent:

Knowledge of the physical phase (including solid, semi-solid, liquid, and gas) of the effluent that is coming out of the bag can be clinically significant. In the case of urostomates and colostomates, the phase of the output can be generally fixed for both groups of patients, with the output being of liquid and solid phases, respectively. However, in the case of ileostomy patients, the output may be of porridge-like consistency, meaning it can be a mix of solid, liquid, or semi-solid. Moreover, both colostomy and ileostomy patients may have gas in the output. The knowledge of the phase of the output can give early signs of dehydration, functionality of the GI tract of the patient, and information about the lifestyle of the patients such as their dietary habits or hydration habits. Combined with the mobile application discussed above, clinically significant data and events can be determined and relayed to doctors rapidly. Moreover, detection of gas output can enable a more accurate calculation of bag fill, as discussed below in more detail.

Skin Irritation and Leakage of the Effluent Around the Stoma:

Leakage as a phenomenon, is particularly common with patients who have more fluid-like output, but can also occur with colostomy patients who have more firm output, through so-called "pancaking" of the stool around the stoma. Leakage can occur when the effluent/output of the patient does not entirely enter the bag. Instead, some of it bypasses the bag and starts to accumulate between the adhesive side of the wafer (skin-side facing) and the skin surrounding the stoma (also called the peristomal skin, which lies behind the wafer). The output encompasses biological and chemical enzymes, which when in contact with the skin for long periods of time, and as a function of their accumulation, can start to "erode" and thus irritate and scar the skin. The method by which skin is irritated in this scenario can be called Irritant Contact Dermatitis (ICD) or Incontinence Associated Dermatitis (IAD). For ease of description, this specification often refers to ICD and IAD interchangeably.

Leakage can be caused by a number of reasons, with some of the main reasons being the loss of tackiness of the hydrocolloid adhesive as a function of long wear times or sweat and/or moisture accumulation between the wafer and the skin behind it. The accumulation of this enzymatic output, behind the wafer, can also promote erosion of and can destroy the hydrocolloid. In doing so, this erosion can break down the adhesive too, destroying its tackiness and therefore ultimately making it redundant. Long wear times are very common with ostomy bags, with 3-5 days being the average wear time per patient before disposal to utilize a new bag. Thus, it can be imagined that over this long period of continuous wear, the hydrocolloid is likely to be exposed to significant amount of moisture, resulting in its ultimate inability to be utilized without leaking.

Moisture and sweat can also act as catalysts to exacerbate the symptoms of leakage because as these forms of moisture start to saturate the hydrocolloid, which has a maximum saturation limit, beyond which it cannot absorb further moisture, then they effectively prevent the hydrocolloid from absorbing the leaking effluent. As a result, the leaking effluent accumulates in between the peristomal skin and the back of the wafer, causing ICD.

ICD is a major concern and issue with a large number of patients, but so far the interventions made by the major bag companies to prevent leakage and subsequently skin irritation, include the utilization of products such Eakin seals which limit the leakage or wipes that form a protective barrier that protect the skin from damage of the adhesive, effluent and enzymes or integration of components like ceramide into the barrier to maintain good skin health and maintain good peristomal skin health. Despite these interventions, many patients are still struggling with peristomal skin complications. One disadvantage that patients face is the lack of sensation of the leakage occurrence. By the time the patient realizes that leakage has occurred, it can become too late because the active enzymes species may have already done significant damage to their peristomal skin. The skin irritation that occurs can be on multiple levels, which WOCNs (Wound Ostomy Care Nurses) can assess via the DET (Discoloration, Erosion and Tissue Overgrowth) score. This scoring system is described as an ostomy skin tool utilized by nurses as a standardized way of assessing the peristomal skin conditions and complications in ostomy patients. This scoring tool is scored for skin irritation promoted by chemical irritation which encapsulates IAD or ICD, mechanical trauma (due to frequent change of the bag wafer), disease related irritation and infection related irritation, as seen in the previous citation. The infection around the stoma can be a symptom of the initial skin irritation coupled with moisture and the presence of sweat.

As yet, based on inventor knowledge, there has been no commercial interventions to provide a technological solution which can indicate the in-situ occurrence of leakage or the saturation and/or breakdown of the hydrocolloid or potential skin irritation at an early stage. However, example devices and algorithms described herein can give users a warning to change their flange/wafer and thus take preventative action to minimize their skin conditions worsening.

Further, there has been no commercial technological solution, based on inventor knowledge, for the detection of the volume in the bag, assimilation of the physical phase in the bag and the flow rate, where temperature is being used as a marker. Solutions to be able to detect these metrics from a technological perspective, with an overall motive to communicate this information (for example, in real-time) to a variety of different stakeholders (for example, patients, nurses, doctors, care givers, care takers) via a smart phone or smart tablet platform as illustrated further below, would be of great value to the healthcare and patient communities.

An example smart ostomy bag (or "smart bag"), which can also encompass a wafer, can have integrated sensors that can track one or more in-situ physical events inside the bag. These events can include volumetric analysis, flow rate, physical phase of the effluent, viscosity of the effluent, possible skin irritation, and/or leakage occurrence around the stoma and saturation of the hydrocolloid. The smart bag can also track more detailed clinical/analytical metrics of the bag such as electrolytic measurements, pH, and other markers, which can be explained in further detail below.

One physical marker that can allow for the detection of some or all of the metrics described above is heat/temperature. The following section will explain why heat can be a relevant marker in order to detect one or more metrics of interest.

As mentioned previously, peristomal skin irritation is one of the top-ranked complications for ostomy patients, which can be caused by frequent change of the wafer, allergy, folliculitis, or leakage of the skin barrier/wafer (a leakage can occur when the stoma output seeps between the skin and the skin barrier/wafer, which may eventually extend outside of the skin barrier/wafer).

Despite the variety of factors that cause ICD, which can collectively be termed irritants, each of these factors can lead to an increased subcutaneous blood flow, and resultantly, an increased skin surface temperature. Though specific clinical data on peristomal skin temperature is not available in literature, other studies on chronic wounds and ulcers have shown evidence of a 3-4° C. difference in skin temperature between the irritated skin and the contralateral unaffected reference skin irritation. Therefore, the in-situ monitoring of the peristomal region skin surface temperature, as well as a region further away from this periphery (in order to have an un-irritated reference area of measure), can provide information about the skin health and can indicate early signs of skin irritation.

Since stoma output can be associated, at least initially as the output leaves the stoma, with internal body temperatures (at or about 37° C.) which is higher than the external skin temperature (specifically the abdominal skin surface) (about 32-35° C.), temperature can also be utilized as a marker to warn of leakage occurrence behind the skin barrier/wafer and therefore to alert the on-coming of early-stage peristomal skin irritation. When the leakage occurs, it would be expected that the temperature in the wafer may increase very rapidly—even appearing to be an instantaneous increase. This rapid or instantaneous temperature change can be monitored as a function of the leakage occurrence to detect the leakage in-situ.

The wafer of the ostomy bag made with hydrocolloid-based materials can have advantages including but not limited to: 1) it adheres to the skin surrounding the stoma, whether it is moist or a dry skin site, 2) in the case of wound exudates, which are a very common occurrence in ostomy applications, the hydrocolloid dressing absorbs fluids and swells, protecting the wound, causing less pain and faster healing and 3) given that in ostomy applications most bags are commonly changed after about a 1-1½ day, 1-3 day, or 3-5 day period in the USA (commonly about 1-2 days in the UK), and the baseplates being changes after about every 5-6 days, the wear life of the hydrocolloid dressing can be sufficiently long such that, once worn, the dressing needs not be replaced in between bag changes, causing less disruption to the wound.

Given that the hydrocolloid absorbs exudates as well as moisture from the body, for example sweat, it is expected that it will expand as a function of the absorption of the fluids. The expansion of the hydrocolloid as a function of the absorption is suggestive of a change in temperature between the hydrocolloid adhesive and the peristomal region as the hydrocolloid effectively moves away from the skin as a function of the exudate absorption. Therefore, the route to detect the saturation of the hydrocolloid, can be via detecting the temperature change as a function of time, which can give early indication of the saturation of the hydrocolloid. This can be important as many patients do not have the sensation of leakage or of the hydrocolloid saturating until they can visually see or feel the flange detach off their bodies, which occurs naturally as a function of the reduced tackiness of the hydrocolloid adhesive.

Apart from temperature, another useful marker for detecting one or more metrics of interest, via the wafer or bag, can be the pH. The pH can be useful due to the leakage occurrence of the exudate and its contribution to the saturation of the hydrocolloid wafer. Given that the effluent contains enzymes of a biological and chemical nature, and the fact that they are able to erode the hydrocolloid and cause chemical damage to the skin, is suggestive an acidic or alkali nature of the effluent. Essentially the skin chemistry as well as the nature of the hydrocolloid wafer is changing as a function of the chemical and/or biological attack. By detecting the change in pH of the hydrocolloid as a function of the leakage occurrence, or its saturation and/or alternatively detecting the pH of the skin as a function of the enzymatic attack, a powerful combination of sensors (temperature and pH) can give early indication of leakage/skin irritation/saturation of the hydrocolloid wafer. By embedding (for example) a thread-based microfluidic pH sensor into the wafer, oversaturation and leakage can be detected. Of course, pH monitoring is optional.

Heat/temperature as an example marker for measuring metrics from the front (and potentially the back) of the main body of the bag will be described in greater detail below.

Some ostomy bag can include a volumetric sensor, based on a resistive flex sensor, which can measure the volumetric fill in bags and warn the patients for the draining points (for example, the times to empty their pouches). The nature of the flex sensor causes it to suffer from noise because of patients' natural movements (sitting, standing sleeping, running) and movements of the content within the ostomy bag.

As mentioned above, effluent is likely to be initially at internal human body temperature (at or about 37° C.) which is higher than the external skin (specifically the abdominal skin surface) temperature (about 32-35° C.). Therefore, the utilization of heat/temperature as a marker to understand the volumetric fill in the bag can be used to determine the volume in the bag. The effluent is likely to be the warmest when it exits the stoma, and as it travels from the top of the bag to the bottom of the bag where it settles, it may gradually cool down. The movement of the effluent from the top of the bag to the bottom of the bag, as well optionally as the possible settlement of effluent, can be heat mapped and thus be indicative of the volume in the bag. 2D or 3D heat mapping of the bag can be used to understand the volumetric activity in the bag.

Temperature measurements can permit visualizing the thermal signatures and heat patterns across the front and/or back of the bag, as the effluent enters the bag. The thermal signatures of the effluent can therefore be traced from the point where the effluent enters the bag to the point where it settles. Given that the output can be of different physical forms depending on the type of ostomy a patient has, such as urostomy (fluid-urine), colostomy (firm stool-solid) and ileostomy (porridge like output semi-solid/solid-liquid), the flow rate can be visually mapped by understanding the rate at which an array of thermal sensors is fired up, as the effluent crosses their path whilst heat is evolving/dissipating from the waste at the same time.

Heat dissipation, or more specifically rate of the heat dissipation, and cooling, can vary between the different physical phases, as can the flow rate. The rate of heat dissipated can depend on the heat capacities of the different phases as well as if the waste is in motion or stagnant. The flow of each phase can depend on the viscosity, with the liquid urine samples likely to be less viscous as the particles in liquid are to some extent free-flowing, allowing this phase to flow and travel quickly into the bag, and cross the path of the thermal sensors very fast. In the case of solid waste, the flow rate can be significantly slower due to the less free-flowing particles in the phase, and hence where an array of temperature sensors would be present, this phase is likely to cross the path of the thermal sensors more slowly. Therefore, it is possible to tell from the rate at which essentially an array of thermal sensors fires up—for example, the sensors' response time to the rate of movement of the effluent whilst it is entering the bag at internal body temperature and crossing the path of the array of thermal sensors—the viscosity and therefore the phase of the effluent. The timeframe of how long the thermal signature of the volumetric output lasts can also allow for indirectly determining the viscosity and phase of the effluent (such as liquid, solid, semi-solid, and gas). It would be expected (depending on the rate of heat dissipation) that the temperature of the output may drop back to baseline within a certain timeframe, but this timeframe can be different for different phases and viscosities.

The integration of arrays of thermal sensors into ostomy bags and/or wafers can aid patients as well as their care givers, nurses and specialist doctors to manage peristomal skin complications and to take early action to prevent the skin condition of the ostomy patient from worsening. Further, patients and caregivers may be able to understand more about the patient's output and the function of their GI system. Specific temperature sensor technologies, as well as other sensor technologies, for wafers and bags are described in greater detail below with respect to the drawings.

The smart ostomy bag can also detect the volume/fill inside the bag, such as by using the same thermistor technology mentioned above. The thermistor technology described above can detect the volume from the thermal signature of the effluent output; such as by placing the thermistor sheet in front of or in back of the bag (e.g., in either a front wall or a back wall of the bag). The time frame of the thermal signature of the volumetric output can indirectly indicate viscosity and eventually phase of the effluent (such as liquid, solid, semi-solid, and potentially even gas).

The thermistor based sensor technology can have a twofold functionality in the smart bag: 1) indicating skin irritation and leakage in the peristomal region and 2) indicating volume fill in the bag as well as phase of the effluent released. Both data sets can be generated based on heat. Below is an explanation of the processes and principles used by the device to generate output for each of these measures.

Because the transduction principle of the thermistor sheet can be based on temperature change and not on bending as the flex sensor is in U.S. Pat. No. 9,642,737, the thermistor technology can be more immune from noise caused by movement and therefore a new candidate for volumetric indication in the bag. Additionally, in example implementations where this thermistor sheet is placed at the front of the bag, the sheet can detect the temperature distribution/diffusion of the content within the bag and also the flow pattern of the stoma output. This can further allow analyzing the rheology properties of the stoma output, and potentially allows identifying the phase of the output.

The temperature readings themselves can be derived from resistance readings of the thermistors at a particular temperature as a function of time. The thermistor can be a semiconductor based device that changes its electrical resistance as a function of applied temperature. The resistance value can then be converted to a temperature value via the Steinhart-Hart equation:

$$\frac{1}{T} = A + B\ln(R) + C[\ln(R)]^3$$

where T is the temperature (in Kelvin), R is the resistance at T (in ohms), and A, B, and C are the Steinhart-Hart coefficients which can vary depending on the type and model of thermistor and the temperature range of interest.

The sensors can send data to an electronic hub, which can packetize the data and send the packets to a cloud server and/or to a mobile application on a user device. The mobile application can read the wireless packets and convert them to their appropriate data types. The mobile application can also be in electrical communication with the cloud server to download the data. The mobile application can output, for presentation to a user, a map of the heat distribution throughout the wafer and the front side of the bag, a temperature versus time scattered plot, and/or as visual representation of the total volume of output in the bag.

Example Ostomy Monitoring System

Figure 1B:
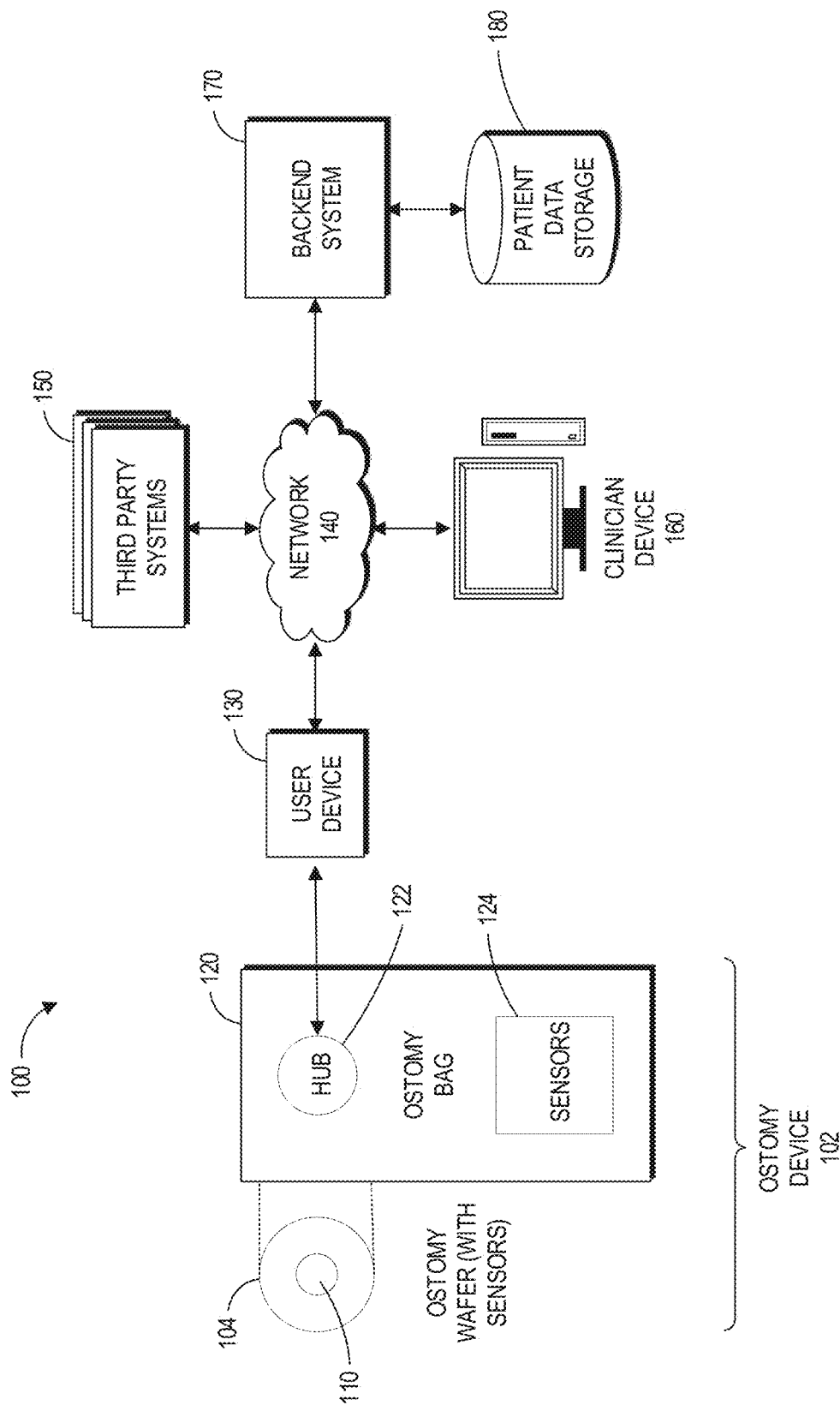
FIGS. 1B and 1C illustrate schematic overviews of example ostomy monitoring environment according to the present disclosure.
Figure 1C:
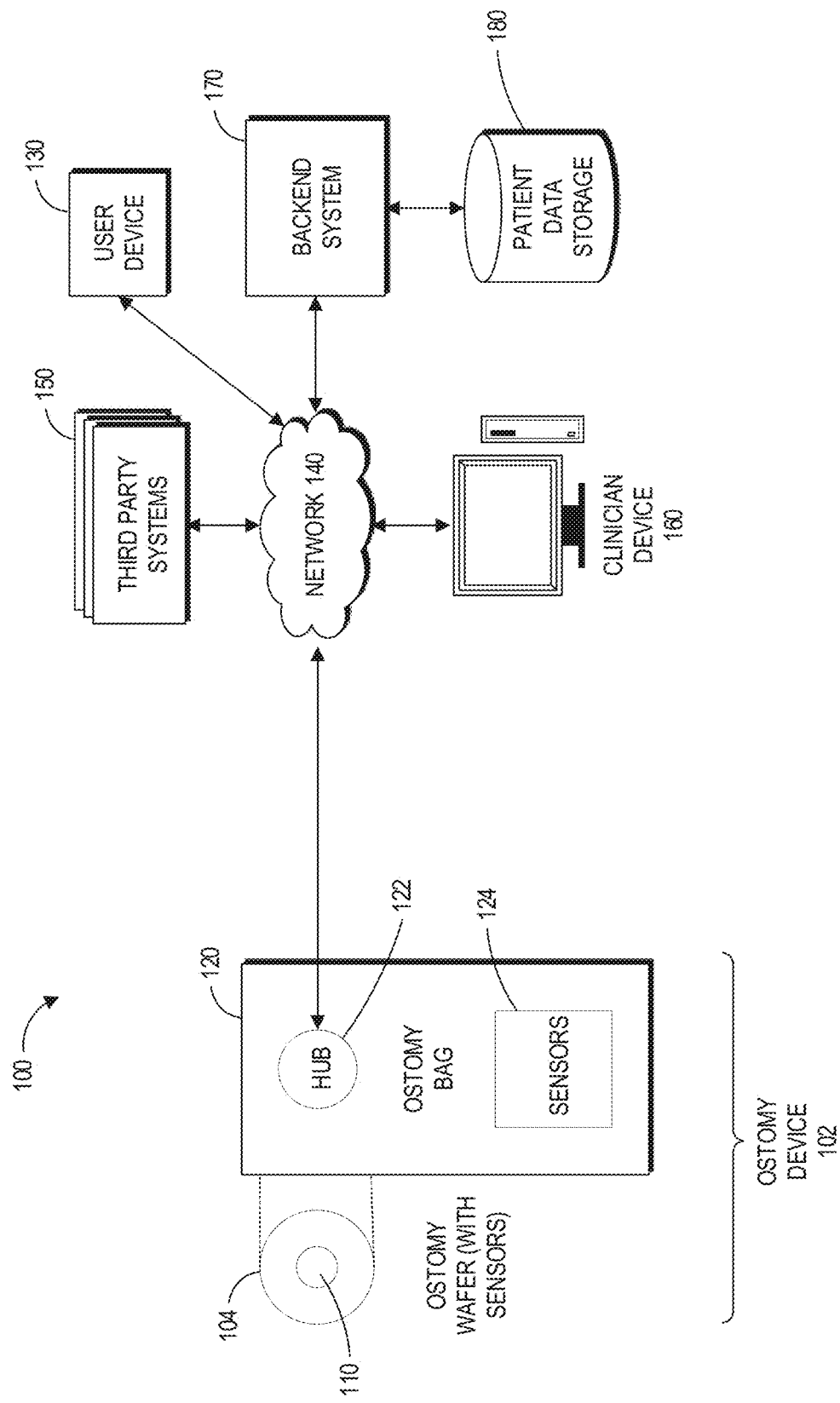

In FIGS. 1B and 1C, a schematic overview of an ostomy monitoring environment 100 is provided in which an ostomy device 102—as well as optionally a patient (not shown) using that device 102—may be monitored. In this environment 100, a hub 122 of the ostomy device 102 is shown in communication with a user device 130 (see FIG. 1B), which can transmit data from the hub to a backend system 170 (such as a remote server or cloud server) over a network 140, or directly with the backend system 170 over the network 140 (see FIG. 1C). The user device 130, the backend system 170, and other devices can be in communication over the network 140. In some cases, such as shown in FIGS. 1B and 1C, the user device 130 can download processed data from the backend system 170 after the hub 122 transmits the data to the backend system 170 for further processing (although in FIG. 1C, the backend system 170 can communicate directly with the hub 122 instead of through the user device 130). These other devices can include, in the example shown, a clinician device(s) 160, and third party systems 150. The ostomy monitoring environment 100 depicts an example environment, and more or fewer devices may communicate with the ostomy device 102 in other systems or devices. The ostomy monitoring environment 100 can enable a user and others (such as clinicians) to monitor various aspects related to the user's ostomy device 102, such as ostomy bag fill, leaks, and skin irritation.

The ostomy device 102 can be a one-piece or two-piece device including an ostomy wafer 104 and an ostomy bag 120.

The ostomy wafer 104 can include a patient-facing side that has an adhesive pad, flange, or the like that attaches to a patient's skin around a stoma 110 and a bag-facing side that is opposite the patient-facing side. The stoma 110 can include any stoma disclosed herein, for example, an aperture or hole in a patient's abdomen (or other location) resulting from a colostomy, ileostomy, urostomy, or other similar medical procedure. The ostomy bag 120 can removably attach to the bag-facing side of the ostomy wafer 104 (such as via adhesives or a Tupperware click mechanism) and receive and store output (for example, effluent) from the stoma 110. The ostomy bag 120 can be flexible so that when the bag 120 can be substantially flat when empty and can expand as effluent enters the bag 120. Once the ostomy bag 120 has reached its designed capacity, the patient (or caregiver) may remove the ostomy bag 120 from the ostomy wafer 104, discard and/or empty it, and attach a new ostomy bag 120 (or clean and reattach the old ostomy bag 120). In another example, the ostomy bag 120 is provided or sold together with the ostomy wafer 104 as a single device, with the ostomy wafer 104 integrally formed with the ostomy bag 120. The ostomy bag 120 collects human waste (such as stools and/or urine) from patients who cannot excrete waste naturally due to medical issues, which span from cancer, trauma, inflammatory bowel disease, bowel obstruction, infection, and incontinence. In such cases, a procedure is performed where a waste passage is created (colostomy, ileostomy, or urostomy) and diverted to a section of the abdominal wall. The ostomy bag 120 can be made of non-porous sterile plastic materials such as, but not limited to, polyvinyl chloride, polyethylene, ethylene vinyl acetate, polypropylene, and copolyester ether.

The ostomy bag 120 can include one or more sensors 124 and a hub 120, which can be located on a side facing away from the wafer 104. The sensors 124 can include any of the sensors described herein. For instance, the sensors 124 can include a plurality of temperature sensors, capacitive sensors, a camera (infrared or visible light), a gas sensor, a magnetic sensor such as an AMR sensor, and/or microfluidic sensor(s), among others. The bag 120 can include multiple layers. One or more sensor layers may be provided in which sensors are embedded or otherwise attached. Different types of sensors may be on different layers, or different types of sensors may be on a single layer. The sensors can also be located on the same and/or different sides of a single layer.

The ostomy bag 120 can include a measurement sheet. The side of the ostomy bag 120 facing away from the wafer 104 can include the measurement sheet. The measurement sheet can include a plurality of layers (such as layers made of polyimide, polyurethane, or the like). As will be described in greater detail below, four or two layers can be used. Other numbers of layers can be used. A layer of temperature sensors and/or a layer of capacitive sensors, for instance, may be provided that detects temperature and/or capacitance changes as effluent enters the bag 120 and disperses about an interior of the bag 120. The temperature and/or capacitive sensors may each be arranged in a matrix or matrix-like arrangement. A processor, whether in the hub 122 (discussed below), the user device 130, or the backend system 170, can process the temperature and/or capacitance data obtained from the temperature and/or capacitive sensors to detect leakage and/or skin irritation metrics, such as an increase in temperature and/or bag fill. Electronics in communication with the sensors can also be provided on one or more of the layers. Other examples of the sensors with respect to the bag are discussed in greater detail below.

The ostomy wafer 104 can be a flexible sheet with one or more layers, and optionally, multiple layers including one or more sensor layers. The layers can be made of the same or similar materials as the layers of the bag 120 described above. One or more of the layers of the ostomy wafer 104 may include one or more of the following sensors: temperature sensors (such as thermistors, temperature sense integrated circuits (ICs), thermocouples, infrared (IR) temperature sensors, etc.), capacitive sensors, flex sensors, odor sensors, microfluidic sensors, leak sensors, combinations of the same, or the like.

The sensors (such as temperature sensors and/or other types of sensors disclosed herein) of the ostomy wafer 104 can be disposed in a sensor layer (described in detail below).

The sensor layer can have a similar or the same shape outline as the ostomy wafer 104. For example, if the ostomy wafer 104 is shaped like a donut or annulus, the sensor layer may include a generally annular shape. The sensor layer can also have a shape that differs from the general shape of the wafer 10, such as a partially annular or partial ring shape. Optionally, the ostomy bag 122 can include a carbon filter port to allow gas to escape. An optional gas sensor placed on or near the port can detect a characteristic about the gas, such as the pungency of the gas to determine the status of the user's gut.

The ostomy wafer 104 can be any size. The size of the ostomy wafer 104 can depend on the type of stoma that the wafer 104 is used with. For example, a colostomy stoma can be larger than a urostomy stoma. Thus, the ostomy wafer 104 can be sized larger for some colostomy stomas than for some urostomy stomas. The ostomy wafer 104 may be a "one-size fits all" wafer that has punch-out sections in the center for adapting to various different stoma sizes. The ostomy wafer 104 can also come in different versions, which have stoma holes 110 of different sizes to accommodate different stoma sizes.

The ostomy wafer 104 can also be in any of a variety of different shapes. For example, the ostomy wafer 104 can have a generally annular, ovular, or circular shape, such as a ring, donut, or the like. The ostomy wafer 104 can also have a more rectangular, oblong, or square shape (optionally with rounded corners).

As described above, the ostomy wafer 104 can be layered in structure to encapsulate the sensors. Encapsulation can improve fixation of the temperature sensors in position in the flexible sheet and/or reduce corrosion of the sensors by the external environment. As an alternative to encapsulation, the temperature sensors may be protected from corrosion by a coating, such as a conformal coating. Some example wafers (and bags, discussed below) can have at least one temperature sensor in a second region of the flexible sheet that is protected by a conformal coating.

As described above, the patient-facing side of the ostomy wafer 104 can have an adhesive side that adheres to skin around a stoma 110 and/or directly to the stoma 110. The adhesive can be a double-sided adhesive. The adhesive may be a hydrocolloid adhesive.

The sensors of the ostomy wafer 104 and/or the bag 120 can detect information based on the output of the stoma 110. The sensors can sense the constituents of the effluent or output of the stoma 110. Temperature sensors can be used to determine whether there is likelihood of inflammation at the site of the stoma and/or a leak. Temperature sensors may also be used to detect the phasing of the constituents, which can be used to determine, for example, how much gas and/or solid is in the bag. A capacitive sensor in the wafer 104 (and/or in the bag 120) may serve as a fallback, provide redundancy to, and/or supplement a temperature sensor to determine if there is a leak. For example, the temperature sensors on the wafer 104 can detect a leak due to the effluent not entering the bag for various reasons as described above in addition to overfill of the bag 120 (such as when the bag 120 is relatively empty but the adhesives on the wafer become loose). As another example, the temperature and/or capacitive sensors on the bag 120 can detect bag fill and output an indication of an imminent overfill or leak, before an actual occurrence of a leak. In another example, capacitive sensors can be used instead of temperature sensors to detect leaks or skin irritation.

If microfluidic sensors are used on the wafer 104 and/or the bag 120, the sensors can be used to detect electrolyte or inflammation markers within the constituents. This data can be used to show the user what he or she could intake or do to obtain a healthier balance of electrolytes and other chemical compositions in the user's body. An odor sensor can be incorporated into the bag 120 and/or the wafer 104 to determine whether there is bacterial growth in the digestive tracts. An inertial measurement unit ("IMU") sensor, a form of positional indicator, can also be integrated into the bag 120 and/or the wafer 104. An optical sensor, such as a camera, may also be integrated into the bag 120 and/or the wafer 104 where the sensor looks down over the stoma and/or into bag in order to detect a degrading stoma, blood in stool, or etc. An audio sensor, such as a microphone, can be included in the bag and/or the wafer to detect gas output and/or bowel movement sounds. pH sensors may also be integrated into the bag 120 and/or the wafer 104 to determine the acidity of the constituents of the bag.

The ostomy wafer 104 and the ostomy bag sensor(s) 124 can collect patient data related to the stomal output and can transmit the data wirelessly or with wires to the hub 122. The hub 122 can include electronics that can facilitate one or both of (1) processing sensor data and (2) transmitting sensor data. For instance, the hub 122 can include a hardware processor, memory, and a wireless transmitter. The hub 122 can also optionally have a display for outputting data related to the sensors (such as an indication of a leak, bag fill, or the like). The hub 122 can also optionally include a speaker that outputs an audible warning indicative of a leak, bag fill, or the like.

The optional wireless transmitter of the hub 122 can send data received from sensors (wafer or bag) to a user device 130. The data can then be sent to a network 140, third-party systems 150, a clinician device 160, a backend system 170, or to a patient data storage device 180 (each of which is discussed in greater detail below). In order to preserve battery life, the wireless transmitter may be switchable to an active mode and idle mode. The wireless transmitter of the hub 122 can also send data received from the sensors on the wafer 104 and/or the bag 120 to the backend system 170, such as shown in FIG. 1C. The wafer 104 and/or the bag 120 can send data periodically, for example, over Bluetooth. The data transmitted by the hub 122 can include unprocessed, or conditioned (such as filtered, demodulated, and so on) signal data. The backend system 170 can process the received signal data to calculate the metrics disclosed herein, such as temperature and/or capacitance values, bag fill volumes, and/or leakage detection. The user device 130 and/or other devices can download the calculated metrics from the backend system 170. Performing the calculation on the backend system 170 can reduce the need for processing power in the hub 122, which can in turn reduce battery consumption and/or frequency in changing or recharging a battery in the hub 122.

The optional wireless transmitter of the hub 122 may include a near-field communication (NFC) reader and/or writer, a Bluetooth transmitter, a radio transmitter, or a Wi-Fi (802.11x) transmitter. The NFC reader and/or writer can be coupled to NFC antennas on the hub for communicating with NFC antennas on the bag 120 and/or the wafer 104 to receive sensor data from the sensors on the bag 120 and/or the wafer 104. The NFC reader and/or writer can have sufficient power or current (for example, with an output current up to about 250 mA) to receive data transmitted by the NFC antennas on the wafer 104 (and/or the antennas on the bag) when the bag 120 is filled to its apparent capacity and/or when the wafer 104 is separated from the hub 122 by a certain (for example, maximum) distance. The NFC reader and/or writer can serve as the main wireless communication tool with the sensors on the bag 120 and/or the wafer 104, and Bluetooth communication can optionally serve as a backup tool. Different wireless communication protocols can also optionally be used for transmitting data among the hub, the ostomy bag, and/or the wafer. The Bluetooth transmitter may include a Bluetooth module and/or a Bluetooth low energy (BLE) module. A Bluetooth module may be, but is not limited to, a Bluetooth version 2.0+EDR (Enhanced Data Rates) module. A Bluetooth low energy module may be a Bluetooth module such as, but not limited to, a Bluetooth version 4.0 (Bluetooth smart), a Bluetooth version 4.1, a Bluetooth version 4.2 or a Bluetooth version 5. The Bluetooth sensor module may include a Bluetooth module using IPv6 Internet Protocol Support Profile (IPSP).

The hub 122 can be in various positions on the device 102. The hub 122 can be placed in many areas on the ostomy bag 120. The hub 122 can be placed in the front, the back, next to a gas filter (not shown), or the like. The hub 122 can also be placed in a pocket on the ostomy bag 120 or the hub 122 could be a replaceable feature on the ostomy bag 120. The hub 122 can also come in different forms. When the hub is removed from an ostomy bag 120 it can use previous collected data and carry over that data to the next subsequent ostomy bag 120 that it is placed upon. Hub removability can save money for the user.

The hub 122 can include a plurality of electronics, including but not limited to the wireless transmitters and/or receivers, motion sensor (such as a three-axis accelerometer), temperature sensors (such as far infrared (FIR) temperature sensors, ambient temperature sensor, and/or the like), camera module, lighting for the camera (such as LED lighting), a microphone (such as a microelectromechanical (MEMS) microphone), battery charging circuitry, and/or other electronics. The ambient temperature sensor, which can be any type of temperature sensor, can be mounted on a side of the hub 122 facing away from the bag and the patient. Temperature measurements from the ambient temperature sensor can approximate a room or ambient temperature, and/or serve as reference for the temperature sensors on the bag 120 and/or the wafer 104. The microphone can record audio information related to the stomal output and/or monitor the metrics related to the stomal output (for example, gas output, bowel movement, or others).

The user device 130 can be any device with a processor and a wireless receiver that can communicate with the hub 122. For example, the user device 130 can be a phone, smart phone, tablet, laptop, desktop, audio assistant or smart speaker (such as an AMAZON ECHO™, GOOGLE HOME™, APPLE HOMEPOD™, or the like), television, or the like, that may pair automatically to the wireless transmitter and may include a mechanism that advises the user of the existence of a wireless link between the wireless receiver and the wireless transmitter. The user device 130 may have software and algorithms to process the data to show the user the status of the fill of the bag, the nearest restroom, nearest sources of electrolytes, nearest source of food, patterns and contents of discharge, hydration levels, and recommendations to improve the user's condition. The user device 130 may also transmit the data wirelessly to a network 140. The network 140 can be a local area network (LAN), a wide area network (WAN), the Internet, an Intranet, combinations of the same, or the like.

The third-party systems 150 can be a data processing tool/feature; backend servers for audio assistants; or fitness trackers, personal health monitors, or any third party systems that can use or manipulate the data collected by the device 102. These third-party systems 150 may also include algorithms and software to calculate and process the data.

Third party systems 150 and audio assistants can fetch data from the ostomy device 102 to announce reminders or alerts for the user such as to empty the bag, change the bag, change the hub, intake or stop intaking certain types of food, intake water, and/or providing periodic check-ins. Other third party systems may use data collected from other users to create a better feedback system or to identify patterns within a demographic of ostomy patients and/or bag users.

The clinician device 160 can be a data processing tool or monitoring program used by a clinician. These clinician devices 160 may receive data from the device 102 to provide a remote clinician to diagnosis the user, recommend actions to the user, or function as an augmented reality system for the clinician. These clinician devices 160 may also include algorithms and software to calculate and process the data.

The backend system 170 (such as cloud servers) can also use algorithms and software to perform data processing. For instance, the backend system 170 can process any data received from the sensors on the wafer and/or bag and return information based on that processing to the user device 130 or other devices. Another optional feature is an inclusion of a patient data storage system 180. From here the backing system can send the data to the patient data storage wirelessly or the patient data storage can access the data from the network 140.

Algorithms and software can show when the user should replace the bag, alert the user when the bag is nearly full or when there is a leak in the wafer or bag. Software features include, but are not limited to, identifying the nearest restrooms within the user's radius, the volume of the user's bag, alarms for different fill levels, a hydration and electrolyte tracker which calculates the user's recommended daily hydration goal with an algorithm. The hydration and electrolyte software can notify the user based on their effluent output or constituents what his or her dietary needs may be throughout the day.

Example Ostomy Wafers and Ostomy Wafer Layers

An ostomy wafer (also called an ostomy flange or an ostomy barrier) is an example of an article designed to adhere to the peristomal skin of a stoma patient. The wafer can protect the skin from chemical and biological erosion caused by stomal output.

Figure 2:
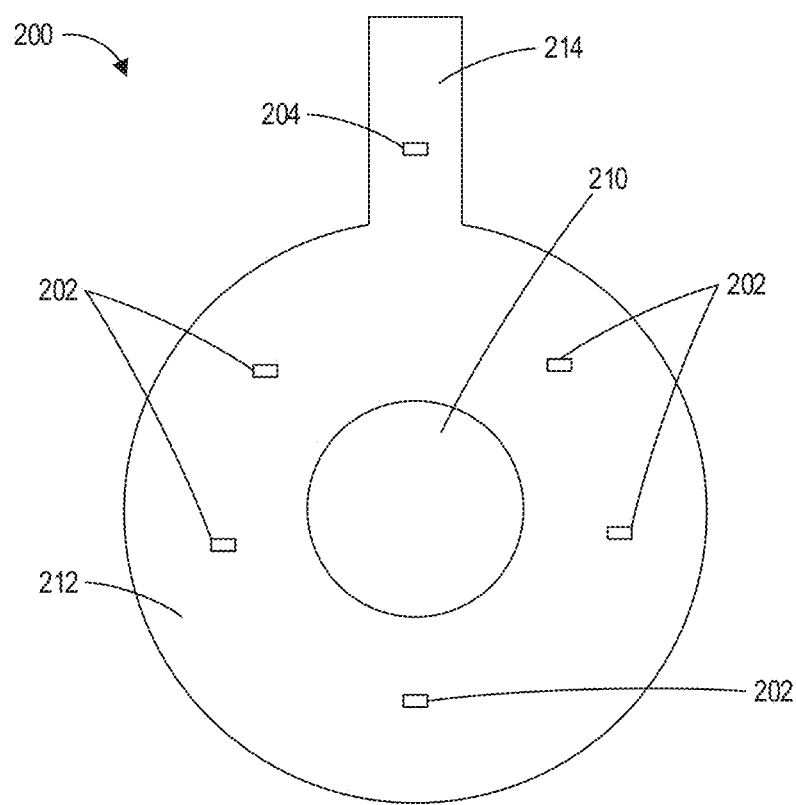
FIG. 2 shows an example sensor layer of an ostomy wafer.

FIG. 2 shows an example sensor layer 200 of an ostomy wafer, such as the wafer 104 of FIGS. 1B-C, which contains sensors 202 such as temperature sensors (for example, thermistors) or any of the other sensors discussed herein. The sensor layer 200 includes a body 212 surrounding a hole 210 (which may be a punch-out or cut-out to fit a user's stoma) and a neck 214. The example sensor layer 200 can be made out of a flexible sheet material.

The sensors 202 shown are placed in the body 212 in a roughly circular path around the hole 210. Any number of sensors 202 may be included. Having sensors 202 disposed in a roughly circular distribution concentric with the hole 210 can facilitate detecting leaks or irritation in different directions or any direction. More sensors may be provided in some implementations to increase a granularity of measurement, to potentially more accurately predict which direction a leak or irritation occurs, for example.

Also depicted is a sensor 204 disposed on the neck 214 extending away from the hole 210. The neck 214 may be resiliently deformable, such that it is able to lengthen in response to movement of the stoma patient and subsequently return to its original form. The sensor 204 can act as a reference sensor for comparing a temperature difference between the sensors 202 and the sensor 204. Because the sensor 204 is farther from the hole 210 than the other sensors 202 in this example, temperature detected by the sensor 204 may represent a baseline temperature of the patient's skin. Thus, comparison of the temperature output from the sensors 202 with the temperature output of the sensor 204 can be indicative of a leak or irritation. More generally, in order to detect the presence or absence of inflammation in the peristomal skin, at least one temperature sensor in the sensor layer 200 may be positioned remote from the hole 210 (once formed). This could be, for example, in the peripheral region of the body 212 or in the neck 214. The use of a sensor in the peripheral region of the body 212 to measure a user's reference body temperature signature in certain instances may be cheaper than manufacturing a sensor 204 in the neck 214.

Although the body 212 of the sensor layer 200 is shown as having a circular or annular shape, the sensor layer 200 may have other shapes. For example, the sensor layer 200 may be oblong, square, or ovular. Additional example shapes for the sensor layer are described in greater detail below.

Also, the sensor layer 200 may be one of multiple layers of material that form the ostomy wafer 104. For instance, the sensor layer 200 may be sandwiched between two or more layers to form the ostomy wafer 104. For example, the ostomy wafer 104 may include at least one layer formed of a protective plastics such as, but are not limited to, polyethylene, polypropylene, polystyrene, polyvinyl chloride, polyurethane, acrylonitrile butadiene styrene, phenolic, polyetheretherketone, polyamides, or combinations thereof. In certain examples of the device, the ostomy wafer 104 includes at least two layers of a protective plastics material, dimensioned to fully encapsulate at least the plurality of temperature sensors in the first body 212 and/or the neck 214. Encapsulation ensures or attempts to ensure that the temperature sensors are held in position in the sensor layer 200 and that they are protected from corrosion by the external environment.

Encapsulation may be achieved, for example, by sandwiching the temperature sensors between two layers of a protective plastics material, and subsequently heat welding or adhering the two protective layers together to form the ostomy wafer 104. In order to encapsulate the temperature sensors and still conform to the shape of the body, the ostomy wafer 104 can be from 0.15 mm to 0.7 mm thick or some other range. As an alternative to encapsulation, the temperature sensors may be protected from corrosion by a coating, such as a conformal coating. In certain systems, at least one temperature sensor in the second region, for example, in the neck 214 can be protected by a conformal coating.

In order to detect inflammation through temperature changes on the ostomy, temperature sensors placed in the positions of sensors 202 can be used. Temperature sensors may be thermistors, resistance temperature detectors (RTDs), thermocouples, integrated circuit sensors or infrared temperature sensors. The temperature sensors can be thermistors. Thermistors may be particularly suitable temperature sensors due to their high sensitivity. The thermistors may be commercially available thermistors that provide a large temperature coefficient of resistance, for example, in the range of about 30° C. to about 50° C. or some other range. Such thermistors are widely commercially available, for example, thermistors from Panasonic, the NTC thermistors NCP15WF104D03RC or NCP15XH103D03RC from Murata Manufacturing Co., Ltd or the NTC thermistor NTCG103JX103DT1 from TDK Corporation. When the temperature sensors are thermistors, the system (e.g., the hub 122) may include a processor that can periodically poll the electrical resistance of each thermistor.

Figure 3:
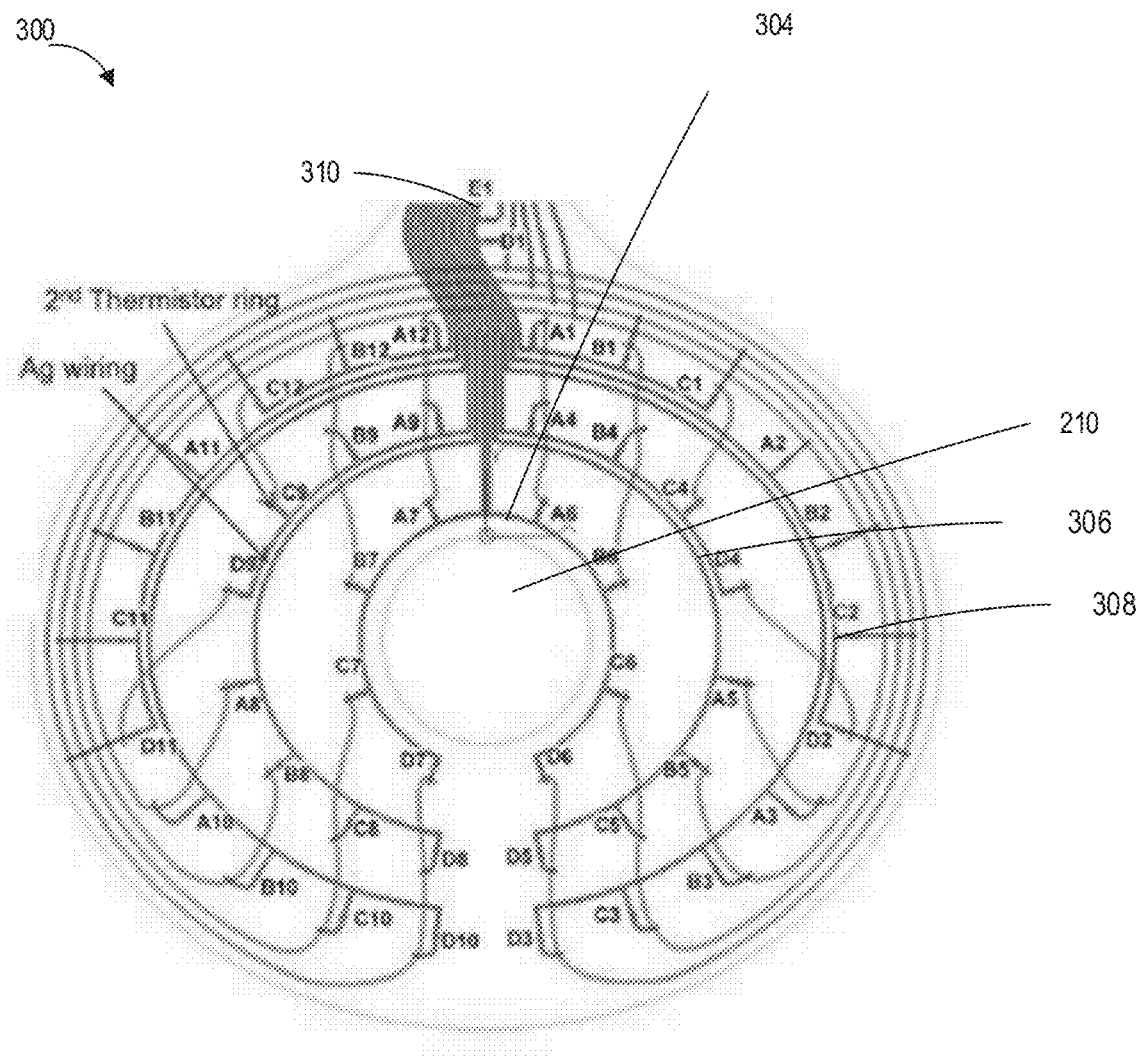
FIG. 3 shows another example sensor layer of an ostomy wafer.

FIG. 3 shows an example sensor layer 300. Like the sensor layer 200, the sensor layer 300 may be part of an ostomy wafer, such as the wafer 104. Accordingly, the sensor layer 300 may be sandwiched between two or more layers to form an ostomy wafer.

The sensor layer 200 may be a "pre-cut," a "cut-to-fit," or a "moldable" wafer. When the wafer is a "pre-cut" wafer, the size of the opening 210 may be in the range of from about 20 mm to about 100 mm in diameter. Other sizes are possible. When the wafer is a "cut-to-fit" wafer, the ostomy wafer may include a pattern of indicia defining at least one severance region. This arrangement can allow the user to size the opening to their stoma, by selecting the appropriate part of the ostomy wafer to remove. The sensor layer 200 may include severance regions which can include a plurality of concentric circles or partial circles (or concentric ovals or partial ovals), such that severing the sensor layer 200 at each of the concentric circle or partial circle (or concentric ovals or partial ovals) can provide an opening of a different size. For example, the severance region may include a pattern of three, four, five, or more concentric circles or partial circles.

The sensor layer 300 includes a plurality of thermistors indicated by letters and numbers on the figure. In particular, these thermistors are numbered A1 through D10. The thermistors are arranged annularly about a hole 210 (or cutout 210 that may be removed to form a hole). In particular, the thermistors are arranged in concentric rings 304, 306, 308. These rings are connected by wiring, shown in blue and red. Thus, although the thermistors are arranged approximately circularly around the hole 210, the connections formed by the conductors connected to the thermistors form approximate partial circles or partial rings around the hole 210. An area 310 of conductors represents an example bottom of the neck 214 of FIG. 2 and is shown truncated for illustration purposes.

In this example, the sensor layer 300 has a plurality of temperature sensors in three rings 304, 306, 308, measuring the temperature in an inner region of the sensor layer 300 (for example, the ring 304 or in the neck 310); at least one temperature sensor in an outer region of the sensor layer 300 for measuring the temperature in the outer region of the sensor layer 300 (for example, the ring 308), the outer region being remote from the inner region. Although not shown, a comparator or processor may be provided (e.g., in the hub 122 and/or the backend system 170) that can compare the temperature in the first region of the sensor layer 300 with the temperature in the second region of the sensor layer 300, and thereby produce a difference signal indicative of the presence or absence of skin inflammation in a region of skin in contact with the first region of the sensor layer 300.

In some systems, the system can be arranged to facilitate skin inflammation detection around a wound. For example, the temperature sensors may be positioned in the sensor layer 300 such that when the wafer 104 including the sensor layer 300 is applied around a stoma on the skin surface, the plurality of temperature sensors in the first region of the sensor layer 300 can detect the temperature of skin adjacent to the wound and at least one temperature sensor in the second region of the sensor layer 300 can detect the temperature of skin remote from the wound. This arrangement can allow a temperature difference between skin adjacent the wound and skin remote from the wound to be attributed to inflammation. By providing a system with the ability to compare the temperature in a first region of the sensor layer 300 with the temperature in a second, remote, region of the sensor layer 300, and transmit to a receiver a signal corresponding to the detected temperature difference, the system can detect the presence or absence of skin inflammation in a region of skin in contact with the first region of the sensor layer 300 and report on its detection to a user.

Figure 4:
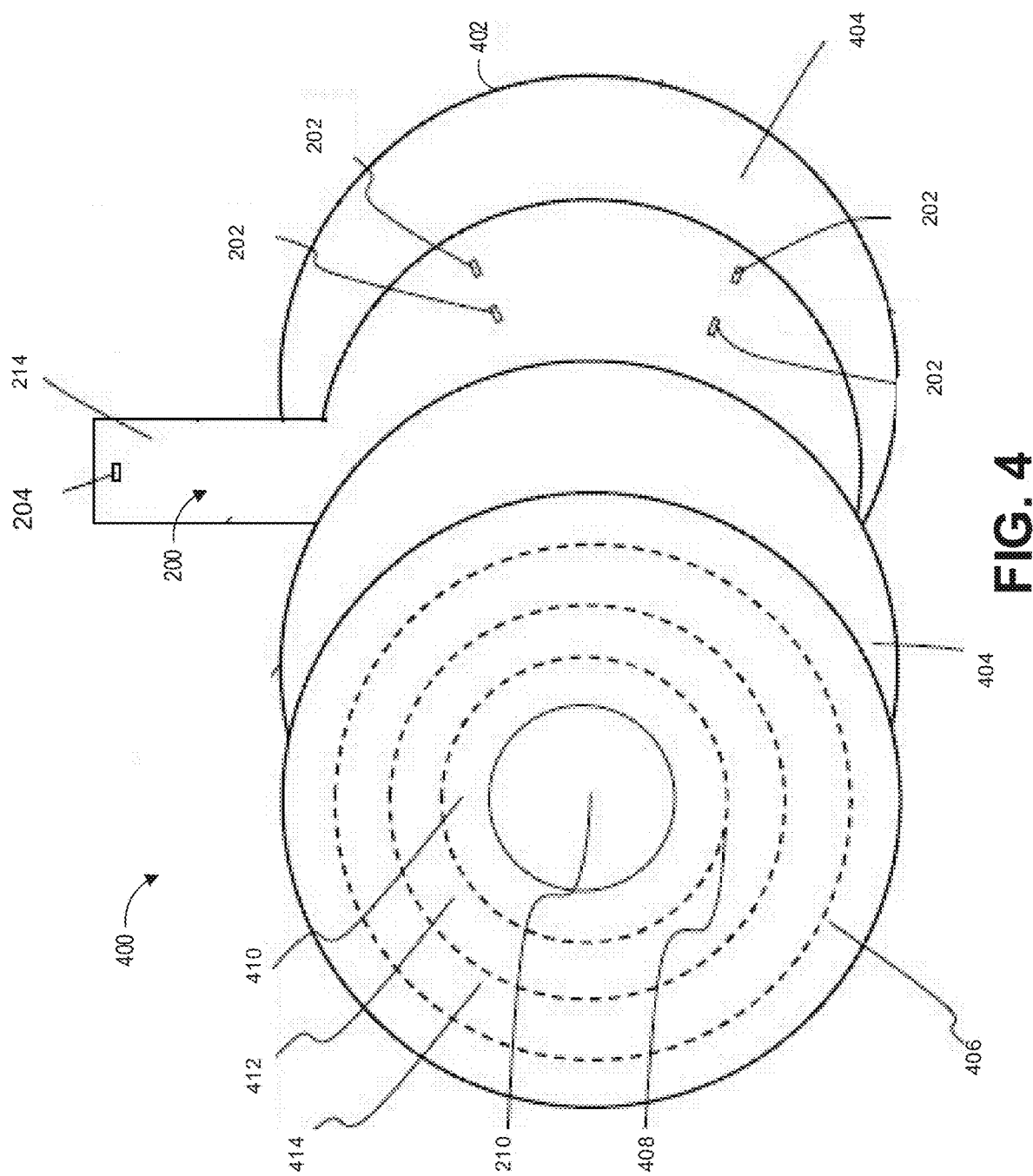
FIG. 4 shows example layers of an ostomy wafer.

FIG. 4 shows example components of the sensor layer 200 in an example ostomy wafer 400. The ostomy wafer 400 may have all the functionality of the ostomy wafer 140 and other example ostomy wafers discussed herein. Although incorporating the sensor layer 200 for illustration purposes, the sensor layer 300 may be used in an example implementation.

The example ostomy wafer 400 also has an adhesive layer 406 at least on the peristomal skin contact side 408 of the ostomy wafer 400 for adhering to skin. A bag interface layer 402 of the ostomy wafer 400 can also have an adhesive (on opposite side from figure; not shown) that can attach on an ostomy bag such as the ostomy bag 120.

Encapsulation sheets 404 can be protective plastics such as, but are not limited to, polyethylene, polypropylene, polystyrene, polyvinyl chloride, polyurethane, acrylonitrile butadiene styrene, phenolic, polyetheretherketone, polyamides, or combinations thereof. Before encapsulation, the sensors 202 may be mounted on, or integrated into, a support sheet 401. The support sheet 401 may be formed of a plastics material, such as polyethylene terephthalate (PET), polyurethane (PU), or combinations thereof, or of a polyimide film, such as Kapton (the condensation product of pyromellitic dianhydride and 4,4'-oxydianiline). The use of a support sheet 401 can ensure or attempt to ensure that the temperature sensors are held in position during the encapsulation process. This enables the temperature sensors to be strategically positioned on the wafer. The example severance circles 408 depicted with inner circle 410, middle circle 412, and outer circle 414, can function as a guide for a user to customize the size of the ostomy hole 210 by cutting along the severance circle traces. In some variation, the wafer may not include the encapsulation sheets, but can include other types of protective material to protect the electronics of the wafer.

The adhesive 406 may be a hydrocolloid adhesive. Hydrocolloid can be a biocompatible material consisting of pectin, carboxymethylcellulose (CMC), gelatin, polymers and other adhesives, for example. The use of a hydrocolloid adhesive may be suitable in ostomy applications because it can adhere to the skin surrounding the stoma, whether it is a moist or a dry skin site. In the case of wound exudates, which are very common in ostomy applications, the polymer in the hydrocolloid dressing can absorb the fluid and swell, protecting the wound, causing less pain and faster healing. In the case of ostomy applications, where bags are changed only after 2 or 3 days, the hydrocolloid dressing may be beneficial, as it has a long wear life once worn, causing reduced disruption to the wound. Furthermore it may be impermeable or less permeable to bacteria than other materials.

Figure 5:
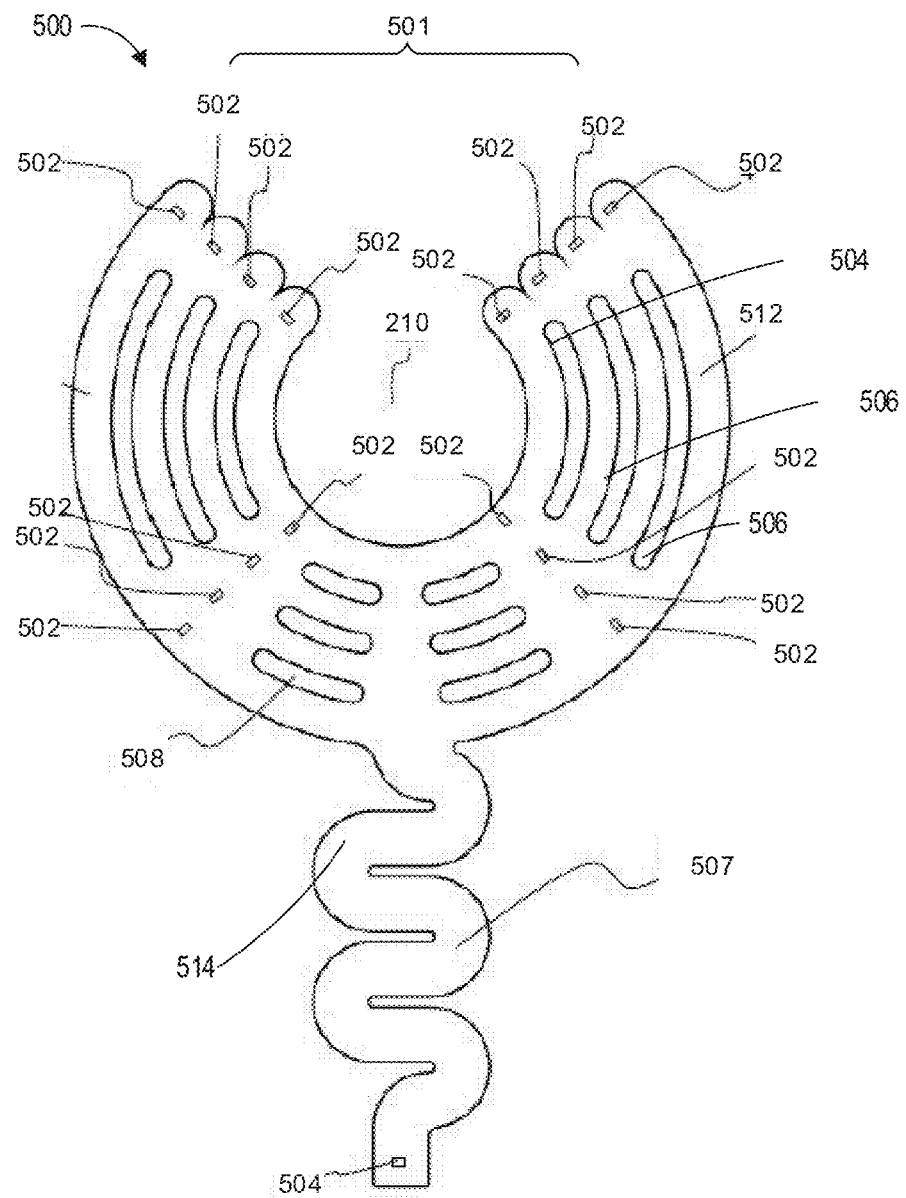
FIG. 5 shows another example of a sensor layer that may be included in an ostomy wafer.

FIG. 5 shows another example of a sensor layer 500 that may be included in the ostomy wafer 104 or in any other ostomy wafer discussed herein. The sensor layer 500 is similar in some respects but different in other respects from the sensor layer 200 and the sensor layer 300. In general, the sensor layer 500 can include many of the features of either the sensor layer 200 or the sensor layer 300. For example, the sensor layer 500 includes sensors 502, which may be thermistors or other sensors as discussed herein. The sensors

502 are disposed in a body 512 of the sensor layer 500. The body 512 connects to a neck 514. The sensor layer 500 may also be disposed between two or more other layers to form an ostomy wafer, as discussed above with respect to FIGS. 2 through 4.

The sensor layer 500 differs from previously described sensor layers in that sensor layer 500 includes a gap 501 between portions of the sensor layer 500. This gap 501 creates a structure that looks approximately like a menorah. The sensor layer 500 can include a plurality of partial rings formed by cutout regions or sections. The sensor layer 500 can include a first cutout section 504, a second cutout section 506, a third cutout section 508, and a fourth cutout section 508. These cutout sections, similar to the severance regions 408 of the ostomy wafers described above, can aid in customization of a stoma size hole 210. A user can use the cutouts as guides to resize the stoma hole 210.

The neck 514 has a serpentine design with zigzags 507 to aid in flexibility. The neck 514 can include conductors much like the neck 214 described above.

Figure 6:
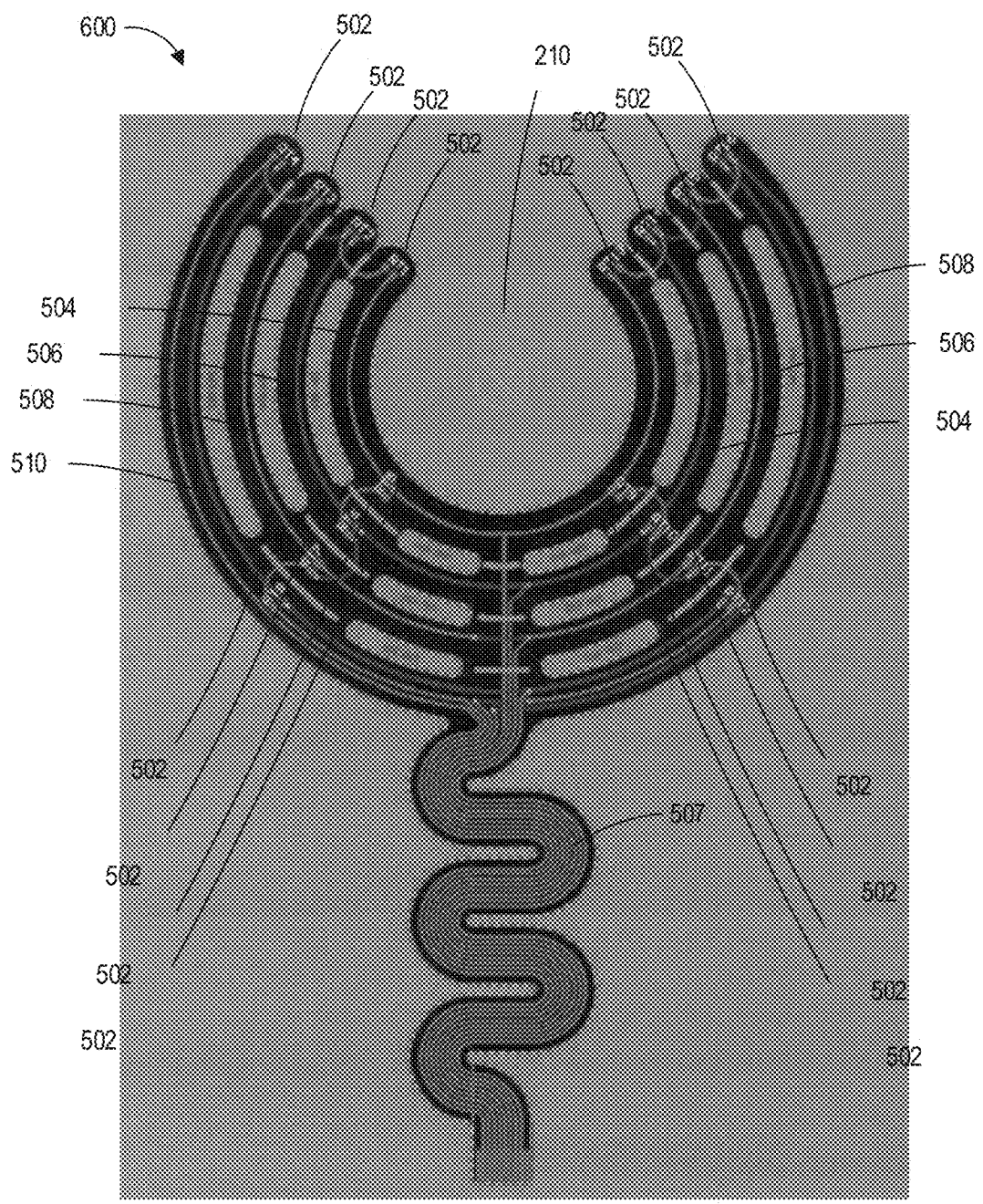
FIG. 6 shows an example implementation of the sensor layer of FIG. 5.

FIG. 6 shows an example implementation of the sensor layer 500, the sensor layer 600. Sensor layer 600 includes all functionality of the sensor layer 500 and also depicts wiring between thermistors 502. The wiring includes curved wiring between the thermistors, which takes the shape of half circles, some of which alternate direction.

Figure 7:
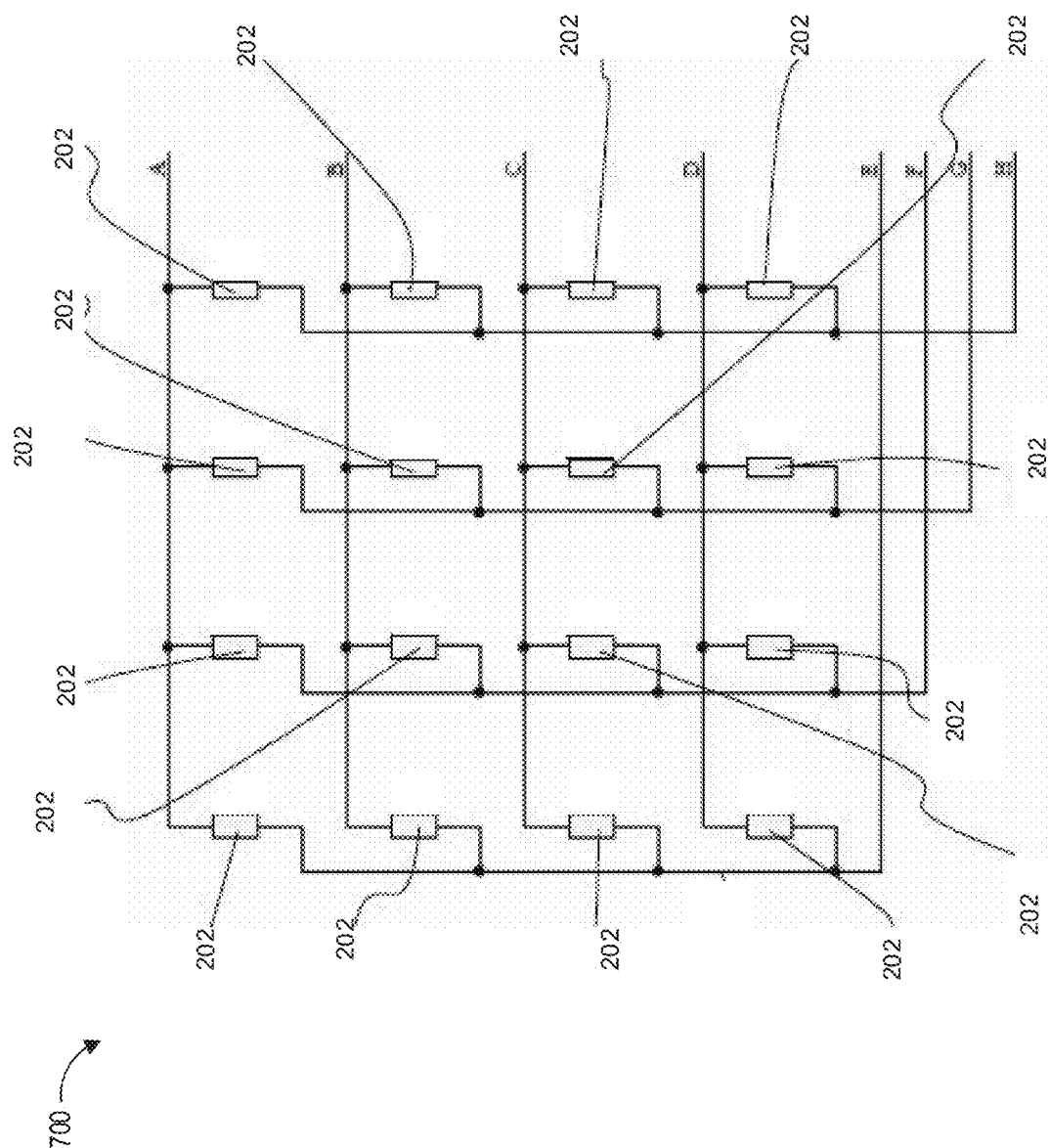
FIG. 7 shows an example circuit schematic of a sensor layer that may be included in an ostomy wafer.

FIG. 7 shows an example circuit schematic 700 that represents schematic arrangement of the sensors 202 (as well as 302 or 502). In the example schematic 700 shown, a matrix of 4×4 sensors 202 is shown. Any of the sensor layers described herein can connect the sensors together in a matrix such as shown in FIG. 7. Although the matrix in FIG. 7 is depicted as rectangular, this is an option but is also merely schematic and can be varied in layout. For example, the layouts of the sensors in the previous figures differs from the rectangular layout as shown, but the sensors in those figures may have the same interconnections in a matrix topology as shown in FIG. 7.

FIGS. 32-35C illustrate an example sensor layer 3200 of an ostomy wafer, such as the wafer 104 described above. The sensor layer 3200 can have any of features of the sensor layers 200, 300 described above. The sensor layer 3200 can be incorporated into the wafer 104, 400 described herein. For example, the wafer including the sensor layer 3200 can include an adhesive layer on a patient contact side, an adhesive layer on an ostomy bag contact side, and/or one or more encapsulation sheets made of polyimide film (such as KAPTON™), polyurethane, or the like.

Figure 32:
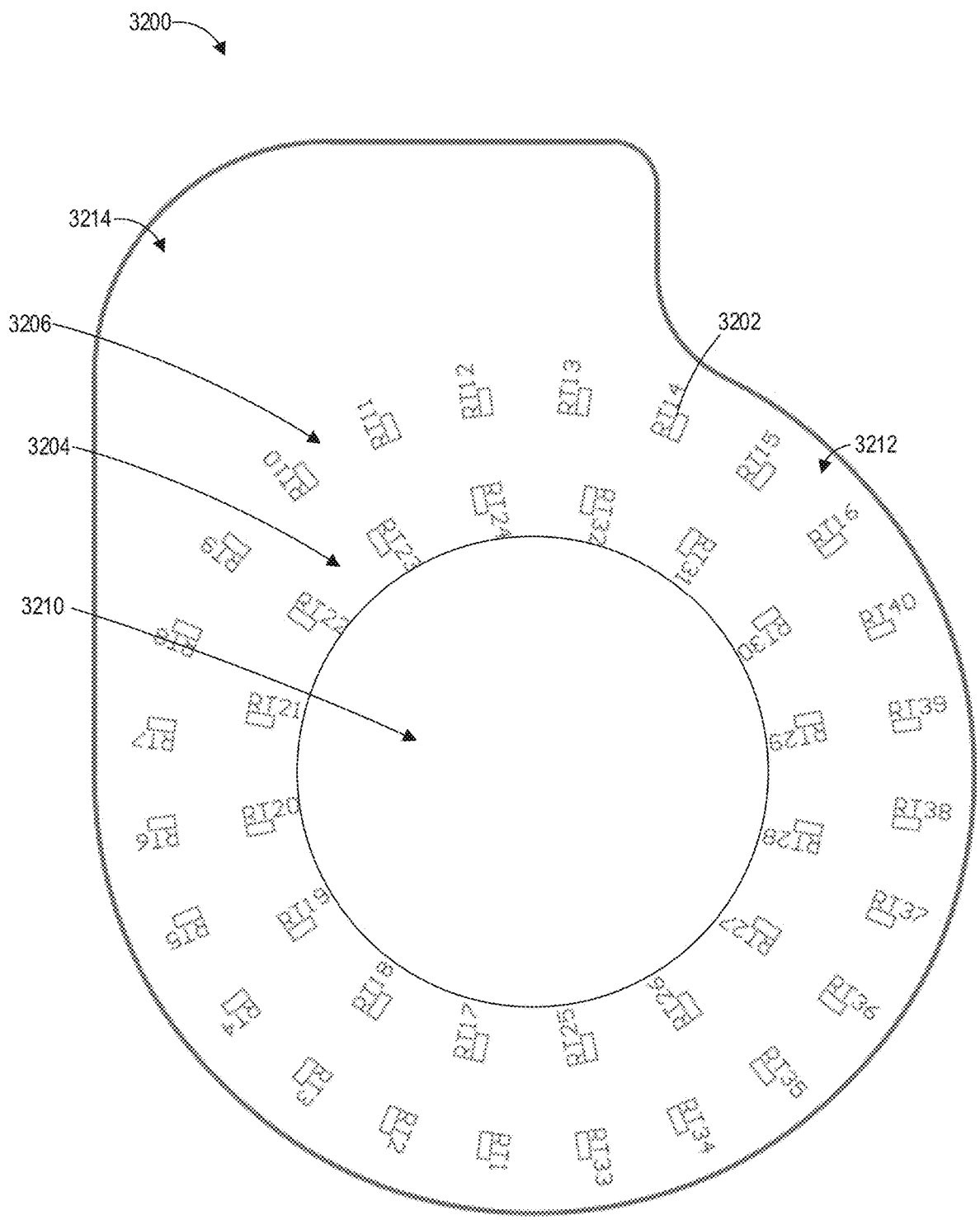
FIG. 32 illustrates schematically temperature sensors on an example sensor layer of an ostomy wafer.
Figure 33A:
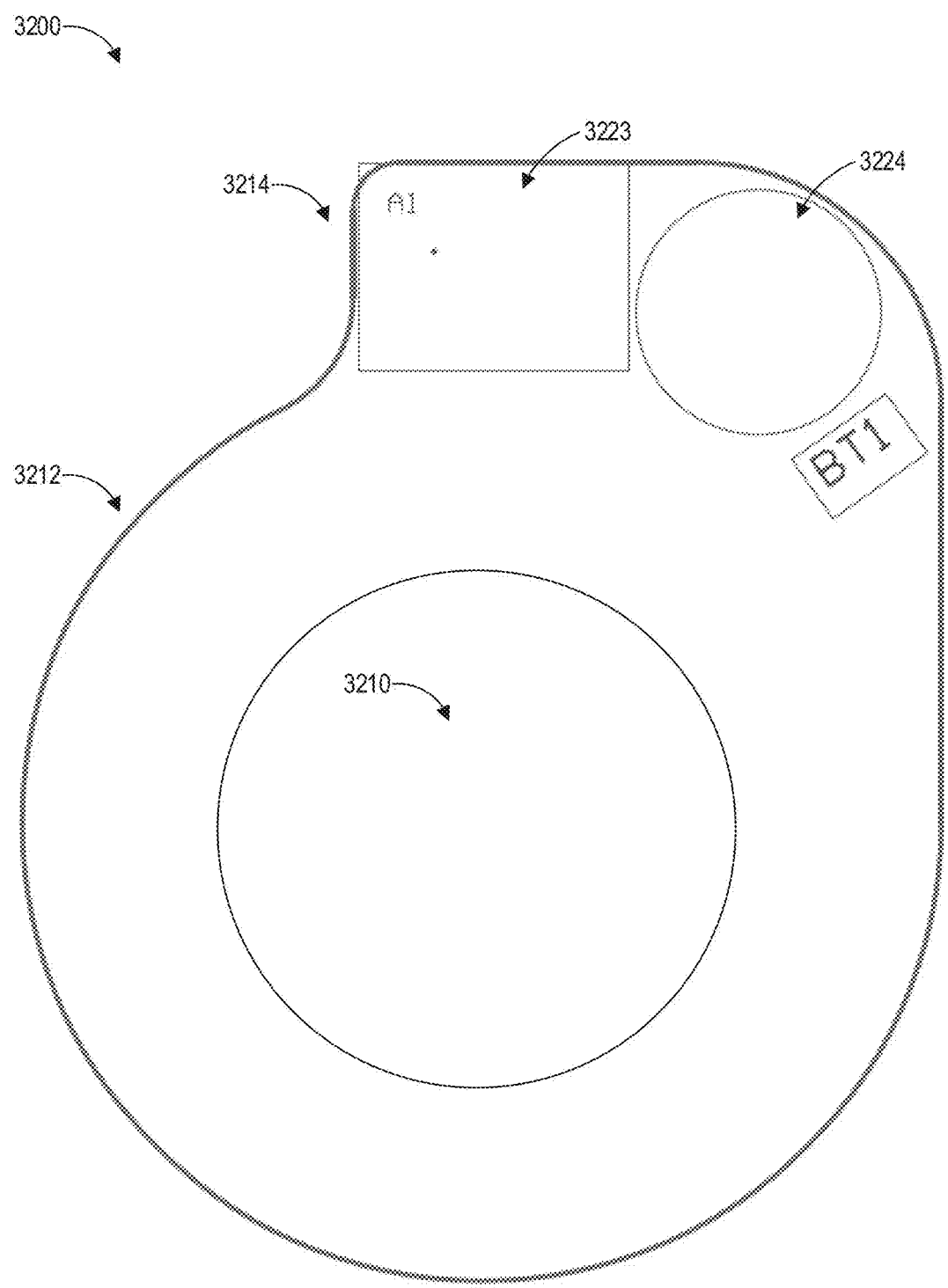
FIGS. 33A-33B illustrate top and bottom views of the sensor layer of FIG. 32.
Figure 33B:
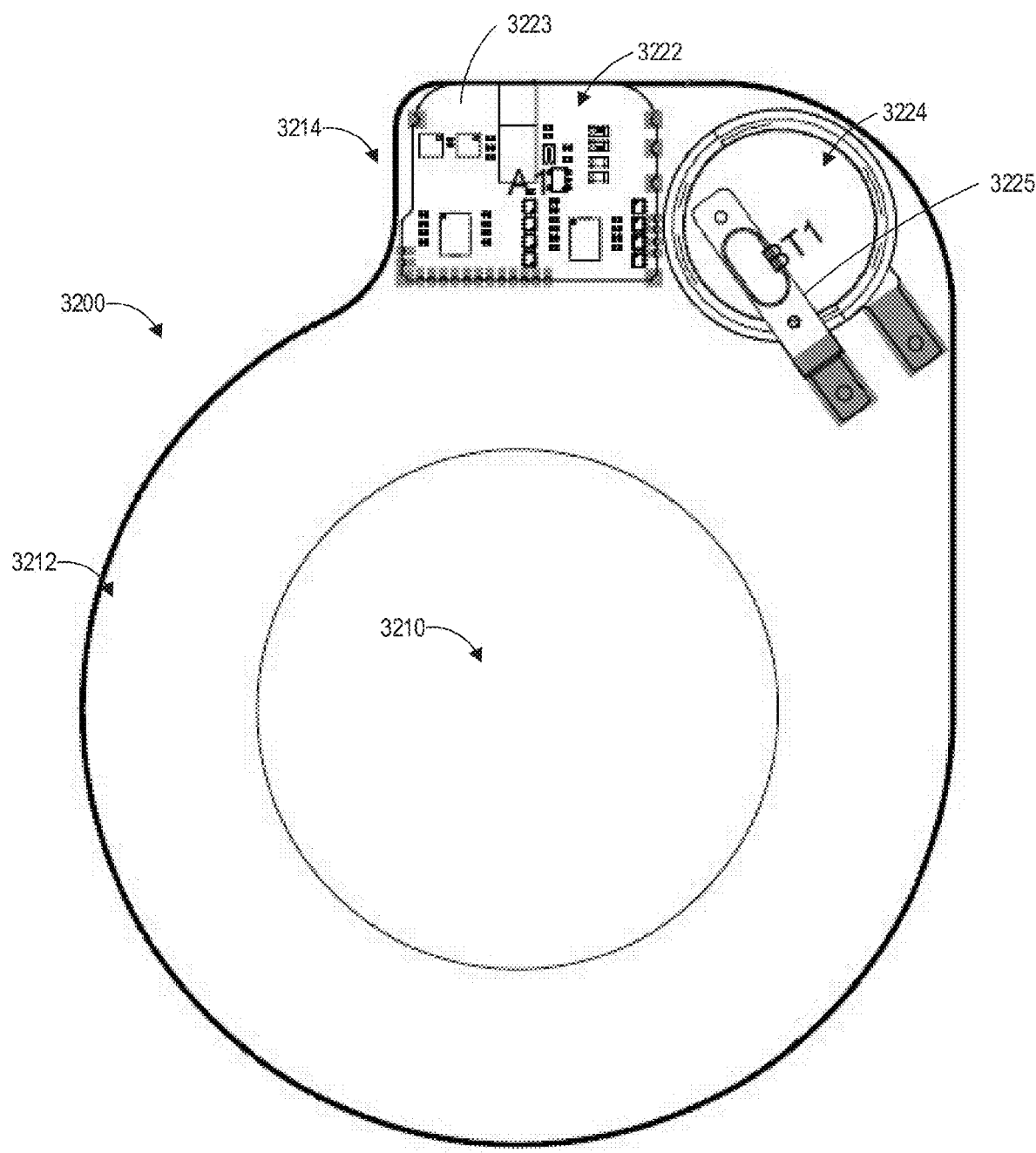

As shown in the schematic drawings in FIGS. 32-33B, the sensor layer 3200 can include a body 3212 and a neck 3214. The body 3212 can be generally circular or ovular. The neck 3214 can be generally rectangular and can extend from the body 3212. The relative position of the neck to the body is not limiting. The body 3212 can include a stoma hole 3210 configured for fitting over a user's stoma. The hole 3212 can have a variable diameter (for example, about 38 mm, or about 45 mm, or others) according to the size of the stoma. The body of the adhesive layer, and optionally the sensor layer and/or encapsulation layer described herein, can also have different sizes and/or shape to, for example, accommodate different stoma sizes, offer different amount of surface area for attachment to the skin, or otherwise. In some configurations, the wafer examples described herein can have an increased border size and/or border tape to reduce peeling off of the wafer from the user's skin. The wafer may include a border ring surrounding the adhesive layer. In some implementations, the border ring can have a greater outer dimension than that of the adhesive layer. The border ring of the wafer can include acrylic adhesives and/or the hydrocolloid adhesives. The hydrocolloid adhesive at the border may have a different thickness than the hydrocolloid adhesive of the remainder of the wafer. The border ring can also be referred to as a tapered edge.

The body 3212 can accommodate a plurality of temperature sensors 3202 (such as thermistors disclosed herein). As shown in FIG. 32, the body 3212 can include forty temperature sensors 3202. The temperature sensors 3202 can be distributed generally over the body 3212. The temperature sensors 3202 can be arranged in a generally circular pattern that is substantially concentric with the hole 3210. As shown in FIG. 32, the temperature sensors 3202 can be arranged in an inner ring 304 and an outer ring 306. Different numbers and/or different arrangements of temperature sensors can also optionally be used. The surface on which the temperature sensors 3202 are mounted can be facing the patient.

The body 3212 can also optionally accommodate one or more capacitive sensors. Any other wafer examples described herein can include one or more capacitive sensors. For example, one or more capacitive sensors can monitor a moisture content of the hydrocolloid in the adhesives, which can provide an indication that the adhesives have dried up and/or the wafer needs to be replaced.

As shown in the schematic drawings in FIGS. 33A-B, which illustrate a surface of the layer 3200 opposite the surface on which the temperature sensors 3202 are mounted, the neck 3214 can accommodate electronic components 3222 and/or power source 3224 on that surface. The electronic components 3222 can be mounted (for example, surface mounted) on a printed circuit board (PCB) 3223, such as shown in FIG. 33B. The PCB 3223 can be mounted on the layer 3200. The PCB 3223 can be sufficiently rigid to protect the electronic components 3222 and/or the circuitry on the PCB 3223 from breaking due to the bending of the flexible layer 3200. The electronic components can be mounted directly on the layer 3200 (for example, without a PCB), with stiffening material(s) (for example, fiber glass, plastic, or others that are more rigid than the material of the layer 3200) mounted on the layer 3200 adjacent to the electronic components to protect the electronic components from breaking. Mounting the electronic components 3222 on the PCB 3223 can reduce the number of encapsulation layers (for example, from four layers for directly mounted electronics to two layers for PCB-mounted electronics) in the sensor layer of the wafer, which can reduce the use and/or waste of the encapsulation materials, and/or make the wafer more affordable to users.

The electronic components 3222 can be electrically coupled to the temperature sensors 3202 (as will be described in greater detail below). The electronic components 3222 can receive data from the temperature sensors 3202. When the temperature sensors 3202 include thermistors, the resistance of the thermistors can vary with respect to temperature changes (such as when there is a leak of the effluent from the stoma). The electronic components 3222 can receive resistance signals from the temperature sensors 3202 and/or condition the resistance signals. The electronic components 3222 can send ADC values and/or other minimally processed signals to the hub, such as the hub 122 described above, for calculating the temperature values on a cloud and/or a user's device to reduce power consumption by the wafer electronic components 3222. The wafer electronic components 3222, the user device, and/or the hub can also optionally perform the calculation of the temperature values.

As shown in FIG. 33B, the power source 3224 can include a battery (such as a coin cell battery). More than one battery can also optionally be mounted to the neck 3214. The battery can be surface-mounted to the neck 3214 adjacent to the electronic components 3222. As shown in FIG. 33B, one or more mounting arms 3225 can be attached to the neck 3214 for holding the battery in place.

Figure 34A:
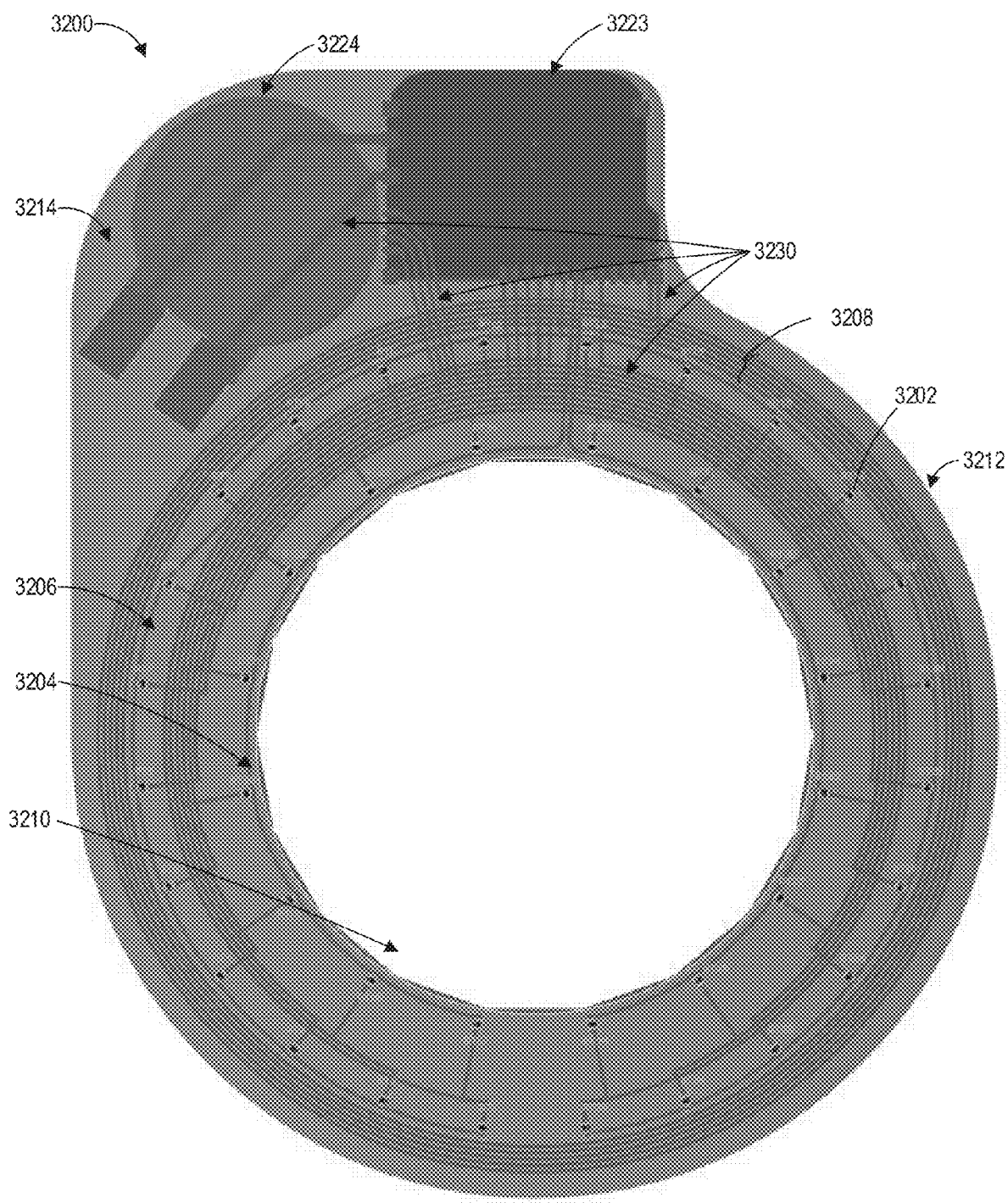
FIG. 34A illustrates a top view of the example sensor layer of an ostomy wafer.
Figure 34B:
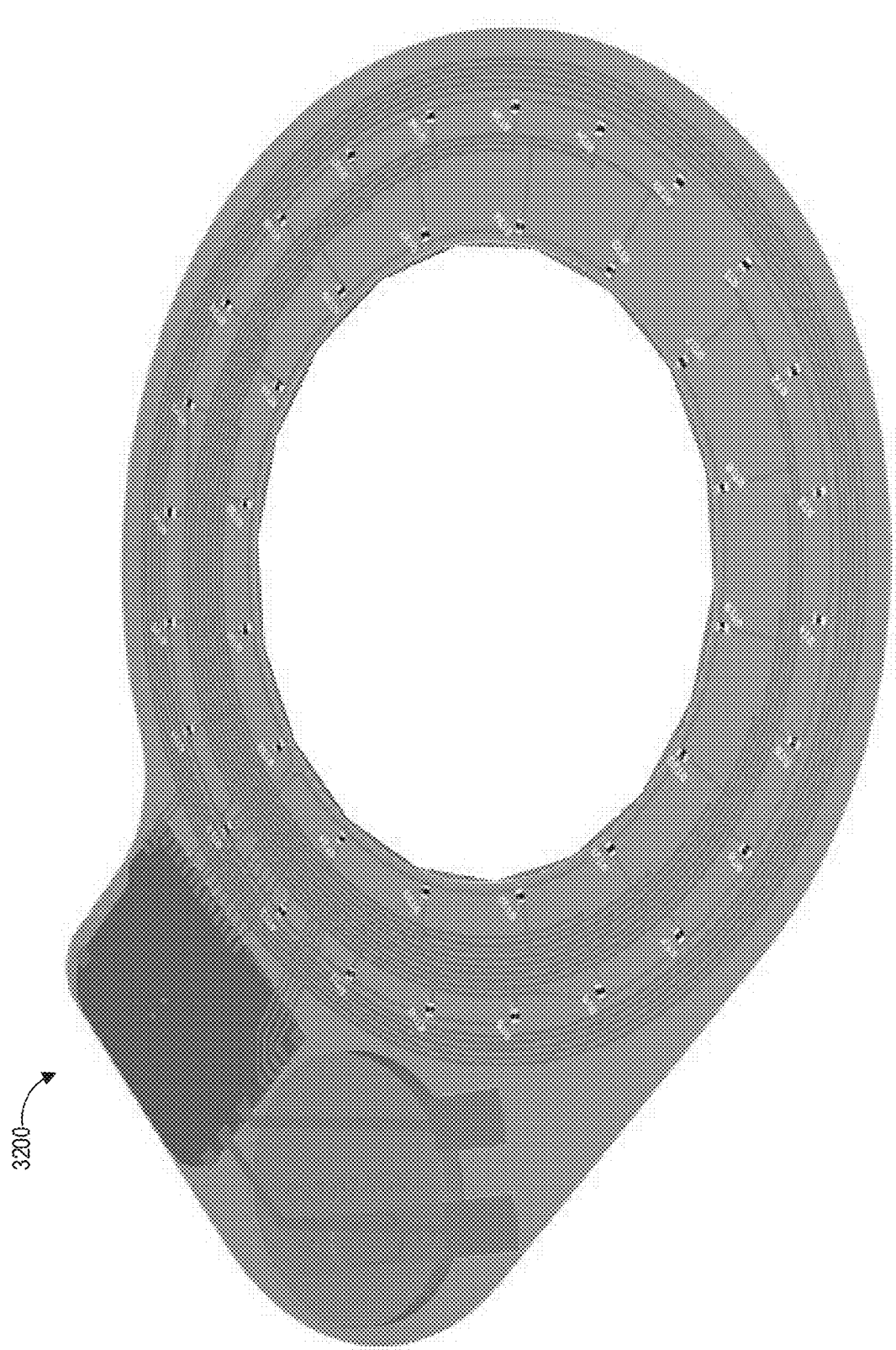
FIG. 34B illustrates a perspective view of the sensor layer of FIG. 34A.
Figure 34C:
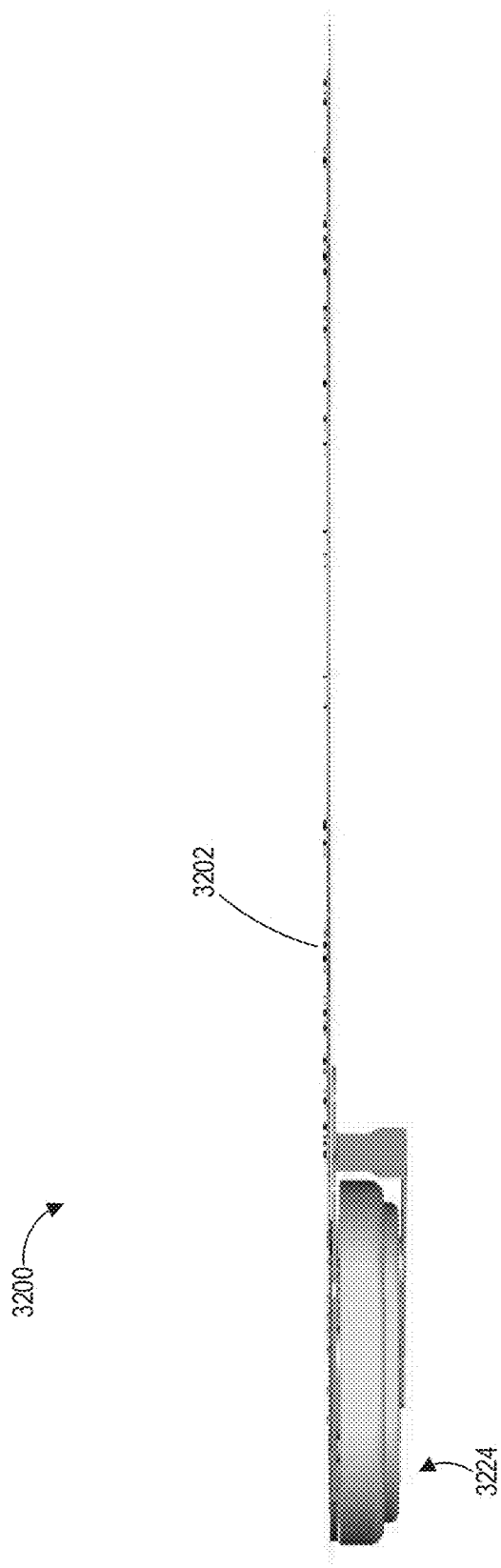
FIG. 34C illustrates a side view of the sensor layer of FIG. 34A.

FIGS. 34A-C illustrate top, perspective, and side views of the example sensor layer 3200. As shown, the sensor layer 3200 can also include a plurality of NFC antenna rings 3208. The NFC antenna rings 3208 can be located radially outwardly from the outer ring 3206 of the temperature sensors 3202. The NFC antenna rings 3208 can be generally concentric with the inner and/or outer rings 3204, 3206 of the temperature sensors 3202. The NFC antenna rings 3208 can be manufactured onto the layer 3200 (for example, printed or etched). When in use, the ostomy bag, such as the ostomy bag 120 described above, can be coupled to (for example, adhesively attached to) the wafer such that the NFC antenna rings 3208 on the sensor layer 3200 substantially coincide with NFC antenna rings on the sensor layer of the bag (described in greater detail below) and/or the NFC antenna rings on the hub. The NFC antenna rings on the wafer, the bag, and the hub can have substantially the same dimensions to facilitate better data transmission between the wafer and the hub and between the bag and the hub. The NFC antennas on the wafer, the bag, and/or the hub can also optionally have other shapes and/or sizes, such as ovular, square, rectangular, or polyhedral shapes.

Figure 35B:
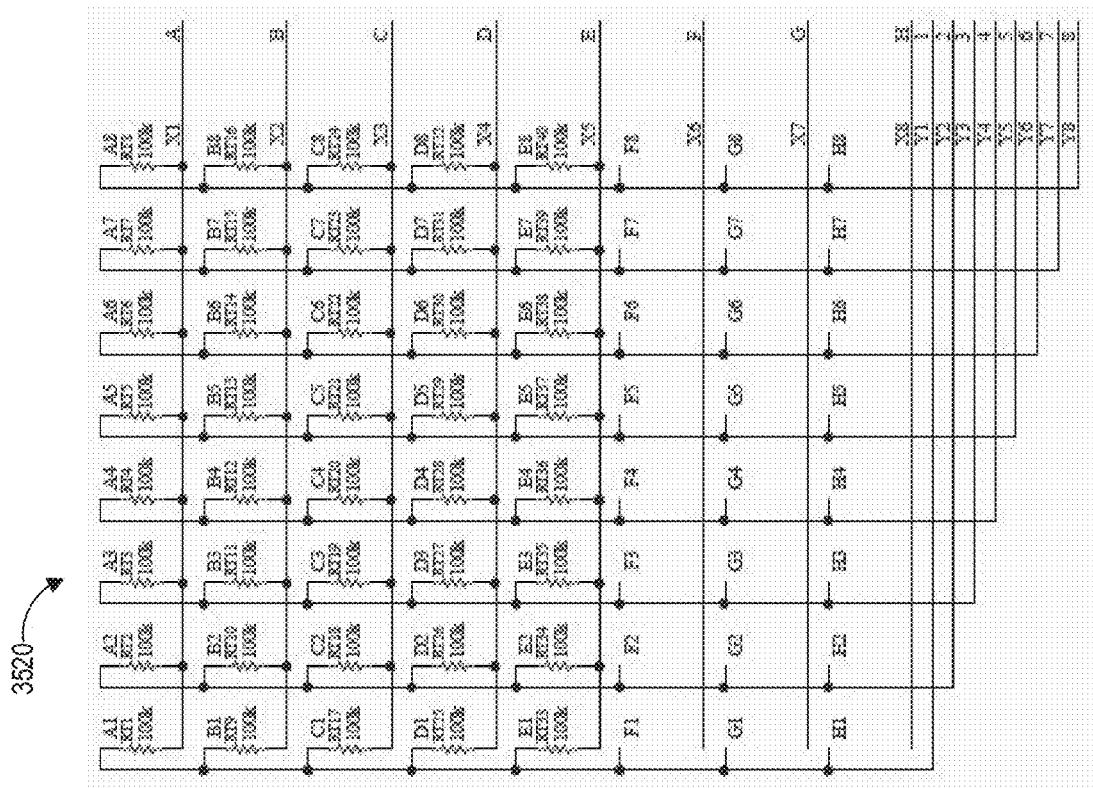
FIG. 35B illustrates an example schematic circuit diagram of temperature sensors on a sensor layer of an ostomy wafer.
Figure 35A:
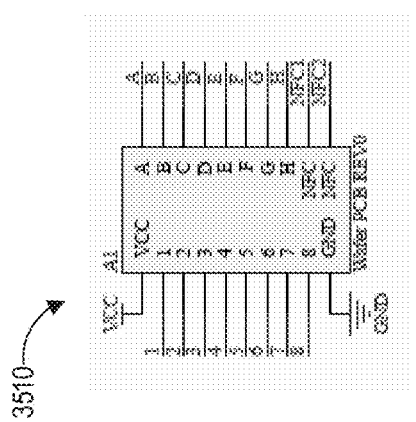
FIG. 35A illustrates an example schematic circuit diagram of a wafer PCB.
Figure 35C:
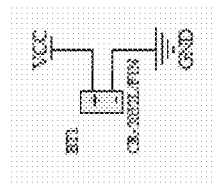
FIG. 35C illustrates an example schematic circuit diagram of a battery on a sensor layer of an ostomy wafer.

As also illustrated in FIGS. 34A-B, conductive traces 3230 (such as copper traces) can connect the temperature sensors 3202, the NFC antenna rings 3208, and/or the power source 3222 to the electronic components on the PCB 3223. The sensor layer can also include more rings, such as more NFC antenna rings and/or conductive traces rings as illustrated. FIGS. 35A-C illustrate example schematic circuit diagrams of the sensor layer 3200. FIG. 35A illustrates an example schematic circuit diagram 3510 of the wafer PCB 3223. The actual arrangement of the electronic components can be varied in the wafer PCB layout. FIG. 35B illustrates an example schematic circuit diagram 3520 of the temperature sensors 3202. As described above, the actual arrangement of the temperature sensors can be varied on the wafer. However, those temperature sensors can have the same interconnections in a matrix topology as shown in FIG. 35B by conductive traces 3230 or wires. FIG. 35C illustrates an example schematic circuit diagram 3530 of the battery.

As also illustrated in FIGS. 34A-B, the traces 3230 connected to the temperature sensors 3202 and the traces 3230 connected to the NFC antenna rings 3208 can cross at various locations. When the hub needs to communicate with the electronic components 3222, the hub communicates using the NFC antennas on the hub with the NFC antenna rings 3208 to establish connection between the hub and the electronics 3208. The hub can turn on its NFC, which powers the antenna to allow the hub to communicate with the ostomy bag and wafer. The electronics 3208 can read data from the temperature sensors 3202 (such as the ADC values or other values described above). The hub can then turn off the temperature sensor circuit on the wafer before the electronics 3208 transmit the temperature sensor data to the hub via NFC communication. The hub can also turn on the temperature sensor circuit when the wafer stops transmitting data to the hub. Deactivating the temperature sensor circuit during data transmission between the wafer and the hub can reduce interference due to the crossing of the traces.

As described above, the sensor layer 3200 (or other sensor layers disclosed herein) can include one or more polyimide films. The sensor layers disclosed herein can also be made of polyurethane. The use of polyurethane can allow silver traces to be used instead of the copper traces. Silver traces can have improved biocompatibility, lower toxicity, and/or better antimicrobial properties than copper traces. Thus, silver traces can reduce irritation for some patients sensitive or allergic to some metals.

Example Ostomy Bags and Bag Layers

Figure 8:
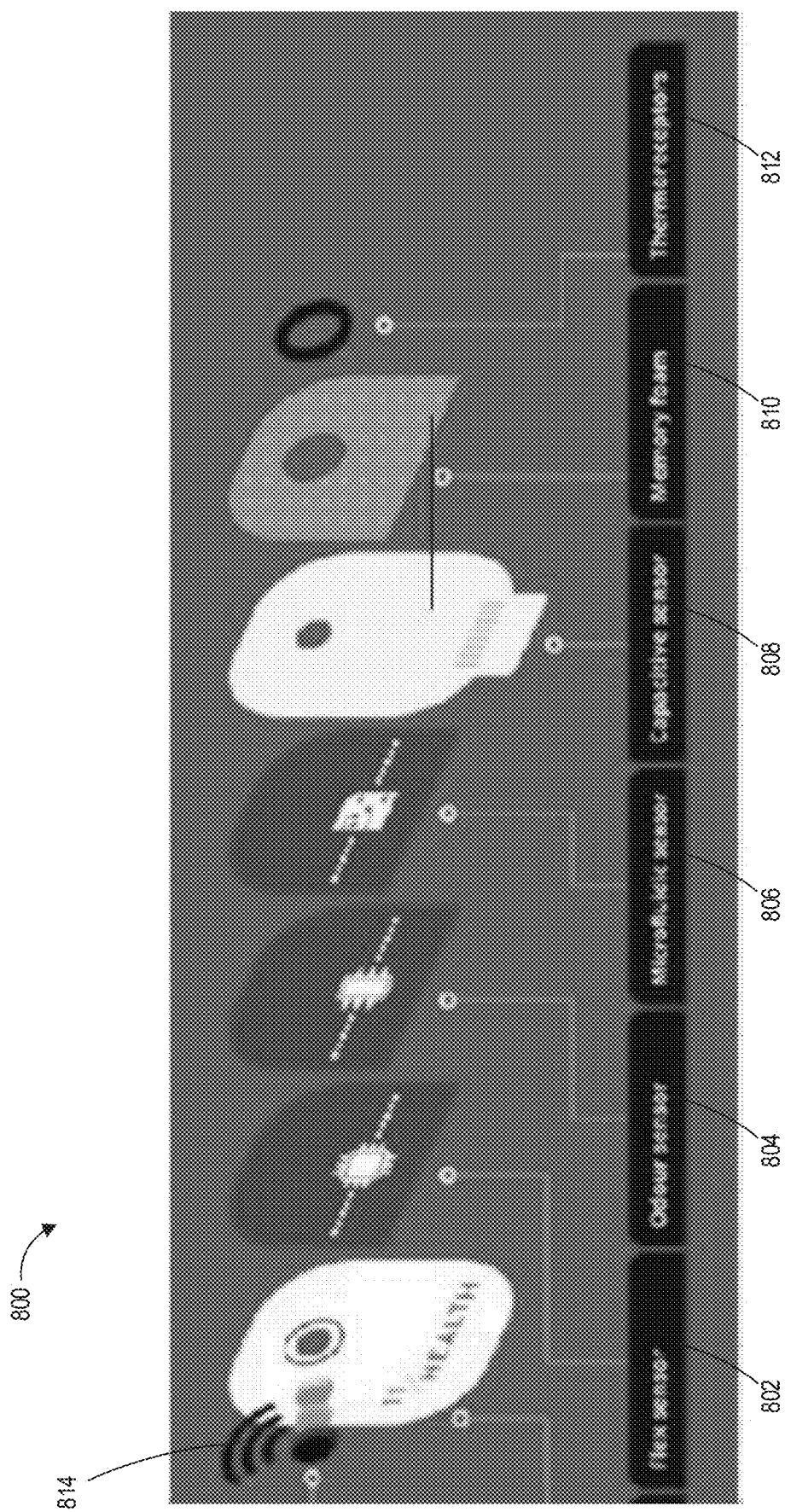
FIG. 8 shows example sensors on or in an ostomy bag

FIG. 8 shows example sensors that can be layered upon or in the ostomy bag 120 of FIG. 1B. This can provide multiple different readings by using a limited amount of space on the device 102. The layered sensor 800 can have, but is not limited to, a flex sensor 802, an odor sensor 804, a microfluidic sensor 806, a capacitive sensor 808, a memory foam layer 810, and a thermoreceptor layer 812. The layered sensors 800 can also have a hub 814, which can be an electronics hub and is an example of the hub 122.

The hub 814 can have any of features of the hub 122 of FIGS. 1B-1C. For example, the hub may contain, among other components, a hardware processor such as a microcontroller/SoC, as well as a wireless circuit or module. The hub 814 can send the data collected by the layered sensors 800 to another device, cloud, server, or any other kind of data storage or data processing system (see, e.g., FIG. 1B).

An optional flex sensor 802 can be used to help determine whether the bag is nearing a full level. An odor sensor 804 can determine whether there is bacterial growth in the gut as reflected in the effluent.

A microfluidic sensor 806 can be used to detect electrolyte concentration, inflammation biomarkers, pH values, and likewise of the fluid. The microfluidic sensor 806 can include a sensor with slots configured to receive the fluid in the output. The microfluidic sensor can be small in size compared to the size of the ostomy bag. This data can be used to show the user what he or she may need to intake to obtain a healthy balance of electrolytes. The data can be obtained from electrical sensors and/or optical sensors with chemical assays. The electrical sensors can detect different amount of electricity generated depending on the concentration of the electrolyte of interest. The optical sensor, such as a camera or a photodiode, can detect color changes in the chemical assays.

The example capacitive sensor 808 may have an onboard microcontroller/SoC (system on a chip), or a capacitive sensor chip that may read in the value received from the capacitive sensor then translate it to "output present/not present." Multiple capacitive sensors could be polled. This data can be processed on the microcontroller/SoC and converted to volume then sent to the application running on the phone or the unprocessed data can be sent directly to the application on the phone for processing. This data can also be transmitted, via the hub, to the backend system for calculating the volume values.

The capacitive sensor(s) 808 may also serve as a fallback to and/or be used in combination with one or more temperature sensors to determine if there is a leak. For example, two capacitive sensor layers can be used with a cloth-like material in between. When the stoma interface is saturated from leaks, the cloth like material may be wet and provide a conduit for the capacitive sensors to activate and alert the user of a leak.

The example thermistors in the thermoreceptor layer 812 can be used to determine leaks and irritation. Leaks may have a sudden direct path pattern heat map signature. Irritation may have a gradual radiating heat map signature.

The thermoreceptor layer 812 could also detect phasing of the material collected in the bag. When a substance phases between liquid, gas, and solid, the speed of temperature change can correlate. Gas often gives false volume readings so that detection of gas may be helpful in filtering false volume readings. In currently available ostomy products, there is no good way to tell how much gas in the output and therefore there are many false readings and leads to wasting not fully utilized bags. Temperature monitoring may allow a device and user to distinguish between volume fill from liquid or gas. This detection can allow the device estimate how much gas is in the bag with the temperature sensor 812. A bag fill algorithm can subtract the estimated gas volume from the fill of the bag.

The thermoreceptor layer 812 can have an onboard microcontroller/SoC (System on a chip) that may poll each thermistor in the array individually by using multiplexer/de-multiplexer. (Of course, this chip may instead be in the electronics hub 814.) The signal from the multiplexer/demultiplexer may then be fed into a series of operational amplifiers which may yield a voltage. That voltage may be read by the microcontroller/SoC using an Analog to Digital converter. From this voltage, the device can calculate the resistance from the thermistor that was polled. From that resistance, the device can calculate the temperature at that specific thermistor. This is repeated for all thermistors. Data from some or all of these sensors can be sent to the application on the user device at any stage. For example, to offload processing from the hub to the backend system and/or to the phone, a thermistor's resistance value or just the ADC values may be sent. The user device may then take that resistance value and calculate temperature. The application on the user device may know which data correlates to which thermistor by the location of the data in the packet being transmitted.

Further sensors, such as any of the sensors disclosed herein, can be integrated into the bag. For example, an inertial measurement unit ("IMU") sensor, a form of positional indicator, can be integrated. The data received from the IMU sensor may be read into the microcontroller/SoC using data lines such as I2C, or SPI. The data is then processed and sent off the application or alternatively can be processed and used internally for the volume calculation. Accelerometers may also be integrated. Accelerometers may be able to tell if the patient is engaged in physical activity, such as running (and hence should have an expected higher skin temperature), and can also help distinguish between whether a user is supine, sitting, or standing. This collected data can then alter the algorithm to determine the reference temperature of the user and compare the temperature data collected by the temperature sensors.

An optical sensor may also be integrated where the sensor looks down over the stoma and into the bag in order to detect a degrading stoma, blood in stool, etc. The optical sensor may use infrared light or a camera. This optical sensor may give augmented reality features or 3D mapping features to a clinician. The patient can be prompted to take a photo of the stoma, for example, after being discharged from the hospital, between time intervals (such as every morning), or whenever the patient puts on a new bag. The patient can be prompted to upload the image to a central server (such as a cloud server) via the application on the user device described herein. The application can process the image to cross-check with the output volume estimated using any of the algorithms described herein to improve accuracy of the output estimation. A user could also use the optical sensor or a camera in their user device to point to the bag or stoma to allow a clinician to help diagnose the issue. This feature could be used in conjunction with operating a remote diagnosis center where clinicians can aid patients in determining how to treat their issues via augmented reality. The stoma image can allow a physician to check the condition of the stoma, such as for signs of infection, presence of blood in the output, and otherwise. The stoma image can be added to a database of stoma images, which help clinicians in building a knowledgebase and/or analytical information about stoma (such as infection or inflammation). Machine learning algorithms or other types of mathematical models can be used to build the knowledgebase. The clinician's input regarding the stoma images can also be fed into the algorithm to further improve accuracy of the knowledgebase.

An audio sensor, such as a microphone can also be integrated. The audio sensor can be used to monitor stoma gas output, and/or bowel sounds. For example, lack of bowel sound can indicate constipation or bowel obstruction. Bowel sounds can also indicate when the user is hungry and should be fed. The bowel sounds collected by the microphone can be also used to build a knowledgebase of how certain bowel sounds may correlate to and predict certain bowel movements. The audio sensor output can be used to correlate the user's feeding and stoma output timing. The optical and audio sensors can be used in combination to detect stoma site observations, such as blood, new wounds, or otherwise. In some implementations, an alarm can be triggered at pre-set protocols upon certain stoma site observations. In some implementations, the audio (such as a microphone) and/or optical (such as a camera) sensors can be selectively turned on and/or off. For example, the optical sensor may be deactivated until the audio sensor detects gas output. Selective activation of the optical sensor and/or audio sensor can save battery usage and increase battery life of the hub.

As described above, microfluidic sensors cannot only include electrolyte detection, but also may detect inflammatory markers such as C-reactive protein detection, fecal calprotectin, and other inflammatory markers. Moreover, pH sensors may also be integrated into the microfluidic sensor as well to determine the acidity of the constituents of the bag 902. Microfluidic sensors may also detect other biological markers, such as dehydration markers, inflammation markers, certain drugs, and others. Using the microfluidic sensors described herein can advantageously allow the electrolytes and other parameters of the stoma output be measured at the stoma site instead of being carried out in a separate procedure in laboratory setting using a patient's urine sample.

Figure 9:
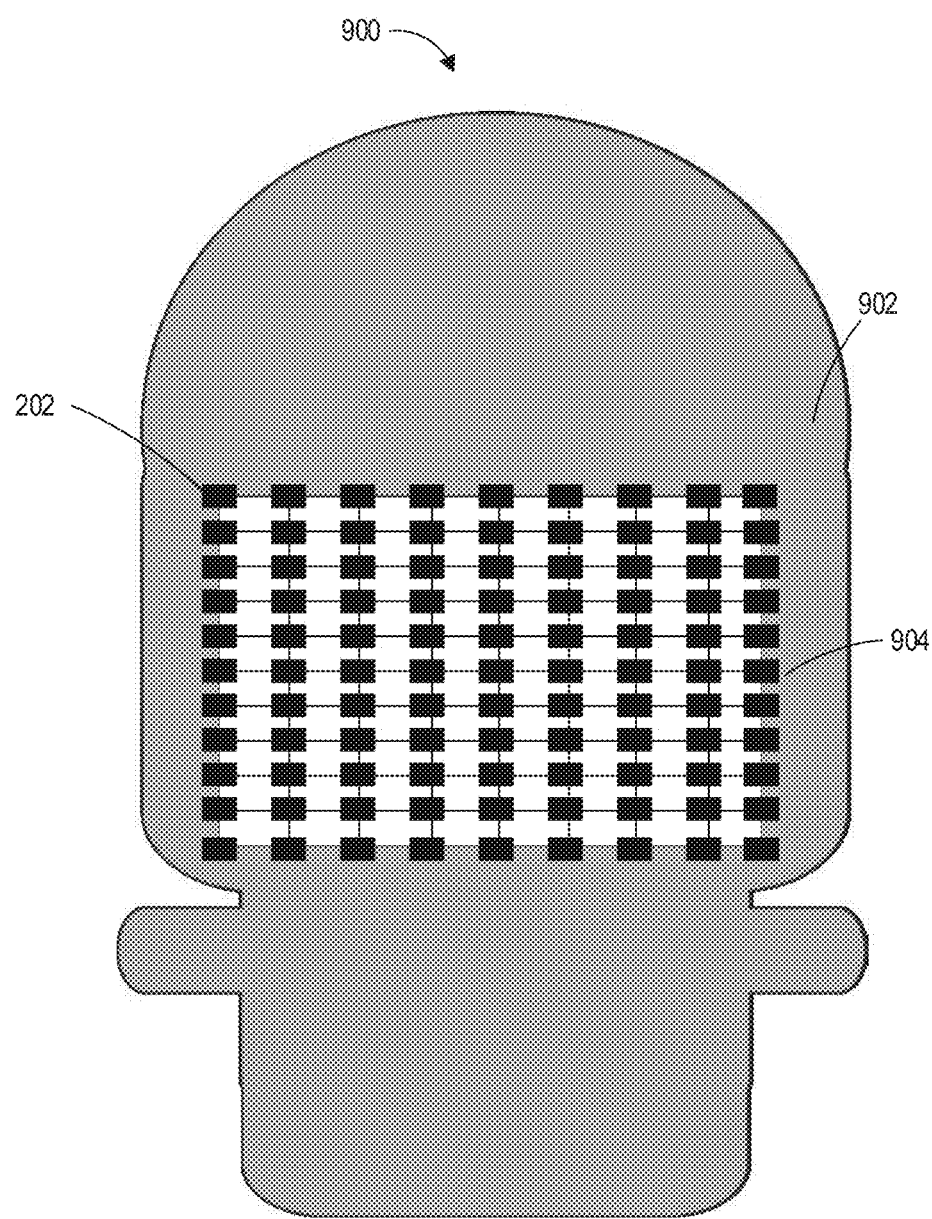
FIG. 9 shows an example ostomy bag with a sensor layer.

FIG. 9 shows an example bag with a single sensor layer 900. The bag 902 has sensors 202 arranged in an array 904. The sensors 202 can be any of the sensors discussed herein, including temperature sensors or any of the sensors described above with respect to FIG. 8.

Figure 10:
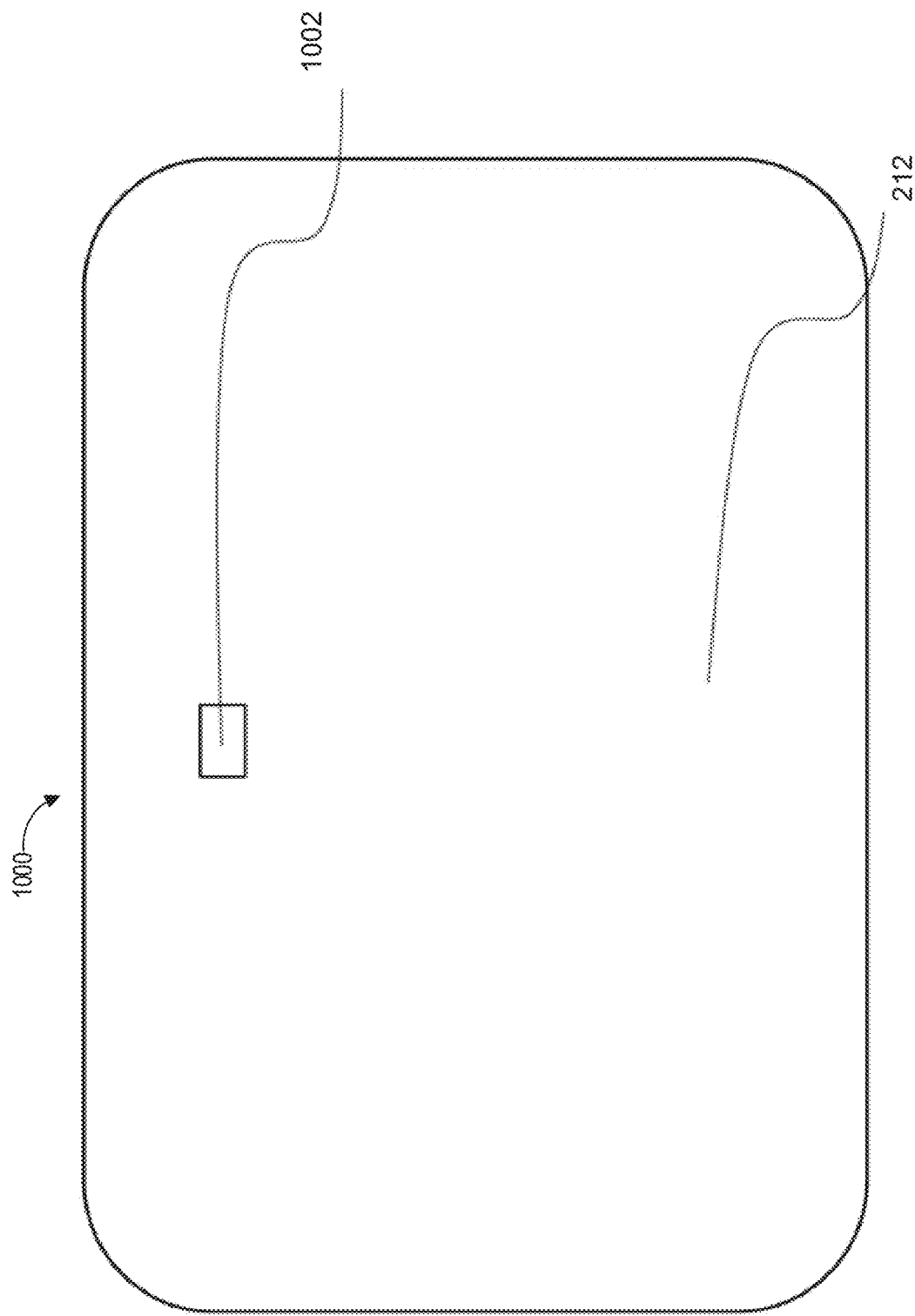
FIG. 10 shows a front view of an example sensor layer of an ostomy bag.

FIG. 10 shows a front view of an example sensor layer 1000. The side of the example sensor layer 1000 facing away from the user shows an example hub 1002 placed upon a sensor layer 200. The hub receives data from the sensor layers.

Figure 11:
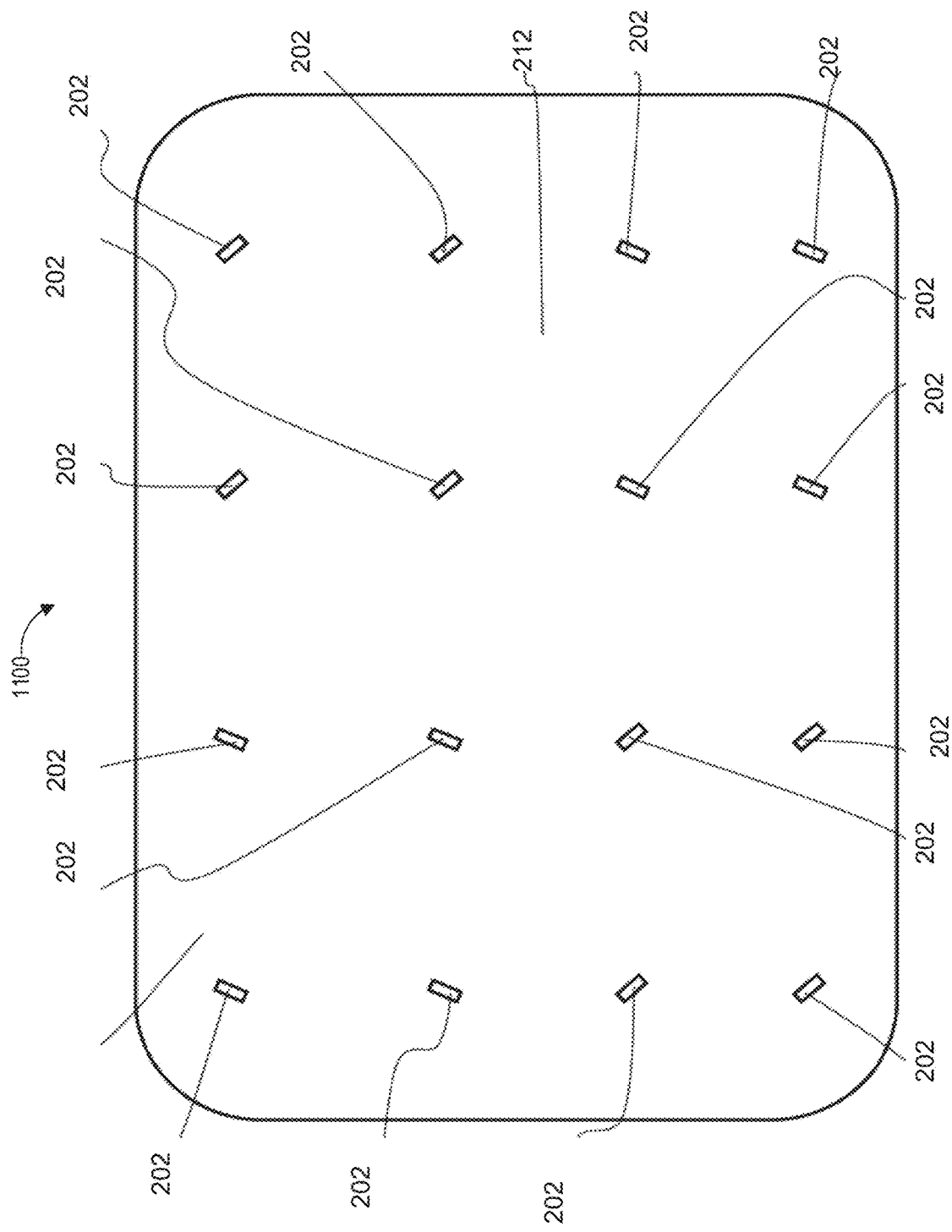
FIG. 11 shows an example back view (user contact side) of an example sensor layer of an ostomy bag.
Figure 12:
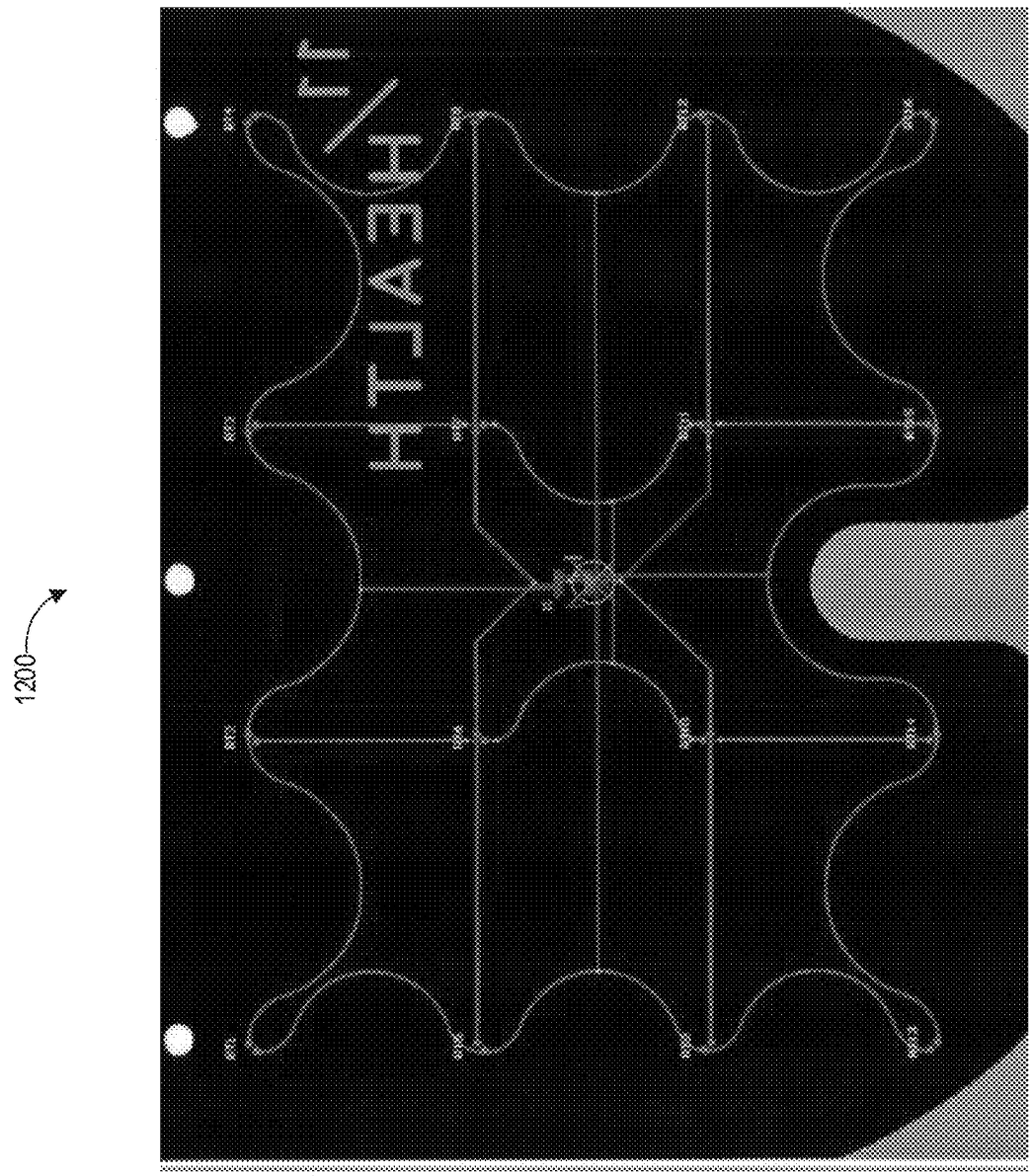
FIG. 12 shows example wiring of a sensor layer of an ostomy bag.

FIG. 11 shows an example user facing side of an example sensor layer 1100. The example sensor layer 1100 can have multiple sensors 202 placed upon a sensor layer 200. FIG. 12 shows example wiring of a layer 1200 that can be placed on a bag 902. The wires may be curved or have half-circle shapes between different sensors to provide for flexibility under patient movement.

Figure 13:
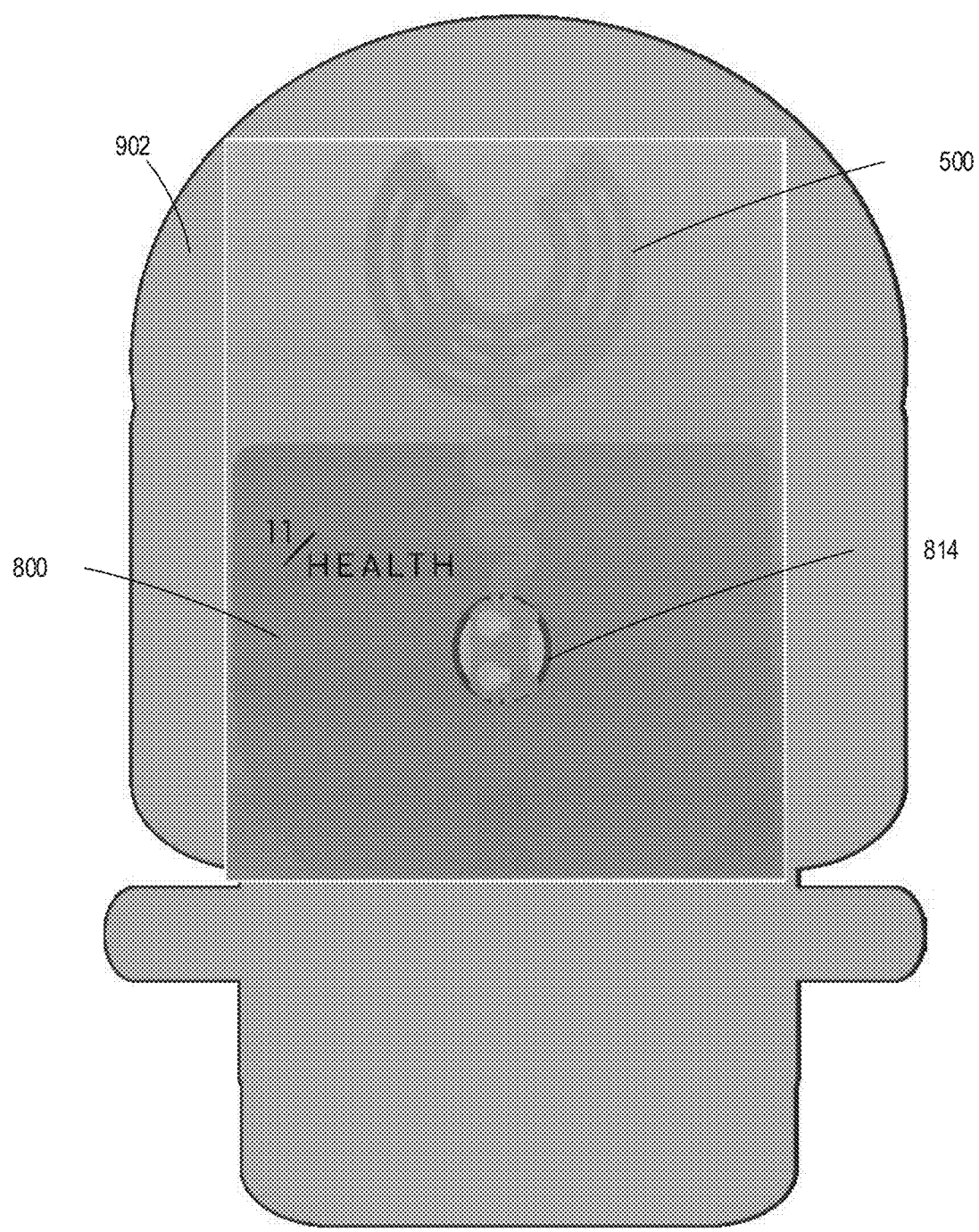
FIG. 13 shows an example ostomy bag with a sensor layer connected to an ostomy wafer layer.

FIG. 13 shows an example bag 902 with a sensor layer 800 that can be connected to a partial ring ostomy wafer 500 layer. The partial ring wafer layer 500 can be connected to the sensor layer 800 at the hub 814. The example sensor layer 500 of an ostomy wafer is also shown. Both sensor layers 500, 800 are connected to an example electronics hub 814. Not shown, but which may be included, are other layers to cover the sensor layers 500, 800 as discussed above.

FIG. 14A shows an example layered ostomy wafer 400 from FIG. 4 placed on an example ostomy bag 902. The example layered ostomy wafer 400 can perform all the functionality of the ostomy wafers discussed above.

Figure 14B:
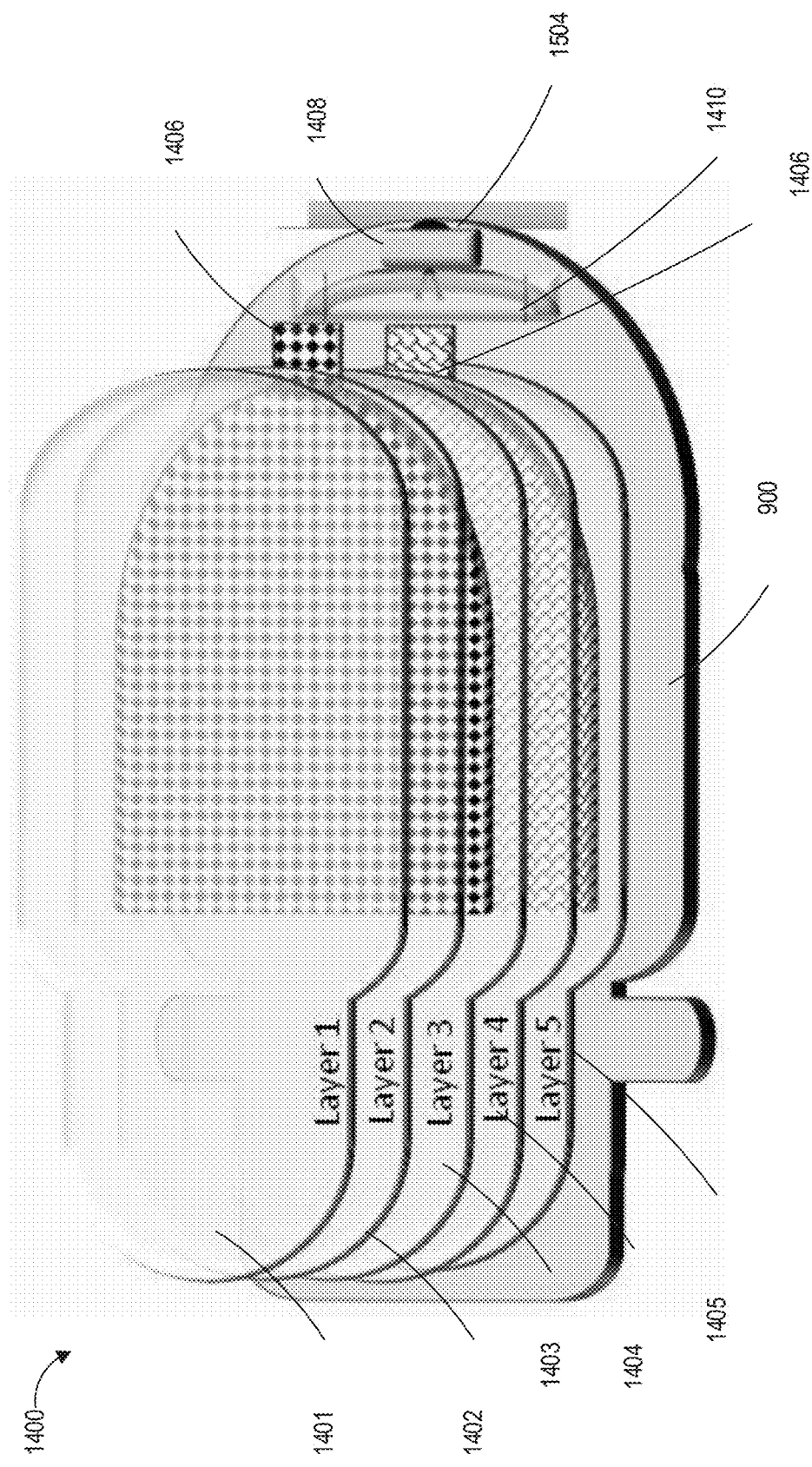
FIG. 14B shows an example ostomy bag with layers of sensors that faces away from the user.

FIG. 14B shows an example ostomy bag 902 with layers of sensors 1400 that faces away from the user. The ostomy bag 902 is another example of the bag 120 of FIG. 1B. Generally speaking, the bag can include two walls, a patient-facing wall and an away-from patient facing wall. The walls may be stitched, pressed, glued, welded, or otherwise connected together at a seam. The bottom of the bag may be sealed or may have a selectively openable portion for draining. Either or both of the walls may include one or more layers.

Figure 44A:
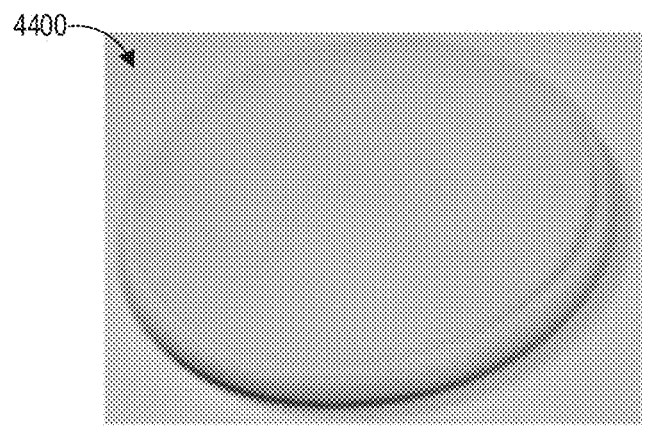
FIGS. 44A-44B illustrate example top and bottom views of an electronic hub of an ostomy bag.
Figure 44B:
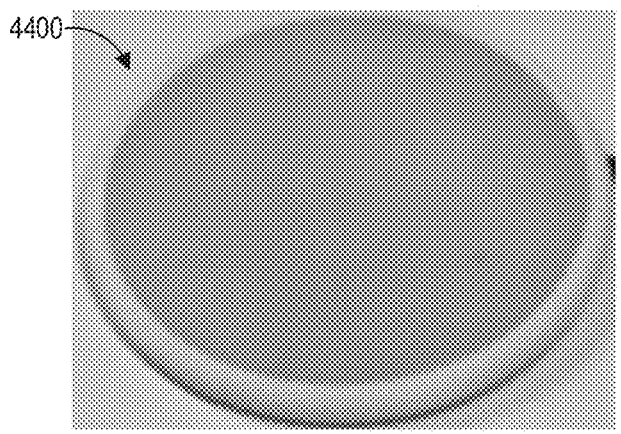
Figure 46B:
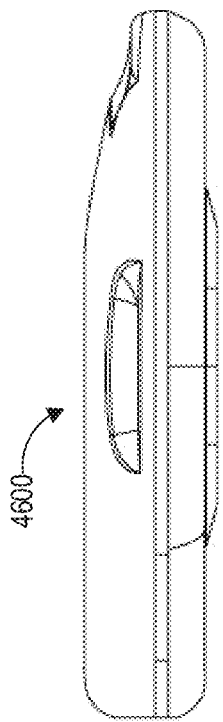
FIGS. 46A-46D illustrate front, back, bottom, and perspective views of another example electronic hub of an ostomy bag.
Figure 46D:
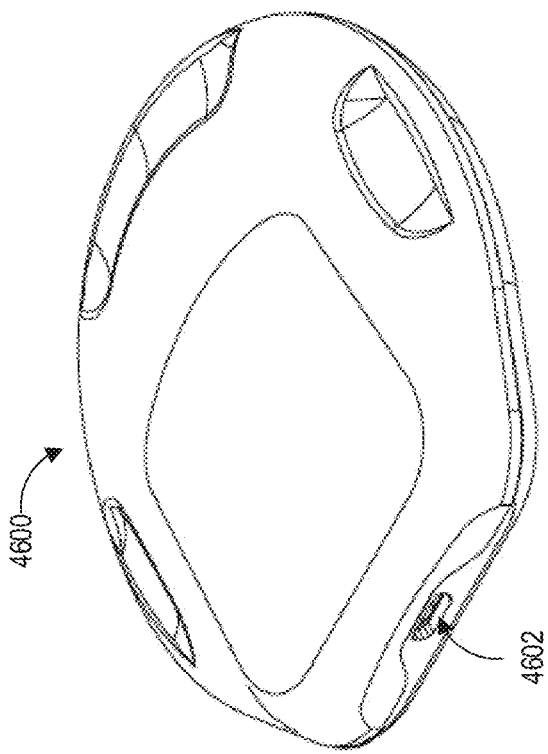
Figure 46A:
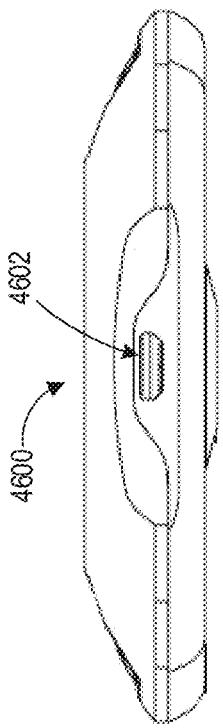
Figure 46C:
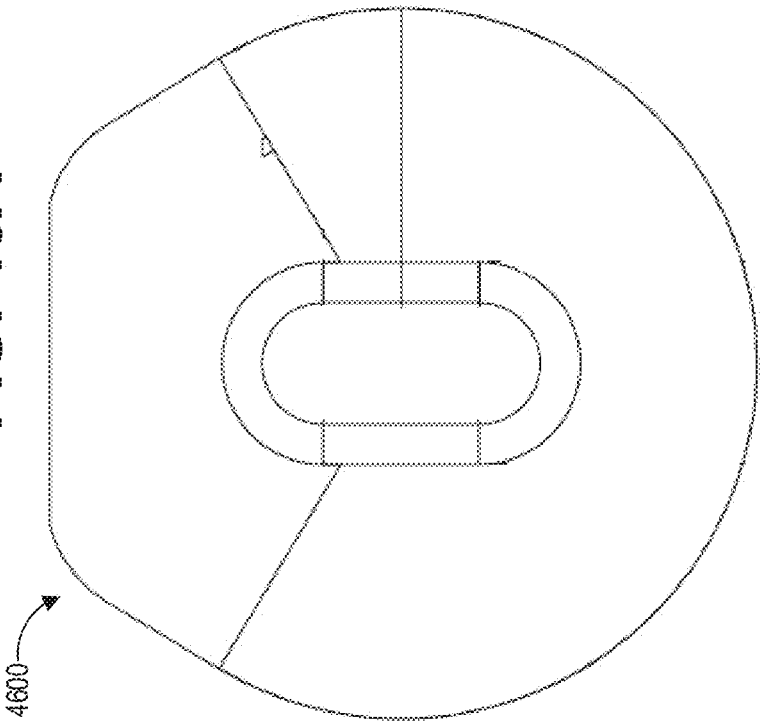
Figure 46E:
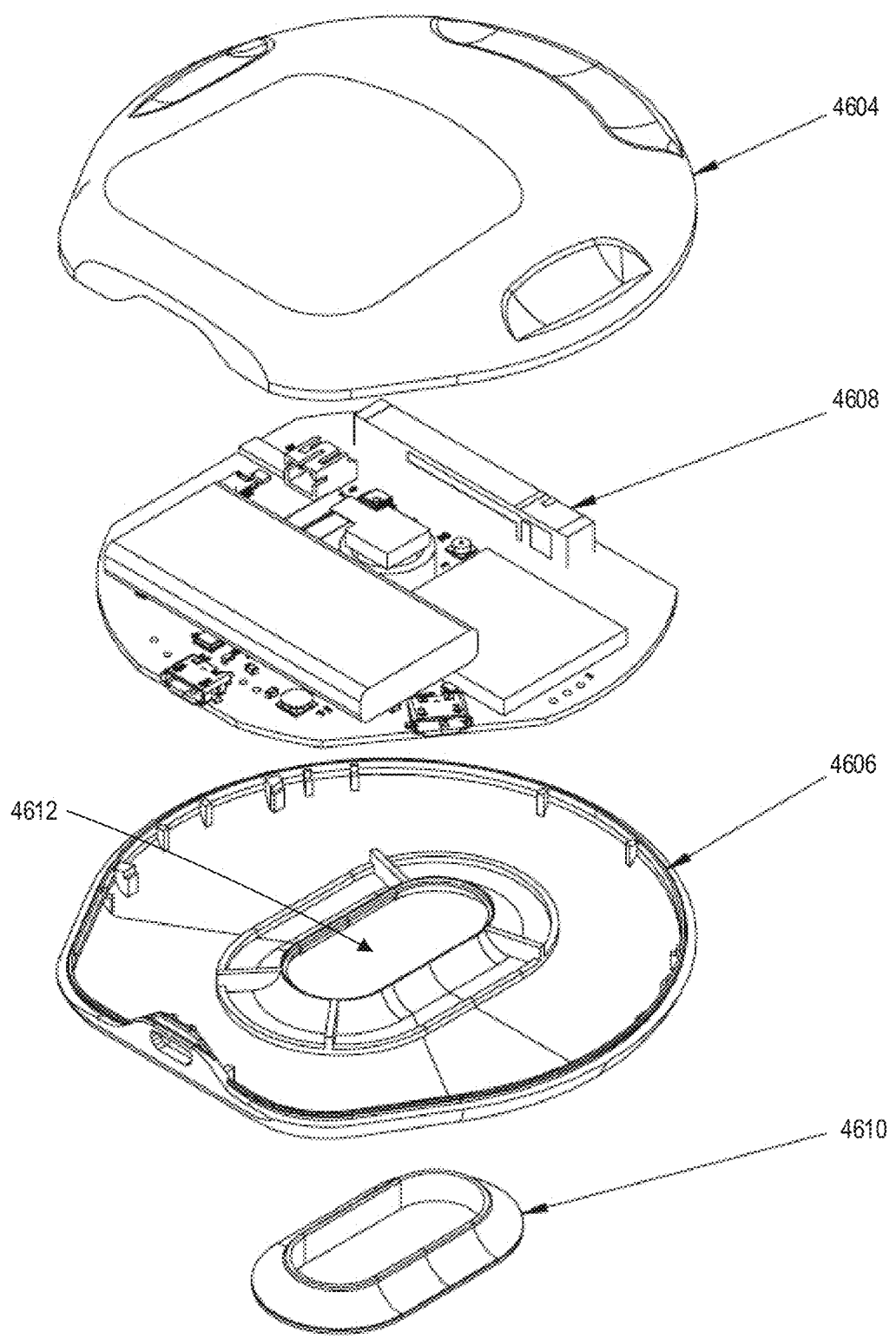
FIG. 46E illustrates an exploded view of the electronic hub of FIGS. 46A-46D.

In this example, a layer of sensors 1400 is connected to an example hub 1410, which in this example is crescent-shaped for improved weight distribution (for example, to avoid the weight of the hub flopping the bag over, which may be irritating to users). The hub can have a generally circular cross-section, such as shown in FIGS. 44A-44B, which illustrate example front and back views of a generally circular hub 4400. The hub can have a generally circular cross-section with a flat side, such as shown in FIGS. 46A-46E. A connection port 4602 can be accessed on the flat side. As shown in FIG. 46E, the hub 4600 can include a hub roof 4604 and a hub base 4606 enclosing electronic components 4608 between the roof 4604 and base 4606. The hub can also include a lens cover 4610 configured to be disposed around a camera opening 4612 to protect the lens of a camera installed in the hub 4600.

An outer dimension of the hub can accommodate the NFC antenna rings in the hub, which can be of substantially the same size as the NFC antenna rings on the ostomy bag. The layer of sensors 1400 can collect data off the material (effluent) that is collected in the bag 902. In this example, Layer 1 1401 is the outermost layer that contains no sensors. In this example, Layer 2 1402 is free of sensors but in other examples, this layer could be populated with sensors. In this example, Layer 3 1403 is populated with a capacitive sensor array to detect volumetric fill (this is not fixed and the sensor could change or its position in the bag could change). In this example, Layer 4 1404 is free of sensors but in other examples, this layer could be populated with sensors. In this example, Layer 5 1405 is the closest layer to the bag. In this example, Layer 5 has a thermistor sheet to detect volumetric fill, and sensors to detect the phase and the viscosity of the output. Layer 3 and Layer 5 can be switched in position. The capacitive sensor array and the thermistor sensor array can also be located on the same layer. This layer of the bag may also use an analytical microfluidic sensor (as it is the closest to the output) and the thermistor sheet may then be placed in another position in the bag. The stomal output in this example can reside between Layer 3 and Layer 4.

In this example, the necks 1406 of the layers of the sensor sheets can be coated with conformal coating, such as protective plastics such as, but are not limited to, polyethylene, polypropylene, polystyrene, polyvinyl chloride, polyurethane, acrylonitrile butadiene styrene, phenolic, polyetheretherketone, polyamides, or combinations thereof.

In this example, a gas sensor 1408 may also be placed over the carbon filter gas valve 1504. The carbon filter gas valve can allow gas to escape the bag 902 while being treated for the odor. The gas sensor 1408 can be used to detect the constituency of the gas. Too pungent a gas can be an indicator of bacterial overgrowth. A strong pungency can correlate to overly-high effluent output, which may be dangerous for a user. The more pungent the odor, the more issues the user's gut may have that may warrant possible medical attention.

The crescent hub 1410 is used on the top of the bag in this example. Hub placement may influence weight distribution of the bag. In some examples, a round hub concentrates weight in a single area with the weight of the gas sensor 1408 and may be too heavy for the device and lead to bag movement. If the weight is spread in a crescent shape, the weight can be distributed more evenly on the top of the bag and thereby reducing bag movement.

Figure 14C:
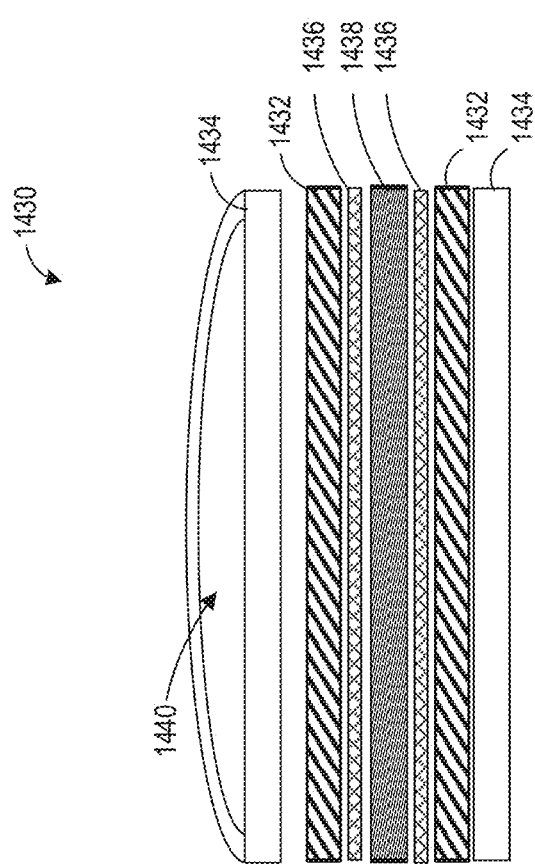
FIG. 14C shows a side view of layers of an example ostomy bag having an insulation layer.

FIG. 14C illustrates another example ostomy bag 1430 having a plurality of layers including an insulation layer 1432 located between an outer cover layer 1434 and the ostomy bag layer 1436. The ostomy bag layer 1436 can be made of any of the materials disclosed herein, such as non-porous sterile plastic materials including but not limited to, polyvinyl chloride, polyethylene, ethylene vinyl acetate, polypropylene, and copolyester ether. A sensor layer 1438 can be located on one side of the ostomy bag 1436, such as a side away from the user. In this manner, the sensor sheet can be placed in front of the layer behind which the output occurs, so the output can be monitored while it comes out. This arrangement of layers may of course be varied. The sensor layer 1438 can have any of the sensor arrays disclosed herein. In some configurations, the sensors and electronics can be printed on the ostomy bag layer so that the bag may not include a separate sensor layer. The insulation layer 1432 on the patient-facing side of the bag can protect the sensor layer from the heat from the patient body. The insulation layer 1432 on the side of the bag that faces away from the patient can also protect the sensor layer from noise from the ambient environment. The insulation layer can be made of any nonconductive material with highly insulating properties, such as PET felt (polyester), polyurethane or polyester foams, any thermally insulating fabrics or textiles, STYROFOAM™, or aerogels. The insulation layer can also include memory foam material so as to better conform the bag to the contour of the patient's body.

Figure 14D:
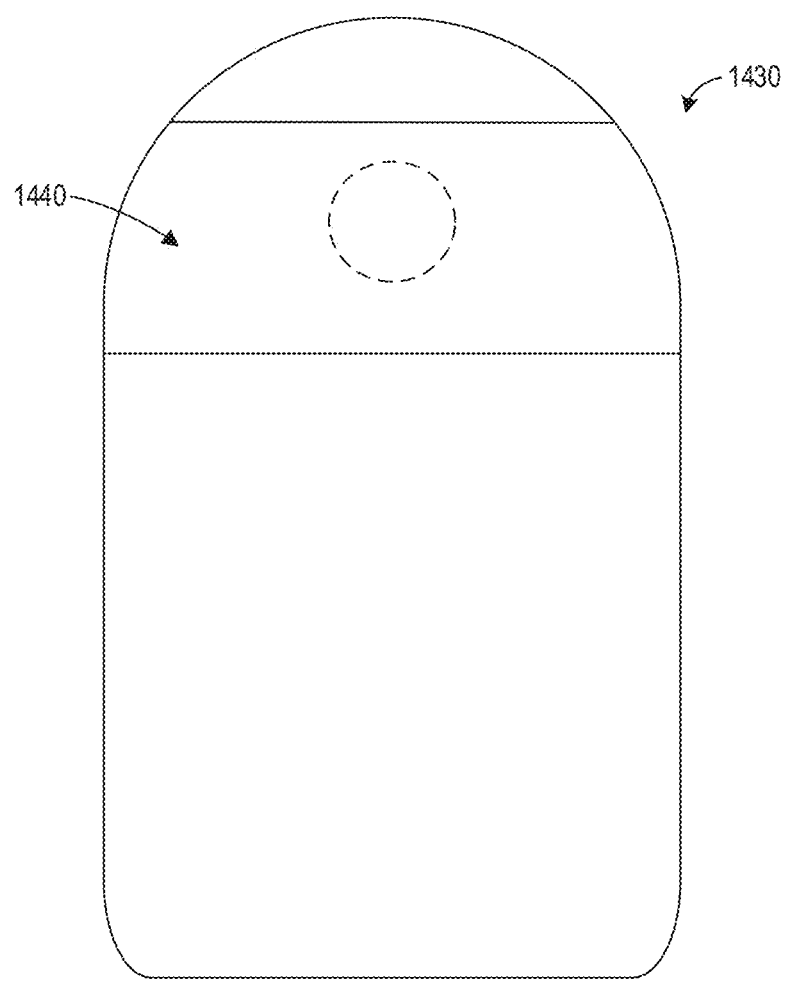
FIG. 14D shows an example ostomy bag with a pocket for an electronic hub.

As shown in FIGS. 14C-14D, the outer cover layer 1434 on the side of the bag facing away from the patient can include a pocket 1440 configured for accommodating an electronic hub. The hub can be removed from the bag 1430 that is about to be discarded and be used on a subsequent new bag. The hub can use data on previously collected a preceding ostomy bag to improve algorithm processing for subsequent bags.

FIGS. 15A-15G depict an example ostomy wafer 400 attached to example ostomy bags 902 with additional different example electronics hub 814 placements. As disclosed above, different hub placements may affect the weight distribution of the bag, which can affect bag movement. Different hub placements can also affect the wearability of the device. The figures depict a patient surface view 1500 that has the example ostomy wafer 400 and a front surface 1502 with a sensor layer 800. There is also a carbon filter 1504 in this example. The carbon filter can help gas escape the bag and eliminate the odor. Additionally, some examples have a gas sensor 1408 which may be used to determine the bacterial activity of the user's gut. Some examples include hook and loop patches 1503 in the shapes of circles or rectangles with neck flaps 1505 to enable the bottom portion of the bag to be selectively opened for draining and closed for receiving effluent.

Figure 15A:
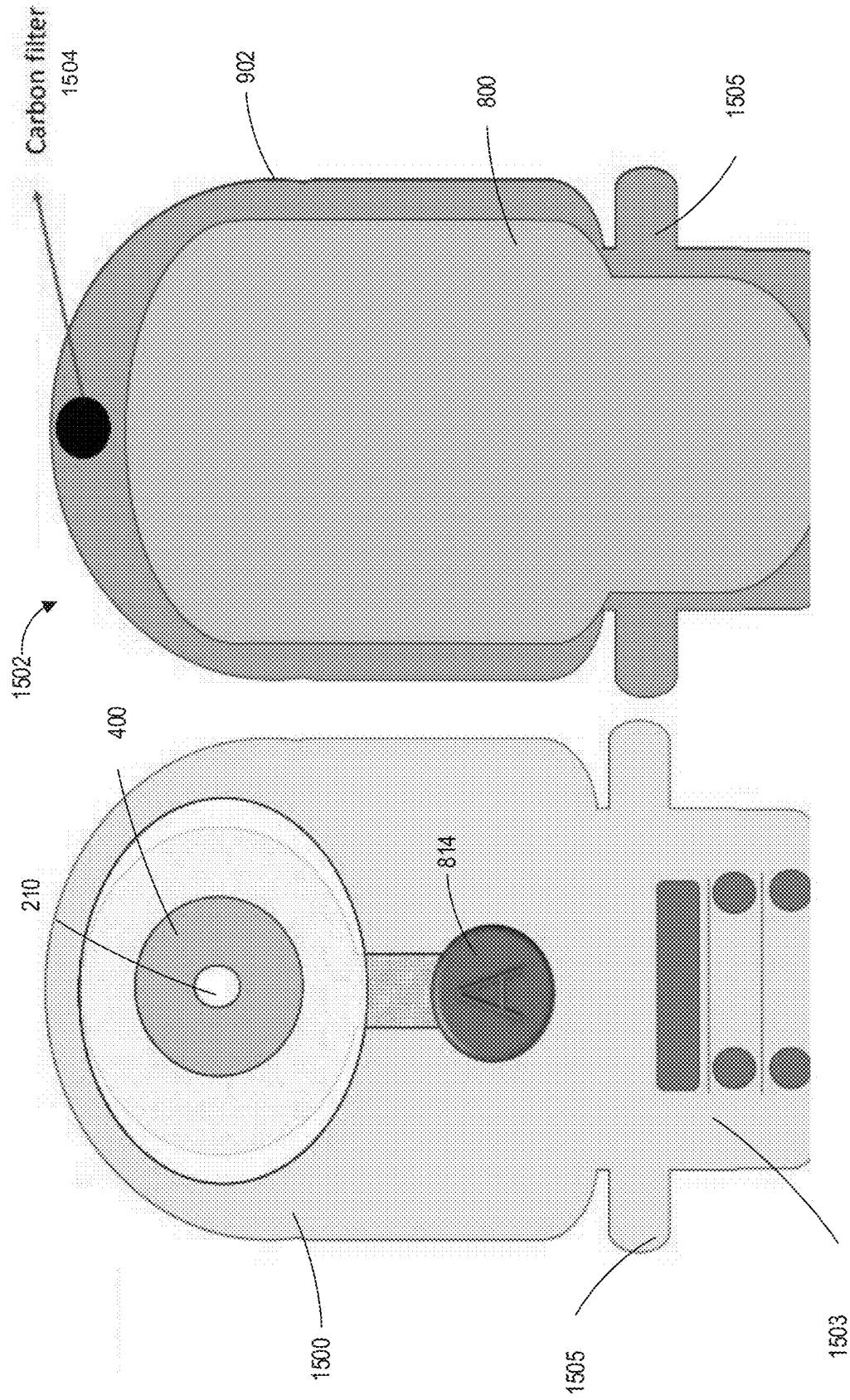
FIGS. 15A-15G illustrate an example ostomy wafer attached to example ostomy bags with different example electronics hub placements.
Figure 15B:
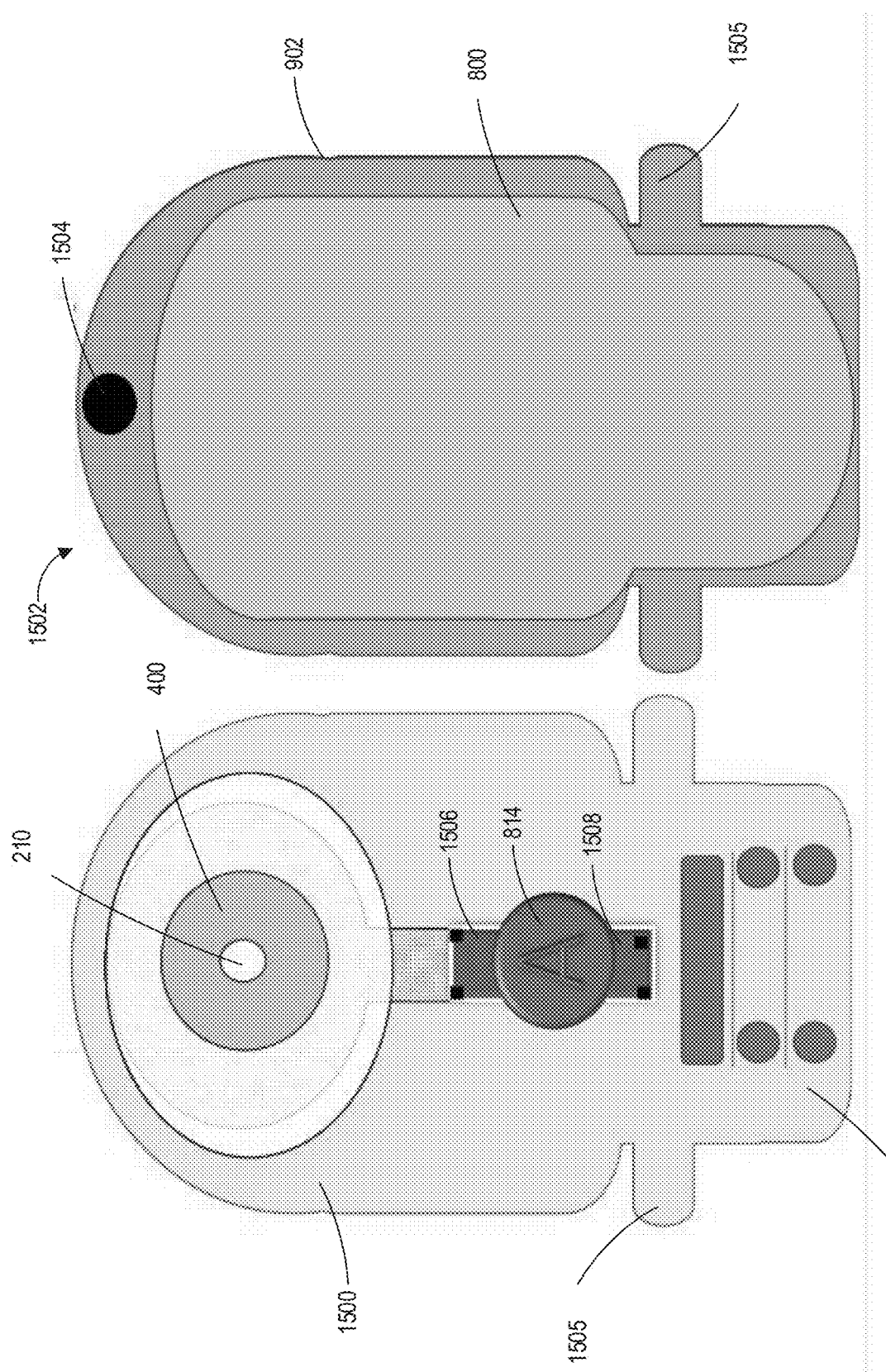

FIG. 15A shows an example device that has a hub 814 in the middle of the bag. FIG. 15B shows an example device with a hub 814 with two USB ports 1506, 1508. The USB ports can be MicroUSB or USB-C ports, among other variations. The USB port feature may create some rigidity in the center of the bag. The hub 814 may also plug in and pull out like a USB device. This modularity can allow a hub 814 to be reused in a different bag. This modularity can also allow an alternate way for the sensors to be in communication with the hub. The connection between the sensor and the hub could be via USB. In this scenario, some or all the circuitry from the different sensors could be affixed to a single port and the USB inlet could affix into a USB inlet in the hub. Other connection methods can include the hub connecting to the bag sensors or wafer sensors using mezzanine-style connectors and/or FPC/FFC connectors, among many other possible variations.

Additional devices may also be plugged in to the USB connectors to give the device additional functionality. For example, a visualization device such as a display, a speaker, a battery, a USB memory stick to obtain hub data, an external data source, or a hard drive with updated or customized algorithms may be inserted to these USB ports 1506, 1508. One USB port instead of two may be provided, or more than two may be provided.

Figure 15C:
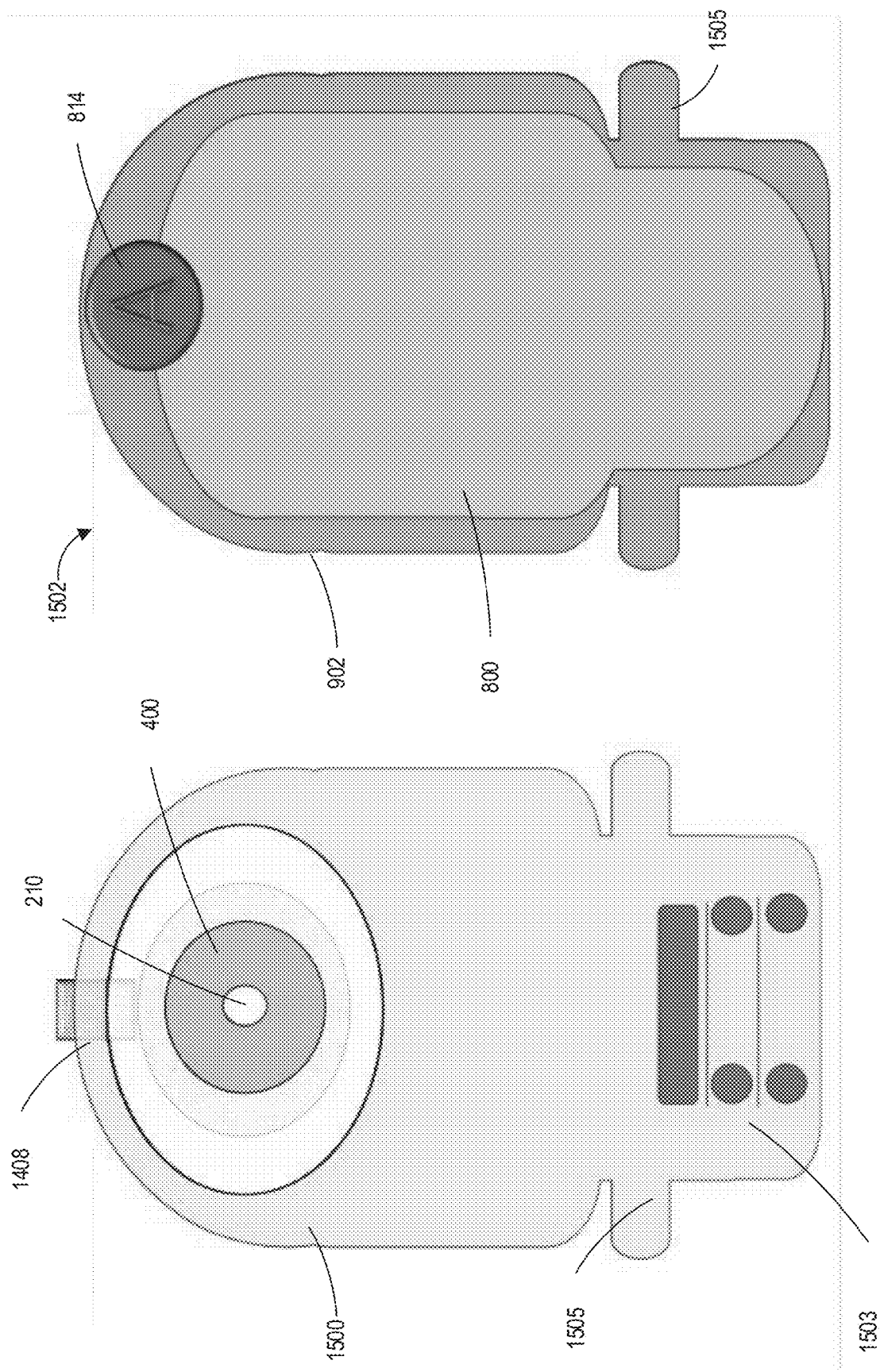
Figure 15D:
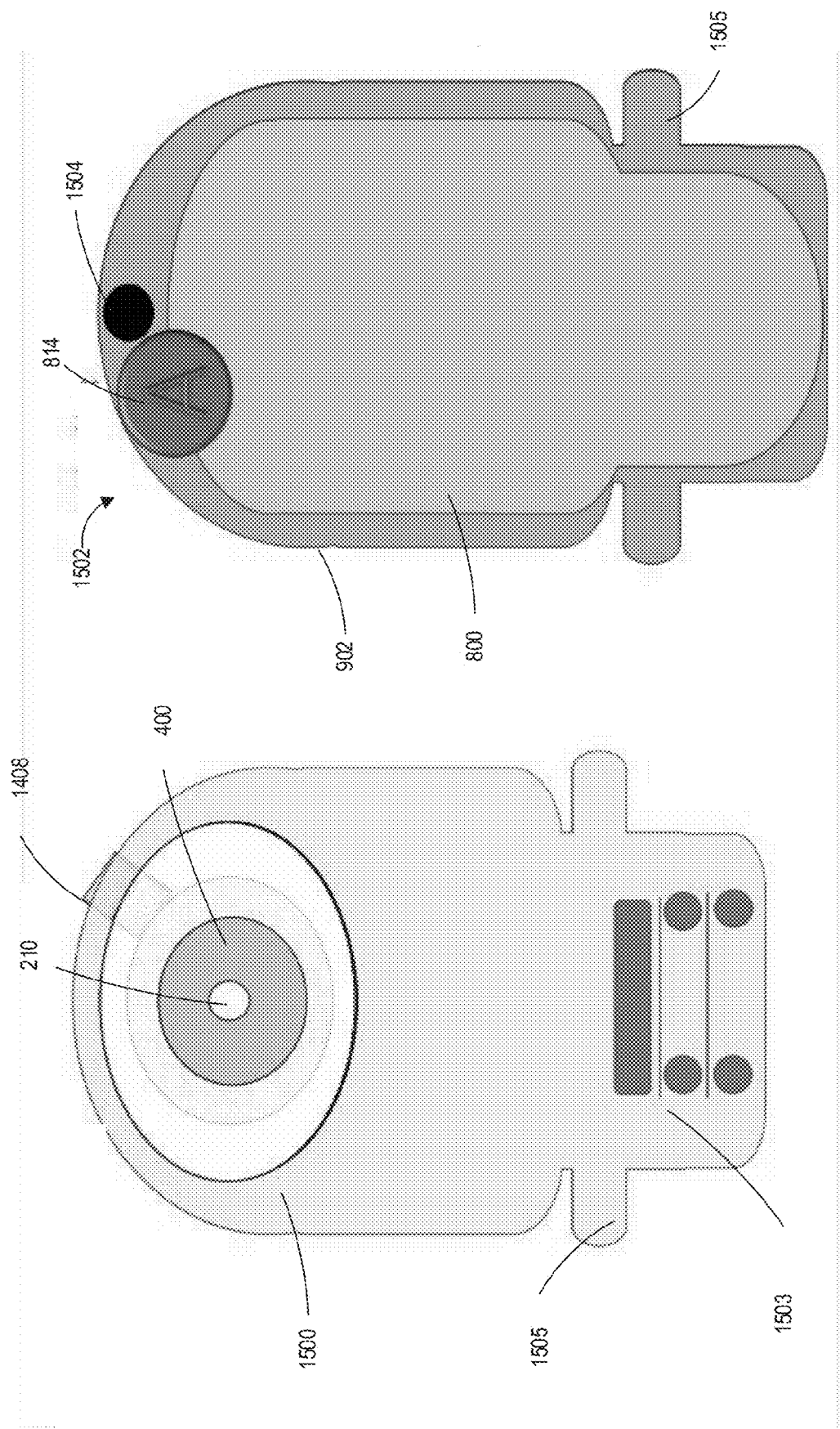
Figure 15E:
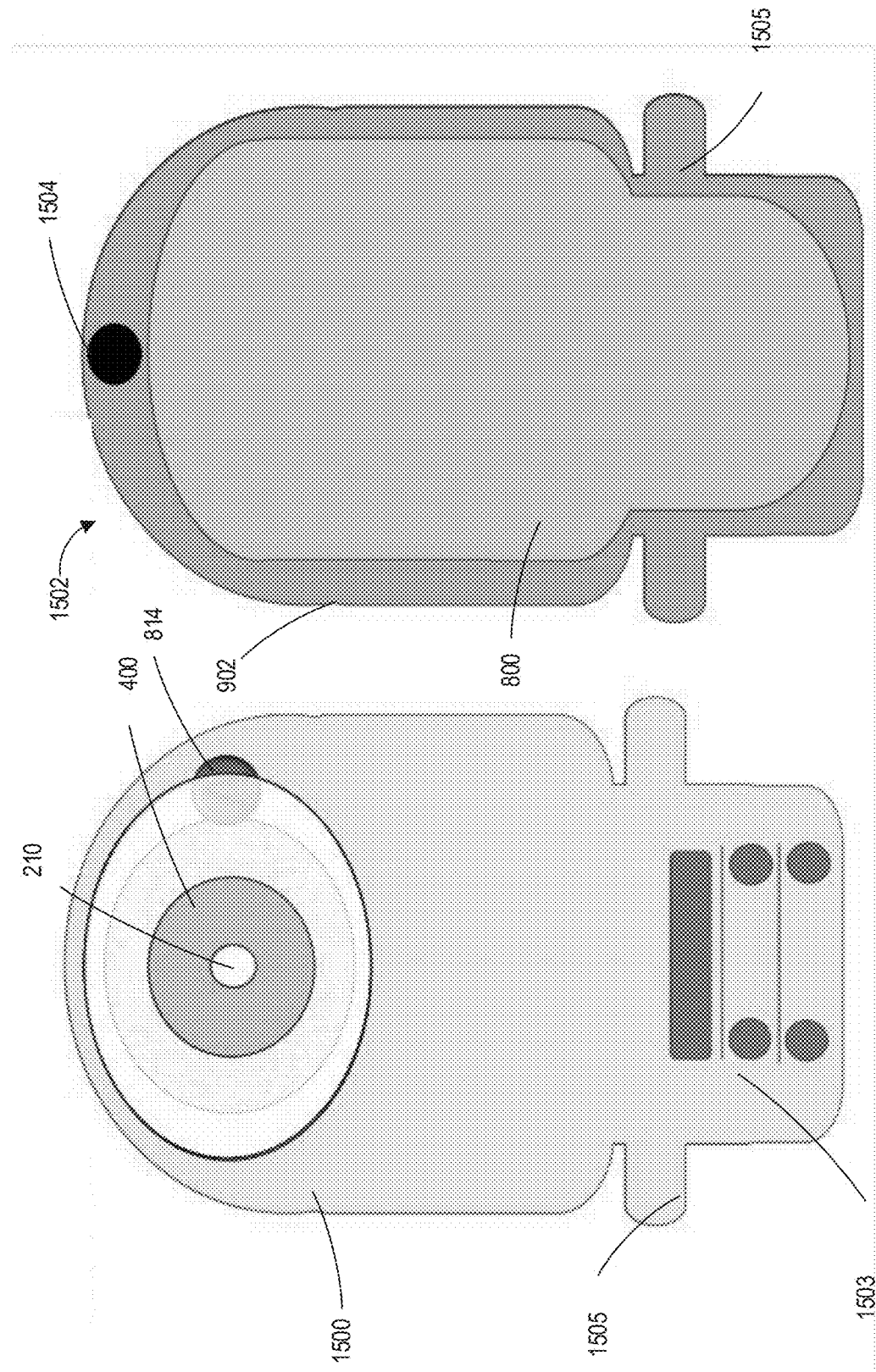
Figure 15F:
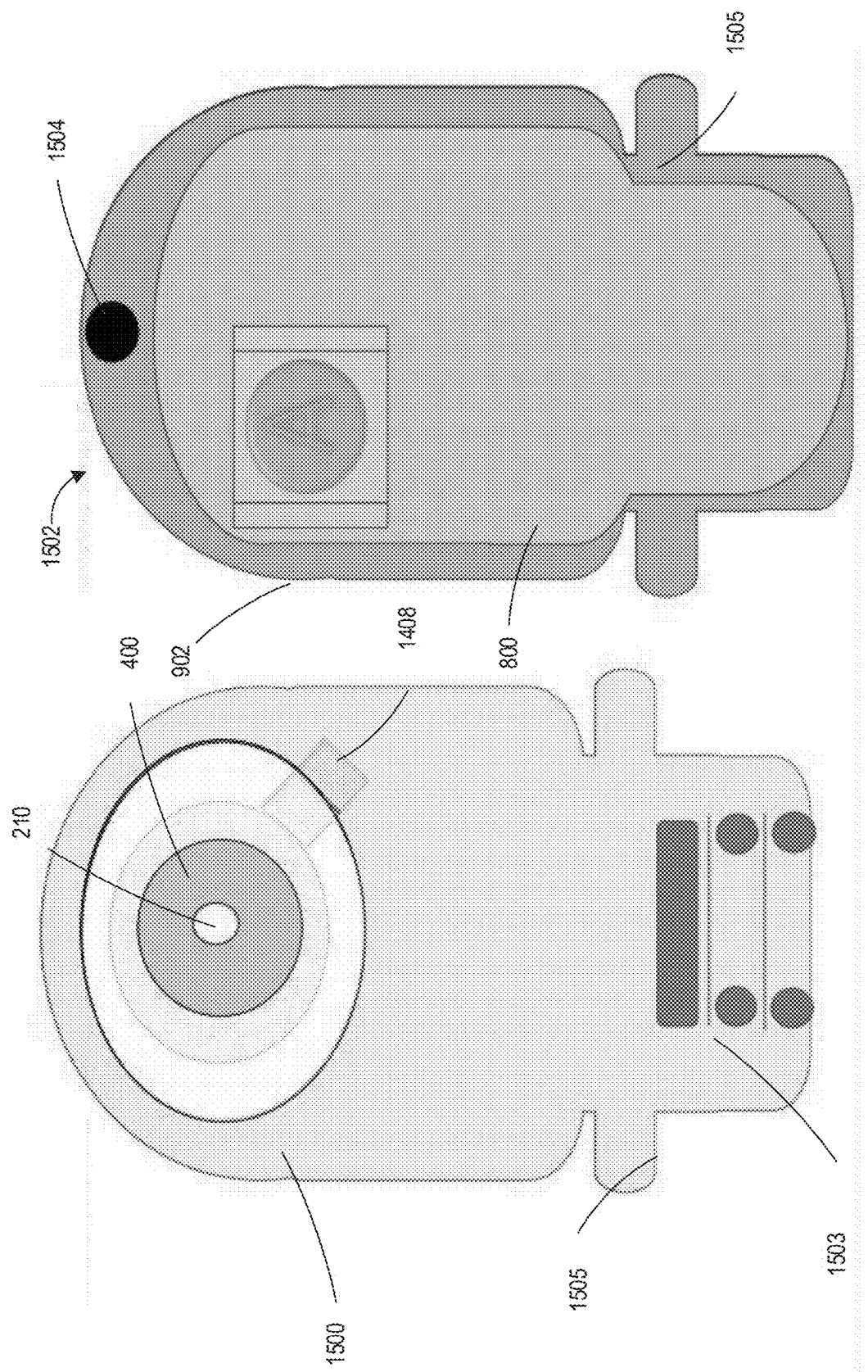

FIG. 15C shows an example hub 814 placed over the charcoal filter 1504 on the top of the bag 902. FIG. 15D shows a hub 814 placed next to a carbon filter 1504 near the top of the bag. FIG. 15E shows a hub 814 placement behind the hydrocolloid layer of the example ostomy wafer 400 but on top of the bag 902. FIG. 15F shows a hub 814 in a pocket 1510. This design is another example of a reusable hub. The hub can be removed from a bag 902 that is about to be disposed and then be used on a subsequent new bag 902. The hub can use previously collected data on a preceding ostomy bag 902 to improve algorithm processing for subsequent bags.

Figure 15G:
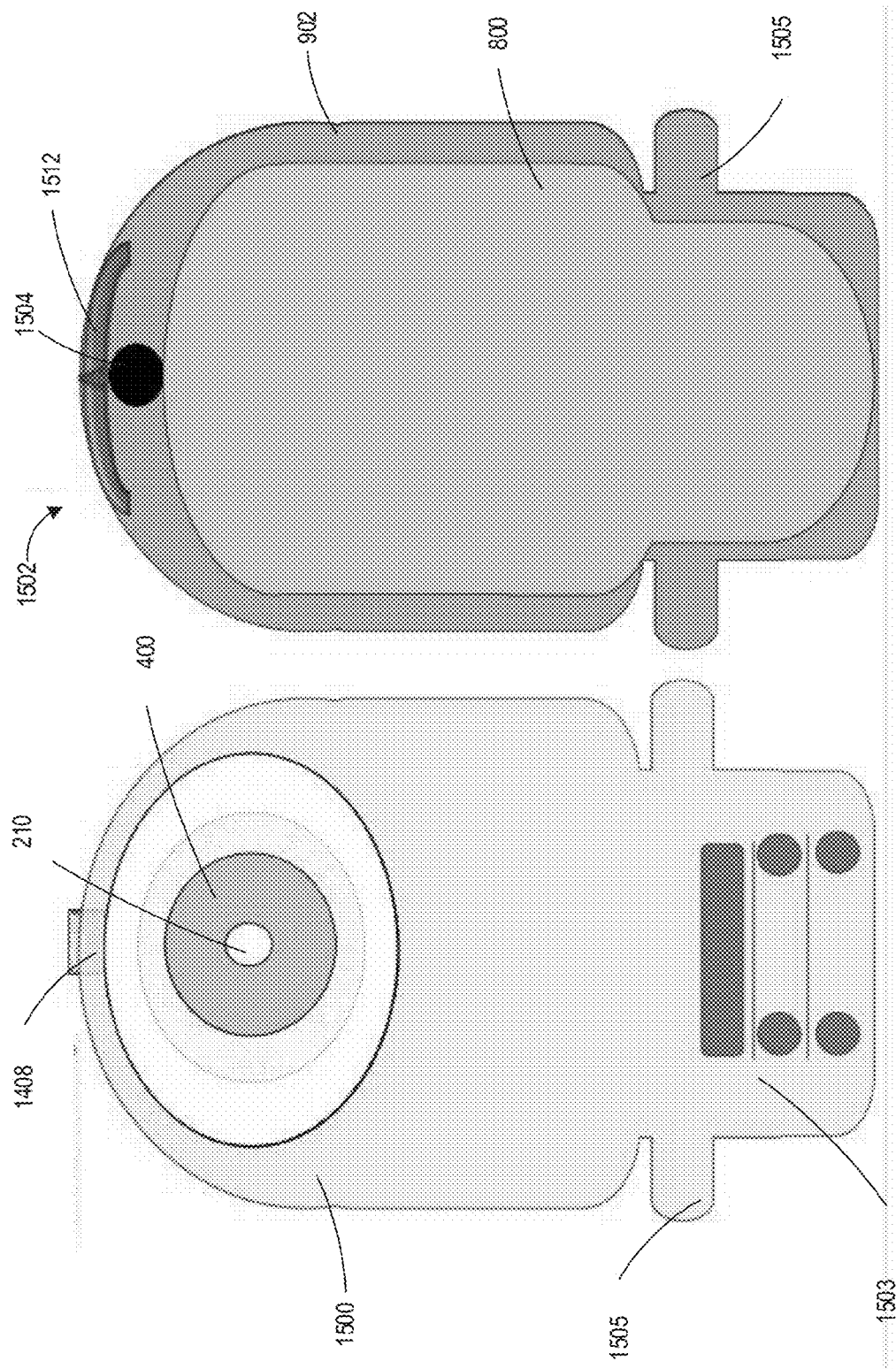

FIG. 15G shows an example approximately crescent-shaped hub 1410 placed at the top of the ostomy bag 902. For the examples that show a hub placement at the top of the bag, a visualization element such as an optical sensor, camera, or IR camera may be connected to the hub via a USB port and descend into the bag to give visualization input of the contents of the bag 902. These example additional parts and device components mentioned in FIGS. 14A-15G can be seamlessly integrated so that there may be little difference in user experience in using and installing these components. The parts may be standardized for easy user use and can be designed to be used in a modular function where a user can pick and choose which sensors are more pertinent to their condition.

In some examples, the device 102 may be manufactured in different configurations. In one configuration, several sensors may be used in a bag and/or wafer. The device may be targeted for new stoma patients and new users where a large collection data may be beneficial for the user. An ostomy bag according to the present disclosure can include any (such as all) of the sensors, biomarkers (for example, for cancer cells, blood, and the like), and/or electronics. Such a bag can be a diagnostic bag configured to be worn by a patient after surgery and before being discharged. It can be more critical to monitor a variety of parameters of the patient immediately after a surgery. However, a diagnostic bag can be expensive. Other configurations may provide a user to choose which sensors pertain to their condition and provide a cheaper alternative. Other configurations may have the bare minimum of sensors for advanced patients who may be acclimated to their stoma condition, such as only temperature sensors in the wafer and/or bag. A simpler and less expensive ostomy bag, such as an analytics bag with fewer sensors, biomarkers and/or electronics than the diagnostic bag, can also be used to monitor phases of the stoma output, skin temperature changes (and thereby skin infections), and/or stoma/output images/sounds via a camera and/or microphone in the electronic hub in addition to detecting output volume and leak. The analytics bag can be used a predetermined period of time after the surgery, such as two weeks, one month, three months, six months, twelve months, or any ranges between those values, or after being discharged from the hospital. The patient can also optionally switch to another ostomy bag, a maintenance bag, that includes just sensors and electronics for volume and leak detection. The maintenance bag can also optionally include sensors and electronics for tracking hydration or dehydration of the patient. The patient can switch to the maintenance bag a predetermined time after the surgery, such as six months, nine months, twelve months, eighteen months, twenty-four months, or any range between those values. In some implementations, a medical kit can include one or more of the diagnostic bags, one or more of the analytics bags, and one or more of the maintenance bags.

FIGS. 36-42D illustrate an example sensor layer 3600 of an ostomy bag, such as the bag 120 described above. The sensor layer 3600 can have any of features of the sensor layers 800, 1100 described above. The sensor layer 3200 can be incorporated into the bag 120, 902 described herein. For example, an ostomy bag incorporating the sensor layer 3200 can include a plurality of sensors, a hub interface, an ostomy wafer interface, and/or encapsulation sheets made of polyimide film, polyurethane, or the like.

As shown in the schematic drawings in FIGS. 36-40B, the bag sensor layer 3600 can have an outline shaped and sized generally like the ostomy bag. The sensor layer 3600 can have a first portion 3612 and a second portion 3614. When in use, the first portion can substantially coincide with the stoma hole of the wafer, such as described with reference to FIGS. 32-34B, and/or with the effluent entrance of the bag. When in use, the second portion 3614 can substantially coincide with a remainder of the bag configured to hold the effluent.

When in use, the bag can be attached to the hub generally within the first portion 3612. As shown in FIGS. 36-40B, the first portion 3612 can include an opening 3632 (such as an oblong opening extending along a longitudinal axis of the sensor layer 3600). The opening 3632 can allow light to travel unobscured between a camera on the hub from one side of the layer 3600 to an opposite side of the layer 3600, or allow the camera on the hub to protrude at least partially through the opening 3632. The opening 3632 can allow monitoring of the stoma via the camera on the hub. The camera can be configured to capture a central portion of the stoma due to the proximity of the camera lens and the stoma. Camera with wider angle or smaller focal lens can also be used to capture images showing a larger area of the stoma.

Figure 36:
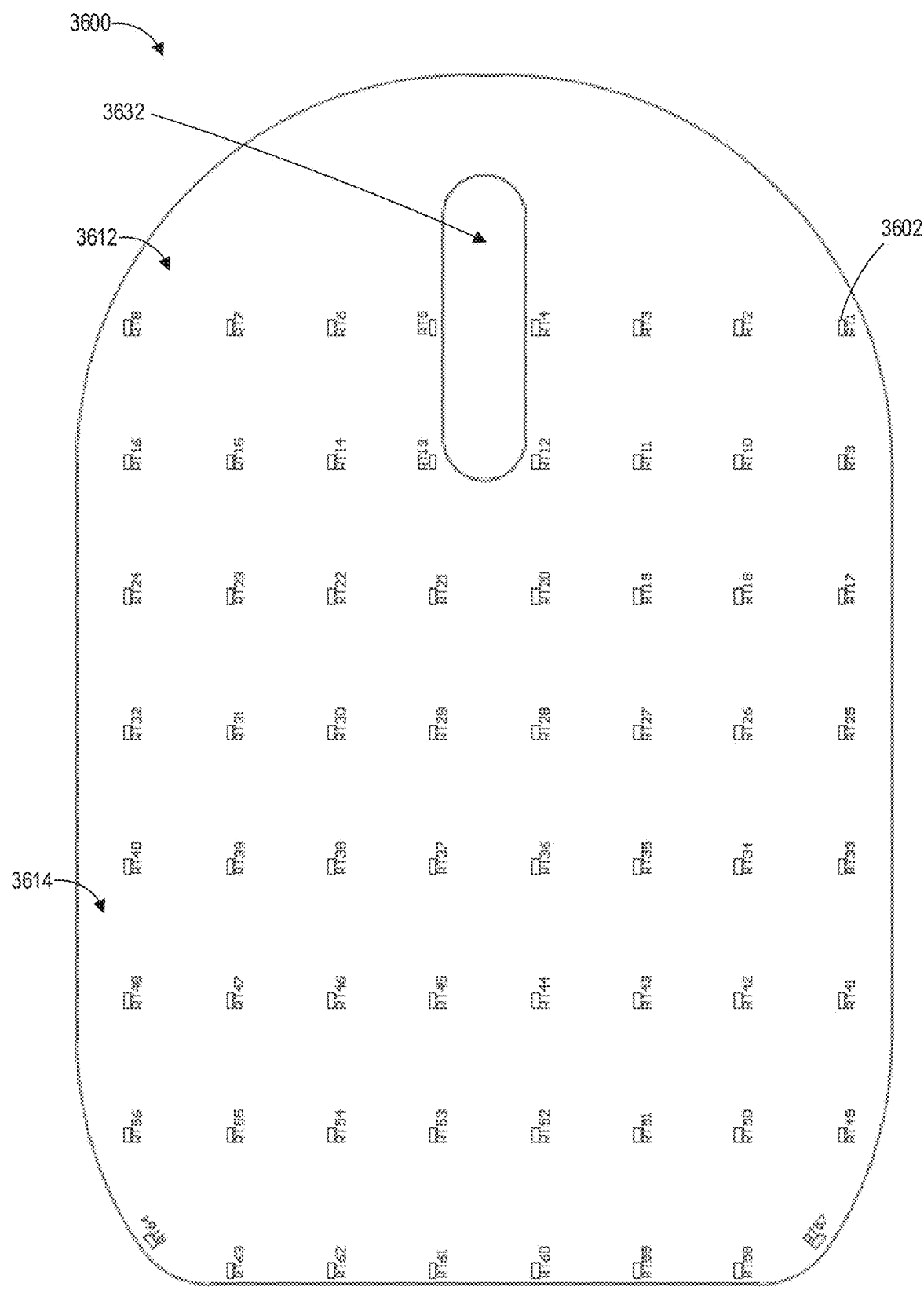
FIG. 36 illustrates schematically temperature sensors on an example sensor layer of an ostomy bag.

As shown in FIG. 36, the second portion 3614 and at least a part of the first portion 3612 immediately adjacent to the second portion 3614 can accommodate a plurality of temperature sensors 3602 (such as thermistors disclosed herein). The sensor layer 3600 can include sixty-four temperature sensors 3602. The temperature sensors 3602 can be arranged in an 8×8 matrix, which can improve an even distribution of the temperature sensors across the part of the sensor layer 3600 that may more likely come into close proximity with the effluent during normal use of the ostomy bag to detect temperature changes due to changes in the bag fill level. Different numbers and/or different arrangements of temperature sensors can also optionally be used. In some configurations, fewer temperature sensors (such as about 20) can be used. The temperature sensors can measure a plurality of metrics related to the stomal output as disclosed herein.

Figure 37:
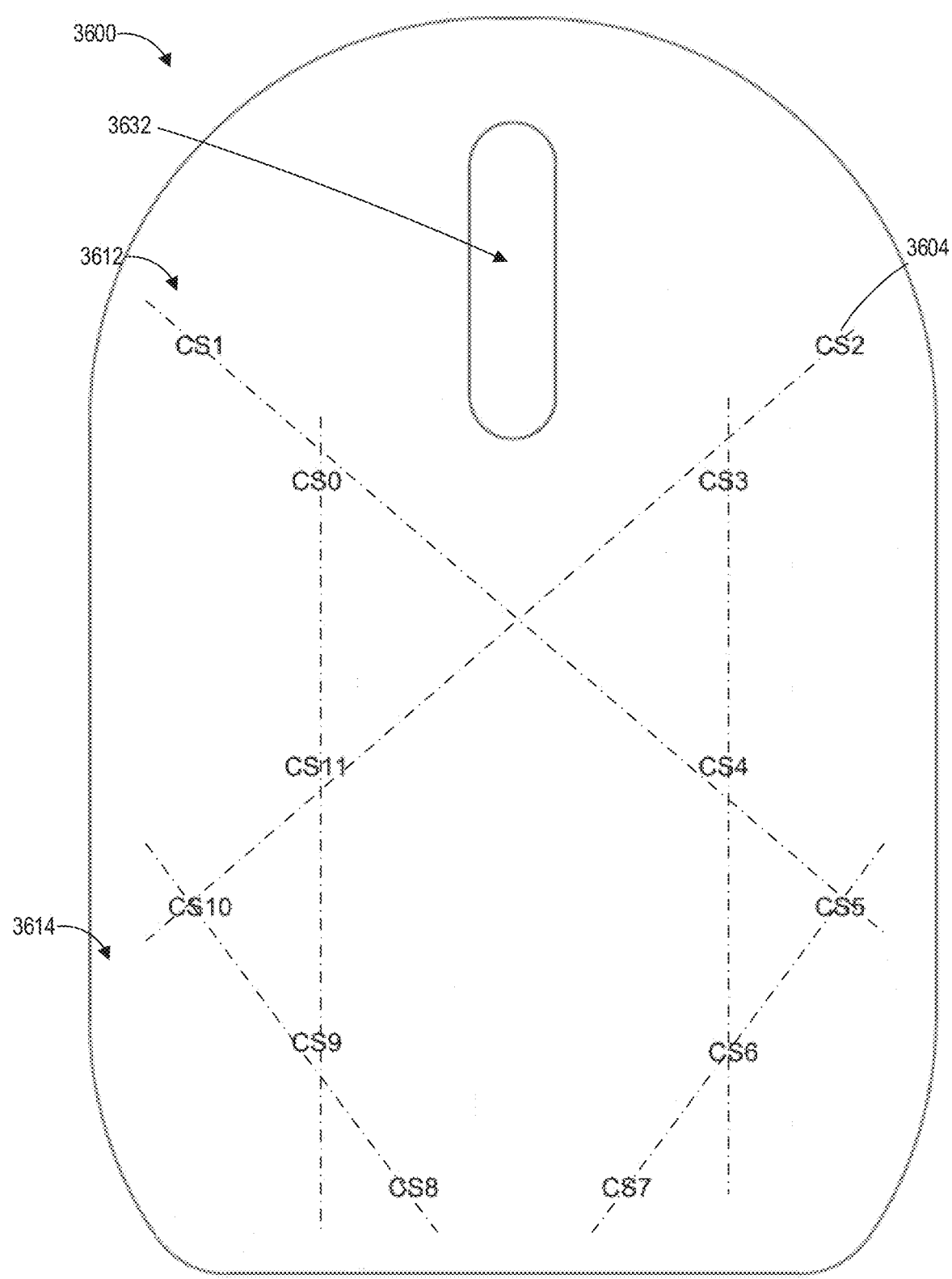
FIG. 37 illustrates schematically capacitive sensors on an example sensor layer of an ostomy bag.

As shown in FIG. 37, the second portion 3614 and at least a part of the first portion 3612 immediately adjacent to the second portion 3614 can accommodate a plurality of capacitive sensors 3604. The sensor layer 3600 can include twelve capacitive sensors 3604. The capacitive sensors 3604 can each include an electrode (such as silver or gold electrodes) coupled to a capacitive sensor chip, which will be described in greater detail below. The capacitive sensors 3604 can measure a capacitance change when effluent enters the bag as the solid and/or liquid contents of the effluent have different capacitance values than a capacitance value of the bag or air in the bag.

As shown in FIG. 37, the capacitive sensors 3604 can be distributed over the sensor layer 3600 such that at least some of the capacitive sensors 3604 can detect a bag fill level when the bag is in an upright position and/or a tilted position of various angles. For example, as shown in FIG. 37, the capacitive sensors 3604 can be distributed symmetrically about a central longitudinal axis of the sensor layer 3600. The capacitive sensors 3604 can be located in different vertical and/or horizontal positions on the sensor layer 3600. As shown by the dash-dot lines in FIG. 37, some of the capacitive sensors 3604 can be generally aligned in straight lines inclined at various angles to detect bag fill levels when the bag is tilted to different angles (see FIG. 39B). These angles can be, for example, from about 30° to about 70°, or from about 40° to about 60°, or from about 50° to about 55°, or about 52.57°, or about 52.79°, or about 53.02°, or about 53°. The angles are not limited to the values shown in FIG. 39B. In addition, more capacitive sensors 3604 are located in the second portion 3614 (such as eight, ten, or others) than in the first portion 3612 (such as four, two, or others), which can permit more lines of different angles to be formed by the capacitive sensors 3604 in regions of the bag that are more likely to contain the effluent.

The arrangement of the capacitive sensors 3604 can permit more accurate detection of the bag fill level, such as when compared to arranging the same number of capacitive sensors in a traditional matrix-like row-column arrangement. For example, the matrix-like row-column arrangement of the same number of capacitive sensors can result in a pattern of lines of the sensors with fewer angle variations, which can lead to less accurate detection of the bag fill when the bag is tilted. In the matrix-like row-column arrangement, there is also a more even distribution of the capacitive sensors in the first and second portions 3612, 3614 of the sensor layer, resulting in fewer sensors in the second portion 3614, where the bag is more likely to contain the effluent. For capacitive sensors in a traditional matrix-like row-column arrangement to detect the bag fill level at different positions of the bag to the same or substantially similar degree of accuracy as the capacitive sensor arrangements disclosed herein, a greater number of capacitive sensors would be required. Therefore, the capacitive sensor arrangements disclosed herein can permit more accurate detection of the bag fill level with few numbers of capacitor sensors.

The capacitive sensors 3604 can also be located such that a "bag full" (or close to full) indication can be outputted, such as by the user device, before the bag has reached its designed capacity (for example, about 5 mL, about 10 mL, or any other volumes before the bag reaches its designed capacity). The user can be alerted, for example, by the user device, when the capacitive sensors 3604 that are closer to the opening 3632 (such as CS1, CS0, CS2, CS3) detect a capacitance change that is indicative of the effluent. Detection of the effluent around those capacitive sensors 3604 can indicate the bag is close to reaching its designed capacity. Alerting the user prior to the bag reaching its designed capacity can provide time for the user to get ready for draining and/or changing the bag, thereby reducing the risk of a leak. Different numbers (such as sixteen, or other numbers) and/or different arrangements of capacitive sensors (including the electrodes and/or the capacitive sensor chips) can also optionally be used. In some configuration, more capacitive sensors (such as about 36 to 48) can be used.

Figure 38:
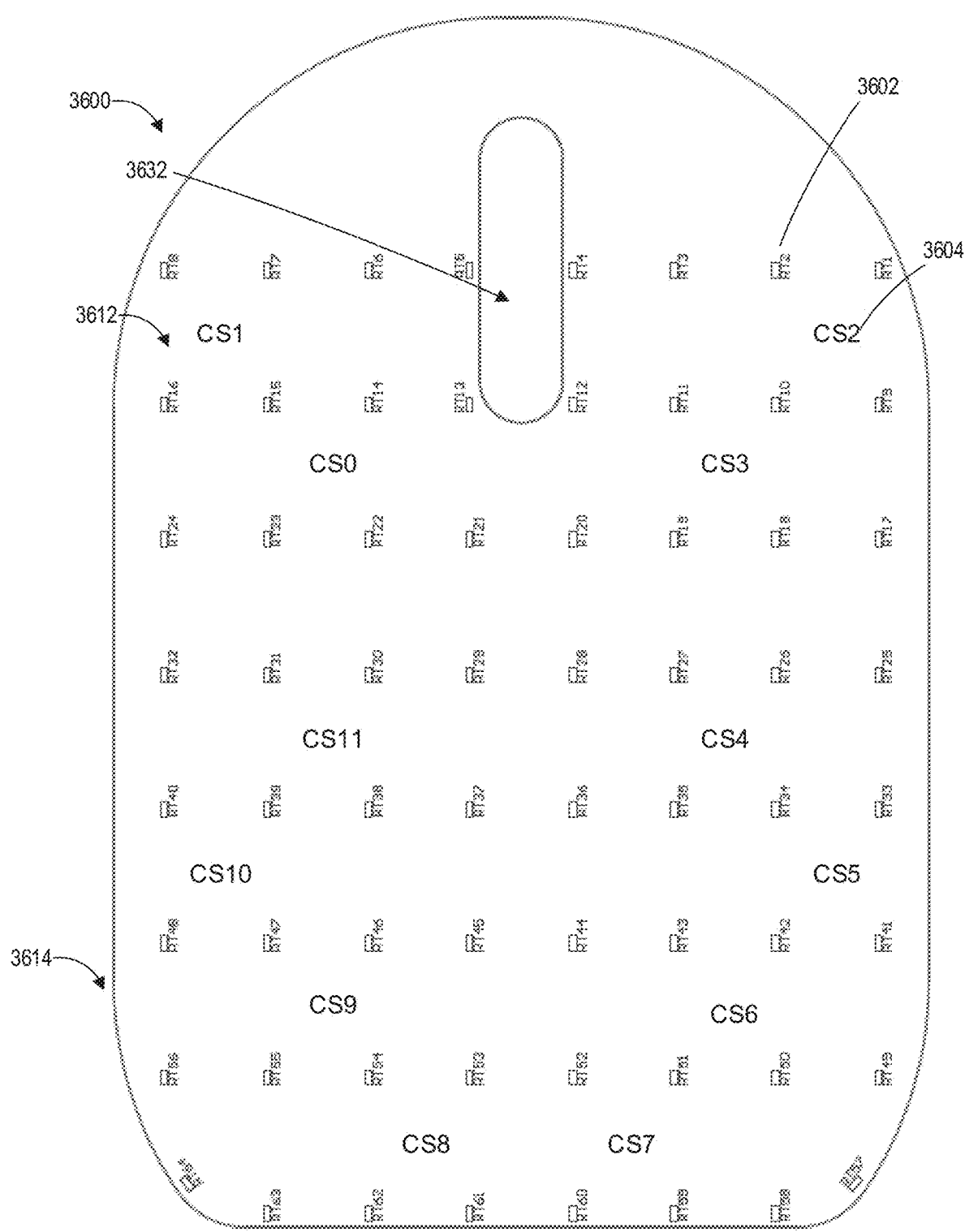
FIG. 38 illustrates schematically temperature and capacitive sensors on an example sensor layer of an ostomy bag.
Figure 39A:
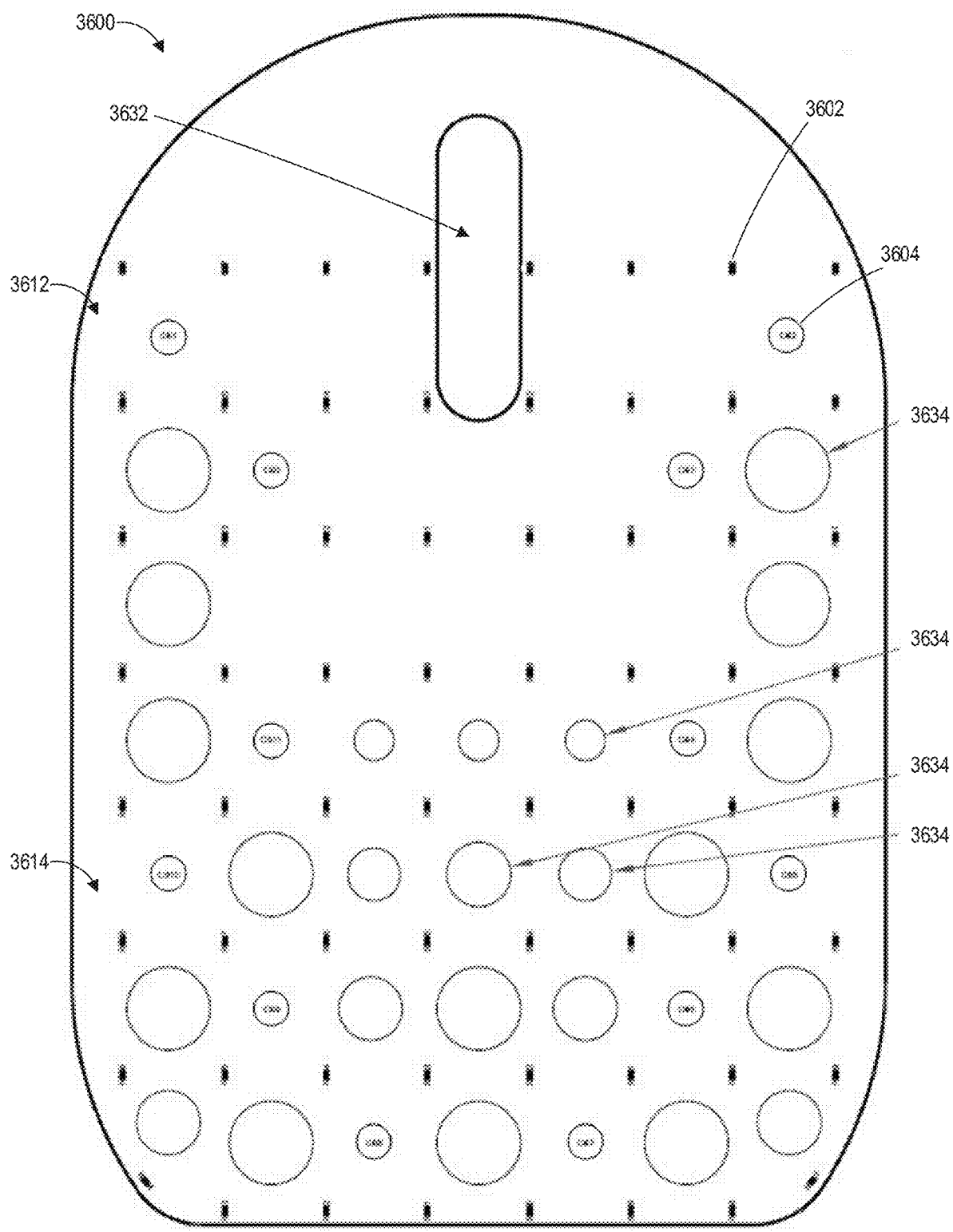
FIGS. 39A-39B illustrates examples of sensor layers of an ostomy bag.
Figure 39B:
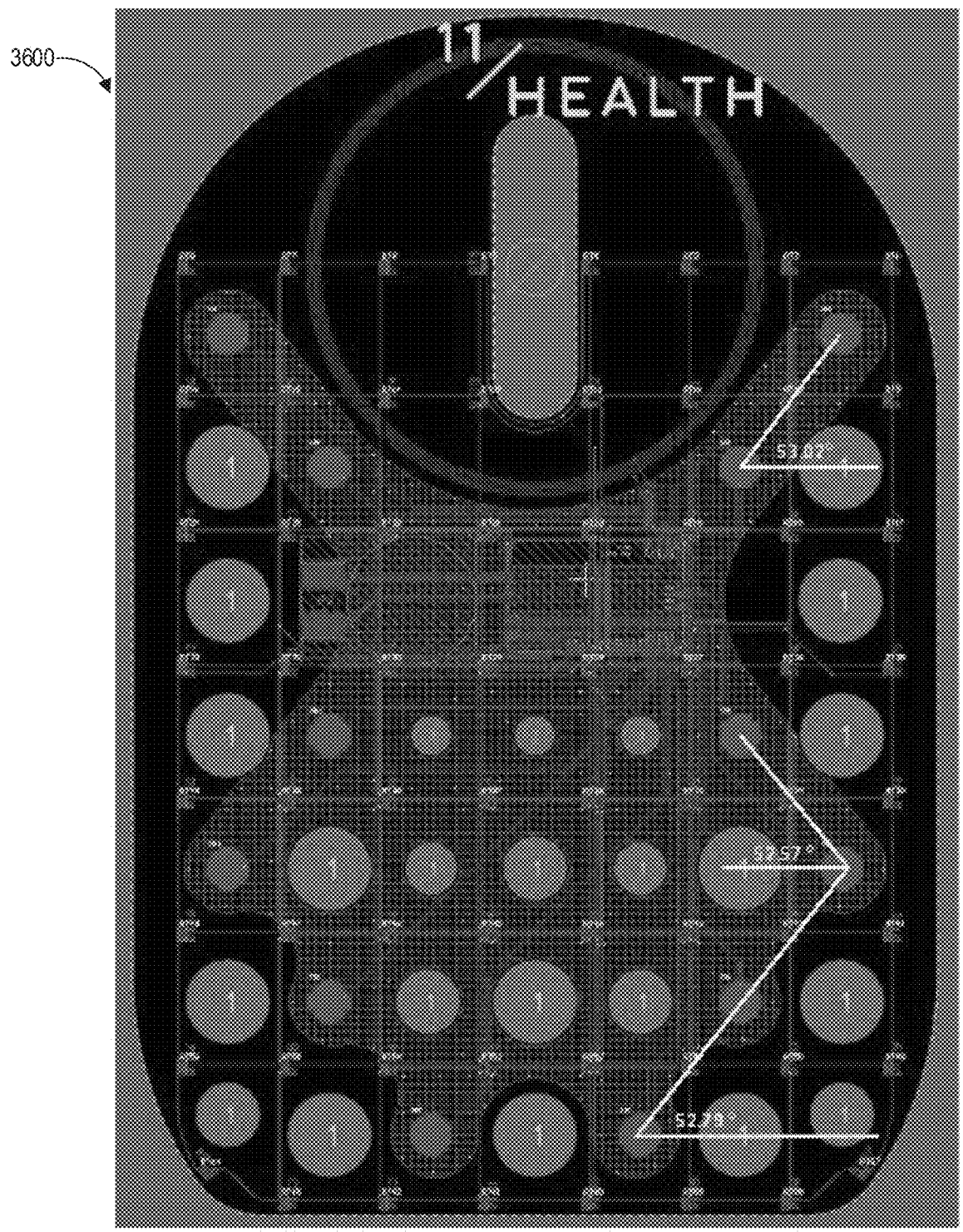

As shown in FIG. 38, the sensor layer 3600 (for example, on a top layer) can include both the plurality of temperature sensors 3602 described with reference to FIG. 36 and the plurality of capacitive sensors 3604 described with reference to FIG. 37. As shown in FIG. 39A, the sensor layer 3600 as shown in FIG. 38 can also further include a plurality of openings 3634 in the layer. The openings 3634 can vary in size, location, and/or number. The plurality of openings 3634 can improve the flexibility of the sensor layer 3600.

Figure 40A:
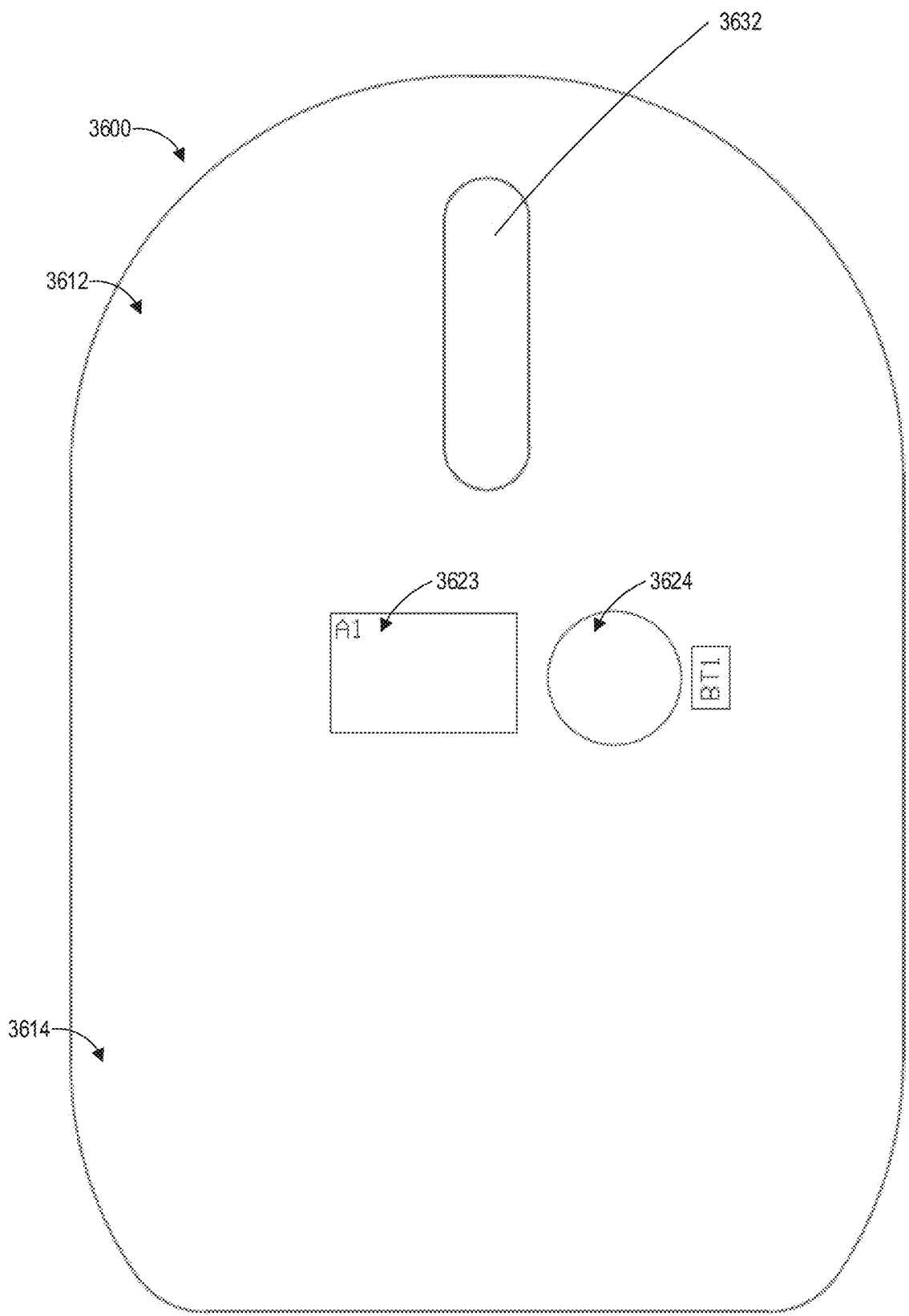
FIGS. 40A-40B illustrate top and bottom views of the sensor layer of FIG. 39A.
Figure 40B:
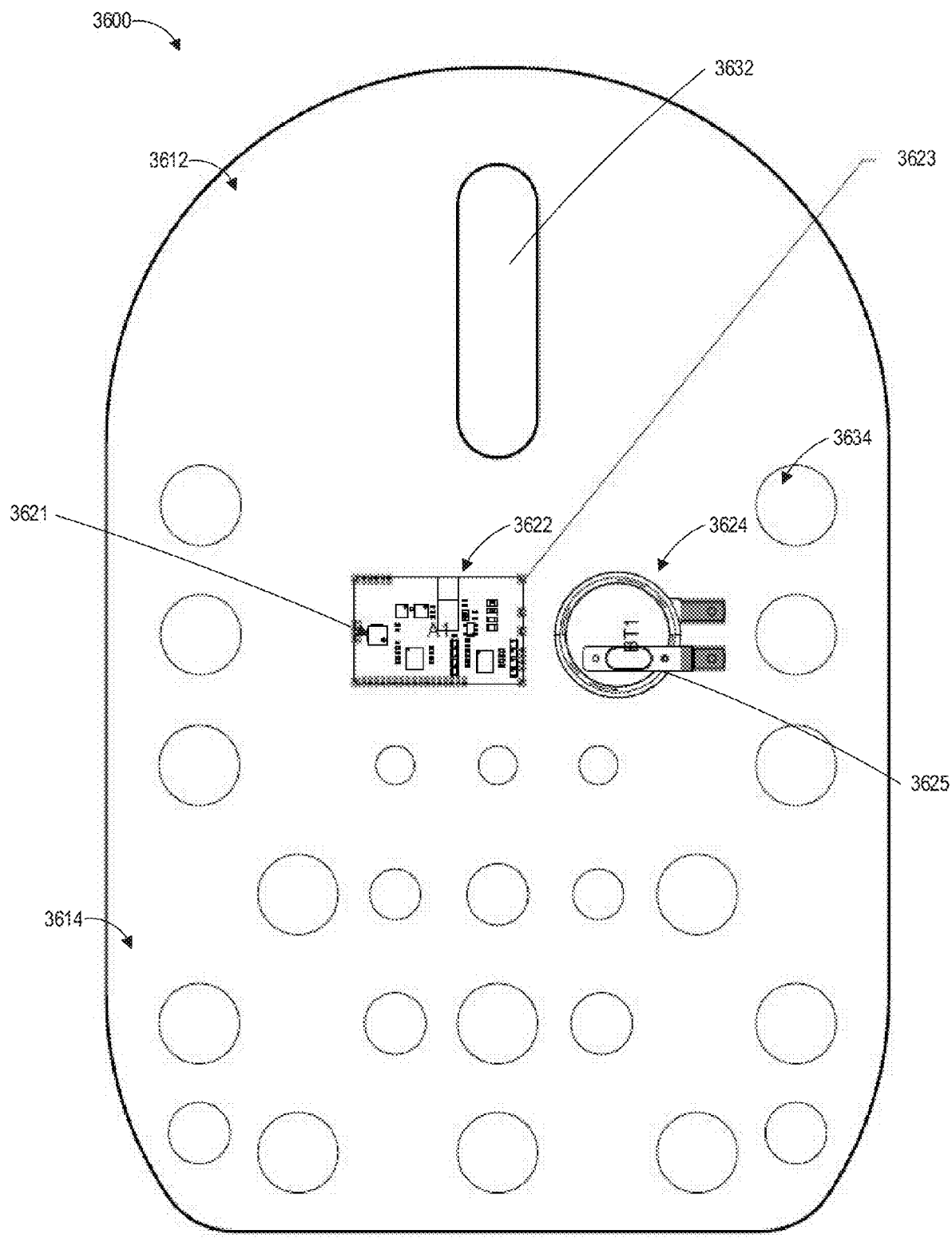

As shown in the schematic drawings in FIGS. 40A-B, which illustrate a surface of the layer 3600 opposite the surface on which the temperature sensors 3602 and/or the capacitor sensors 3604 are mounted, the sensor layer 3600 can accommodate electronic components 3622 and/or power source 3624 on that surface. The electronic components 3622 and/or power source 3624 can be located approximately in the center of the layer 3600.

The electronic components 3622 can be mounted (for example, surface mounted) on a printed circuit board (PCB) 3623, such as shown in FIG. 40B. The PCB 3623 can be mounted on the layer 3600. The PCB 3623 can be sufficiently rigid to protect the electronic components 3622 and the circuitry on the PCB 3623 from breaking due to the bending of the flexible layer 3600. The electronic components can also optionally be mounted directly on the layer 3600, with stiffener material(s) (for example, fiberglass, plastic, or others that are more rigid than the material of the layer 3600) mounted on the layer 3600 adjacent to the electronic components to protect the electronic components from breaking. Mounting the electronic components 3622 on the PCB 3623 can reduce the number of encapsulation layers (for example, from four layers for directly mounted electronics to two layers for PCB-mounted electronics) in the bag sensor layer, which can reduce the use and/or waste of the encapsulation material, and/or make the ostomy bag more affordable to users. The PCB can also optionally include two rigid portions placed adjacent each other. The PCB can be foldable along the adjoining sides of the two portions to improve flexibility of the bag. In some implementations, the electrical circuits, such as including the temperature sensors and any other sensors, can be printed on the ostomy bag layer instead of having a separate sensor layer. Reducing the need for a separate sensor layer can further improve flexibility of the bag and allow the bag to conform better to the user's skin.

The electronic components 3622 can be electrically coupled to the temperature sensors 3602. The electronic components 3622 can also include a capacitive sensor chip 3621 electrically coupled to the capacitive sensors 3604. The electronic components 3622 can receive data from the temperature sensors 3602 and/or the capacitive sensors 3604. For example, the electronic components 3222 can receive resistance signals of the temperature sensors 3602 and/or the capacitive sensors 3604, and/or condition the resistance signals from the temperature sensor 3602 and/or the capacitive sensors 3604. The electronic components 3622 can also send ADC values and/or other conditioned signals to the hub for calculating the temperature and/or capacitance values on a cloud and/or a user's device to reduce power consumption by the bag electronic components 3622. The bag electronic components 3622, the hub, and/or the user device can also optionally perform the calculation of the temperature and/or capacitance values.

As shown in FIG. 40B, the power source 3624 can include a battery (such as a coin-cell battery). More than one battery can also optionally be mounted to the sensor layer 3600. The battery can be surface-mounted to the sensor layer 3600 adjacent to the electronic components 3622. As shown in FIG. 40B, one or more mounting arms 3625 can be attached to the sensor layer 3600 for holding the battery in place.

Figure 41A:
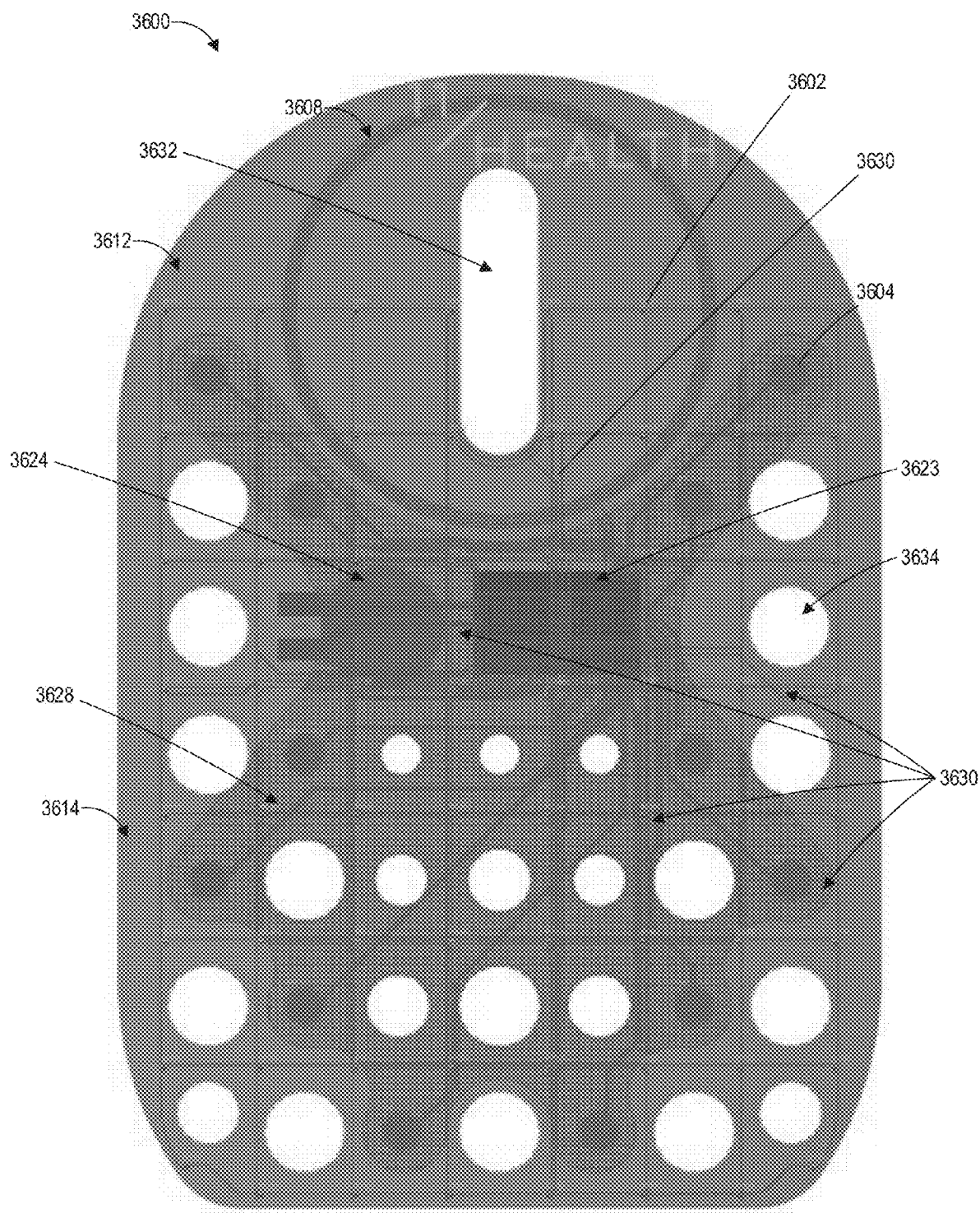
FIG. 41A illustrate a top view of the sensor layer of FIG. 39B.
Figure 41B:
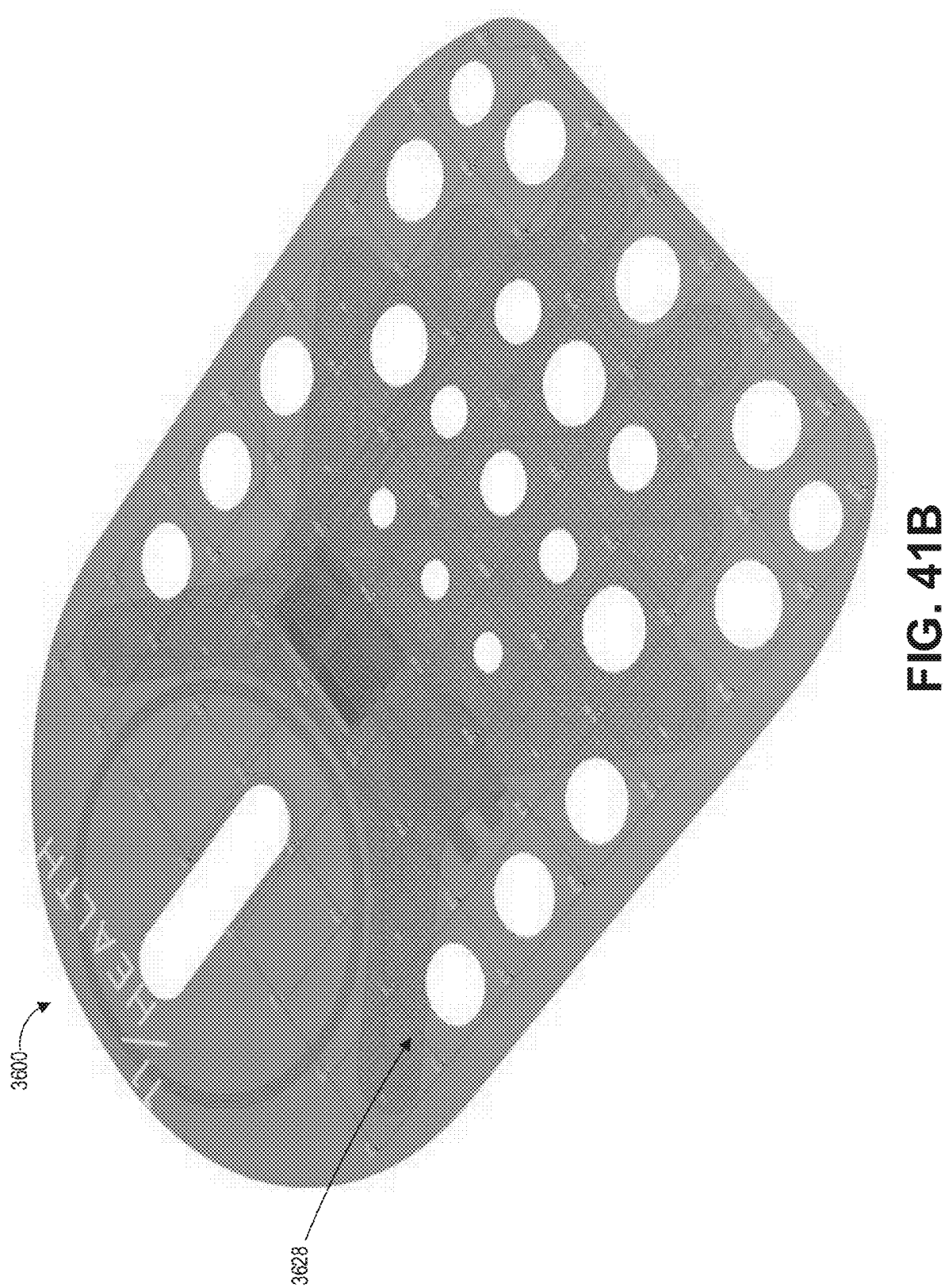
FIG. 41B illustrate a perspective view of the sensor layer of FIG. 39B.
Figure 41C:
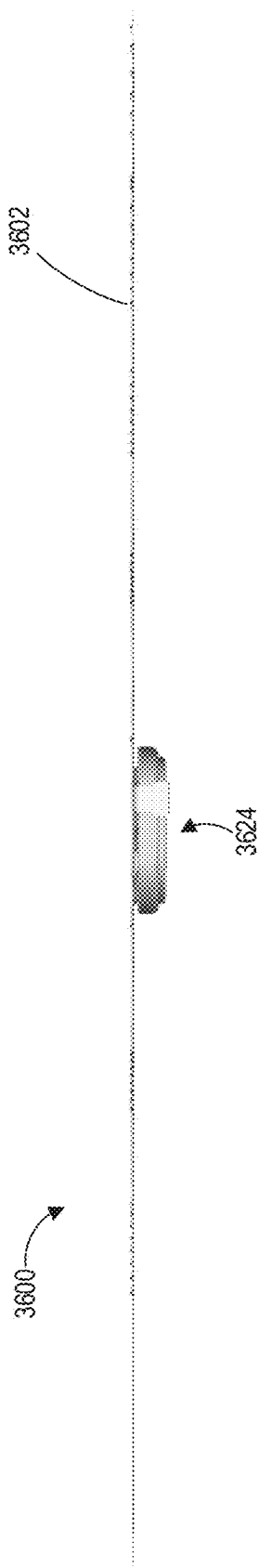
FIG. 41C illustrate a side view of the sensor layer of FIG. 39B.
Figure 45:
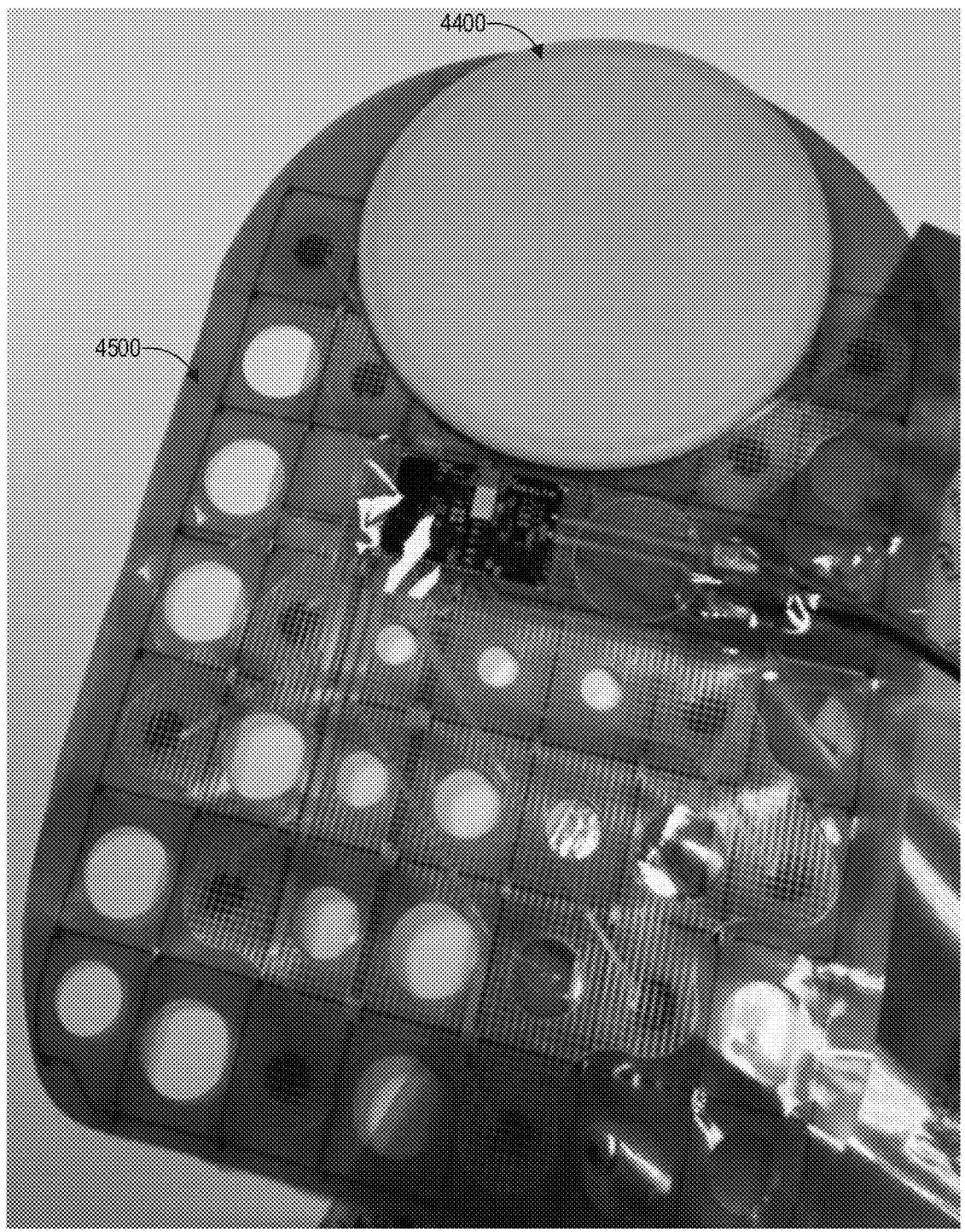
FIG. 45 illustrates the hub of FIGS. 44A-44B coupled to an ostomy bag.

FIGS. 41A-B illustrate top, perspective, and side views of the example sensor layer 3600. As shown, the sensor layer 3600 can also include a plurality of NFC antenna rings 3608. The NFC antenna rings 3608 can extend around the camera opening 3632. A portion of the NFC antenna rings 3608 can also be located near the electronic components 3622 and the power source 3624. The NFC antenna rings 3608 can be generally concentric to one another. Similar to the NFC antennas 3208 on the wafer sensor layer 3200, the NFC antenna rings 3608 can be manufactured onto the sensor layer 3600 (for example, printed or etched). When in use, such as shown in FIG. 45, an ostomy bag 4500, which incorporates the sensor layer 3600, can be coupled to (for example, adhesively, or via hook and loop Velcro dots, attached to) the hub 4400 such that the NFC antenna rings 3608 on the sensor layer 3600 substantially coincide with the NFC antenna rings on the hub.

As also illustrated in FIGS. 41A-B, conductive traces 3630 (such as copper traces, for example, copper plated with ENIG (Electroless nickel immersion gold), or Immersion gold or silver traces as well as Hard Gold or any other PCB surface finish, depending on the material of the layer 3600 as described above) can connect the temperature sensors 3602, the capacitive sensors 3604, the NFC antenna rings 3608, and/or the power source 3622 to the electronic components 3622 on the PCB 3623. FIGS. 42A-D illustrate example schematic circuit diagrams of the bag sensor layer 3600. FIG. 42A illustrates an example schematic circuit diagram 4210 of the bag PCB 3623. The actual arrangement of the electronic components can be varied in the bag PCB layout. FIG. 42B illustrates an example schematic circuit diagram 4220 of the temperature sensors 3602 on the bag sensor layer. As described above, the actual arrangement of the temperature sensors can be varied. However, those temperature sensors can have the same interconnections in a matrix topology as shown in FIG. 42B by the conductive traces 3630 or wires. FIG. 42C illustrate an example schematic circuit diagram 4230 of the capacitive sensors 3604 on the bag sensor layer. As described above, the actual arrangement of the capacitive sensors can be varied. However, those capacitive sensors can have the same interconnections as shown in FIG. 42C by conductive traces 3630 or wires. FIG. 42D illustrates an example schematic circuit diagram 4240 of the battery.

As also illustrated in FIGS. 41A-B, the sensor layer 3600 can further include a ground plane mesh 3628 extending circumferentially around the plurality of capacitive sensors 3604 and between the capacitive sensors 3604. The ground plane mesh 3628 can reduce noise on the readings from the capacitive sensors 3604.

Another difficulty in accurately detecting electronically the level of the fill of an ostomy bag is the residue problem. When the stoma output is more viscous, such as when the output includes feces or other more solids, the more viscous components can cling to the inner surface(s) of the bag. The solids drying out ("pancaking") on the inner surface of the bag can result in misleading or false level reading and thus volume calculation. The dried solids can cause opposing inner surfaces of the bag to be stuck, obstructing entry and/or downward movement of the output discharged or infused into the bag. Prolonged exposure of the stoma to the "pancaked" output can also cause infection.

As will be explained below, recalibration of the capacitive sensors to update the baseline values of those sensors can help reduce the influence of the residue problem in the level and volume determination. Alternatively and/or additionally, more capacitive sensors (such as greater than 12 capacitive sensors, for example, from about 36 to about 48 capacitive sensors) can be used on the sensor layer of the ostomy bag to alleviate the effect of residue problem on the level readings. More capacitive sensors and/or increased capacitive sensor density can provide greater resolution in the sensor reading, which can help detect a residue or "pancaked" output as the residue can have a more random shape than the content of the output that has fallen to the bottom of the bag. Accordingly, more capacitive sensors and/or increased capacitive sensor density can improve the accuracy in predicting the volume of the output. In some configurations, the sensor layer including more than 12 capacitive sensors may also include fewer than 64 temperature sensors (such as about 20 temperature sensors).

Alternatively and/or additionally, the inner surface of the ostomy bag layer can be coated with a material, which can reduce the friction coefficient of the inner surface of the ostomy bag and guide the stoma output toward the bottom of the bag. For example, the material can be hydrophilic or hydrophobic. Coating of the material can be achieved through a variety of ways, such as spraying, dipping, or otherwise. The coating can be effective throughout a life cycle of the bag and can be more convenient than having to wash the inner surface of the bag with lubricating materials each time after the bag is drained. The coating can also be more convenient than applying an adhesive layer of hydrophilic lubricating material to the inner surface of the bag, wherein the hydrophilic layer requires substantial moisture to become hydrated and lubricious, so the beneficial effects of reducing the residue problem the may not be realized unless the output discharged into the bag is sufficiently liquid to activate the hydrophilic coating material.

Example Algorithms

Figure 16:
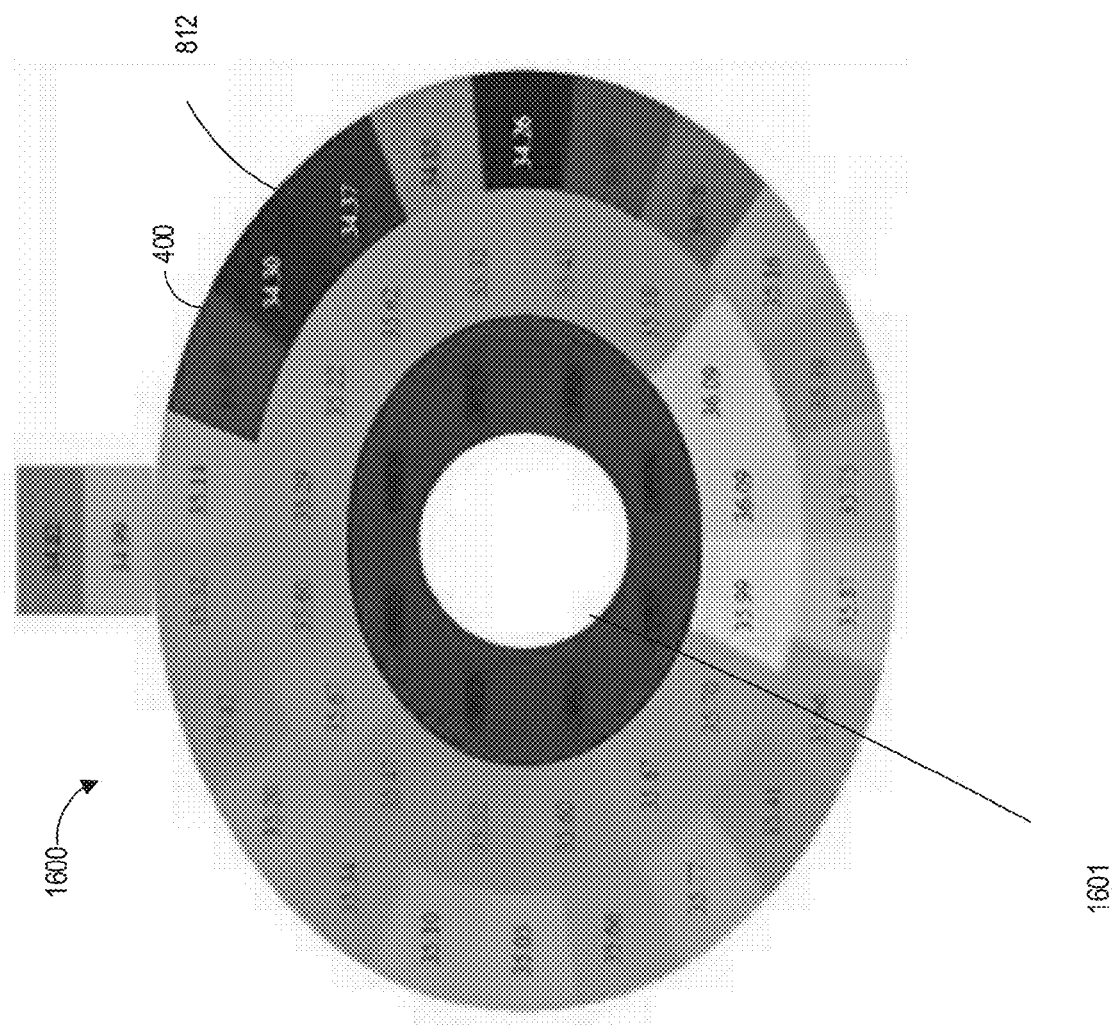
FIG. 16 shows an example heat map that represents the heat signature of a thermistor layer of an ostomy wafer.

FIG. 16 shows a heat map 1600 generated by an algorithm that represents the heat signature of the thermistor layer 812 of an ostomy wafer 400. The heat map may be output for display to a user, e.g., on the user device. The heat map can be used by the device 102 to determine whether the heat is an indication of a leak or inflammation. A user can use the heat map image to see how the effluent of a stoma is entering the bag. Data extraction by the user from the interface or, more succinctly, the experience of interpreting data may be visual. Depending on the sensor type, the visuals may be different. A current example that can be provided is temperature data from the thermistor layer. Here, the output may be in the form of a visual heat map. Each coordinate in the heat map (in the software interface) can be positioned such that it represents each thermistor in the approximately same position in the sheet. Hence the temperature sensed by the thermistor can be seen visually in the map.

The data from the software on the hub, user device, or in the cloud (e.g., at the backend server) can also be extracted into a spreadsheet format which allows more detail data analysis through the formulation of graphs through either Excel and other graphical software such as Origin. In bouts of inflammation, the center near the stoma 1601 may be at a higher temperature than most of the outer edges and areas of the ostomy wafer 400. A higher temperature in the center of the ring may represent an area near the stoma that is potentially undergoing inflammation or a leak. In some examples, a reference sensor can be placed on the neck or the reference sensors could be the outer edges of the device. Using the outer edge sensors that are already part of the device as a reference sensor may be a way to save costs instead of implanting a separate sensor on the neck The visuals in the software can include: the temperature range value, indication of the quantitative value of the temperature in each coordinate, the log interval: 1) whether it should be on or off or 2) how frequently the data is collected and recorded. The software may also have the ability to drag across the elapsed time to be able to see the thermistor sheet as a function of time.

Figure 17:
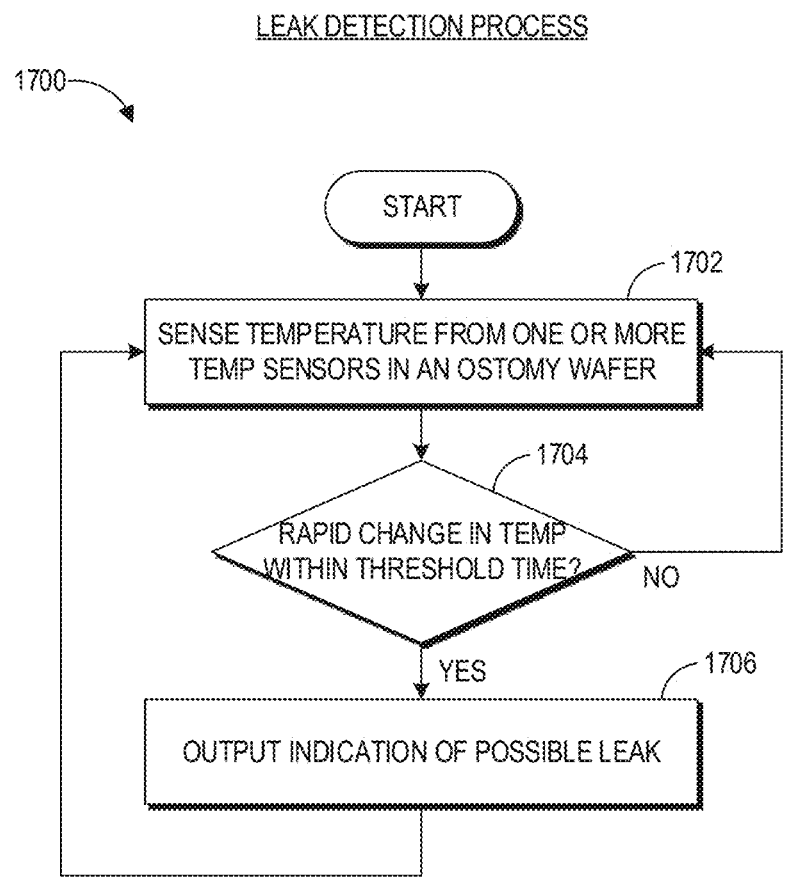
FIG. 17 shows an example ostomy bag leak detection process.

FIG. 17 shows an example leak detection process 1700. The leak detection process 1700 can be implemented by the hub, user device, or backend server as discussed above. More generally, the process 1700 can be implemented by a hardware processor in any of those or another device.

The leak detection process can begin at block 1702, where temperature is sensed from one or more temperature sensors in an ostomy wafer. The temperature may be sensed by the hub, or temperature sensor output signals may be obtained from the hub and transmitted to the user device or backend server to obtain temperature from the temperature sensor output signals.

At block 1704, the processor determines whether there is detected a rapid change in temperature, for example, a change in temperature occurring within a threshold time. If so, the processor outputs an indication of a possible leak at block 1706. A leak of effluent under the ostomy wafer or into the ostomy wafer can cause a rapid rise of temperature—even a near-instantaneous rise in temperature. Thus, detecting such rapid changes in temperature can enable rapid leak detection, which can result in warning the patient on the user device audibly and/or visually. The patient can then address the leak, for example, by changing the ostomy wafer and/or bag. By doing so, the patient can potentially avoid skin irritation and ameliorate a potentially embarrassing situation.

Figures 18A, 18B:
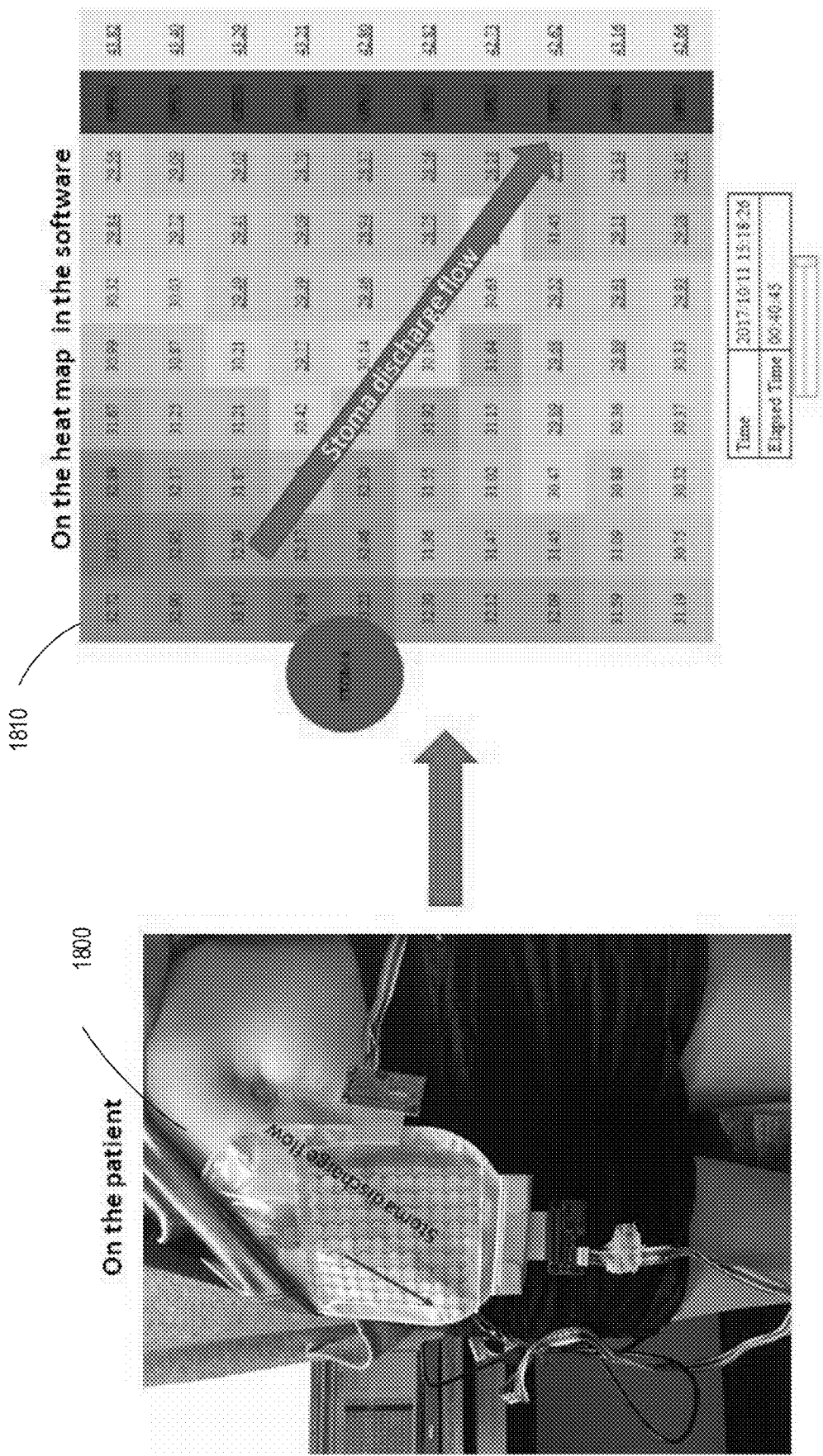
FIG. 18A shows an example device worn by a patient.
FIG. 18B shows an example heat map showing a stoma discharge flow in the device of FIG. 18A.

FIGS. 18A-B shows an example device 1800 worn by a patient and a heat map 1810 showing a stoma discharge flow. The heat map corresponds to an ostomy bag sensor layer, as shown any ostomy sensor bag layer disclosed herein. The discharge flow is represented by an influx of a higher temperature reading across the thermoreceptor map. As effluent flows into a bag, near the top of the bag, the discharge flow moves toward the bottom of the bag. This flow can be tracked by tracking the change in temperature over time in the various rows or columns of the sensor matrix to predict that effluent has entered the bag. As a result, volume of effluent in the bag can be tracked. Further, faster flowing effluent can correspond to liquid and/or gas, while slower flowing effluent can correspond to solid or semi-solid materials. Thus, using a hardware processor to monitor the change in temperature of the sensors over time can indicate the type of effluent emitting from the stoma. Further, since gas can change temperature so quickly, the gas can be detected and its volume excluded from the bag fill calculation.

FIGS. 19 and 20 show example infusions of test materials into the bag and allowing the algorithm to show a heat map. FIG. 19 shows an infusion of heated applesauce at different volumes in a standing position 1900. The volume increasing as a function of the heat dissipated. The thicker apple sauce leaves a greater thermal foot prints on the bag, as the sauce is more viscous. FIG. 20 shows an infusion of water in a standing position 2000 at various volumes from 50 mL up to 350 mL at 50 mL increments. Visual thermal data (alongside the algorithms) can potentially give indication of the position of the patients. This is specifically from the thermistor sheet which can be integrated into the front of the bag to detect the volume inside the bag, as well as other physical parameters such as phase and viscosity. Changing the position from standing to supine, in the case of an ostomy bag for example, results in the orientation of the thermal signature being changed (specifically by rotation). This is because the thermistor sheet is in a fixed position and orientation on the bag and the software is also fixed with respect to a specific orientation of the sheet. As such, the change in the orientation of the patient, by default changes the orientation of the sheets and therefore the thermal signature and hence from the data it is possible to tell a change in position of the patient.

Visual data combined with the power of artificial intelligence, algorithms and software can allow the interpretation of not only output occurrence but also the phase of the output. This is based on the fact that different output types are associated to different viscosities. Liquid, for example, has a low viscosity and can flow. Hence as the liquid crosses the path of thermistors (in the array) and falls into the ostomy bag, its rate of lighting up the thermistors may be faster than a solid or a semi-solid. Solids in contrast may have higher viscosities and may not flow as fast as liquids. This suggests that the rate at which the thermistors light up may be a way to tell the phase of the output. The heat dissipation may also vary with viscosity as may the cooling rate. AI and algorithms such as a neural network model or any other machine learning algorithms, can be developed to be able to differentiate between the different phases. The machine learning algorithms can be trained to recognize a sharp border between thermal foot prints due to the different phases on the heat map. The resolution of the border recognition can be improved with increased number of temperature sensors over the ostomy bag.

The volumetric build-up in the bag can also be seen as a function of greater and greater output with time. Further incremental addition of volume in the bag to the volume that is already present in the bag, can also be differentiated between where the fresh "waste" can be differentiated from waste that was already present in the bag. The heat changes in the thermistor sheet can be used to assess the heat distribution as a function of time with leakage and the on-coming of skin irritation expected to raise the observed temperature around the stoma and alter the heat distribution. Although contributing factors such as humidity and sweat can act to also alter the temperature, reference sensors as well as AI and algorithms may be used differentiate between temperature increases due to background noise (sweat, humidity) and hone in on the active noise (due to sporadic active leakage occurrence and skin inflammation due to active skin irritation).

Figure 21:
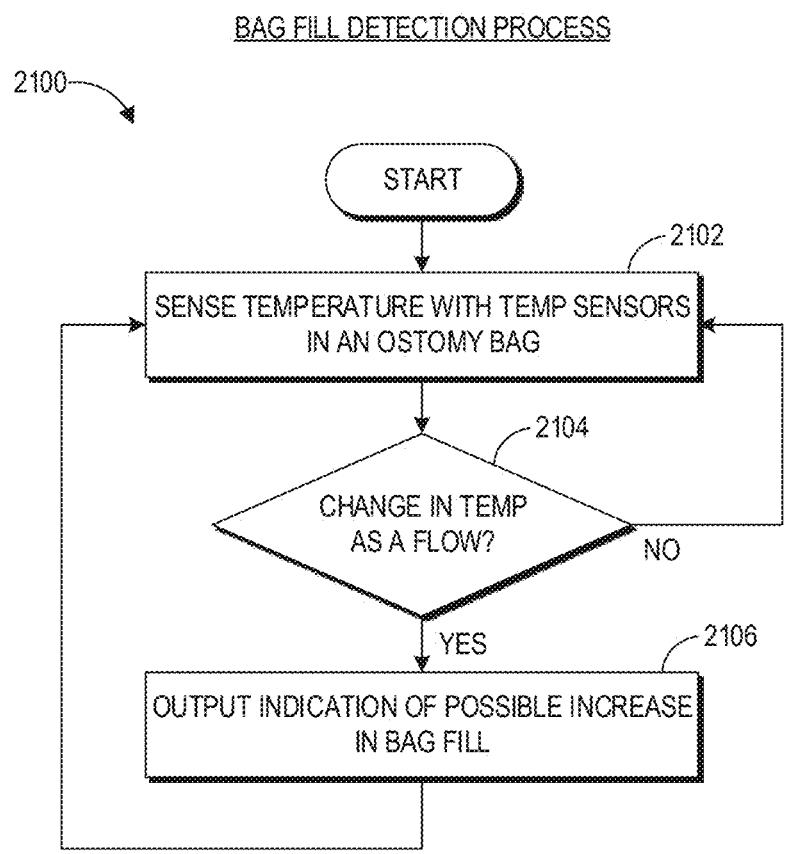
FIG. 21 shows an example ostomy bag fill detection process.

FIG. 21 shows an example bag fill detection process 2100. The process 2100 can be implemented by the hub, user device, or backend server as discussed above. More generally, the process 2100 can be implemented by a hardware processor in any of those or another device.

At block 2102, the hardware processor senses temperature with temperature sensors in an ostomy bag. At block 2104, a change in temperature as a flow is detected. For instance, referring to the preceding figures, the processor can detect the flow of effluent by detecting changing temperatures in different rows or columns of the bag over time. The process 2100 can output at block 2106 an indication of possible increase in bag fill, and/or a warning that the bag may be full.

Figure 43:
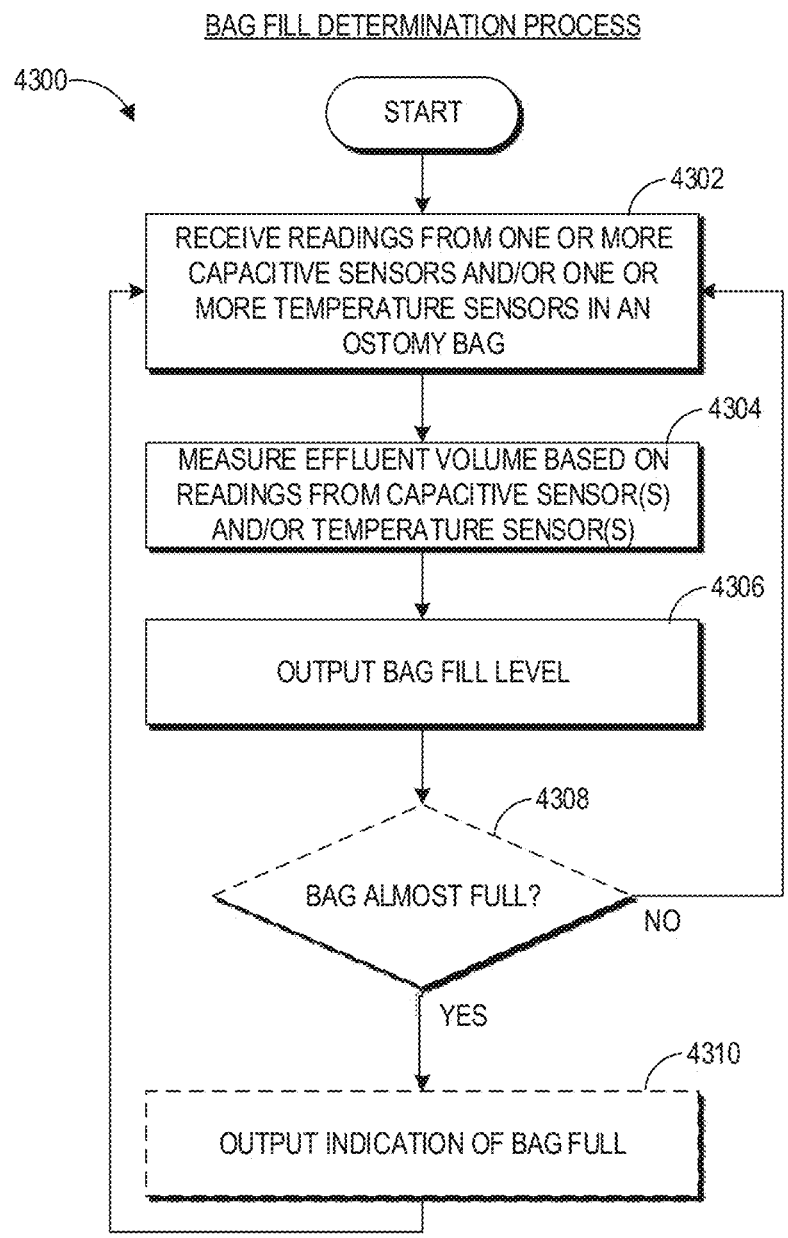
FIG. 43 shows another example ostomy bag fill determination process.

FIG. 43 shows an example bag fill determination process 4300. The process 4300 can be implemented by the hub, user device, or backend server as discussed above. More generally, the process 4300 can be implemented by a hardware processor in any of those or another device.

The process 4300 can begin at block 4302, where the processor receives readings from one or more capacitive sensors and/or one or more temperature sensors described above, such as with respect to FIGS. 37-42D. The readings can include resistance readings of the capacitive and/or temperature sensor(s) from which the processor can calculate the capacitance and/or temperature values, or calculated capacitance and/or temperature values (for example, performed by the electronic components on the ostomy bag).

At block 4304, the processor can measure an effluent volume based on the readings from the capacitive sensor(s) and/or temperature sensor(s). The processor can calculate the effluent volume based solely on changes in the capacitance values, solely on the changes in the temperature values, and/or a combination of changes in the capacitance values and the temperature values (for example, using statistical methods). At block 4306, the processor can output a bag fill level.

At decision block 4308, the processor can also optionally determine whether the bag is full or almost full (for example, at a volume close to the designed capacity, effluent having been detected by the capacitive and/or temperature sensors at certain locations, or others that are disclosed herein). If the bag is full or close to being full, the processor can optionally output a "bag full" indication in block 4310. The outputted indication can be displayed on the user device. If the bag is not full or close to being full, the processor can return to block 4302 to repeat the bag fill determination process 4300.

Figure 47A:
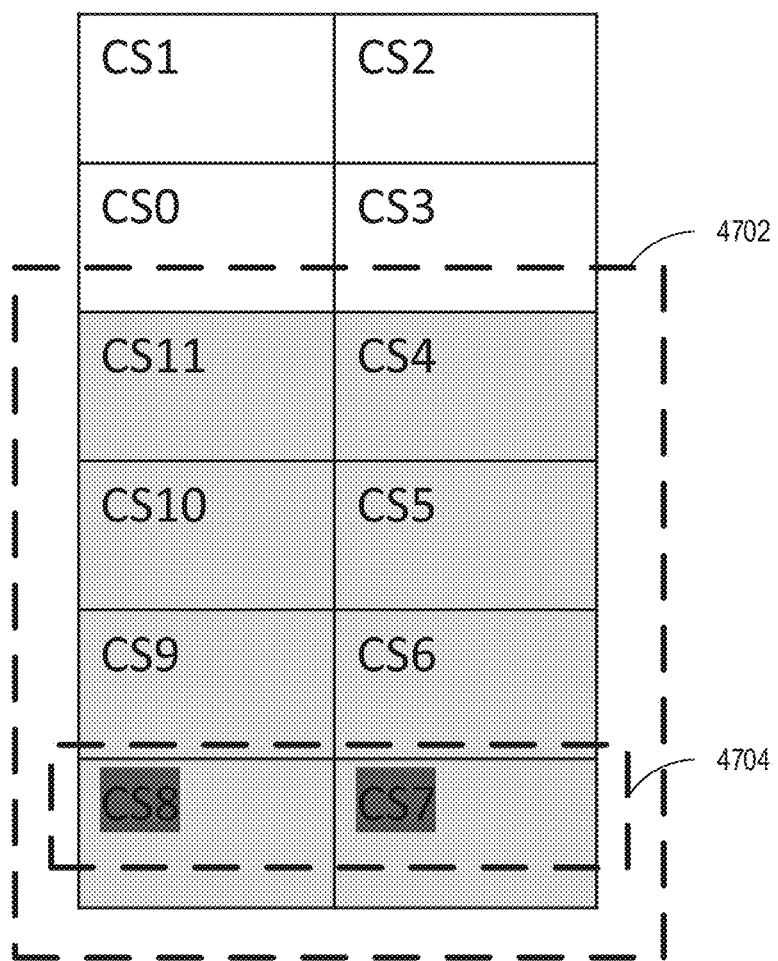
FIG. 47A illustrates schematically a plurality of capacitive sensors on an example ostomy bag.

The smart ostomy bag can also detect the volume/fill inside the bag, such as by using an array of capacitive sensors. At least some of the capacitive sensors on the bag can be used to detect the level of the fill in the bag, which can be converted to the volume of the output. As shown in FIG. 47A, an example ostomy bag may include twelve capacitive sensors, CS0 to CS11 (which may be arranged as shown in FIGS. 37-39B). The capacitive sensors within the dashed line 4702 can be used for level detection.

At least some of the capacitive sensors can also be used to detect draining of the bag. As shown in FIG. 47A, the capacitive sensors within the dashed line 4704, which can be located toward a lower portion of the sensor layer of the ostomy bag, can be used for drain detection. The processor can determine whether the bag is being drained using a first drain criteria $\Sigma_{i=7,8} \Delta CS_i > C_3$, where $CS_i$ are the capacitive sensor readings and $C_3$ is a constant that can be determined empirically, such as based on patient studies data analysis. In some implementations, $C_3$ can be 3. The processor can stop detecting level when the bag is being drained. The processor can also automatically calibrate the capacitive sensors after drain is complete.

Figure 47B:
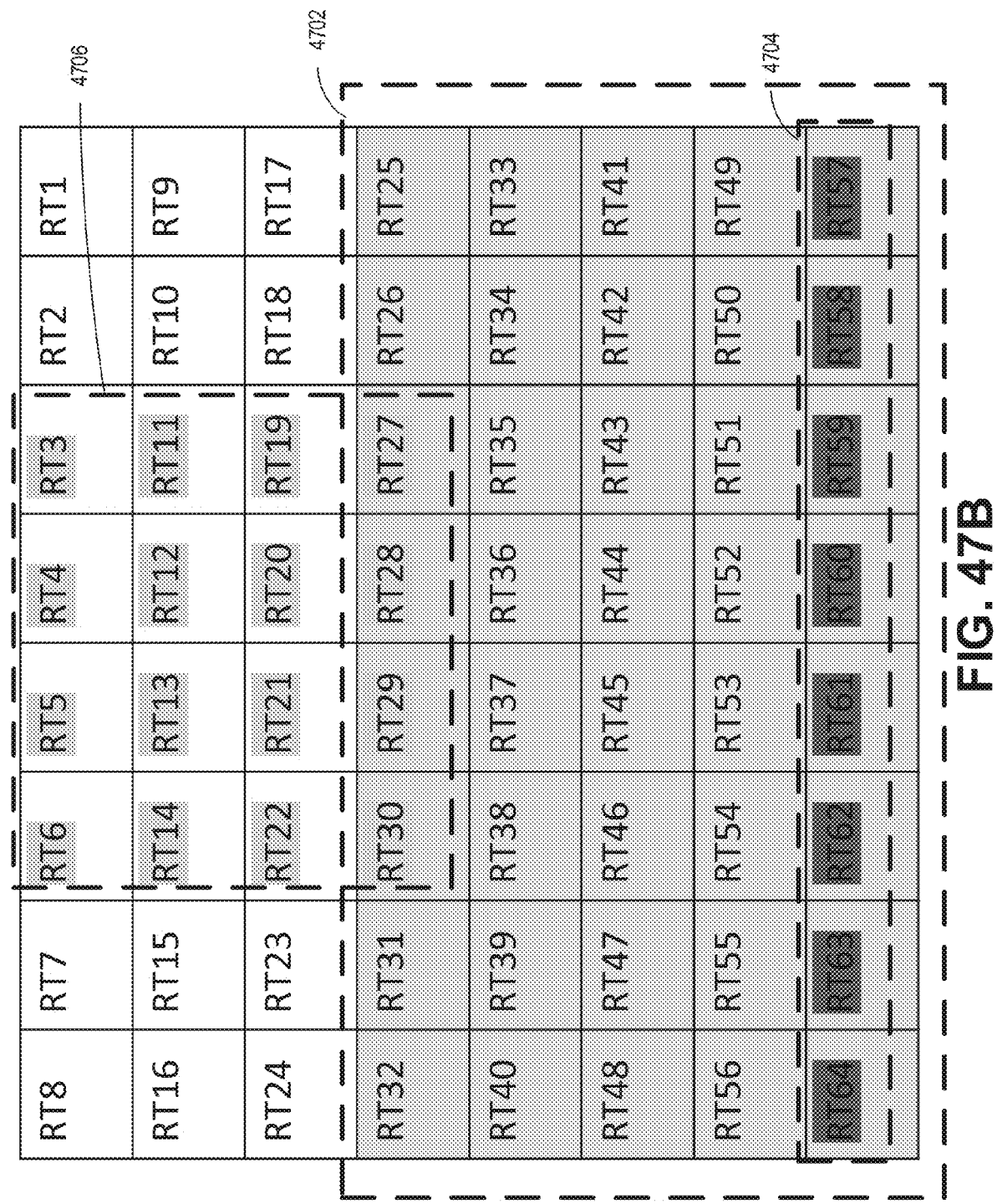
FIG. 47B illustrates schematically a plurality of temperature sensors on an example ostomy bag.

Readings from the temperature sensors can optionally be used in combination with readings from the capacitive sensors in calculating the volume/fill inside the bag and/or draining of the bag. Capacitive sensors may be better at detecting level as capacitive sensors may be more resistant to noise, such as due to the residue problem, than temperature sensors. As shown in FIG. 47B, an example ostomy bag may include sixty-four temperature sensors, RT1 to RT64 (which may be arranged as shown in FIGS. 36 and 38-39B). The temperature sensors within the dashed line 4702 can be used for level detection. The temperature sensors within the dashed line 4704, which can be located toward a lower portion of the sensor layer of the ostomy bag, can be used for drain detection. The processor can determine whether the bag is being drained using a second drain criteria $$\sum_{i=57}^{64} \Delta T_i < C_4,$$

where $T_i$ are the temperature sensor readings and $C_4$ is a constant that can be determined empirically, such as based on patient studies data analysis. In some implementations, $C_4$ can be −15. The processor can use the first and/or second drain criteria in determining whether the bag is being drained.

At least some of the temperature sensors can also be used to detect whether the bag is being worn by the patient and/or whether there is infusion into the bag. As shown in FIG. 47B, the temperature sensors within the dashed line 4706, which can be located toward an upper portion of the sensor layer of the ostomy bag, can be used for infusion detection. The temperature sensors within the dashed line 4706 can be located near or in front of the stoma. The processor can determine whether the bag is on the patient's body using an on-body criteria $$\sum_{\substack{i=3+8n \\ n=0,1,2,3}}^{6+8n} T_i > C_2,$$

where $T_i$ are the temperature sensor readings and $C_2$ is a constant that can be determined empirically, such as based on patient studies data analysis. In some implementations, $C_2$ can be 525. The processor can determine whether the bag is on the patient's body using an infusion criteria $$\sum_{\substack{i=3+8n \\ n=0,1,2,3}}^{6+8n} \Delta T_i > C_1,$$

where $T_i$ are the temperature sensor readings and $C_1$ is a constant that can be determined empirically, such as based on patient studies data analysis. In some implementations, $C_1$ can be 3.5. Detecting onset of infusion when the patient is wearing the bag can trigger the capacitive sensors (and also optionally the temperature sensors) to begin level detection. Performing level detection after infusion is detected can reduce false readings as level readings caused by increase in the output content in the ostomy bag. For example, false readings can be caused by a variety of reasons, such as due to residue on the ostomy bag inner surface, temporary pressure change, or otherwise.

Figure 48:
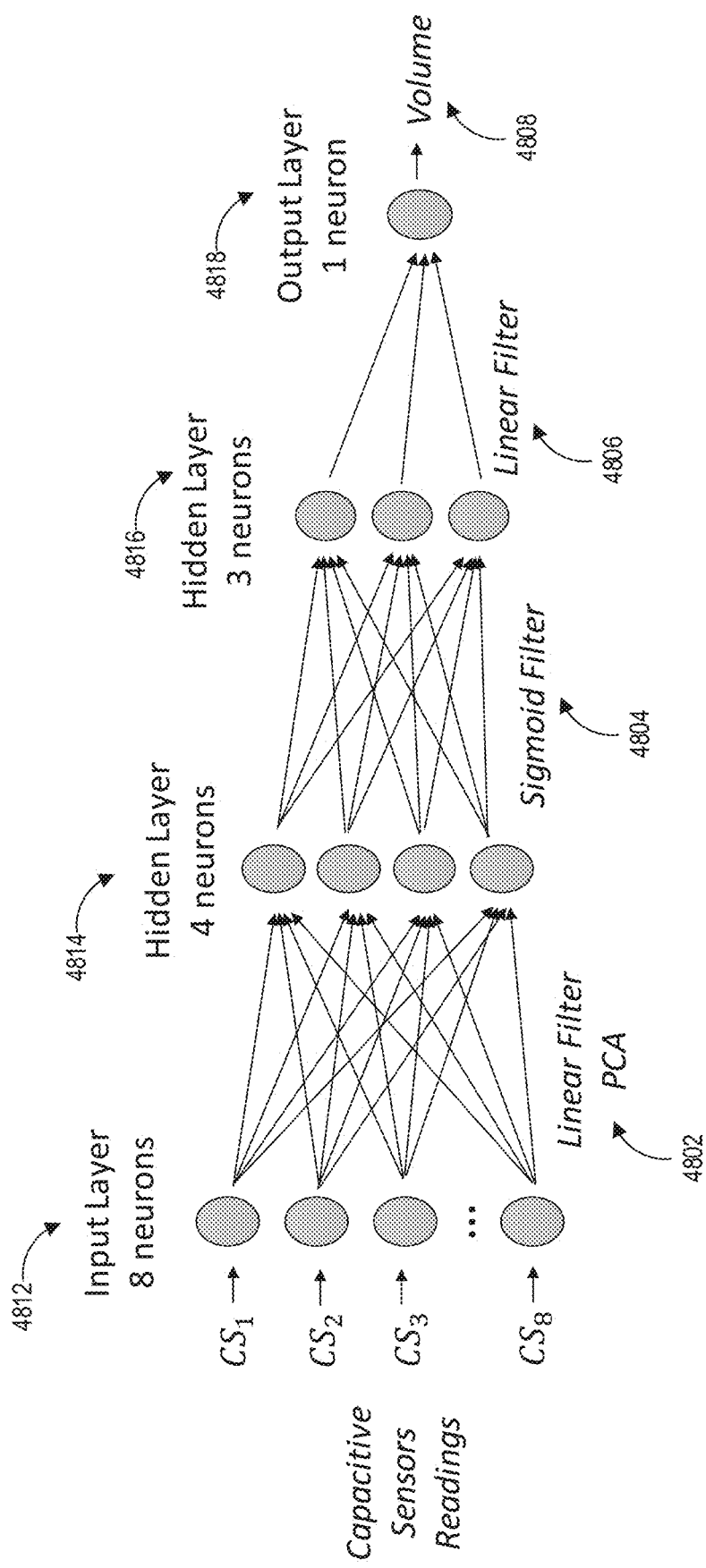
FIG. 48 illustrates schematically an example neural network model for calculating output volume of an ostomy bag.

Machine learning can be used to train the computer to detect the level of the fill in the bag and thereby to predict an actual output based on a set of data from the capacitive sensors. Examples of machine learning modes can include neural network, regression analysis, and/or the like. FIG. 48 illustrates an example neural network model for calculating the volume of the output in the bag. Although the illustrated example uses only capacitive sensor readings, such as readings from eight capacitive sensors, which can be the eight capacitive sensors within the dashed line 4702 in FIG. 47A, readings from the temperature sensors, such as those within the dashed line 4702 in FIG. 47B can also be used in the volume calculation. Resilient backpropagation (RPROP) algorithm can be used for supervised training of feedforward artificial neural network (multilayer perceptron). The neural network model can employ multiplayer perceptron architecture. As shown in FIG. 48, Principal Component Analysis (PCA) 4802 can be applied to the capacitive sensors data in the input layer 4812 to derive linearly uncorrelated variables (principal components) and decrease dimensionality from eight to four. A sigmoid filter 4804 can be applied to the hidden layer of four neurons 4814 obtained from the application of the PCA to decrease dimensionality from four to three. A linear filter 4806 can be applied to the hidden layer of three neurons 4816 to derive an output layer of one neuron 4818, which can be used to determine the value of the volume 4808.

As each capacitive sensor may be different, calibration of each capacitive sensor may be performed to get the baseline value of each capacitive sensor. Each capacitive sensor may have its own calibration values. Calibration can be done after the first measurements are done when the patient puts on the bag for the first time. The timing of calibration can reduce the effect of moisture from the stoma, which can cause baseline drift of the capacitive sensor when the patient puts on the bag for the first time. The on-bag detection described above can also be used to inform the processor to take a first measurement and then calibrate the capacitive sensors. The output residue on the ostomy bag can also result in capacitive sensors baseline drifting. FIGS. 49A-49B illustrate capacitive sensors readings 4900 after the first measurement is taken and after the bag is drained. As shown, at least four readings of the capacitive sensors, which are bounded by dashed lines 4902, have shifted their baseline values between the first measurement (when the bag is empty) and after the bag is drained (and therefore also empty). Recalibration of each capacitive sensor can be performed to reduce the baseline drifting. Recalibration can be performed after each drain and/or before the first infusion. The drain detection algorithm described above can be used to determine when recalibration is needed.

Figure 50:
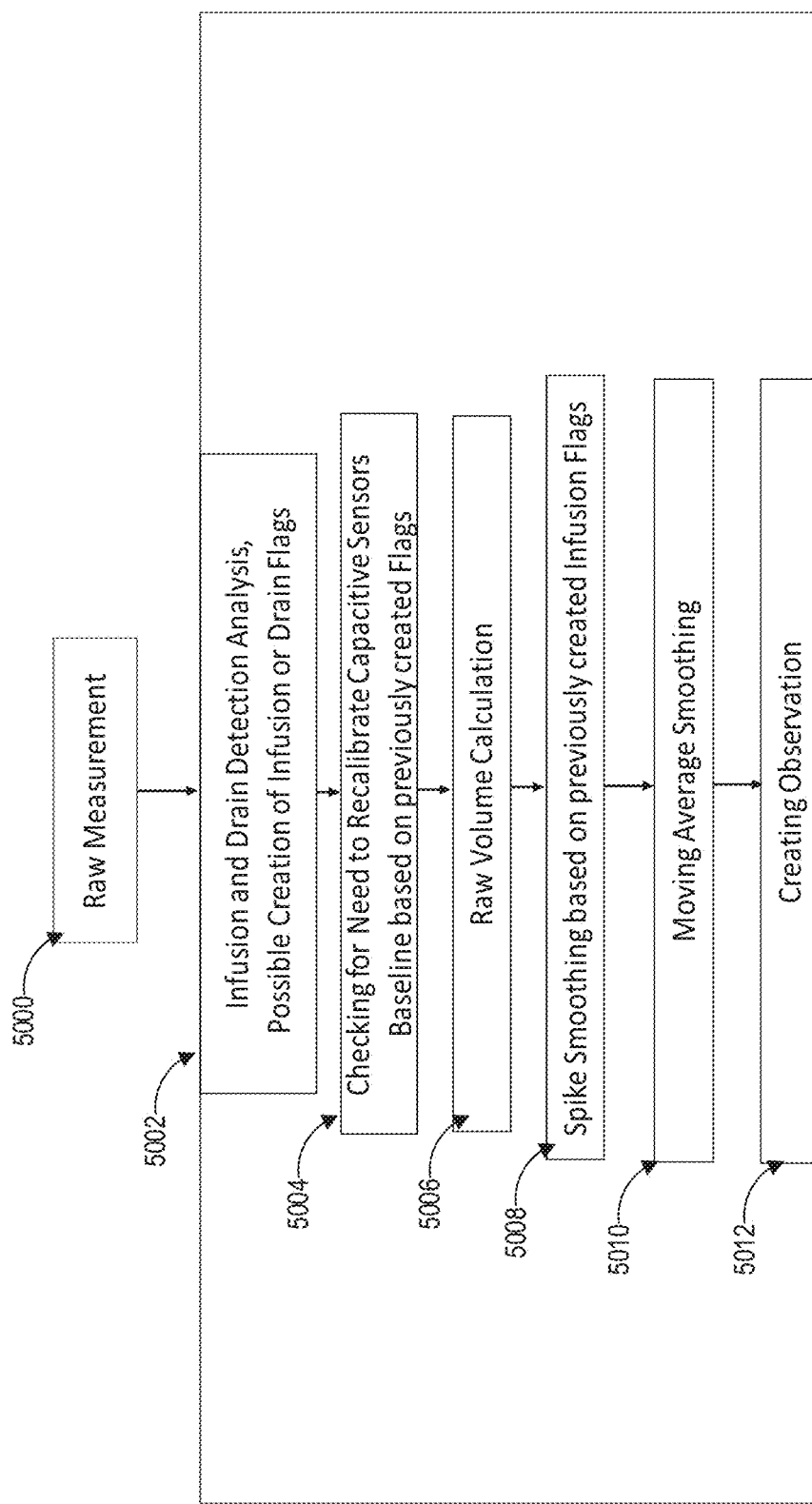
FIG. 50 illustrates example algorithm logics for detecting infusion, drain, and output of an ostomy bag using capacitive and temperature sensors.

FIG. 50 illustrates certain algorithm logics used in volume calculation. When raw measurements 5000 are obtained from the sensors, which can be the capacitive sensors and/or temperature sensors described herein, the processor can perform the infusion detection and/or drain detection analysis 5002, such as using the criteria described above. The processor can optionally create infusion and/or drain flags. The processor can check for need to calibrate or recalibrate the capacitive sensors baseline 5004 based on the previously created flags, such as on-bag detection, drain detection, and/or infusion detection flags. After performing any necessary calibration or recalibration, the processor can perform a raw volume calculation 5006. As described above, the raw volume calculation can be performed using a variety of machine learning tools, such as the neural network model shown in FIG. 48. The processor can perform spike smoothing based on the previously created flags, such as infusion and/or drain detection flags 5008. Certain logics derived from clinical observations can also be used for spike smoothing. For example, a spike in volume calculation at a rate exceeding any possible infusion rate is likely not caused by an increase in output volume. In some implementations, the spikes can be caused by patient movements or sudden pressure change. The smoothing can be performed using a variety of ways, such as by applying a low pass filter, a median filter, or otherwise. The processor can also perform moving averages smoothing 5010 to improve accuracy of the volume calculation before outputting an observation of the volume calculation 5012.

Example User Interfaces

Figure 22:
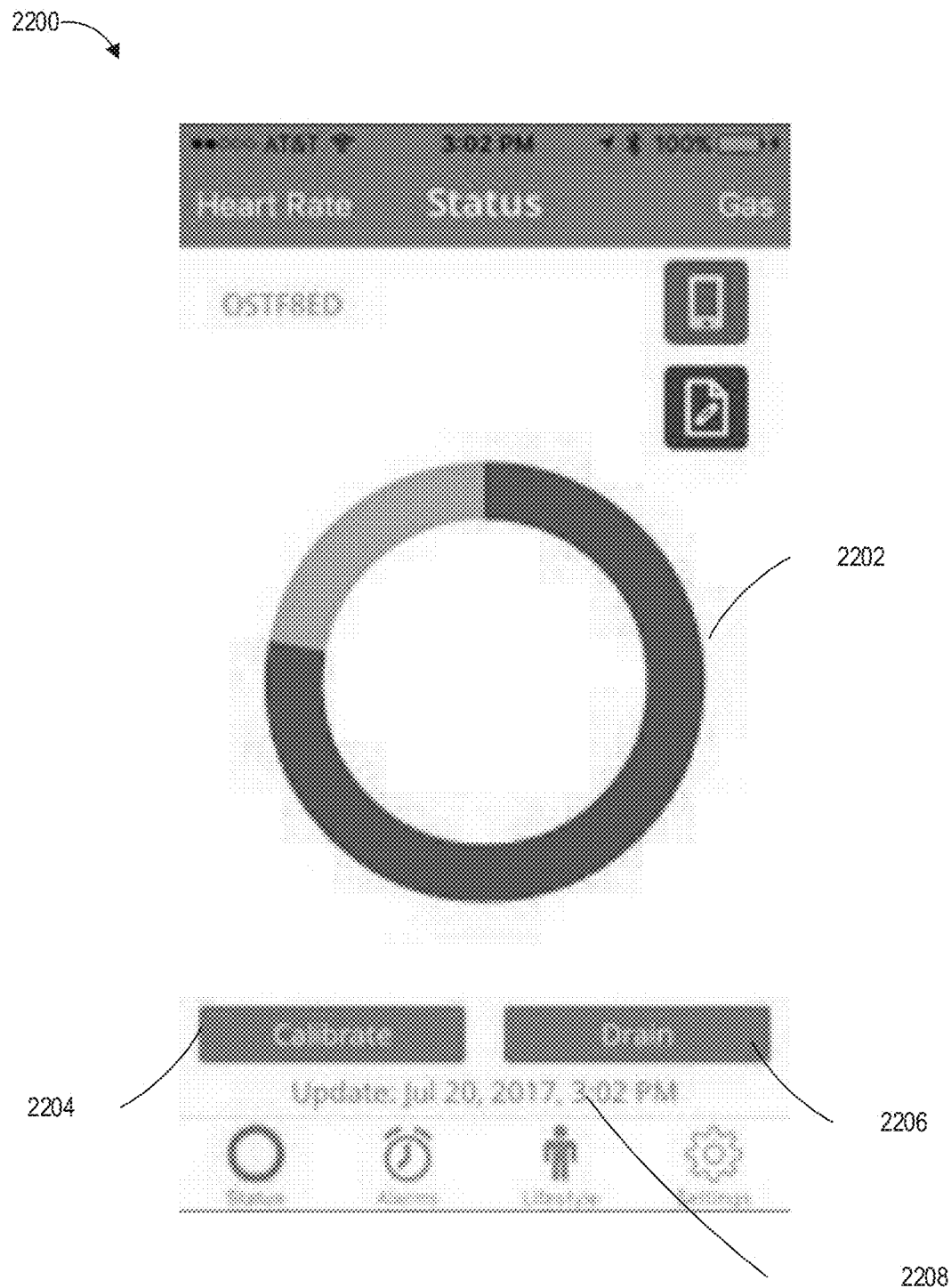
FIG. 22 shows an example user interface for a "Status Screen" of a patient application in electrical communication with an electronic hub of an ostomy bag.

FIG. 22 shows an example user interface for a "Status Screen" 2200 or "Alfred Alert." The Status Screen 2200 can display the current volume of the user's bag. In this example, there is a volume tracking circle 2202, a calibration button 2204, a drain button 2206, and an update tracker 2208. The volume tracking feature can be achieved through Apple's native iOS library CoreBluetooth or another personal device's equivalent native library. CoreBluetooth is the library responsible for the communication between the iOS device and the sensor device. The app can receive Bluetooth packets ranging from 7 to 11 bytes. The application can perform volume bag fill tracking using the process 2100 of FIG. 21. Alternatively, the application can perform the bag fill tracking algorithm based on data received from a resistance sensor, rather than or in addition to a temperature sensor array. The application can also perform bag fill and/or volume calculation based on a plurality of capacitive sensors and/or a plurality of temperature sensors as described above with reference to FIGS. 47A-50.

In the temperature and capacitance examples, the application can convert readings from the temperature and/or capacitive sensors to volume using the algorithms disclosed herein. As described above, the controller of the ostomy device can perform drain detection and/or calibrate or recalibrate the sensors based on detection of drain, infusion, and likewise. Additionally, the user can manually instruct the controller of the ostomy device to calibrate the sensors by pressing the calibration button 2204, and/or inform the controller that the bag is empty by pressing the drain button 2206.

The user device can pair to the sensor device under the pretense that the device is the master and the sensor is the slave. The device may send specific UUID's to the sensor to be able to read its data. This may be done after the device pairs to the sensor. When the user disconnects from the device, the application may call the DisconnectPeripheral method from CoreBluetooth or the native library. This can handle disconnection as well as unpairing the device. If the sensor device comes out of range with the user device, it may disconnect but not unpair. Once the device is back in range, the device may repair with the sensor. This is accomplished using the following method from the CoreBluetooth or native library framework.

Figure 23:
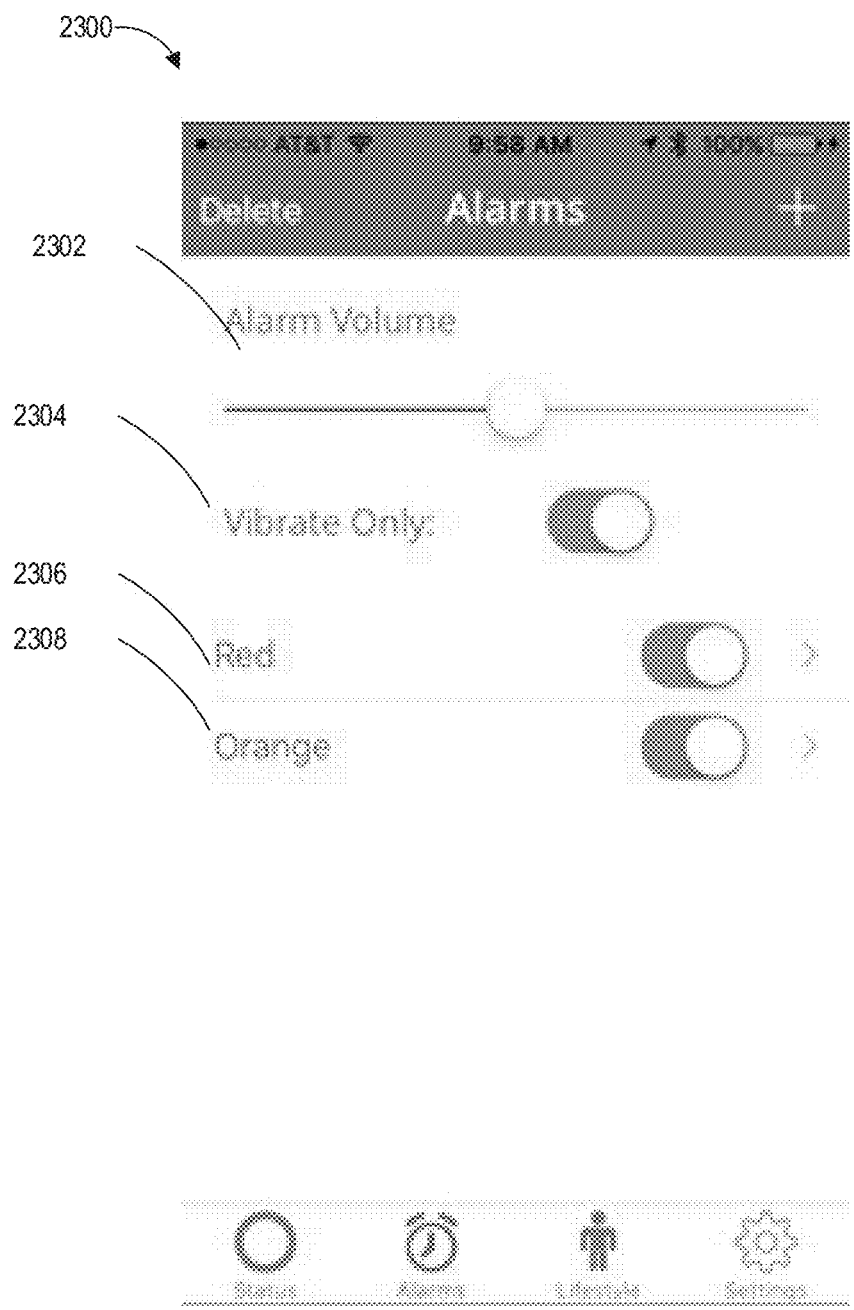
FIG. 23 shows an example alarm user interface of the patient application.

FIG. 23 shows an example alarm user interface 2300. In this example, there is an alarm volume slider 2302, a vibration mode toggle 2304, and a red toggle 2306, and an orange toggle 2308. Users can set alarms for different fill levels of the bag. When each measurement is taken and recorded, the application may check whether the measurement should trigger any of the current alarms. If measurement should trigger one or more alarms, the application may present notification(s) to the user that one of their alarms has been triggered. Additional alarm features could include alerts to manually check the bag, to replace reusable hubs, to remind a user to not be in a supine position, and the like.

Figure 24:
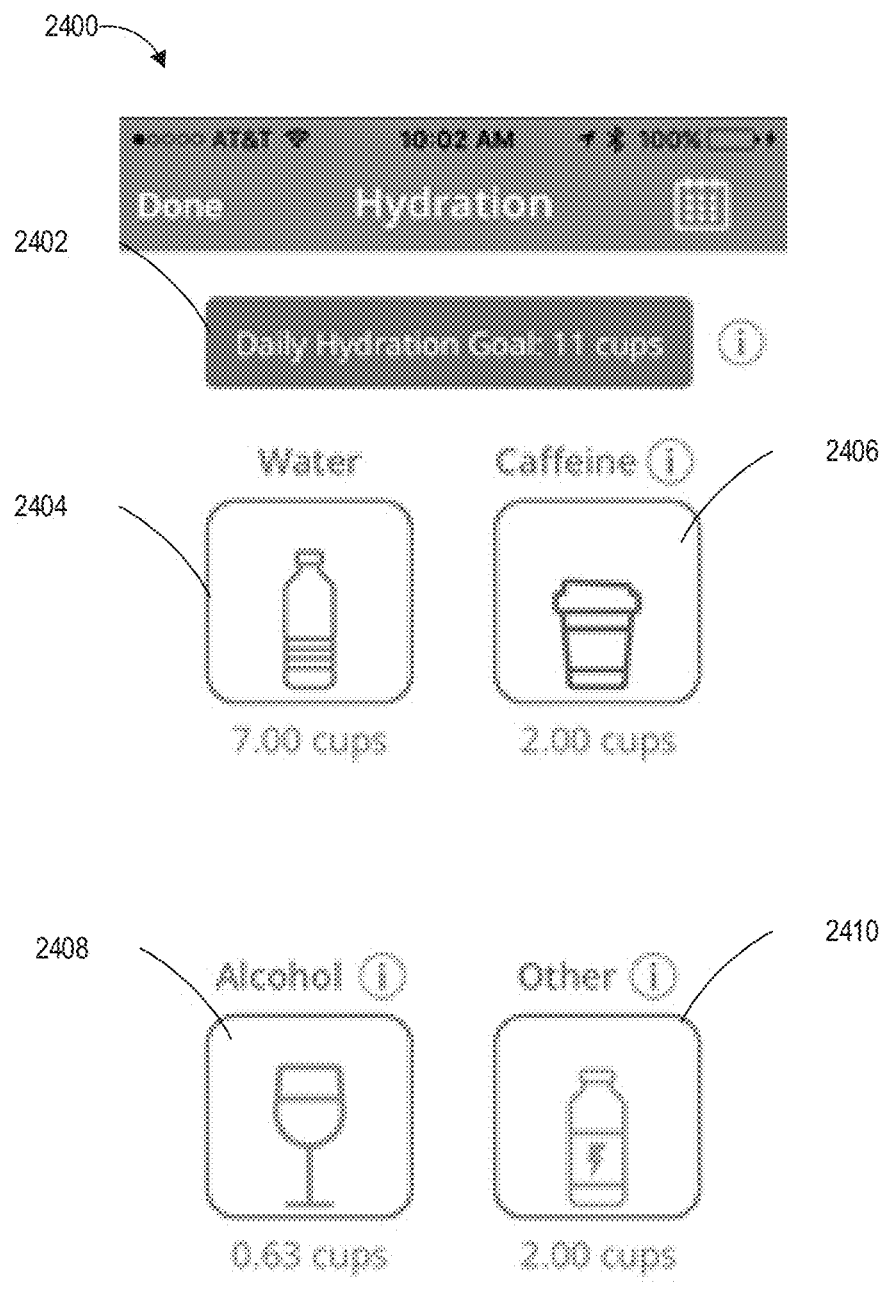
FIG. 24 shows an example user interface of a hydration tracker feedback feature of the patient application.
Figure 25:
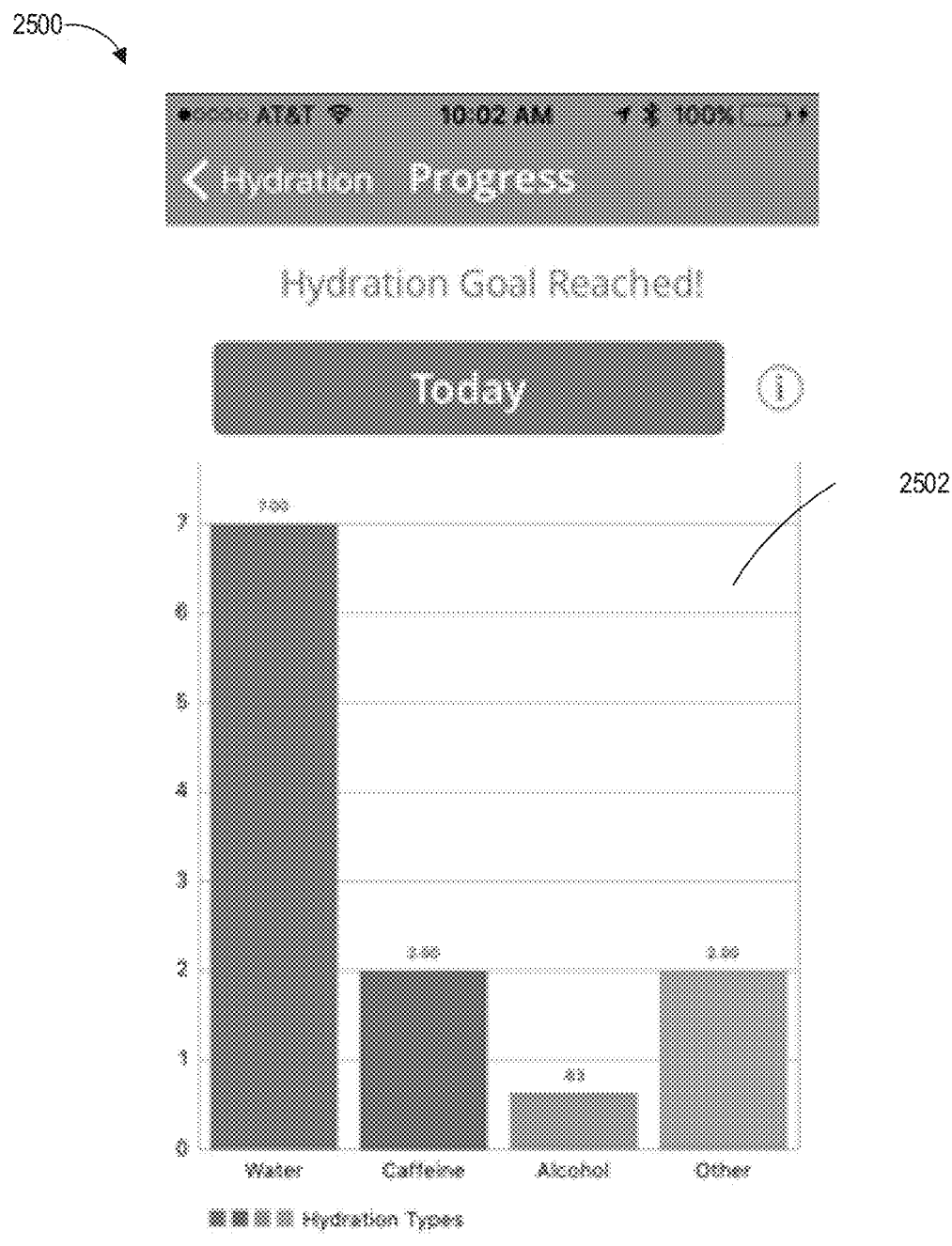
FIG. 25 show a user interface of an example hydration progress screen of the patient application.

The application may also have an additional feedback feature. For example, the additional feedback feature may be called the "Alfred Connect." This feature provides additional feedback to the user. This feature may use the same functionality above. The additional feedback feature can have multiple Bluetooth sensors connected to multiple patients at once. This can be achieved by assigning each patient and sensor a unique ID for pairing. FIG. 24 shows an example user interface of an additional hydration tracker 2400 feedback feature. The example hydration tracker 2400 has a daily hydration goal counter 2402, a water tracker 2404, a caffeine beverage tracker 2406, an alcoholic beverage tracker 2408, and another beverage tracker 2410. Additional types of liquid intakes could also be used such as soup, soda, sports drinks, and etc. FIG. 25 show a user interface of an example hydration progress screen 2500. The example hydration progress screen 2500 shows whether a user's hydration goal is met. The example screen 2500 can display one or more bar graphs 2502 to track different types of liquid intake the user has ingested. The hydration summary can be retrieved by using an API that fetches the user's hydration data from the backend server. The data retrieval can be from a selected date, which can be displayed at the top of the screen, to a current date. The hydration feature can also be used in tandem with the alarm page 2300 to remind the user to intake liquid throughout the day or notify when the user needs to ingest more liquid or electrolytes.

Figure 26A:
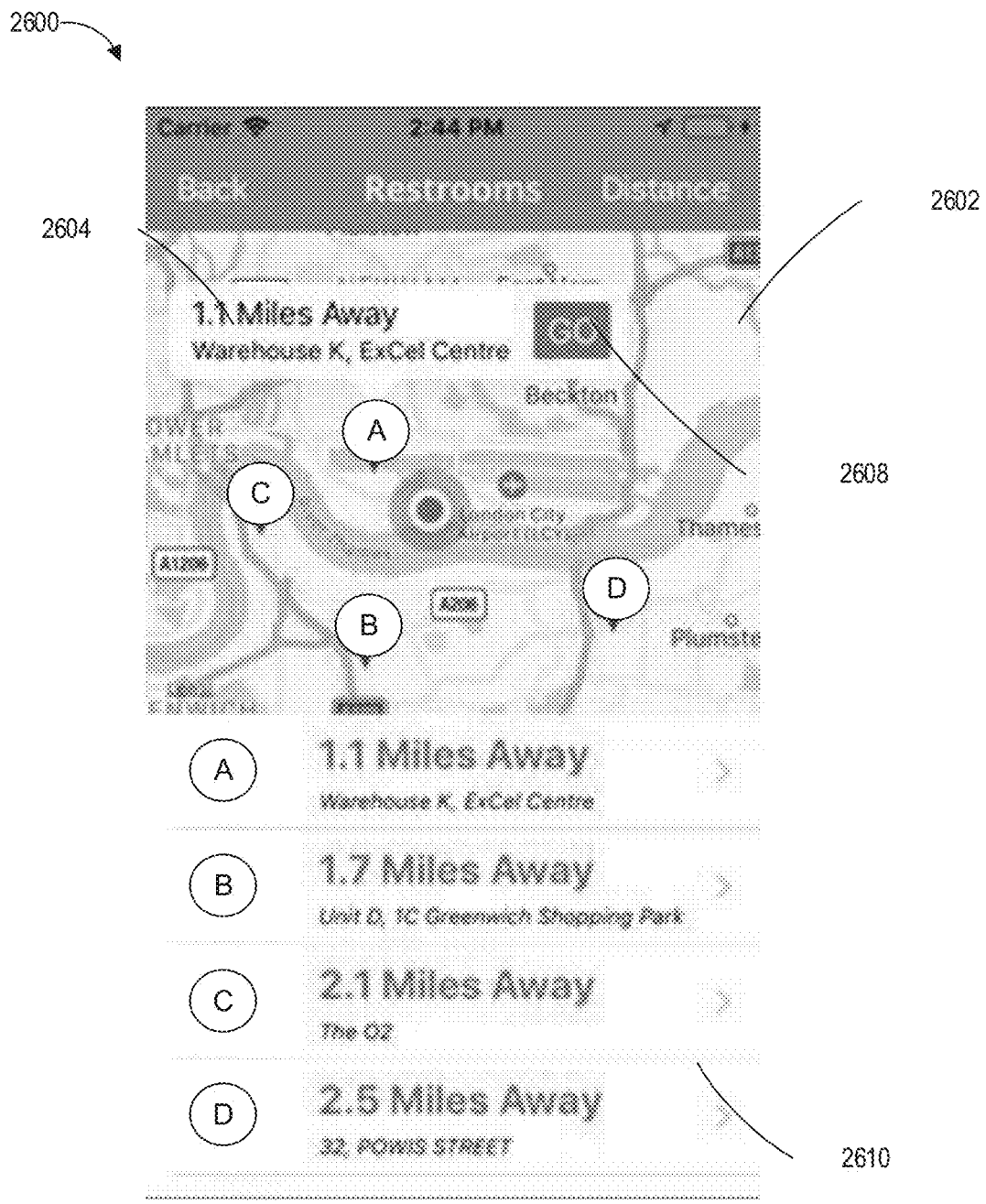
FIG. 26A shows an example of an additional user interface of a restroom locator feature of the patient application.

FIG. 26A shows an example of an additional user interface of a restroom locator 2600. This feature shows the nearest restrooms for the user so he or she may empty the ostomy bag. The user interface of the application can display a map 2602. The map 2602 showing the nearest restrooms 2604 may also provide directions, such as with a "GO" button 2608 or a button with similar instructions. When the user taps the "GO" button 2604 or tap on one of the locations 2610 in the table view, the user can be directed to the maps app with the restroom location set as their desired destination. The restroom locator can work as follows: 1) the backend server can contain a data table with all the restroom locations and/or their coordinates and cross streets. 2) The app retrieves a set amount of restroom locations based on the desired radius of the user. This is achieved through an API that returns restroom locations based on the radius and coordinates of the user. 3) The distance between the user's location and each restroom is calculated using an algorithm function.

Figure 26B:
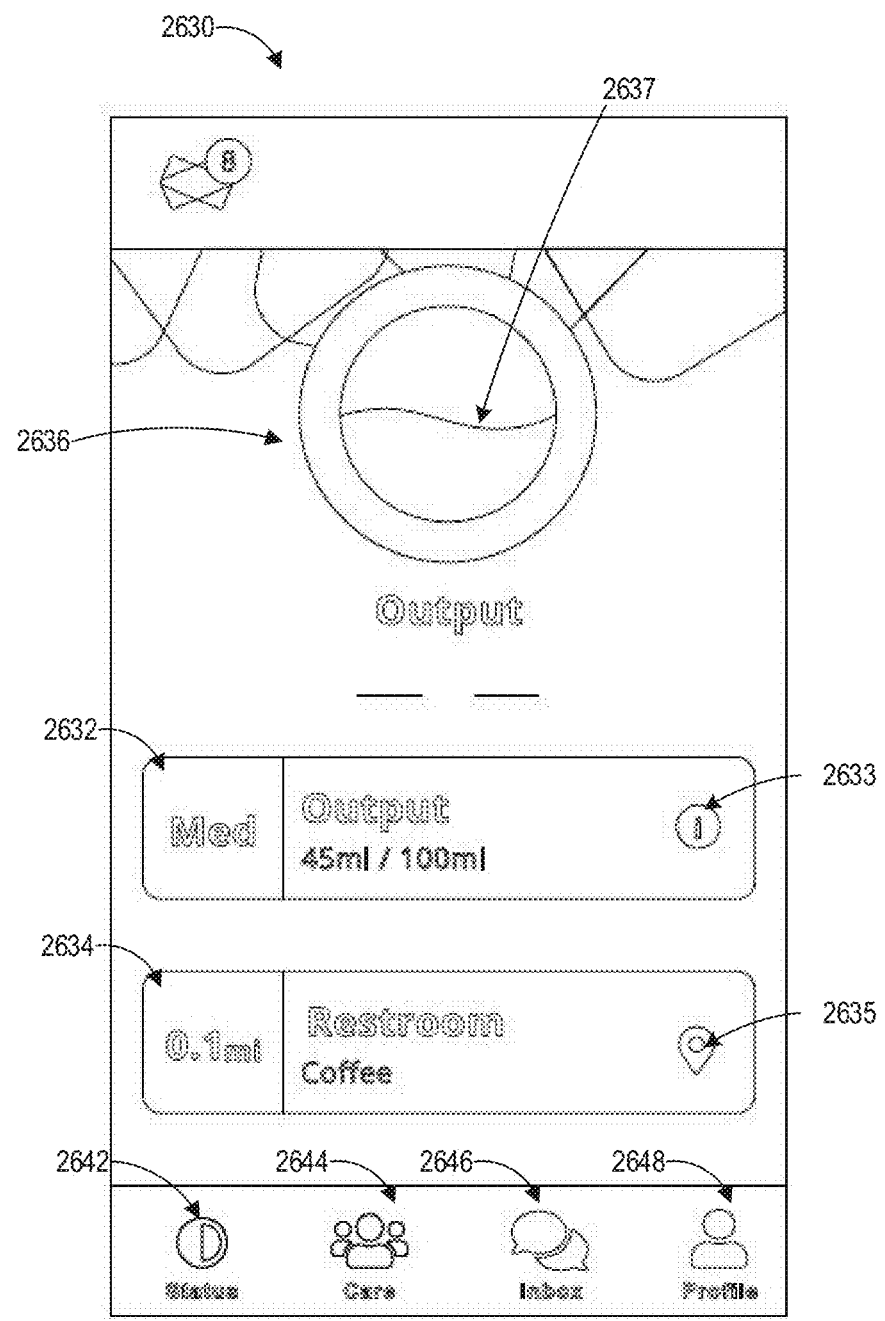
FIGS. 26B-26C show examples of a user interface illustrating output and restroom location feature of the patient.
Figure 26C:
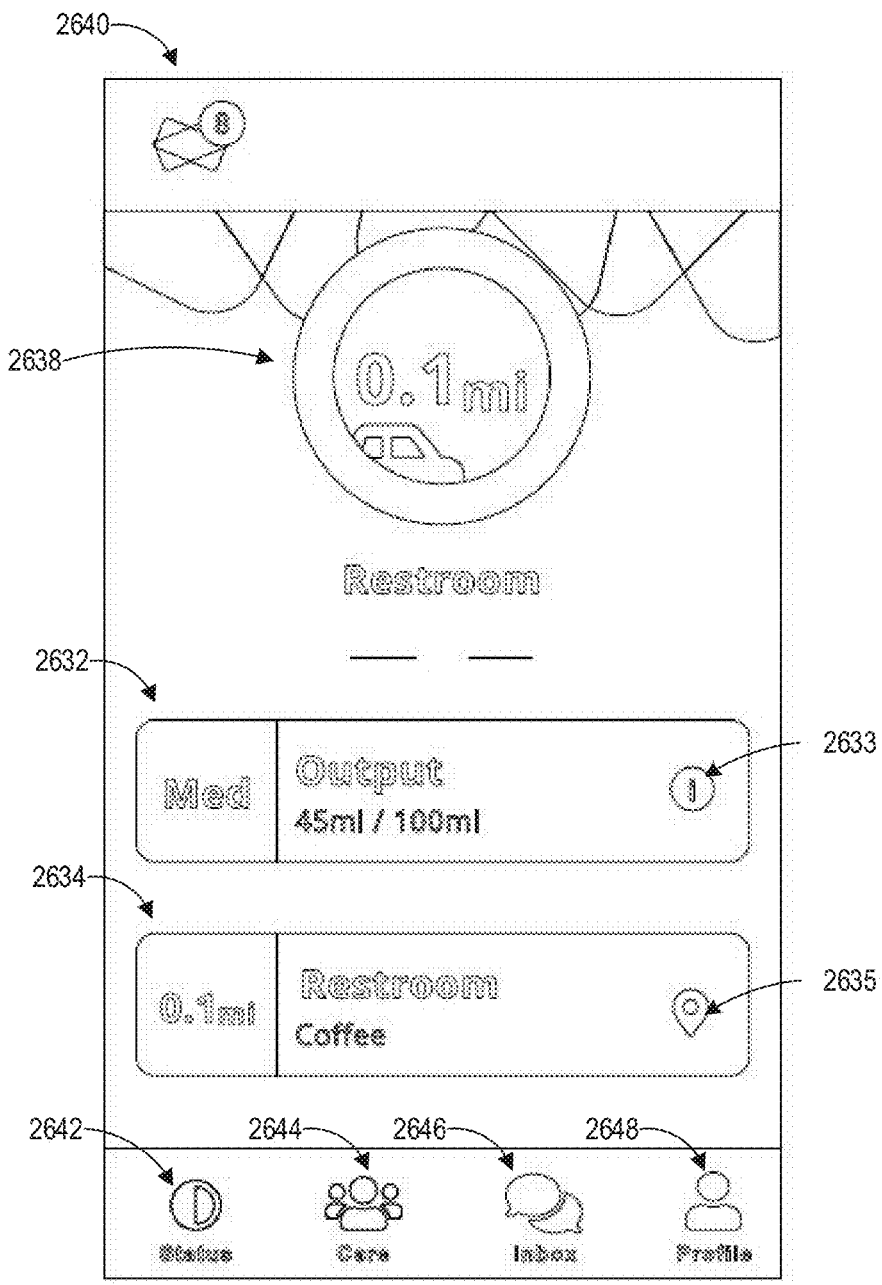
Figure 26D:
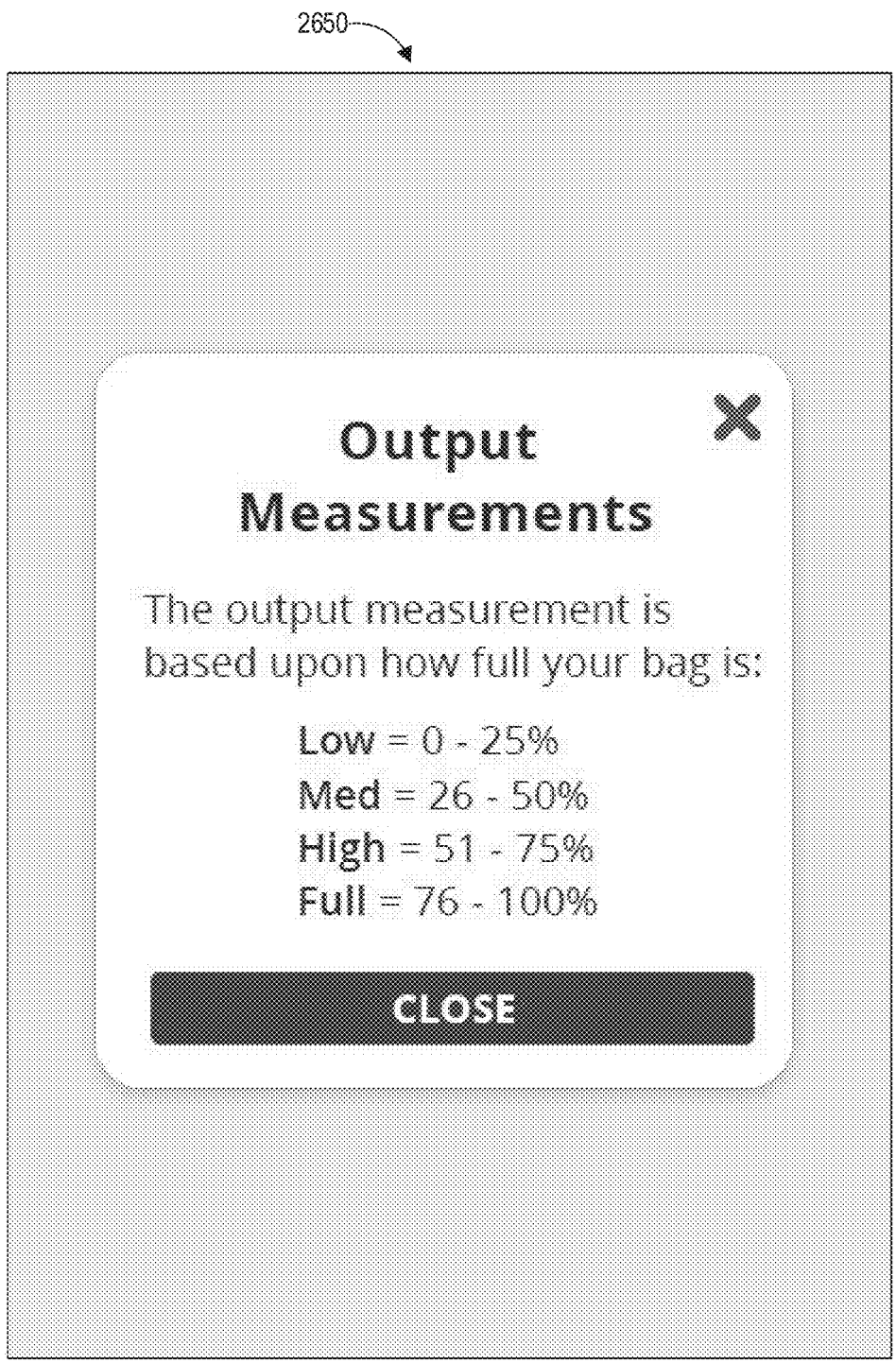
FIG. 26D illustrates an example user interface illustrating additional information relating to output.
Figure 26E:
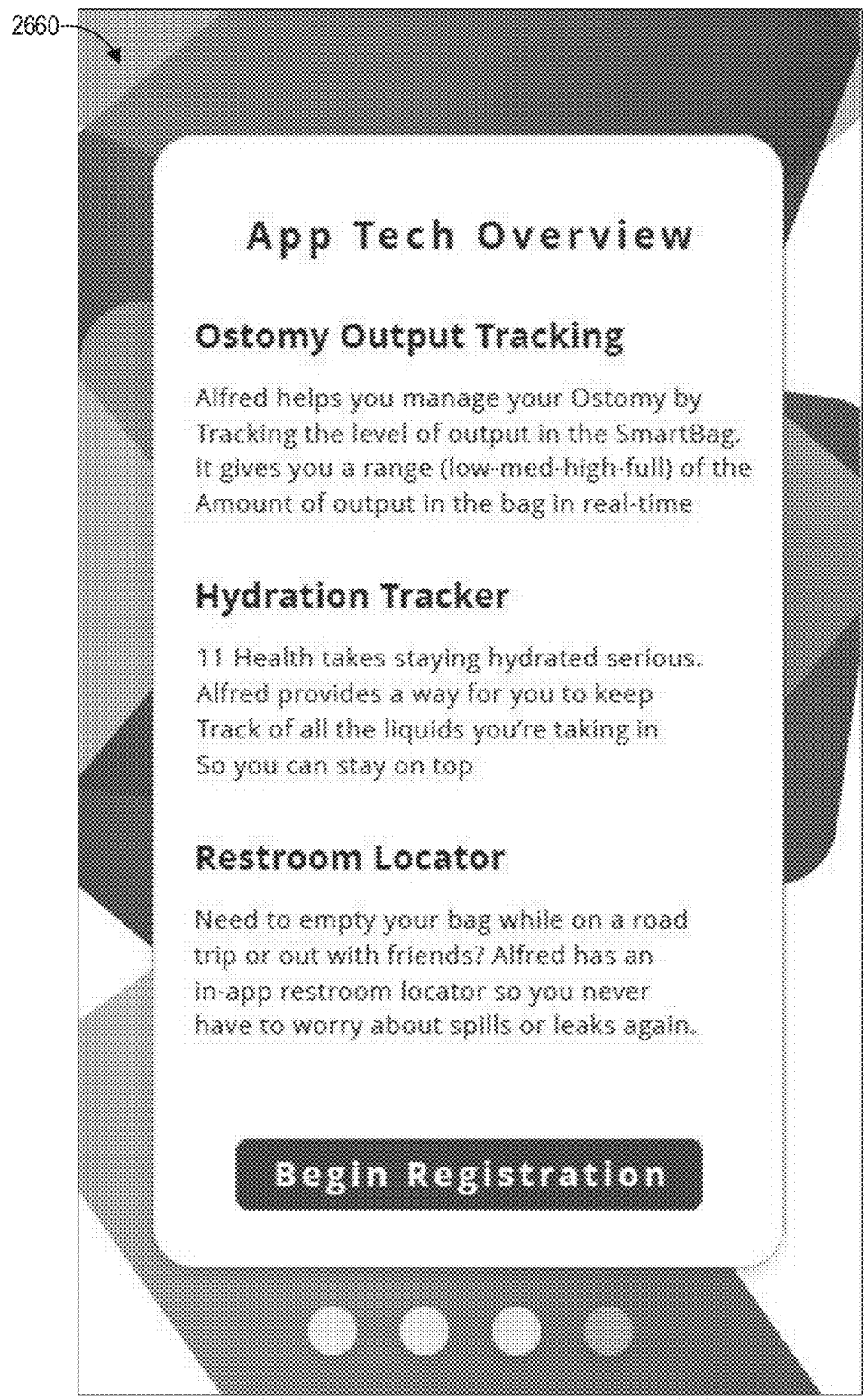
FIG. 26E illustrates an example user interface illustrating an application overview display page.

FIGS. 26B-26C show example user interfaces 2360, 2640 displaying both estimated stoma output 2632 and restroom location 2634. The user can toggle between an animated graphic indicator displaying output 2636 (FIG. 26B) and an animated graphic indicator displaying distance to a nearby restroom 2638 (FIG. 26C). The animated graphic indicator for output 2636 can include a circle with a changing fill level 2637 to visually inform the user about an estimate volume of the bag. The user can tap an information icon 2633 in FIG. 26B to be directed to an output measurement user interface 2650, such as shown in FIG. 26D, to obtain more information relating to the output. The distance value in the animated graphic indicator for distance to a restroom 2638 can change as the user moves toward or away from the target restroom. The user can also click the location icon 2635 to be taken to a map interface, such as shown in FIG. 26A. The user interfaces also can include other icons, such as "Status" 2642 for checking the state of the connected ostomy bag, "Care" 2644 for connecting with a medical professional, "Inbox" 2646 for connecting with the ostomy bag user community, and/or "Profile" 2648 to set up a user profile. A user may be able to change the bag size by accessing "Profile." The name of these icons are provided as examples and are not limiting. Other icons can be included in the user interface. The user interface examples in FIGS. 26B-26C can also optionally include a hydration tracker so that the application can provide tracking of the output, the restroom locator, and the hydration status, such as explained in an application overview display page 2660 shown in FIG. 26E.

Each of the example user interfaces shown can include one or more user interface controls that can be selected by a user, for example, using a browser or other application software (such as a mobile application). Thus, each of the user interfaces shown may be output for presentation by electronic hardware as graphical user interfaces, which may optionally include a browser or any other application software installed thereon that outputs the user interfaces.

The user interface controls shown are merely illustrative examples and can be varied. For instance, any of the user interface controls shown may be substituted with other types of user interface controls that provide the same or similar functionality. Some examples of user interface controls that may be used include buttons, dropdown boxes, select boxes, text boxes or text fields, checkboxes, radio buttons, toggles, breadcrumbs (e.g., identifying a page or interface that is displayed), sliders, search fields, pagination controls, tags, icons, tooltips, progress bars, notifications, message boxes, image carousels, modal windows (such as pop-ups), date and/or time pickers, accordions (e.g., a vertically stacked list with show/hide functionality), and the like. Additional user interface controls not listed here may be used.

Further, user interface controls may be combined or divided into other sets of user interface controls such that similar functionality or the same functionality may be provided with very different looking user interfaces. Moreover, each of the user interface controls may be selected by a user using one or more input options, such as a mouse, touch screen input (e.g., finger or pen), or keyboard input, among other user interface input options. Although each of these user interfaces are shown implemented in a mobile device, the user interfaces or similar user interfaces can be output by any computing device, examples of which are described above.

Thermal Imaging Examples

As described above (for example, with respect to FIGS. 1 and 2), the temperature sensors in the ostomy wafer and/or the ostomy bag can be infrared (IR) temperature sensors, which may be thermal imaging sensors or infrared thermometers. IR temperature sensors can provide temperature outputs similar to the thermistors described above. Thus, any of the algorithms described herein for analyzing temperature output from thermistors or other temperature sensors can apply to IR temperature sensors. Thermal imaging using IR temperature sensors, for instance, has a potential advantage over thermistors in that no contact may be required to measure temperature with a thermal imaging sensor. Thus, if an ostomy wafer peels away from the skin, an IR temperature sensor in the ostomy wafer may still be able to detect temperature of the skin.

Example output of IR temperature sensors can be conceptualized by analyzing the example output of a test thermal imaging camera, as shown in FIGS. 27-32. In FIG.

27, a test setup 2700 of an ostomy bag 2720 using a thermal imaging camera 2730 is shown. The ostomy bag 2720 is shown attached to a dummy 2722, which can be filled from the back (not shown) with food or liquid to cause that food or liquid to enter the ostomy bag 2720. The thermal imaging camera 2730 takes a thermal image of the ostomy bag 2720 to identify temperature changes in the bag as food or liquid enters the bag and as that food or liquid remains in the bag over time. The test setup 2700 shown can be used to validate the use of temperature sensors in an ostomy bag.

Figure 28:
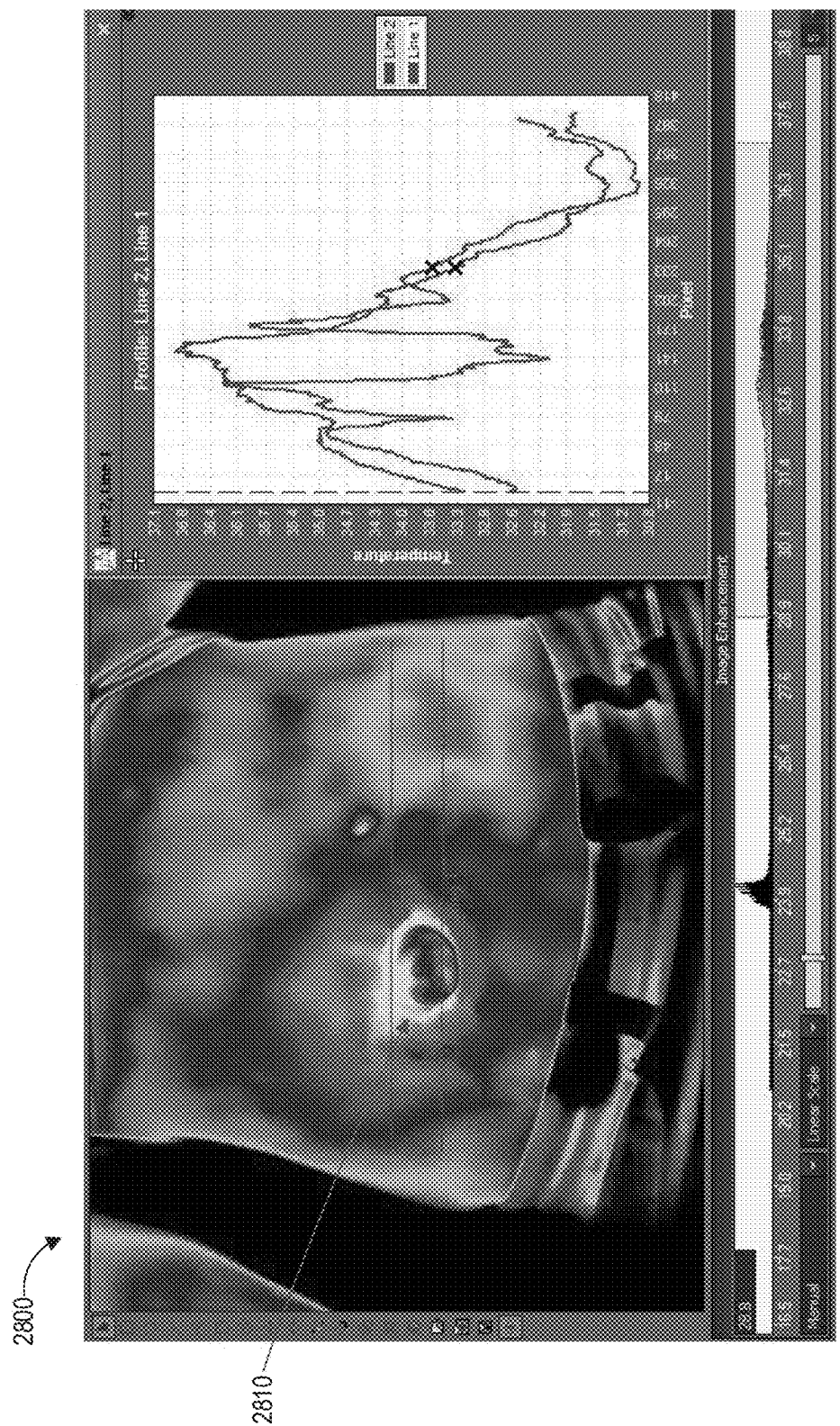
FIG. 28 depicts an example thermal image of a patient's stoma using a test thermal imaging camera.

FIG. 28 depicts an example thermal image 2800 of a patient's stoma 2810. The thermal image 2800 may have been taken using a camera such as the camera 2730. The thermal image 2800 provides an indication of example temperatures at and around a stoma.

Figure 27:
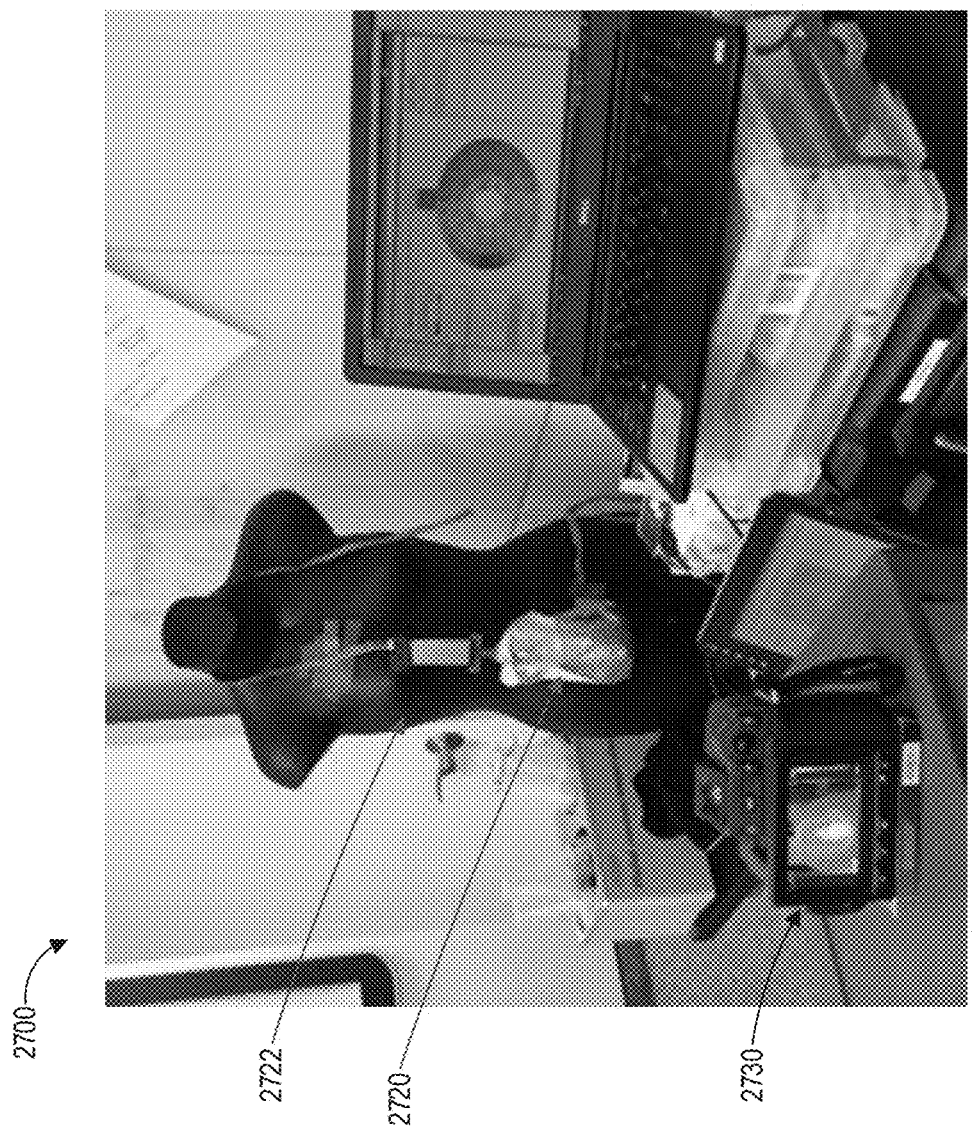
FIG. 27 illustrates an example test setup of an ostomy bag on an anatomical model using a thermal imaging camera.
Figure 29:
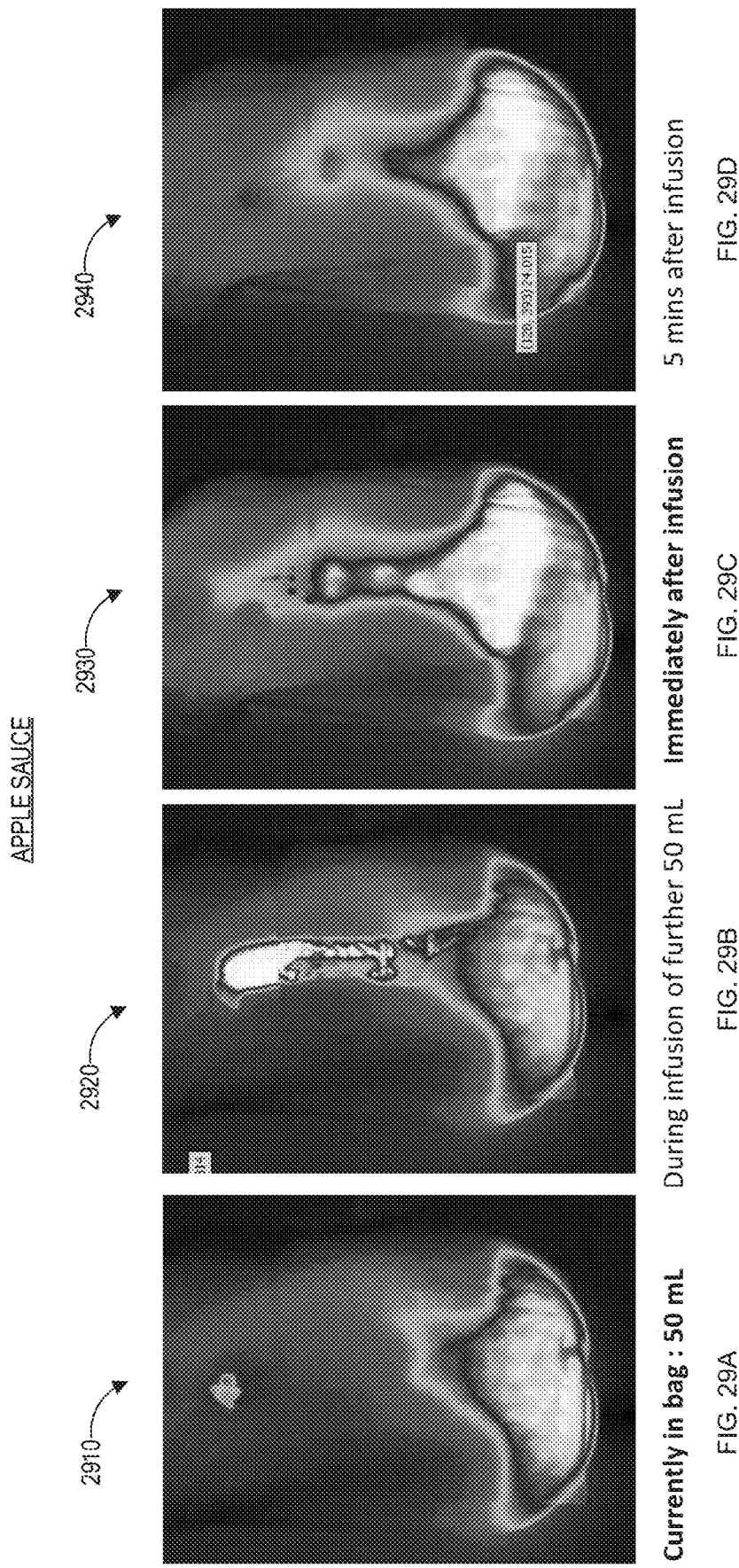
FIGS. 29A-29D depict example thermal images of apple sauce infusion of the ostomy bag of FIG. 27.
Figure 30:
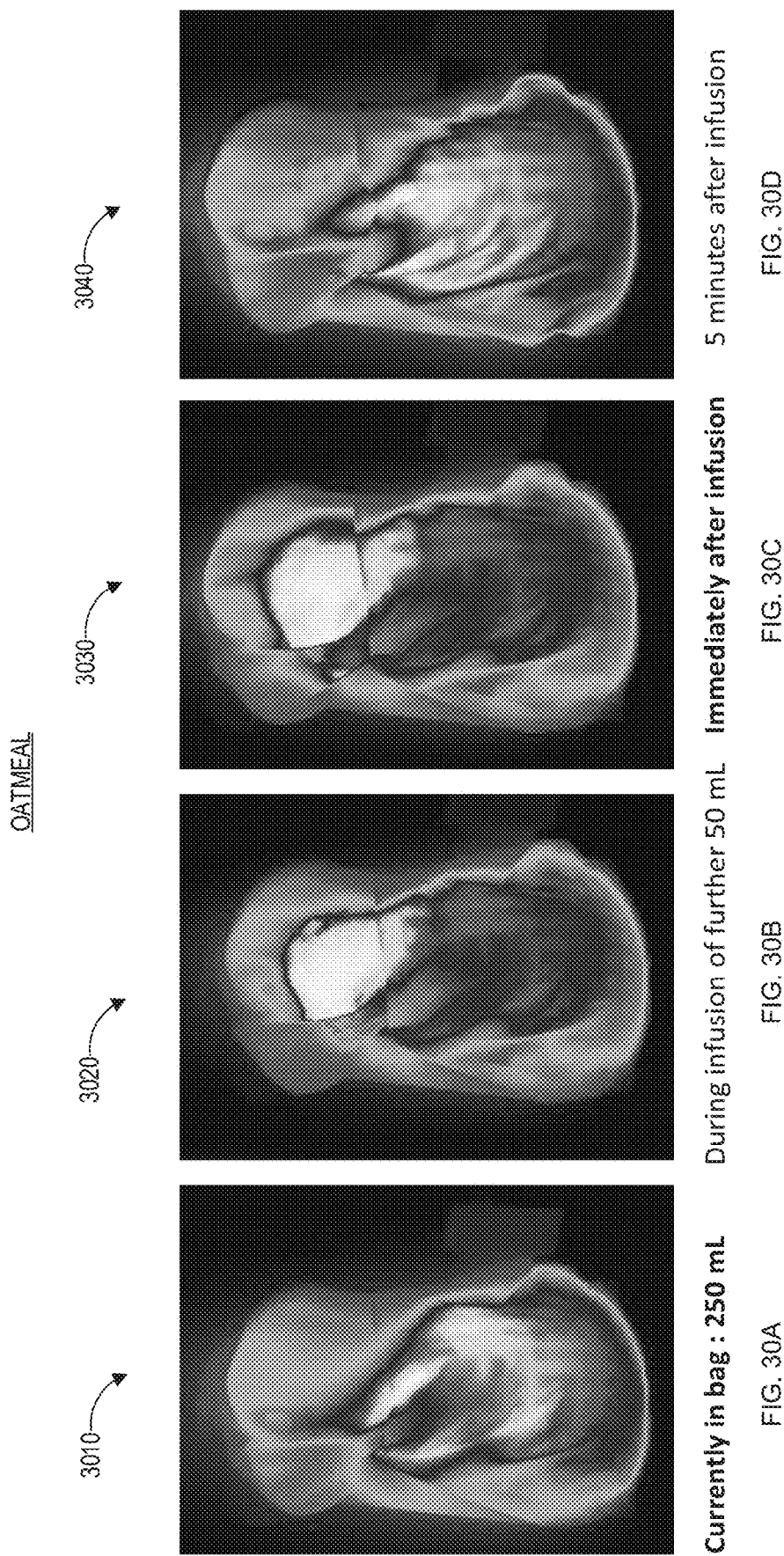
FIGS. 30A-30D depict example thermal images of oatmeal infusion of the ostomy bag of FIG. 27.
Figure 31:
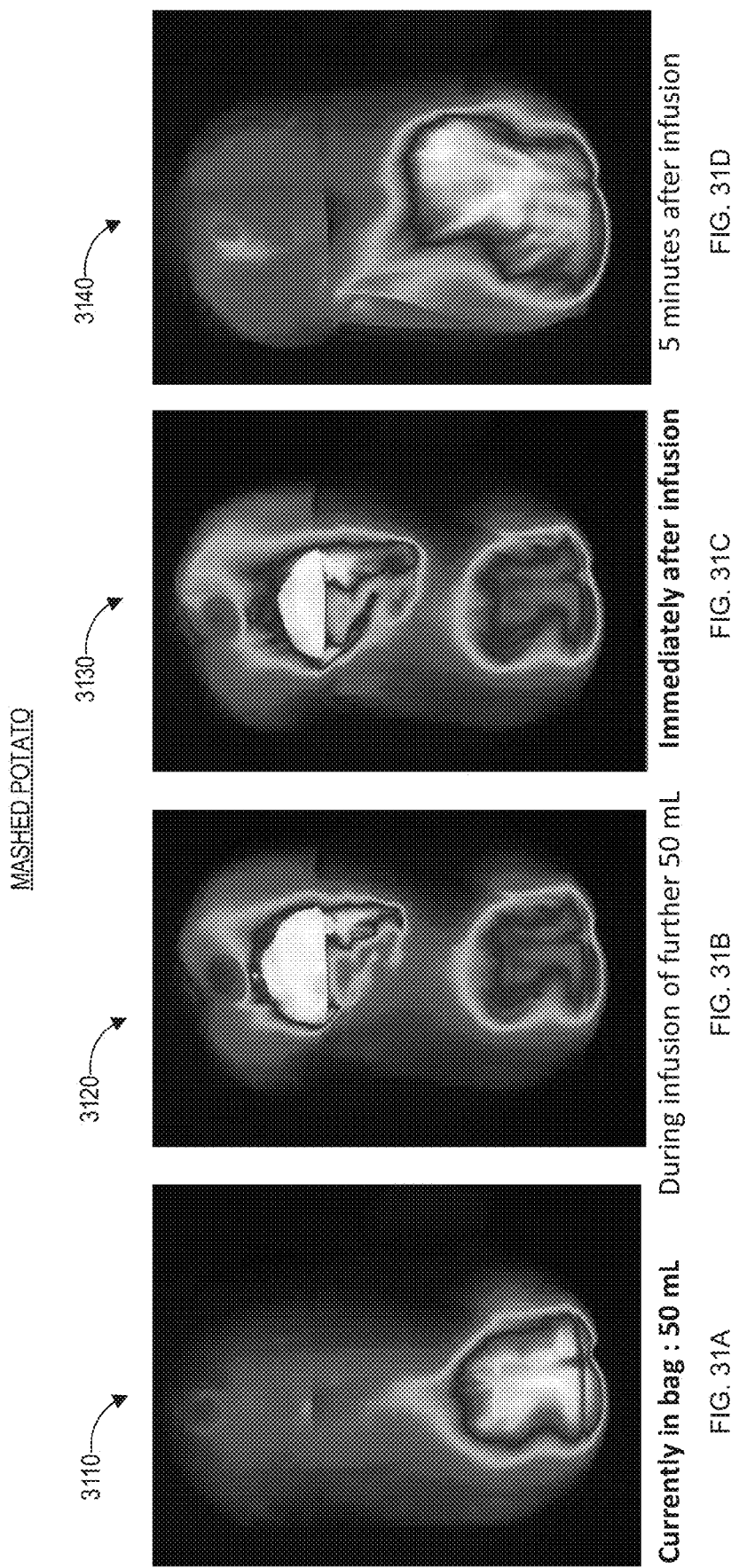
FIGS. 31A-31D depict example thermal images of mashed potatoes infusion of the ostomy bag of FIG. 27.

FIGS. 29-31 depict example thermal images of the ostomy bag 2720 of FIG. 27. In FIG. 29, images 2910-2940 depict an apple sauce infusion. In image 2910, the image depicts material currently in the bag. The image 1920 depicts image during an infusion of apple sauce. The image 1930 depicts the bag immediately after the infusion. The final image, 1940, depicts the bag five minutes after the infusion. FIGS. 30 and 31 depict similar images 3010-3040 and 3110-3140 for oatmeal and mashed potatoes, respectively.

The ostomy wafer or the ostomy bag can include one or more IR temperature sensors. A plurality of IR temperature sensors can be dispersed about the ostomy wafer or the ostomy bag. These sensors would be generally far closer to the patient's skin than the thermal imaging camera 2730 of FIG. 27. Accordingly, the images or temperatures output by each sensor in the wafer and/or the bag may individually depict just a portion of the temperature at the wafer and/or the bag. Collectively, a plurality of IR temperature sensors can provide temperature data for a large area of the wafer and/or bag.

The hub 122 can poll the IR temperature sensors periodically, such as every second, every minute, every five minutes, or at some other interval. The outputs from these sensors can be provided to a processor, which can average or otherwise combine the images or temperatures into a single image for further analysis. The processor could also analyze the images or temperatures separately without combining them together. The processor can be in the hub 122, user device 130, or the backend system 170 (which may be in the cloud). The processor can use any of the leak detection, irritation detection, bag fill, or other algorithms described herein to analyze the output of the IR temperature sensors.

Additional Example Combinations of Features

In some configurations, a system for detecting skin inflammation can include a flexible sheet, having an adhesive on at least a first surface for adhering to skin; a plurality of temperature sensors in a first region of the flexible sheet for measuring the temperature in the first region of the flexible sheet; at least one temperature sensor in a second region of the flexible sheet for measuring the temperature in the second region of the flexible sheet, the second region being remote from the first region; a wireless transmitter configured to transmit data derived from the temperature sensors to a wireless receiver; and a comparator adapted to compare the temperature in the first region of the flexible sheet with the temperature in the second region of the flexible sheet, and thereby produce a difference signal indicative of the presence or absence of skin inflammation in a region of skin in contact with the first region of the flexible sheet.

In one configuration, the system can further include a wireless receiver for receiving the signal transmitted by the wireless transmitter and communicating the detected presence or absence of skin inflammation to a user.

In one configuration, the wireless receiver can include a visual display for presenting to the user a visual representation of the difference in temperature between the first region of the flexible sheet and the second region of the flexible sheet.

In one configuration, the wireless receiver can include an alarm for alerting the user when the detected difference in temperature between the first region of the flexible sheet and the second region of the flexible sheet exceeds a preselected threshold.

In some configurations, the data transmitted from the wireless transmitter to the wireless receiver can be data indicative of the comparison of the temperature in the first region of the flexible sheet with the temperature in the second region of the flexible sheet, and the comparator is mounted on or proximate to the flexible sheet.

In some configurations, the data transmitted from the wireless transmitter to the wireless receiver can be data indicative of the temperature in the first region of the flexible sheet and the temperature in the second region of the flexible sheet, and the comparator is incorporated in the wireless receiver.

In some configurations, a system for detecting skin inflammation can include a flexible sheet, having an adhesive on at least a first surface for adhering to skin; a plurality of temperature sensors in a first region of the flexible sheet for measuring the temperature in the first region of the flexible sheet; at least one temperature sensor in a second region of the flexible sheet for measuring the temperature in the second region of the flexible sheet, the second region being remote from the first region; an electrical connector to enable connection of a processor to the temperature sensors, wherein each said temperature sensor can be connected to the electrical connector by at least one electrical conductor; and a pattern of indicia defining at least one severance region, such that severing the flexible sheet in the severance region enables the removal of a part of the flexible sheet, together with one or more of the temperature sensors, thereby creating an opening in the flexible sheet, such that any said electrical conductors which are connected to temperature sensors which are not thereby removed can remain intact after the severance process.

In some configurations, the severance region can include a plurality of concentric circles or partial circles, such that severing the flexible sheet at each said concentric circle or partial circle provides a circular opening of a different size.

In some configurations, the system can include a processor connected to the electrical connector for obtaining the temperature values reported by each said temperature sensor.

In some configurations, the system can include a wireless transmitter configured to transmit data derived from the temperature sensors to a wireless receiver.

In some configurations, the system can include a wireless receiver for receiving the signal transmitted by the wireless transmitter and communicating the data derived from the temperature sensors to a user.

In some configurations, the wireless receiver includes a visual display for presenting to the user a visual representation of the difference in temperature between the first region of the flexible sheet and the second region of the flexible sheet.

In some configurations, the wireless receiver includes an alarm for alerting the user when the detected difference in temperature between the first region of the flexible sheet and the second region of the flexible sheet exceeds a preselected threshold.

In some configurations, the system can include a comparator adapted to compare the temperature in the first region of the flexible sheet with the temperature in the second region of the flexible sheet, and thereby produce a difference signal indicative of the presence or absence of skin inflammation in a region of skin in contact with the first region of the flexible sheet.

In some configurations, the system can include a wireless transmitter, wherein the data transmitted from the wireless transmitter to the wireless receiver is data indicative of the comparison of the temperature in the first region of the flexible sheet with the temperature in the second region of the flexible sheet, and the comparator is mounted on or proximate to the flexible sheet.

In some configurations, the system can include a wireless transmitter and a wireless receiver, wherein the data transmitted from the wireless transmitter to the wireless receiver can be data indicative of the temperature in the first region of the flexible sheet and the temperature in the second region of the flexible sheet, and the comparator can be incorporated in the wireless receiver.

In some configurations, the temperature sensors can be positioned in the flexible sheet such that when the device is applied to a wound on the skin surface, the plurality of temperature sensors in the first region of the flexible sheet detect the temperature of skin adjacent to the wound and the at least one temperature sensor in the second region of the flexible sheet detects the temperature of skin remote from the wound In some configurations, the flexible sheet can form part of an ostomy wafer and is dimensioned so as to be positioned around a colostomy stoma, an ileostomy stoma or a urostomy stoma.

In some configurations, the temperature sensors can be thermistors or IR temperature sensors.

In some configurations, an ostomy system for detecting peristomal skin inflammation can include an ostomy wafer comprising a flexible sheet, having an adhesive on at least a first surface for adhering to skin; a plurality of temperature sensors in the peristomal region of the ostomy wafer for measuring the temperature in the peristomal region of the ostomy wafer; at least one temperature sensor in a second region of the ostomy wafer for measuring the temperature in the second region of the ostomy wafer, the second region being remote from the peristomal region; and an electrical connector to enable connection of a processor to the temperature sensors, wherein each said temperature sensor can be connected to the electrical connector by at least one electrical conductor; and an ostomy bag having means for receiving a wireless transmitter configured to transmit data derived from the temperature sensors to a wireless receiver.

In some configurations, the system can include a processor connected to the electrical connector for obtaining the temperature values reported by each said temperature sensor.

In some configurations, the system can include a wireless transmitter mounted on the ostomy bag and configured to transmit data derived from the temperature sensors to a wireless receiver.

In some configurations, the system can include a wireless receiver for receiving the signal transmitted by the wireless transmitter and communicating the data derived from the temperature sensors to a user.

In some configurations, the wireless receiver can include a visual display for presenting to the user a visual representation of the difference in temperature between the peristomal region of the ostomy wafer and the second region of the ostomy wafer.

In some configurations, the wireless receiver includes an alarm for alerting the user when the detected difference in temperature between the peristomal region of the ostomy wafer and the second region of the ostomy wafer exceeds a preselected threshold.

In some configurations, the system can include a comparator adapted to compare the temperature in the peristomal region of the ostomy wafer with the temperature in the second region of the ostomy wafer, and thereby produce a difference signal indicative of the presence or absence of skin inflammation in the peristomal skin.

In some configurations, the system can include a wireless transmitter, wherein the data transmitted from the wireless transmitter to the wireless receiver can be data indicative of the comparison of the temperature in the peristomal region of the ostomy wafer with the temperature in the second region of the ostomy wafer, and the comparator is mounted on or proximate to the flexible sheet.

In some configurations, the system can include a wireless transmitter and a wireless receiver, wherein the data transmitted from the wireless receiver to the wireless receiver can be data indicative of the temperature in the peristomal region of the ostomy wafer and the temperature in the second region of the ostomy wafer, and the comparator is incorporated in the wireless receiver.

In some configurations, the system can include a pattern of indicia defining at least one severance region, such that severing the ostomy wafer in the severance region can enable the removal of a part of the ostomy wafer, together with one or more of the temperature sensors, thereby creating an opening in the ostomy wafer, such that any said electrical conductors which are connected to temperature sensors which are not thereby removed remain intact after the severance process.

In some configurations, the severance region can include a plurality of concentric circles or partial circles, such that severing the ostomy wafer at each said concentric circle or partial circle provides a circular opening of a different size.

In some configurations, A method for detecting skin inflammation can include adhering a flexible sheet to the skin, the flexible sheet having a plurality of temperature sensors in a first region for measuring the temperature in the first region of the flexible sheet and at least one temperature sensor in a second region of the flexible sheet for measuring the temperature in the second region of the flexible sheet, the second region being remote from the first region; measuring the temperature in the first region and the second region of the flexible sheet; and comparing the temperature in the first region of the flexible sheet with the temperature in the second region of the flexible sheet, thereby detecting the presence or absence of skin inflammation in a region of skin in contact with the first region of the flexible sheet.

In some configurations, an ostomy bag can include two walls joined together along a seam around at least a portion of an edge of the ostomy bag, a first one of the walls configured to be placed facing skin of a user and a second one of the walls configured to face away from the user when the first wall faces the skin of the user; an opening in the first wall, the opening configured to be disposed around a stoma of the user and to receive effluent from the stoma; and a plurality of temperature sensors and a plurality of capacitive sensors, wherein the plurality of temperature sensors measure a temperature change due to the effluent entering the bag, and wherein the plurality of capacitive sensors measure a capacitance change due to the effluent entering the bag, the sensor layer further comprising one or more wireless communication antennas, wherein when in use, the one or more antennas are in electrical communication with one or more antennas on an ostomy wafer configured to couple the first one of the walls of the ostomy bag to the skin of the user, and/or one or more antennas on a hub configured to be coupled to the ostomy bag on the second one of the walls.

In some configurations, the plurality of temperature sensors and the plurality of capacitive sensors are located on a sensor layer disposed in, on, or between one of the two walls of the ostomy bag.

In some configurations, the plurality of temperature sensors and the plurality of capacitive sensors are printed on one or both of the two walls of the ostomy bag.

In some configurations, the capacitive sensors are arranged in a pattern of lines at non-90 degree angles with respect to one another.

In some configurations, the capacitive sensors are configured to detect a fill level of the effluent in the bag when the bag is in an upright position and tilted.

In some configurations, an ostomy bag can include two walls joined together along a seam around at least a portion of an edge of the ostomy bag, a first one of the walls configured to be placed facing skin of a user and a second one of the walls configured to face away from the user when the first wall faces the skin of the user; an opening in the first wall, the opening configured to be disposed around a stoma of the user and to receive effluent from the stoma; and a sensor layer disposed in, on, or between one of the two walls of the ostomy bag, the sensor layer comprising a plurality of temperature sensors and a plurality of capacitive sensors, wherein the plurality of temperature sensors measure a temperature change due to the effluent entering the bag, and wherein the plurality of capacitive sensors measure a capacitance change due to the effluent entering the bag, the sensor layer further comprising one or more wireless communication antennas, wherein when in use, the one or more antennas are in electrical communication with one or more antennas on an ostomy wafer configured to couple the first one of the walls of the ostomy bag to the skin of the user, and/or one or more antennas on a hub configured to be coupled to the ostomy bag on the second one of the walls.

In some configurations, the capacitive sensors can be arranged in a pattern of lines at non-90 degree angles with respect to one another.

In some configurations, an ostomy bag can include two walls joined together along a seam around at least a portion of an edge of the ostomy bag, a first one of the walls configured to be placed facing skin of a user and a second one of the walls configured to face away from the user when the first wall faces the skin of the user; an opening in the first wall, the opening configured to be disposed around a stoma of the user and to receive effluent from the stoma; and a sensor layer disposed in one of the two walls of the ostomy bag, the sensor layer comprising temperature sensors configured to measure temperature of the effluent.

In some configurations, a method of detecting skin irritation around a stoma can include under control of a hardware processor, sensing temperature readings of a plurality of temperature sensors disposed in a ring about an ostomy wafer; detecting a slow change in the temperature of one or more of the temperature sensors, the rapid slow change occurring greater than a threshold time; and outputting an indicating that irritation has occurred at a location in the ostomy wafer corresponding with the one or more temperature sensors.

In some configurations, the method can be implemented with any of the features of an ostomy device disclosed herein.

In some configurations, a method of detecting fill of an ostomy bag can include under control of a hardware processor, sensing temperature with readings of a plurality of temperature sensors disposed in an ostomy bag; detecting a change in the temperature of a plurality of the temperature sensors as a flow; and outputting an indicating that a volume of bag fill has increased responsive to detecting the change in the temperature.

In some configurations, the plurality of temperature sensors are disposed in a matrix in the ostomy bag.

In some configurations, the hardware processor can be configured to detect the change in temperature as a change in temperature progressing from first ones of the temperature sensors at an upper part of the ostomy bag and to second ones of the temperature sensors at a lower part of the ostomy bag.

In some configurations, the hardware processor is further configured to detect a phase of the effluent based on a speed of the change in temperature.

In some configurations, the hardware processor is further configured to consider the temperature change to correspond to effluent but to reject a second temperature change that does not correspond to temperature changes flowing from the first temperature sensors to the second temperature sensors.

In some configurations, the hardware processor is further configured to reject a second temperature change that is below a threshold rate.

In some configurations, the hardware processor is further configured to calibrate based on detecting body temperature prior to flow of the effluent.

In some configurations, the hardware processor is further configured to cause temperature changes to be ignored that are due to gas.

In some configurations, the hardware processor is further configured to subtract a volume of effluent due to gas from a volume calculation based on the fill detection.

In some configurations, the hardware processor is further configured to detect the gas based on output from a gas sensor disposed in the ostomy bag.

In some configurations, the method can include causing to be displayed on a user device in electrical communication with the bag a volume of bag fill.

In some configurations, the method can include causing to be displayed on a user device in electrical communication with the bag a distance to a nearby restroom.

In some configurations, the method can include causing to be displayed on a user device in electrical communication with the bag a hydration tracker.

In some configurations, the method can be implemented with any of the features of an ostomy device disclosed herein.

In some configurations, a method of detecting phasing of effluent in an ostomy bag can include under control of a hardware processor, sensing temperature values of a plurality of temperature sensors disposed in an ostomy bag, the plurality of temperature sensors being in contact with the output; and determining a phase of the effluent based in part on the temperature values.

In some configurations, the detecting is based in part on a rate of change of the temperature values of the plurality of temperature sensors in contact with the effluent.

In some configurations, the detecting is based in part on a flow rate determined from the temperature values of the plurality of temperature sensors.

In some configurations, the temperature values are presented as a heat map.

In some configurations, a heavier thermal print on the heat map indicates a more viscous effluent.

In some configurations, the calculating is performed by machine learning.

In some configurations, the calculating is performed by a trained neural network model.

In some configurations, the trained neural network model is configured to recognize borders between effluents of different phases on the heat map.

In some configurations, a system for monitoring an ostomy patient can include a wireless device configured to receive sensor signals from an ostomy device, the sensor signals comprising signals related to temperature; a memory device storing processor-executable instructions; a hardware processor configured to execute the processor-executable instructions to perform any of the features of using the ostomy device disclosed herein or optionally to provide the sensor signals to a backend server that performs any of the features of using the ostomy device disclosed herein; and a display configured to output a result of execution of the processor-executable instructions, the result comprising one or more of: an indication of a leak, an indication of skin irritation, and an indication of volume of effluent in the ostomy device.

In some configurations, the hardware processor can be further configured to output one or more of the following: a user interface comprising functionality for a user to specify hydration and/or food input, a user interface configured to output information related to the specified hydration and/or food input, a user interface configured to alert the user to a need to obtain more hydration and/or food input, a user interface configured to indicate a nearby restroom location, and a user interface configured to indicate that hydration and/or food input is available at the restroom location.

Terminology

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a hardware processor comprising digital logic circuitry, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. An ostomy wafer configured to be coupled to an ostomy bag, the ostomy wafer comprising:
    an adhesive layer configured to adhere to skin around a stoma of a living person;
    a flexible sensor layer coupled with the adhesive layer, the flexible sensor layer comprising a plurality of temperature sensors; and
    a plurality of conductors wired to the plurality of temperature sensors, the plurality of conductors configured to be electrically coupled with a processor located at or proximate to the ostomy bag so that signals from the plurality of temperature sensors are electrically communicated to the processor,
    wherein the flexible sensor layer comprises a neck and a body, the plurality of conductors being disposed in part on the neck.

2. The ostomy wafer of claim 1, wherein the ostomy wafer further comprises a third layer configured to cover the flexible sensor layer such that the flexible sensor layer is sandwiched between the adhesive layer and the third layer.

3. The ostomy wafer of claim 2, wherein the third layer comprises an adhesive configured to adhere to an ostomy bag.

4. The ostomy wafer of claim 1, wherein the temperature sensors are arranged in concentric rings or concentric partial rings.

5. The ostomy wafer of claim 4, wherein one or more of the concentric partial rings are severable so as to fit the ostomy wafer to different sized stomas.

6. The ostomy wafer of claim 4, wherein the concentric partial rings comprise two or more rings.

7. The ostomy wafer of claim 1, wherein the plurality of conductors comprise curved portions between the temperature sensors.

8. The ostomy wafer of claim 1, wherein the plurality of temperature sensors are electrically connected in a matrix circuit.

9. The ostomy wafer of claim 1, further comprising one or more capacitive sensors.

10. The ostomy wafer of claim 9, wherein the one or more capacitive sensors are disposed on the flexible sensor layer or a second flexible sensor layer.

11. The ostomy wafer of claim 9, wherein the one or more capacitive sensors are configured to detect moisture in adhesives of the adhesive layer.

12. The ostomy wafer of claim 1, wherein a first temperature sensor of the plurality of temperature sensors is disposed on the neck as a reference sensor.

13. The ostomy wafer of claim 12, wherein all other ones of the temperature sensors other than the first temperature sensor are disposed on the body.

14. The ostomy wafer of claim 1, wherein the temperature sensors comprise first temperature sensors disposed in a first region closer to a center of the body and second temperature sensors disposed in a second region farther from the center of the body.

15. The ostomy wafer of claim 14, wherein the second temperature sensors are used as reference temperature sensors.

16. The ostomy wafer of claim 1, wherein the adhesive layer comprises hydrocolloid adhesives.

17. The ostomy wafer of claim 1, further comprising a border ring surrounding the adhesive layer, the border ring comprising an adhesive side configured to adhere to the skin around the stoma.

18. The ostomy wafer of claim 17, wherein the adhesive side of the border ring comprises acrylic adhesives or hydrocolloid adhesives.

19. The ostomy wafer of claim 1, further comprising a printed circuit board (PCB) in electrical communication with the plurality of temperature sensors, the PCB configured to send the signals from the plurality of temperature sensors to the processor located at or proximate to the ostomy bag.

20. The ostomy wafer of claim 1, in combination with an ostomy bag comprising a plurality of sensors.

21. The ostomy wafer of claim 1, further comprising at least one antenna ring for wireless communication with the processor located at or proximate to the ostomy bag, the at least one antenna ring comprises conductive traces.

22. The ostomy wafer of claim 21, wherein the at least one antenna ring is concentric with and located radially outward from the plurality of conductors, wherein the plurality of conductors comprise concentric rings.

23. The ostomy wafer of claim 21, wherein the at least one antenna ring and the plurality of conductors cross at one or more locations.

* * * * *